(12) United States Patent
Shimizu et al.

(10) Patent No.: US 9,023,882 B2
(45) Date of Patent: May 5, 2015

(54) 5-MEMBERED NITROGEN CONTAINING HETEROCYCLIC DERIVATIVES AND PHARMACEUTICAL COMPOSITIONS COMPRISING THE SAME

(75) Inventors: Kazuo Shimizu, Azumino (JP); Yasushi Takigawa, Azumino (JP); Hideki Fujikura, Azumino (JP); Masato Iizuka, Azumino (JP); Masahiro Hiratochi, Azumino (JP); Norihiko Kikuchi, Azumino (JP)

(73) Assignee: Kissei Pharmaceutical Co., Ltd., Matsumoto-shi (JP)

( * ) Notice: Subject to any disclaimer, the term of this patent is extended or adjusted under 35 U.S.C. 154(b) by 0 days.

(21) Appl. No.: 13/494,380

(22) Filed: Jun. 12, 2012

(65) Prior Publication Data
US 2012/0289506 A1 Nov. 15, 2012

Related U.S. Application Data

(63) Continuation of application No. 12/595,437, filed as application No. PCT/JP2008/057093 on Apr. 10, 2008, now Pat. No. 8,227,500.

(30) Foreign Application Priority Data

Apr. 11, 2007 (JP) ................................. 2007-104094

(51) Int. Cl.
| | | |
|---|---|---|
| A61K 31/4025 | (2006.01) |
| C07D 231/10 | (2006.01) |
| C07D 207/30 | (2006.01) |
| A61K 31/4155 | (2006.01) |
| C07D 403/04 | (2006.01) |
| A61K 31/402 | (2006.01) |
| A61K 31/165 | (2006.01) |
| A61K 31/404 | (2006.01) |
| A61K 31/415 | (2006.01) |
| A61K 31/427 | (2006.01) |
| A61K 31/4439 | (2006.01) |
| A61K 31/454 | (2006.01) |
| A61K 31/5377 | (2006.01) |
| A61K 45/06 | (2006.01) |

(Continued)

(52) U.S. Cl.
CPC ............. *A61K 31/402* (2013.01); *A61K 31/165* (2013.01); *A61K 31/404* (2013.01); *A61K 31/415* (2013.01); *A61K 31/4155* (2013.01); *A61K 31/427* (2013.01); *A61K 31/4439* (2013.01); *A61K 31/454* (2013.01); *A61K 31/5377* (2013.01); *A61K 45/06* (2013.01); *C07D 207/34* (2013.01); *C07D 231/14* (2013.01); *C07D 231/16* (2013.01); *C07D 231/20* (2013.01); *C07D 231/38* (2013.01); *C07D 231/40* (2013.01); *C07D 401/04* (2013.01); *C07D 403/04* (2013.01); *C07D 405/04* (2013.01); *C07D 405/06* (2013.01); *C07D 409/04* (2013.01); *C07D 409/12* (2013.01); *C07D 417/04* (2013.01)

(58) Field of Classification Search
USPC ........................................ 514/403; 548/356.1
See application file for complete search history.

(56) References Cited

U.S. PATENT DOCUMENTS

| 5,085,686 A | 2/1992 | Vogelbacher et al. |
| 5,187,185 A | 2/1993 | Outcalt et al. |

(Continued)

FOREIGN PATENT DOCUMENTS

| EP | 0 770 610 A1 | 5/1997 |
| EP | 1932833 A1 | 6/2008 |

(Continued)

OTHER PUBLICATIONS

Patani et al., Chem Rev, 1996, vol. 96 (8), especially p. 3149.*

(Continued)

*Primary Examiner* — Michael Barker
*Assistant Examiner* — Po-Chih Chen
(74) *Attorney, Agent, or Firm* — Westerman, Hattori, Daniels & Adrian, LLP

(57) ABSTRACT

5-membered heterocyclic derivatives represented by general formula (I) having xanthine oxidase inhibitory activities and useful as agents for the prevention or treatment of a disease associated with abnormality of serum uric acid level, prodrugs thereof, or salts thereof. In the formula (I), T represents nitro, cyano and the like; ring J represents aryl or heteroaryl; Q represents carboxy, 5-tetazolyl and the like; Y represents H, OH, NH$_2$, halogen, haloalkyl and the like; X$^1$ and X$^2$ independently represent CR$^2$ or N; R$^2$ represents H, alkyl and the like; R$^1$ represents halogen, cyano, haloalkyl, A-D-E-G-L-M, —N(-D-L-M)$_2$ and the like, A represents a single bond, O, S and the like; D, G and M independently represent optionally substituted alkylene, cycloalkylene, heterocycloalkylene, arylene, heteroarylene and the like; E and L independently represent a single bond, O, S, COO, SO$_2$ and the like.

(I)

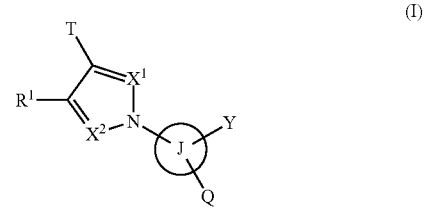

24 Claims, No Drawings

(51) Int. Cl.
| | |
|---|---|
| *C07D 207/34* | (2006.01) |
| *C07D 231/14* | (2006.01) |
| *C07D 231/16* | (2006.01) |
| *C07D 231/20* | (2006.01) |
| *C07D 231/38* | (2006.01) |
| *C07D 231/40* | (2006.01) |
| *C07D 401/04* | (2006.01) |
| *C07D 405/04* | (2006.01) |
| *C07D 405/06* | (2006.01) |
| *C07D 409/04* | (2006.01) |
| *C07D 409/12* | (2006.01) |
| *C07D 417/04* | (2006.01) |

(56) References Cited

U.S. PATENT DOCUMENTS

| | | | |
|---|---|---|---|
| 5,215,994 | A | 6/1993 | Oku et al. |
| 5,506,260 | A | 4/1996 | Outcalt et al. |
| 5,760,068 | A | 6/1998 | Talley et al. |
| 5,824,691 | A | 10/1998 | Kuno et al. |
| 5,859,215 | A | 1/1999 | Rodriguez-Ubis et al. |
| 6,015,829 | A | 1/2000 | Ishibuchi et al. |
| 6,355,386 | B1 | 3/2002 | Helber et al. |
| 6,369,002 | B1 | 4/2002 | Kunz et al. |
| 6,511,974 | B1 | 1/2003 | Dusza et al. |
| 6,894,067 | B2 * | 5/2005 | Minich et al. .......... 514/352 |
| 7,947,707 | B2 | 5/2011 | Toyoshima et al. |
| 2003/0069242 | A1 | 4/2003 | Toriyabe et al. |
| 2003/0144280 | A1 | 7/2003 | Ando et al. |
| 2004/0180889 | A1 | 9/2004 | Suto et al. |
| 2005/0004103 | A1 | 1/2005 | Koshio et al. |
| 2007/0167631 | A1 | 7/2007 | Luthy et al. |
| 2008/0045505 | A1 | 2/2008 | Bruton et al. |
| 2009/0163520 | A1 | 6/2009 | Coulter et al. |
| 2011/0039833 | A1 | 2/2011 | Bruton et al. |

FOREIGN PATENT DOCUMENTS

| | | | | |
|---|---|---|---|---|
| JP | 62-153273 | * | 12/1985 | .......... C07D 231/40 |
| JP | 08-511243 | A | 11/1996 | |
| JP | 2000-001431 | A | 1/2000 | |
| JP | 3220987 | B2 | 10/2001 | |
| WO | 94-26709 | A1 | 11/1994 | |
| WO | 97-46530 | A1 | 12/1997 | |
| WO | 03-042181 | A1 | 5/2003 | |
| WO | 03-073999 | A2 | 9/2003 | |
| WO | 2005040144 | A1 | 5/2005 | |
| WO | 2005-058830 | A1 | 6/2005 | |
| WO | 2006-066937 | A2 | 6/2006 | |
| WO | 2007-043400 | A1 | 4/2007 | |
| WO | 2007-043401 | A1 | 4/2007 | |

OTHER PUBLICATIONS

European Office Action dated Jul. 30, 2012, issued in corresponding European Patent Application No. 08 740 194.9 (4 pages).
Database Registry [Online], 2006, Database accession No. 890715-87-4, American Chemical Society (1 page).
Database Registry [Online], 2006, Database accession No. 890716-01-5, American Chemical Society (1 page).
Database Registry [Online], 2006, Database accession No. 899701-01-0, American Chemical Society (1 page).
Database Registry [Online], 2006, Database accession No. 890715-79-4, American Chemical Society (1 page).
Russian Office Action dated Jun. 28, 2013, issued in Russian Patent Application No. 2009141613/04, which is a Russian National Stage Application of PCT/JP2008/057093.
Balsamo A. et al., "Synthesis of heteroaromatic analogs of (2-aryl-1-cyclopentenyl-1-alkylidene)-(arylmethyloxy) amine COX-2 inhibitors: effects on the inhibitory activity of the replacement of the cyclopentene central core with pyrazole, thiophene or isoxazole ring," European Journal of Medicinal Chemistry, 2003, 38, p. 157-168.
Cobb J. et al., "Synthesis and Reactions of 1-aryl-2-nitropyrroles. Structural and conformational study of ethyl N-[2'-[1'-(2-nitropyrrolyl)]phenyl]-N-toluene-4-sulfonamide glycinate," Tetrahedron, 1996, vol. 52, No. 12, p. 4485-4494.
International Search Report of PCT/JP2008/057093, Mailing Date of Jun. 17, 2008.
Chinese Office Action dated May 12, 2011, issued in corresponding Chinese Patent Appluication No. 200880018819.3.
XP002632443, Database Reaxys [Online], Elsevier Properties SA; 2003, Chemical Structural Formula Database accession No. 9635644 CAS Registry No. 750597-06-9 (From Asiri, Heterocyclic Communications 2003, vol. 9, #5, 483).
European Search Report dated May 25, 2011, issued in corresponding European Patent Application No. 08740194.9.
Oh et al., "Synthesis of celecoxib via 1, 3-dipolar cycloaddition" Tetrahedron Letters, Elsevier, Amsterdam, NL, vol. 47, No. 45, Nov. 6, 2006, pp. 7943-7946, XP005681865.
Patani et al., Chem Rev, 1996, vol. 96 (8), pp. 3147-3176, esp. p. 3149.

* cited by examiner

5-MEMBERED NITROGEN CONTAINING HETEROCYCLIC DERIVATIVES AND PHARMACEUTICAL COMPOSITIONS COMPRISING THE SAME

CROSS REFERENCE TO RELATED APPLICATIONS

This is a continuation of U.S. application Ser. No. 12/595,437 filed Oct. 9, 2009, which is a 371 of PCT/JP2008/057093 filed Apr. 10, 2008, which are incorporated herein by reference.

TECHNICAL FIELD

The present invention relates to 5-membered heterocyclic derivatives useful as medicaments.

More particularly, the present invention relates to 5-membered heterocyclic derivatives having xanthine oxidase inhibitory activities and useful as agents for the prevention or treatment of a disease associated with abnormality of serum uric acid level, prodrugs thereof, or pharmaceutically acceptable salts thereof.

BACKGROUND ART

Uric acid is the final product of purine metabolism in human. In many mammals, unlike human, uric acid is further broken down by urate oxidase (uricase) in the liver into allantoin, which is excreted through the kidney. In human, main pathway of uric acid excretion is the kidney, wherein approximately two thirds of uric acid is excreted in urine. The remaining is excreted in feces. When an excessive production or decreased excretion of uric acid occurs, that causes hyperuricemia. Hyperuricemia is classified into a uric acid overproduction type, a uric acid underexcretion type and a mixed type thereof. This classification of hyperuricemia is clinically important. Aiming for reducing adverse effects of therapeutic agents, therapeutic agents are chosen according to each class (for example, see Non-patent reference 1).

In hyperuricemia with a uric acid overproduction type, urinary excretion of uric acid increases, and when the urinary excretion of uric acid further increases by using of a uricosuric drug, the complication of urinary calculi is possibly developed. Therefore, in principle, allopurinol, a uric acid production inhibitor (or sometimes called a uric acid synthesis inhibitor, hereinafter referred to as "a uric acid production inhibitor"), is used in a uric acid overproduction type.

Uric acid is produced from purine bodies, which are derived from diet and synthesized endogenously, finally by oxidizing xanthine by xanthine oxidase. Allopurinol is developed as a xanthine oxidase inhibitor and an only uric acid production inhibitor used in medical practice. While allopurinol, however, is reported being effective in hyperuricemia and various diseases caused by the same, severe adverse effects such as poisoning syndrome (hypersensitivity angiitis), Stevens-Johnson syndrome, exfoliative dermatitis, anaplastic anemia, liver dysfunction and the like have been also reported (for example, see Non-patent reference 2). As one of the causes, it has been pointed out that allopurinol has a nucleic acid-like structure and inhibits a pathway of pyrimidine metabolism (for example, see Non-patent reference 3).

On the other hand, in hyperuricemia with a uric acid underexcretion type, uric acid excretion decreases. It has been reported that when allopurinol, which is metabolized into oxypurinol to be excreted through the kidney by the same mechanism to uric acid, is used, the excretion of oxypurinol also decreases and that increases the incidence of liver disorders (for example, see Non-patent reference 4). Therefore, in principle, uricosuric drugs such as probenecid, benzbromarone and the like are used in a uric acid underexcretion type. These uricosuric drugs, however, also exert adverse effects such as gastrointestinal disorders, urinary calculi or the like. Particularly, benzbromarone is known as possibly causing fluminant hepatitis in the case of idiosyncratic patients (for example, see Non-patent reference 5).

Thus, it is said that both of the existing uric acid production inhibitor and uricosuric drug have usage restrictions in patients or severe adverse effects. Therefore, the development of an easy-to-use agent for the treatment of hyperuricemia has been desired.

Uric acid is eliminated mainly by the kidney, and the urate dynamics in the kidney has been investigated so far in some experiments using brush-border membrane vesicles (BBMV) prepared from the renal cortex (for example, see Non-patent references 6 and 7). It has been known that in human, uric acid is passed through the kidney glomerulus freely, and there are mechanisms of reabsorption and secretion of uric acid in the proximal tubule (for example, see Non-patent reference 8).

In recent years, the gene (SLC22A12) encoding the human kidney urate transporter has been identified (for example, see Non-patent reference 9). The transporter encoded by this gene (urate transporter 1, hereinafter referred to as "URAT1") is a 12-transmembrane type molecule belonging to OAT family. URAT1 mRNA was specifically expressed in the kidney, and localization of URAT1 in apical side of the proximal tubule was observed on the human kidney tissue section. In an experiment using xenopus oocyte expression system, uptake of uric acid through URAT1 was shown. Furthermore, it was shown that the uptake of uric acid is transported by exchange with organic anions such as lactic acid, pyrazinecarboxylic acid (PZA), nicotinic acid and the like, and the uric acid uptake through URAT1 is inhibited by uricosuric drugs, probenecid and benzbromarone. Thus, as expected by the experiment using membrane vesicles, it was strongly suggested that URAT1 is a urate/anion exchanger. That is, it was shown that URAT1 is a transporter that plays an important role in uric acid reabsorption in the kidney (for example, see Non-patent reference 9).

In addition, the relation between URAT1 and diseases became clear. Idiopathic renal hypouricemia is a disease wherein uric acid excretion is increased due to abnormal urate dynamics in the kidney and the serum uric acid level becomes low. It is known that the disease is often associated with urinary calculi or acute renal failure after exercise. URAT1 was identified as a causative gene of the renal hypouricemia (for example, see Non-patent reference 9). These things also strongly suggest that URAT1 is responsible for controlling the blood uric acid level.

Therefore, a substance having a URAT1 inhibitory activity is useful as an agent for the treatment and prevention of diseases associated with high blood uric acid levels, that is, hyperuricemia, gouty tophus, gouty arthritis, renal disorder associated with hyperuricemia, urinary calculi or the like.

In the treatment of hyperuricemia, it was reported that a combination of allopurinol of a uric acid production inhibitor and an agent having a uricosuric activity lowered the serum uric acid level more strongly than the single use of allopurinol (for example, see Non-patent references 10 and 11). Therefore, when treatment with a single existing agent can not exert effect enough, a higher therapeutic effect can be expected by a combination use of a uric acid production inhibitor and a uricosuric agent. Furthermore, for hyperuricemia with the uric acid underexcretion type, it is considered that since urinary excretion of uric acid can be decreased by lowering blood uric acid level, the risk of urinary calculi caused by the monotherapy with a uricosuric agent can be reduced. In addition, for hyperuricemia with the mixed type, high therapeutic effect is expected. Thus, an agent having both an inhibitory activity of uric acid production and a uricosuric activity is expected to become an extremely useful agent for the prevention or treatment of hyperuricemia or the like.

As a compound having both xanthine oxidase inhibitory activity and URAT1 inhibitory activity, morin, a natural product, is known (see Non-patent reference 12). In addition, as a compound having a uricosuric activity, biaryl or diaryl ether compounds are known (see Patent reference 1).

As 1-phenyl-5-membered heterocyclic derivatives, 1-phenylpyrrole derivatives and 1-phenylpyrazole derivatives are known (for example, see Patent references 2 and 3). However, in any of these references, a 5-membered heterocyclic derivative of the present invention is not disclosed concretely, and anything is neither described nor suggested about that it has a xanthine oxidase inhibitory activity or is useful for the prevention or treatment of a disease associated with abnormal serum uric acid level such as gout, hyperuricemia or the like.

Patent reference 1: Tokkai 2000-001431 (JPA2000-001431)

Patent reference 2: The international publication 2006/012642 pamphlet

Patent reference 3: The international publication 2006/021462 pamphlet

Non-patent reference 1: Atsuo Taniguchi and 1 person, Modern Physician, 2004, Vol. 24, No. 8, pp. 1309-1312

Non-patent reference 2: Kazuhide Ogino and 2 persons, Nihon Rinsho (Japan Clinical), 2003, Vol. 61, Extra edition 1, pp. 197-201

Non-patent reference 3: Hideki Horiuchi and 6 persons, Life Science, 2000, Vol. 66, No. 21, pp. 2051-2070

Non-patent reference 4: Hisashi Yamanaka and 2 persons, Konyosankessyo to Tsufu (Hyperuricemia and gout), issued by Medical Review Co., 1994, Vol. 2, No. 1, pp. 103-111

Non-patent reference 5: edited by Konyosankessyo, tsufu no Chiryo guideline sakuseiiinkai (The Committee establishing a guideline for the treatment of hyperuricemia and gout), The guideline for the treatment of hyperuricemia and gout, Edition 1, issued by Nihon tsuhu kakusan taisya gakkai (Japanese society of gout and nucleic acid metabolism), 2002, pp. 32-33

Non-patent reference 6: Francoise Roch-Ramel and 2 persons, Am. J. Physiol., 1994, Vol. 266 (Renal Fluid Electrolyte Physiol., Vol. 35), F797-F805

Non-patent reference 7: Francoise Roch-Ramel and 2 persons, J. Pharmacol. Exp. Ther., 1997, Vol. 280, pp. 839-845

Non-patent reference 8: Hiroaki Kimura and 3 persons, Nihon rinsyo (Japan Clinical), 2003, Vol. 61, Extra Edition 1, pp. 119-123

Non-patent reference 9: Atsushi Enomoto and 18 persons, Nature, 2002, Vol. 417, pp. 447-452

Non-patent reference 10: S Takahashi and 5 persons, Ann Rheum. Dis., 2003, Vol. 62, pp. 572-575

Non-patent reference 11: M. D. Feher and 4 persons, Rheumatology, 2003, Vol. 42, pp. 321-325

Non-patent reference 12: Zhifeng Yu and 2 persons, J. Pharmacol. Exp. Ther., 2006, Vol. 316, pp. 169-175

DISCLOSURE OF THE INVENTION

Problem that the Invention Aims to Solve

The present invention is to provide an agent which has an inhibitory activity of uric acid production for the prevention or treatment of a disease associated with abnormal serum uric acid level.

Means to Solve the Problem

The present inventors have earnestly to solve the above problem. As a result, it was found that 5-membered heterocyclic derivatives represented by the following general formula (I) exert an excellent xanthine oxidase inhibitory activity and extremely lower serum uric acid levels, and therefore, they can be an agent for the prevention or treatment of a disease associated with abnormal serum uric acid level, thereby forming the basis of the present invention.

That is, the present invention relates to:

[1] A 5-membered heterocyclic derivative represented by the general formula (I):

[Chem. 1]

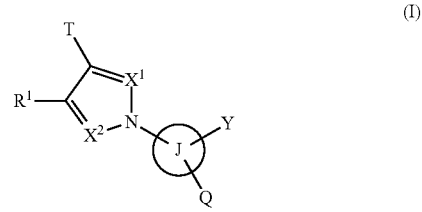

(I)

wherein
T represents nitro, cyano, trifluoromethyl or a halogen atom;
ring J represents an aryl ring or a heteroaryl ring;
Q represents carboxy, lower alkoxycarbonyl, carbamoyl, mono(di)(lower alkyl)carbamoyl, sulfo, sulfamoyl or 5-tetrazolyl;
$X^1$ and $X^2$ independently represent $CR^2$ or N with the proviso that both of $X^1$ and $X^2$ do not represent N at the same time, and when two or more $R^2$ exist, these $R^2$ are optionally the same or different from each other;
$R^2$ represents a hydrogen atom or optionally substituted lower alkyl;
Y represents a hydrogen atom, hydroxy, amino, a halogen atom, perfluoro(lower alkyl), optionally substituted lower alkyl, optionally substituted lower alkoxy, nitro, (lower alkyl)carbonylamino or (lower alkyl)sulfonylamino with the proviso that two or more Y optionally exist on ring J and these Y are optionally the same or different from each other;
$R^1$ represents cyano, perfluoro(lower alkyl), $-A^4$, -A-D-L-M, -A-D-E-G-L-M or $-N(-D-L-M)_2$ with the proviso that two (-D-L-M) are optionally different from each other;
in the formula, $A^4$ represents a hydrogen atom, thiol, —CHO, carboxy, —CONHR³, amino, —N(R³)CHO, —N=CR³NHR⁴, —COCOOH, —COCONHR³, —SO₂NHR³, —N(R³)CONHR⁴ or —N(R³)SO₂NHR⁴;
A represents a single bond, —O—, —S—, —CO—, —COO—, —CON(R³)—, —SO₂—, —NH—, —N(R³)CO—, —N(R³)COO—, —N(R³)SO₂—, —N=CR³N(R⁴)—, —COCOO—, —COCON(R³)—, —SO₂N(R³)—, —N(R³)CON(R⁴)— or —N(R³)SO₂N(R⁴)—, wherein $R^3$ and $R^4$ independently represent a hydrogen atom or lower alkyl;

D represents optionally substituted lower alkylene, optionally substituted lower alkenylene, optionally substituted lower alkynylene, optionally substituted cycloalkylene, optionally substituted heterocycloalkylene, optionally substituted arylene or optionally substituted heteroarylene with the proviso that D is optionally further substituted by -L-M or -E-G-L-M;

E represents a single bond, —O—, —S—, —CO—, —COO—, —CON($R^5$)—, —$SO_2$—, —N($R^5$)—, —N($R^5$)CO—, —N($R^5$)COO—, —N($R^5$)$SO_2$—, —OCON($R^5$)—, —OCOO—, —COCOO—, —COCON($R^5$)—, —$SO_2$N($R^5$)—, —N($R^5$)CON($R^6$)— or —N($R^5$)$SO_2$N($R^6$)—, wherein $R^5$ and $R^6$ independently represent a hydrogen atom or lower alkyl;

G represents optionally substituted lower alkylene, optionally substituted lower alkenylene, optionally substituted lower alkynylene, optionally substituted cycloalkylene, optionally substituted heterocycloalkylene, optionally substituted arylene or optionally substituted heteroarylene;

L represents a single bond, —O—, —S—, —CO—, —COO—, —CON($R^8$)—, —$SO_2$—, —N($R^8$)—, —N($R^8$)CO—, —N($R^8$)COO—, —N($R^8$)$SO_2$—, —OCO—, —OCON($R^8$)—, —OCOO—, —COCOO—, —COCON($R^8$)—, —$SO_2$N($R^8$)—, —N($R^8$)CON($R^9$)— or —N($R^8$)$SO_2$N($R^9$)—, wherein $R^8$ and $R^9$ independently represent a hydrogen atom or lower alkyl; and M represents a hydrogen atom, optionally substituted lower alkyl, optionally substituted lower alkenyl, optionally substituted lower alkynyl, optionally substituted cycloalkyl(lower alkyl), optionally substituted heterocycloalkyl(lower alkyl), optionally substituted aryl(lower alkyl), optionally substituted heteroaryl(lower alkyl), optionally substituted cycloalkyl, optionally substituted heterocycloalkyl, optionally substituted aryl or optionally substituted heteroaryl with the proviso that when M is a hydrogen atom, L is a single bond, —O—, —S—, —CO—, —COO—, —CON($R^8$)—, —N($R^8$)—, —N($R^8$)CO—, —COO—, —OCON($R^8$)—, —COCOO—, —COCON($R^8$)—, —$SO_2$N($R^8$)—, —N($R^8$)CON($R^9$)— or —N($R^8$)$SO_2$N($R^9$)—; with the proviso that when $R^1$ and $R^2$ bound to the neighboring atoms exist, these $R^1$ and $R^2$ optionally bind together to form a ring; respectively, or a prodrug thereof, or a pharmaceutically acceptable salt thereof;

[2] a 5-membered heterocyclic derivative as described in the above [1], wherein Y represents a hydrogen atom, hydroxy, amino, a halogen atom, perfluoro(lower alkyl), optionally substituted lower alkyl or optionally substituted lower alkoxy with the proviso that two or more Y optionally exist on ring J and these Y are optionally the same or different from each other, or a prodrug thereof, or a pharmaceutically acceptable salt thereof;

[3] a 5-membered heterocyclic derivative as described in the above [2], wherein

T represents nitro, cyano or trifluoromethyl;

Q represents carboxy, carbamoyl or 5-tetrazolyl;

Y represents a hydrogen atom, hydroxy, amino, a halogen atom, perfluoro(lower alkyl), optionally substituted lower alkyl, or lower alkoxy which optionally has 1 to 3 the same or different substituents selected from the group consisting of a fluorine atom, hydroxy and amino with the proviso that two or more Y optionally exist on ring J and these Y are optionally the same or different from each other;

$R^1$ represents perfluoro (lower alkyl), -$A^4$, -A-D-L-M, -A-D-E-G-L-M or —N(-D-L-M)$_2$ with the proviso that two (-D-L-M) are optionally different from each other; in the formula, $A^4$ represents thiol, —CHO, —CONH$R^3$, amino, —N($R^3$)CHO, —N=C($R^3$)NH$R^4$, —COCOOH, —COCONH$R^3$, —$SO_2$NH$R^3$, —N($R^3$)CONH$R^4$ or —N($R^3$)$SO_2$NH$R^4$;

A represents a single bond, —O—, —S—, —CO—, —CON($R^3$)—, —$SO_2$—, —NH—, —N($R^3$)CO—, —N($R^3$)COO—, —N($R^3$)$SO_2$—, —N=C$R^3$N($R^4$)—, —CO-COO—, —COCON($R^3$)—, —$SO_2$N($R^3$)—, —N($R^3$)CON($R^4$)— or —N($R^3$)$SO_2$N($R^4$)—, wherein $R^3$ and $R^4$ independently represent a hydrogen atom or lower alkyl;

D represents optionally substituted lower alkylene, optionally substituted lower alkenylene, optionally substituted lower alkynylene, optionally substituted cycloalkylene, optionally substituted heterocycloalkylene, optionally substituted arylene or optionally substituted heteroarylene with the proviso that D is optionally further substituted by -L-M or -E-G-L-M;

E represents a single bond, —O—, —S—, —CO—, —COO—, —CON($R^5$)—, —$SO_2$—, —N($R^5$)—, —N($R^5$)CO—, —N($R^5$)COO—, —N($R^5$)$SO_2$—, —OCON($R^5$)—, —OCOO—, —COCOO—, —COCON($R^5$)—, —$SO_2$N($R^5$)—, —N($R^5$)CON($R^6$)— or —N($R^5$)$SO_2$N($R^6$)—, wherein $R^5$ and $R^6$ independently represent a hydrogen atom or lower alkyl;

G represents optionally substituted lower alkylene, optionally substituted lower alkenylene, optionally substituted lower alkynylene, optionally substituted cycloalkylene, optionally substituted heterocycloalkylene, optionally substituted arylene or optionally substituted heteroarylene;

L represents a single bond, —O—, —S—, —CO—, —COO—, —CON($R^8$)—, —$SO_2$—, —N($R^8$)—, —N($R^8$)CO—, —N($R^8$)COO—, —N($R^8$)$SO_2$—, —OCO—, —OCON($R^8$)—, —OCOO—, —COCOO—, —COCON($R^8$), —$SO_2$N($R^8$)—, —N($R^8$)CON($R^9$)— or —N($R^8$)$SO_2$N($R^9$)—, wherein $R^8$ and $R^9$ independently represent a hydrogen atom or lower alkyl; and M represents a hydrogen atom, optionally substituted lower alkyl, optionally substituted lower alkenyl, optionally substituted lower alkynyl, optionally substituted cycloalkyl(lower alkyl), optionally substituted heterocycloalkyl(lower alkyl), optionally substituted aryl(lower alkyl), optionally substituted heteroaryl(lower alkyl), optionally substituted cycloalkyl, optionally substituted heterocycloalkyl, optionally substituted aryl or optionally substituted heteroaryl with the proviso that when M is a hydrogen atom, L is a single bond, —O—, —S—, —CO—, —COO—, —CON($R^8$)—, —N($R^8$)—, —N($R^8$)CO—, —OCO—, —OCON($R^8$)—, —COCOO—, —COCON($R^8$)—, —$SO_2$N($R^8$)—, —N($R^8$)CON($R^9$)— or —N($R^8$)$SO_2$N($R^9$)— with the proviso that when $R^1$ and $R^2$ bound to the neighboring atoms exist, these $R^1$ and $R^2$ optionally bind together to form a ring; respectively, or a prodrug thereof, or a pharmaceutically acceptable salt thereof;

[4] a 5-membered heterocyclic derivative as described in the above [2] or [3], wherein $X^1$ represents N; and $X^2$ represents C$R^{11}$ wherein $R^{11}$ represents a hydrogen atom or optionally substituted lower alkyl; or a prodrug thereof, or a pharmaceutically acceptable salt thereof;

[5] a 5-membered heterocyclic derivative as described in the above [2] or [3], wherein $X^1$ represents CH; and $X^2$ represents N; or a prodrug thereof, or a pharmaceutically acceptable salt thereof;

[6] a 5-membered heterocyclic derivative as described in the above [2] or [3], wherein $X^1$ and $X^2$ independently represent C$R^{11}$ wherein these $R^{11}$ are optionally different from each other and represent a hydrogen atom or optionally substituted lower alkyl; or a prodrug thereof, or a pharmaceutically acceptable salt thereof;

[7] a 5-membered heterocyclic derivative as described in the above [6], wherein $X^1$ and $X^2$ represent CH, or a prodrug thereof, or a pharmaceutically acceptable salt thereof;

[8] a 5-membered heterocyclic derivative as described in any one of the above [1] to [7], wherein T represents cyano, or a prodrug thereof, or a pharmaceutically acceptable salt thereof;

[9] a 5-membered heterocyclic derivative as described in any one of the above [1] to [8], wherein Q represents carboxy, or a prodrug thereof, or a pharmaceutically acceptable salt thereof;

[10] a 5-membered heterocyclic derivative as described in the above [9], wherein the group represented by the general formula:

[Chem. 2]

(II)

is a group represented by the following general formula (IIa) or (IIb):

[Chem. 3]

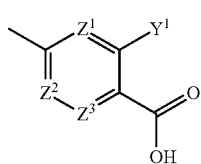
(IIa)

[Chem. 4]

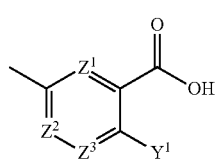
(IIb)

in the formula,
$Z^1$, $Z^2$ and $Z^3$ independently represent $CR^{12}$ or N; and $Y^1$ and $R^{12}$ independently represent a hydrogen atom, hydroxy, amino, a halogen atom, optionally substituted lower alkyl, or lower alkoxy which optionally has 1 to 3 the same or different substituents selected from the group consisting of a fluorine atom, hydroxy and amino with the proviso that when two or more $R^{12}$ exist, these $R^{12}$ are optionally the same or different from each other, or a prodrug thereof, or a pharmaceutically acceptable salt thereof;

[11] a 5-membered heterocyclic derivative as described in the above [10], wherein the group represented by the general formula (II) is a group represented by the general formula (IIa) wherein $Z^1$, $Z^2$ and $Z^3$ independently represent $CR^{13}$ in which $R^{13}$ represents a hydrogen atom or a halogen atom; and $Y^1$ represents a hydrogen atom, hydroxy or amino, or a prodrug thereof, or a pharmaceutically acceptable salt thereof;

[12] a 5-membered heterocyclic derivative as described in the above [10], wherein the group represented by the general formula (II) is a group represented by the general formula (IIb) wherein $Z^1$, $Z^2$ and $Z^3$ independently represent $CR^{13}$ in which $R^{13}$ represents a hydrogen atom or a halogen atom; and $Y^1$ represents a hydrogen atom, hydroxy or amino, or a prodrug thereof, or a pharmaceutically acceptable salt thereof;

[13] a 5-membered heterocyclic derivative as described in the above [10], wherein the group represented by the general formula (II) is a group represented by the general formula (IIa) wherein one of $Z^1$ and $Z^2$ represents N; the other represents CH; $Z^3$ represents CH; and $Y^1$ represents a hydrogen atom, hydroxy or amino, or a prodrug thereof, or a pharmaceutically acceptable salt thereof;

[14] a 5-membered heterocyclic derivative as described in the above [10], wherein the group represented by the general formula (II) is a group represented by the general formula (IIb) wherein $Z^1$ and $Z^3$ independently represent $CR^{13}$ in which $R^{13}$ represents a hydrogen atom or a halogen atom; $Z^2$ represents N; and $Y^1$ represents a hydrogen atom, hydroxy or amino, or a prodrug thereof, or a pharmaceutically acceptable salt thereof;

[15] a 5-membered heterocyclic derivative as described in the above [9], wherein ring J represents a 5-membered heteroaryl ring having 1 to 3 different or the same hetero atoms selected from the group consisting of an oxygen atom, a nitrogen atom and a sulfur atom in the ring, or a prodrug thereof, or a pharmaceutically acceptable salt thereof;

[16] a 5-membered heterocyclic derivative as described in the above [15], wherein the group represented by the general formula:

[Chem. 5]

(II)

is a group represented by the following general formula (IIc):

[Chem. 6]

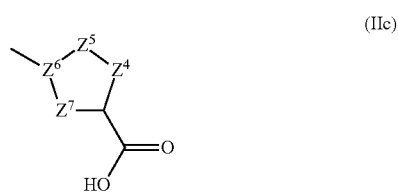
(IIc)

in the formula,
$Z^4$, $Z^5$ and $Z^7$ independently represent an oxygen atom, a nitrogen atom, a sulfur atom with the proviso that both of $Z^4$ and $Z^5$ are not atoms selected from an oxygen atom and a sulfur atom at the same time, or $CR^{14}$ in which $R^{14}$ represents a hydrogen atom, hydroxy, amino, a halogen atom, optionally substituted lower alkyl or optionally substituted lower alkoxy which optionally has 1 to 3 the same or different substituents selected from the group consisting of a fluorine atom, hydroxy and amino with the proviso that when two or more $R^{14}$ exist, these $R^{14}$ are optionally the same or different from each other; $Z^6$ represents a carbon atom; and $Z^4$, $Z^5$, $Z^6$ and $Z^7$ bind together with the carbon atom bound by a carboxy group to form a 5-membered heteroaryl ring, or a prodrug thereof, or a pharmaceutically acceptable salt thereof;

[17] a 5-membered heterocyclic derivative as described in any one of the above [1] to [8], wherein the group represented by the above general formula (II) is a group represented by the following general formula (IIx) or (IIy):

[Chem. 7]

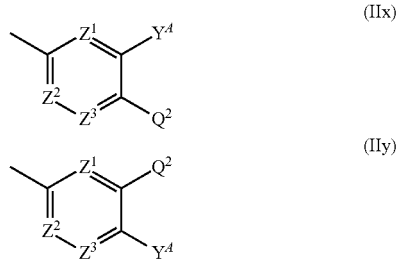

(IIx)

(IIy)

in the formula, $Z^1$, $Z^2$ and $Z^3$ independently represent $CR^{15}$ or N; and $Q^2$ represents carbamoyl; $Y^A$ and $R^{15}$ independently represent a hydrogen atom, hydroxy, amino or a halogen atom with the proviso that when two or more $R^{15}$ exist, these $R^{15}$ are optionally the same or different from each other, or a prodrug thereof, or a pharmaceutically acceptable salt thereof;

[18] a 5-membered heterocyclic derivative as described in any one of the above [1] to [17], wherein $R^1$ represents -$A^1$-D-L-M or -$A^1$-D-E-G-L-M in the formula $A^1$ represents a single bond; and D, E, G, L and M have the same meanings as defined in the above [1], or a prodrug thereof, or a pharmaceutically acceptable salt thereof;

[19] a 5-membered heterocyclic derivative as described in the above [18], wherein $R^1$ represents -$A^1$-D-L-M in the formula $A^1$ represents a single bond; and D, L and M have the same meanings as defined in the above [1], or a prodrug thereof, or a pharmaceutically acceptable salt thereof;

[20] a 5-membered heterocyclic derivative as described in the above [18], wherein $R^1$ represents -$A^1$-D-E-G-L-M in the formula $A^1$ represents a single bond; and D, E, G, L and M have the same meanings as defined in the above [1], or a prodrug thereof, or a pharmaceutically acceptable salt thereof;

[21] a 5-membered heterocyclic derivative as described in any one of the above [1] to [17], wherein $R^1$ represents -$A^2$-D-L-M or -$A^2$-D-E-G-L-M in the formula $A^2$ represents —O—; and D, E, G, L and M have the same meanings as defined in the above [1], or a prodrug thereof, or a pharmaceutically acceptable salt thereof;

[22] a 5-membered heterocyclic derivative as described in any one of the above [1] to [17], wherein $R^1$ represents -$A^3$-D-L-M or -$A^3$-D-E-G-L-M in the formula $A^3$ represents —CO— or —CON($R^3$)—; and D, E, G, L, M and $R^3$ have the same meanings as defined in the above [1], or a prodrug thereof, or a pharmaceutically acceptable salt thereof;

[23] a 5-membered heterocyclic derivative as described in any one of the above [1] to [17], wherein $R^1$ represents -$A^4$-D-L-M, -$A^4$-D-E-G-L-M or —N(-D-L-M)$_2$ with the proviso that two (-D-L-M) are optionally different from each other, in the formula $A^4$ represents —N($R^3$)CO, —N($R^3$)SO$_2$— or —N=C$R^3$N($R^4$)—; and D, E, G, L, M, $R^3$ and $R^4$ have the same meanings as defined in the above [1], or a prodrug thereof, or a pharmaceutically acceptable salt thereof;

[24] a 5-membered heterocyclic derivative as described in any one of the above [1] to [23], wherein optionally substituted lower alkyl, optionally substituted lower alkenyl, optionally substituted lower alkynyl, optionally substituted cycloalkyl and optionally substituted heterocycloalkyl represent lower alkyl which optionally has 1 to 3 the same or different substituents selected from the following substituent group α, lower alkenyl, which optionally has 1 to 3 the same or different substituents selected from the following substituent group α, lower alkynyl which optionally has 1 to 3 the same or different substituents selected from the following substituent group α, cycloalkyl which optionally has 1 to 3 the same or different substituents selected from the following substituent group α and heterocycloalkyl which optionally has 1 to 3 the same or different substituents selected from the following substituent group α, respectively; and optionally substituted aryl and optionally substituted heteroaryl represent aryl which optionally has 1 to 3 the same or different substituents selected from the following substituent group β and heteroaryl which optionally has 1 to 3 the same or different substituents selected from the following substituent group β;

[Substituent Group α]

a fluorine atom, perfluoro (lower alkyl), —$OW^1$, —$SW^1$, carboxy, sulfo, lower alkyl, lower alkylsulfonyl, lower alkoxycarbonyl, —$OCOW^2$, —$N(W^2)COW^3$, —$OCOOW^4$, —$N(W^2)COOW^4$, —NHC(=NH)—$NW^2W^3$, —$NW^2W^3$, —$CONW^2W^3$, —$N(W^5)CONW^6W^7$, —$N(W^2)SO_2W^5$, —$SO_2NW^2W^3$, —$SO_2W^4$; aryl which optionally has any 1 to 3 substituents selected from the group consisting of a halogen atom, hydroxy, lower alkyl, lower alkoxy and trifluoromethyl; and heteroaryl which optionally has any 1 to 3 substituents selected from the group consisting of a halogen atom, hydroxy, lower alkyl, lower alkoxy and trifluoromethyl;

[Substituent Group β]

a halogen atom, perfluoro (lower alkyl), cyano, nitro, —$OW^8$, —$SW^8$, carboxy, lower alkyl, lower alkylsulfonyl, lower alkoxycarbonyl, —$OCOW^2$, —$N(W^2)COW^3$, —$OCOOW^4$, —$N(W^2)COOW^4$, —NHC(=NH)—$NW^2W^3$, —$NW^2W^3$, —$CONW^2W^3$, —$N(W^5)CONW^6W^7$, —$N(W^2)SO_2W^5$, —$SO_2NW^2W^3$, —$SO_2W^4$; aryl which optionally has any 1 to 3 substituents selected from the group consisting of a halogen atom, hydroxy, lower alkyl, lower alkoxy and trifluoromethyl; and heteroaryl which optionally has any 1 to 3 substituents selected from the group consisting of a halogen atom, hydroxy, lower alkyl, lower alkoxy and trifluoromethyl;

in the above, $W^1$ represents a hydrogen atom, lower alkyl, perfluoro (lower alkyl); aryl which may have any 1 to 3 groups selected from the group consisting of a halogen atom, hydroxy, alkyl, lower alkoxy and trifluoromethyl; aryl(lower alkyl); or lower alkyl having 2 to 6 carbon atoms which has a group selected from the group consisting of amino, mono(di)(lower alkyl)amino and lower alkylsulfonamide, with the proviso that the oxygen or sulfur atom bound to $W^1$ and a nitrogen atom in $W^1$ bind to different carbon atoms;

$W^2$, $W^3$, $W^5$, $W^6$ and $W^7$ independently represent a hydrogen atom, lower alkyl, aryl(lower alkyl), or $W^2$ and $W^3$, and $W^5$ and $W^6$, or $W^6$ and $W^7$ may form an alicyclic amino with the binding nitrogen atom;

$W^4$ represents lower alkyl, or $W^2$ and $W^4$ may form an alicyclic amino with the binding nitrogen atom;

and $W^8$ represents a hydrogen atom, lower alkyl, perfluoro (lower alkyl); aryl which may have any 1 to 3 groups selected from the group consisting of a halogen atom, hydroxy, alkyl, lower alkoxy and trifluoromethyl; aryl(lower alkyl); or lower alkyl having 2 to 6 carbon atoms which has a group selected from the group consisting of amino, mono(di)(lower alkyl) amino and lower alkylsulfonamide, with the proviso that the oxygen or sulfur atom bound to $W^8$ and a nitrogen atom in $W^8$ bind to different carbon atoms and when two —$OW^8$ exist on neighboring carbon atoms in an aryl ring, these $W^8$ may bind together to form a methylene chain which may be substituted by 1 or 2 fluorine atoms or an ethylene chain which may be substituted by 1 to 4 fluorine atoms, respectively, or a prodrug thereof, or a pharmaceutically acceptable salt thereof;

[25] a xanthine oxidase inhibitor comprising as an active ingredient a 5-membered heterocyclic derivative as described in any one of the above [1] to [24], or a prodrug thereof; or a pharmaceutically acceptable salt thereof;

[26] a pharmaceutical composition comprising as an active ingredient a 5-membered heterocyclic derivative as described in any one of the above [1] to [24], or a prodrug thereof, or a pharmaceutically acceptable salt thereof;

[27] a pharmaceutical composition as described in the above [26], which is an agent for the prevention or treatment of a disease selected from the group consisting of hyperuricemia, gouty tophus, gouty arthritis, renal disorder associated with hyperuricemia and urinary calculi;

[28] a pharmaceutical composition as described in the above [27], which is an agent for the prevention or treatment of hyperuricemia;

[29] a pharmaceutical composition as described in the above [26], which is an agent for lowering serum uric acid level;

[30] a pharmaceutical composition as described in the above [26], which is a uric acid production inhibitor.

[31] a pharmaceutical composition as described in any one of the above [26] to [30], which comprises a further combination with at least one drug selected from the group consisting of colchicines, a non-steroid anti-inflammatory drug, a steroid and a urine alkalizer as an active ingredient; and the like.

In the 5-membered heterocyclic derivatives represented by the above general formula (I) of the present invention, each term represents the following meaning.

The term "halogen atom" means a fluorine atom, a chlorine atom, a bromine atom or an iodine atom.

The term "lower" means a straight-chained or branched hydrocarbon group having 6 or less carbon atoms. For example, as lower alkyl, methyl, ethyl, propyl, isopropyl, butyl, isobutyl, sec-butyl, tert-butyl, pentyl, isopentyl, neopentyl, tert-pentyl, hexyl and the like can be illustrated, as lower alkenyl, vinyl, allyl, 1-propenyl, isopropenyl, 1-butenyl, 2-butenyl, 2-methylallyl and the like can be illustrated, and as lower alkynyl, ethynyl, 2-propynyl and the like can be illustrated. As lower alkylene, methylene, methylmethylene, dimethylmethylene, ethylene, 1-methylethylene, 2-methylethylene, propane-1,3-diyl, 1-methylpropane-1,3-diyl, 1,1-dimethylpropane-1,3-diyl, 2-methylpropane-1,3-diyl, 2,2-dimethylpropane-1,3-diyl, 3-methylpropane-1,3-diyl, 3,3-dimethylpropane-1,3-diyl, butane-1,4-diyl, 1-methylbutane-1,4-diyl, 1,1-dimethylbutane-1,4-diyl, 2,2-dimethylbutane-1,4-diyl, 3,3-dimethylbutane-1,4-diyl, 4-methylbutane-1,4-diyl, 4,4-dimethylbutane-1,4-diyl, pentane-1,5-diyl, 1-methylpentane-1,5-diyl, 2-methylpentane-1,5-diyl, 3-methylpentane-1,5-diyl, 4-methylpentane-1,5-diyl, 5-methylpentane-1,5-diyl, hexane-1,5-diyl and the like can be illustrated, as lower alkenylene, vinylene, propene-1,3-diyl, 1-butene-1,4-diyl, 2-butene-1,4-diyl, 1,3-butadiene-1,4-diyl, 1-pentene-1,5-diyl, 2-pentene-1,5-diyl, 1,3-pentadiene-1,5-diyl, 1-hexene-1,6-diyl, 2-hexene-1,6-diyl, 3-hexene-1,6-diyl, 1,3-hexadiene-1,6-diyl, 1,3,5-hexatriene-1,6-diyl and the like can be illustrated, and as lower alkynylene, ethnylene, 2-propynylene and the like can be illustrated. As lower alkoxy, methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy and the like can be illustrated, and as lower alkoxycarbonyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl and the like can be illustrated.

The term "perfluoro (lower alkyl)" means the above lower alkyl which is substituted by a fluorine atom, and methyl substituted by 1 to 3 fluorine atoms or ethyl substituted by 1 to 5 fluorine atoms is preferable.

The term "cycloalkyl" means cyclopropyl, cyclobutyl, cyclopentyl, cyclohexyl, cyclohexenyl, cycloheptyl or cyclooctyl, and the term "cycloalkylene" means a divalent group derived from the above cycloalkyl.

The term "heterocycloalkyl" means a 3 to 8-membered aliphatic monocyclic hydrocarbon group having any 1 or 2 hetero atoms selected from the group consisting of an oxygen atom, a sulfur atom and a nitrogen atom in the ring and optionally having 1 or 2 oxo groups such as aziridino, azetidino, morpholino, 2-morpholinyl, thiomorpholino, 1-pyrrolidinyl, piperidino, 4-piperidinyl, 1-piperazinyl, 1-pyrrolyl and the like, or a 5 to 6-membered aliphatic monocyclic hydrocarbon group defined above which is fused with a benzene ring, for example, 1,3-dioxoisoindolin-2-yl and the like. The term "heterocycloalkylene" means a divalent group derived from the above heterocycloalkyl.

The term "aryl" means phenyl or naphthyl, and the term "arylene" means divalent group derived from the above aryl.

The term "cycloalkyl(lower alkyl)" means the above lower alkyl substituted by the above cycloalkyl, the term "heterocycloalkyl(lower alkyl)" means the above lower alkyl substituted by the above heterocycloalkyl, the term "aryl(lower alkyl)" means the above lower alkyl substituted by the above aryl, the term "heteroaryl(lower alkyl)" means the above lower alkyl substituted by the above heteroaryl. A substituent of optionally substituted cycloalkyl(lower alkyl) may be on either cycloalkyl or lower alkyl. It is similar about optionally substituted heterocycloalkyl(lower alkyl), optionally substituted aryl(lower alkyl), and optionally substituted heteroaryl (lower alkyl).

The term "heteroaryl" means a 5 or 6-membered aromatic heterocyclic group having any 1 to 4 hetero atoms selected from the group consisting of an oxygen atom, a sulfur atom and a nitrogen atom in the ring, which is derived from thiazole, oxazole, isothiazole, isoxazole, pyridine, pyrimidine, pyrazine, pyridazine, pyrrole, furan, thiophene, imidazole, pyrazole, oxadiazole, thiadiazole, triazole, tetrazole, furazan or the like, or a 5 or 6-membered aromatic heterocyclic group fused with a 6-membered ring having any 1 to 4 any hetero atoms selected from the group consisting of an oxygen atom, a sulfur atom and a nitrogen atom, which is derived from indole, isoindole, benzofuran, isobenzofuran, benzothiophene, benzoxazole, benzothiazole, benzisoxazole, benzisothiazole, indazole, benzimidazole, quinoline, isoquinoline, phthalazine, quinoxaline, quinazoline, sinoline, indolizine, naphthyridine, pteridine or the like. The term "heteroarylene" means a divalent group derived from the above heteroaryl.

The term "optionally substituted" which may have 1 to 3 the same or different substituents.

As a substituent of optionally substituted lower alkyl, optionally substituted lower alkenyl, optionally substituted lower alkynyl, optionally substituted cycloalkyl and optionally substituted heterocycloalkyl, for example, a fluorine atom, perfluoro (lower alkyl), —$OW^1$, —$SW^1$, carboxy, sulfo, lower alkyl, lower alkylsulfonyl, lower alkoxycarbonyl, —$OCOW^2$, —$N(W^2)COW^3$, —$OCOOW^4$, —$N(W^2)COOW^4$, —$NHC(=NH)$—$NW^2W^3$, —$NW^2W^3$, —$CONW^2W^3$, —$N(W^5)CONW^6W^7$, —$N(W^2)SO_2W^5$, —$SO_2NW^2W^3$, —$SO_2W^4$; aryl which may have any 1 to 3 groups selected from the group consisting of a halogen atom, hydroxy, lower alkyl, lower alkoxy and trifluoromethyl; and heteroaryl which may have any 1 to 3 groups selected from the group consisting of a halogen atom, hydroxy, lower alkyl, lower alkoxy and trifluoromethyl can be illustrated.

As a substituent of optionally substituted lower alkoxy, a fluorine atom, perfluoro (lower alkyl), lower alkyl, hydroxyl group and lower alkoxy preferably can be illustrated.

As a substituent of optionally substituted aryl and optionally substituted heteroaryl, for example, a halogen atom, perfluoro (lower alkyl), cyano, nitro, —$OW^8$, —$SW^8$, carboxy, lower alkyl, lower alkylsulfonyl, lower alkoxycarbonyl, —$OCOW^2$, —$N(W^2)COW^3$, —$OCOOW^4$, —$N(W^2)COOW^4$, —NHC(=NH)—$NW^2W^3$, —$NW^2W^3$, —$CONW^2W^3$, —$N(W^5)CONW^6W^7$, —$N(W^2)SO_2W^5$, —$SO_2NW^2W^3$, —$SO_2W^4$; aryl which may have any 1 to 3 groups selected from the group consisting of a halogen atom, hydroxy, lower alkyl, lower alkoxy and trifluoromethyl; and heteroaryl which may have any 1 to 3 groups selected from the group consisting of a halogen atom, hydroxy, lower alkyl, lower alkoxy and trifluoromethyl can be illustrated.

In the above, $W^1$ represents a hydrogen atom, lower alkyl, perfluoro (lower alkyl); aryl which may have any 1 to 3 groups selected from the group consisting of a halogen atom, hydroxy, alkyl, lower alkoxy and trifluoromethyl; aryl(lower alkyl); or lower alkyl having 2 to 6 carbon atoms which has a group selected from the group consisting of amino, mono(di)(lower alkyl)amino, and lower alkylsulfonamide, with the proviso that the oxygen or sulfur atom bound to $W^1$ and a nitrogen atom in $W^1$ bind to different carbon atoms.

$W^2$, $W^3$, $W^5$, $W^6$ and $W^7$ independently represent a hydrogen atom, lower alkyl, aryl(lower alkyl), or $W^2$ and $W^3$, and $W^5$ and $W^6$, or $W^6$ and $W^7$ may form an alicyclic amino with the binding nitrogen atom;

$W^4$ represents lower alkyl, $W^2$ and $W^4$ may form an alicyclic amino with the binding nitrogen atom;

and $W^8$ represents a hydrogen atom, lower alkyl, perfluoro (lower alkyl); aryl which may have any 1 to 3 groups selected from the group consisting of a halogen atom, hydroxy, alkyl, lower alkoxy and trifluoromethyl; aryl(lower alkyl); or lower alkyl having 2 to 6 carbon atoms which has a group selected from the group consisting of amino, mono(di)(lower alkyl) amino and lower alkylsulfonamide, with the proviso that the oxygen or sulfur atom bound to $W^8$ and a nitrogen atom in $W^8$ bind to different carbon atoms and when two —$OW^8$ exist on neighboring carbon atoms in an aryl ring, these $W^8$ may bind together to form a methylene chain which may be substituted by 1 or 2 fluorine atoms or an ethylene chain which may be substituted by 1 to 4 fluorine atoms, respectively.

The term "mono(di)(lower alkyl)amino" means amino mono- or di-substituted by the above lower alkyl, and the term "mono(di)(lower alkyl)carbamoyl" means carbamoyl mono- or di-substituted by the above lower alkyl. The two lower alkyl groups in a di-substituted group may be different from each other.

The term "alicyclic amino" means 3 to 8-membered cyclic amino optionally having a hetero atom selected from the group consisting of an oxygen atom, a sulfur atom and a nitrogen atom other than a nitrogen atom at the binding position in the ring, such as aziridino, azetidino, morpholino, thiomorpholino, 1-pyrrolidinyl, piperidino, 1-piperazinyl, 1-pyrrolyl and the like, optionally having 1 or 2 oxo groups and optionally having 1 or 2 a double bond in ring, for example, 2-oxo-1-pyrrolidinyl and the like.

When ring J represents a 5-membered heteroaryl ring, The term "5-membered heteroaryl" means the above heteroaryl of 5-membered, such as thiazole, oxazole, furan, thiophene, pyrrole, pyrazole, imidazole and the like can be illustrated.

The term "a ring wherein $R^1$ and $R^2$ optionally bind together to form" means a 3 to 8-membered aliphatic monocyclic hydrocarbon group having any 1 or 2 hetero atoms selected from the group consisting of an oxygen atom, a sulfur atom and a nitrogen atom in the ring and optionally having 1 or 2 oxo groups, such as aziridine, azetidine, morpholine, thiomorpholine, pyrrolidine, piperidine, piperadine, pyrroline or the like can be illustrated, a compound having 1 or 2 hetero atoms in the ring is preferable.

In the 5-membered heterocyclic derivatives represented by formula (I), when $R^1$ represents -A-D-L-M or -A-D-E-G-L-M, in each combination of A and L, A and E or E and L, both represent a group selected from the group consisting of —O—, —S—, —$SO_2$—, —$N(R^{16})$—, —$N(R^{17})CO$—, —$N(R^{17})COO$—, —$N=CR^{17}N(R^{18})$—, —$SO_2N(R^{17})$—, —$N(R^{17})CON(R^{18})$— and —$N(R^{17})SO_2N(R^{18})$— wherein $R^{16}$ represents a hydrogen atom in A; a hydrogen atom or lower alkyl in the L, E or G, and $R^{17}$ and $R^{18}$ independently represent a hydrogen atom or lower alkyl, and D or G between them represents optionally substituted lower alkyl, the lower alkyl unit of D or G has 2 to 6 carbon atoms, and A and L, A and E or E and L preferably bind to different carbon atoms of the lower alkyl chain of D or G, with the proviso that when A; or E in E and G; represent —$N(R^{17})CO$—, it is not necessary so. Similarly, when $R^1$ represents —$N(-D-L-M)_2$, and L represents a group selected from the above group, N and L preferably bind to different carbon atoms of the lower alkyl chain of D. In the formula, M has the same meaning as defined above. To take an example for purposes of illustration, as -A-D-L-M, —O—$CH_2$—$CH_2$—O-M and the like; as -A-D-E-G-L-M, -A-D-O—$CH(CH_3)$—$CH_2$—$N(R^{16})CO$-M and the like; and as —$N(-D-L-M)_2$, —N(—$CH_2$—$CH_2$—O-M)(-D-L-M) and the like are included.

In the 5-membered heterocyclic derivatives represented by formula (I), in case that the group represented by formula (II) is a group represented by formula (IId):

[Chem. 8]

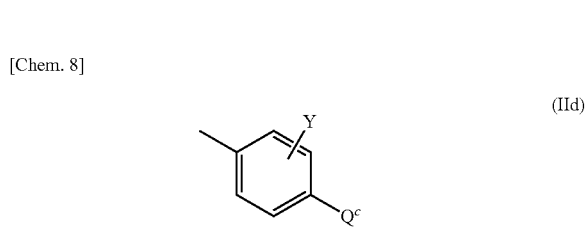

(IId)

wherein $Q^C$ represents carboxy or 5-tetrazoyl and $R^1$ represents -A-D-L-M with the proviso that A represents a single bond; D represents arylene optionally substituted by a substituent selected from the group consisting of lower alkyl, a halogen atom, lower alkyl substituted a halogen atom, and lower alkoxy; or heteroarylene optionally substituted by a substituent selected from the group consisting of lower alkyl, lower alkoxy and a halogen atom with the proviso that when heteroarylene represents a group derived from thiophene, pyrrole or thiazole; L represents a single bond; M represents a hydrogen atom; as Y, hydroxy, amino or a halogen atom is preferable.

A preferable compound among the 5-membered heterocyclic derivatives represented by the above general formula (I) of the present invention also has a URAT1 inhibitory activity. Accordingly, such a compound can exert an uricosuric effect in addition to an uric acid synthesis inhibitory effect, and show a superior lowering effect of serum uric acid level. As a compound which also has a URAT1 inhibitory activity, for example, compounds represented by the following general formula (IIIa) to (IIIc) and the like can be illustrated.

[Chem. 9]

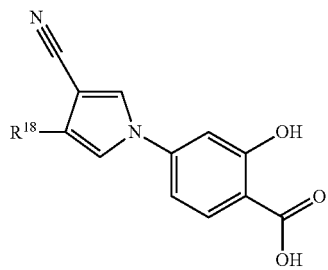

(IIIa)

In the formula, R$^{18}$ represents -A-D-L-M or -A-D-E-G-L-M with the proviso that A represents a single bond, and D, E, G, L and M have the same meanings as defined above.

[Chem. 10]

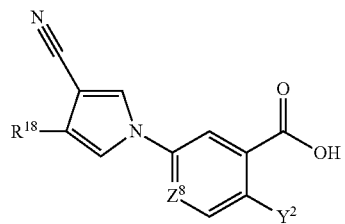

(IIIb)

In the formula, R$^{18}$ has the same meaning as defined above, Y$^2$ represents a hydrogen atom, hydroxy or amino, and Z$^8$ represents N or CR$^{19}$ wherein R$^{19}$ represents a hydrogen atom, a halogen atom or lower alkyl.

[Chem. 11]

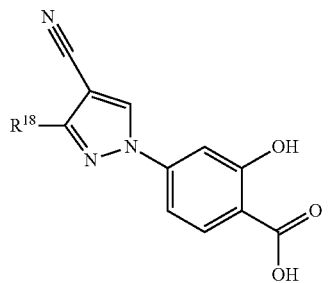

(III c)

In the formula, R$^{18}$ has the same meaning as defined above.

The 5-membered heterocyclic derivatives represented by the above general formula (I) of the present invention can be prepared, for example, by a method described below or a similar method thereto, or a method described in other literatures or a similar method thereto or the like. In addition, when a protective group is necessary, operations of introduction and deprotection can be conducted optionally in combination according to a general method.

[Synthetic Method 1]

[Chem. 12]

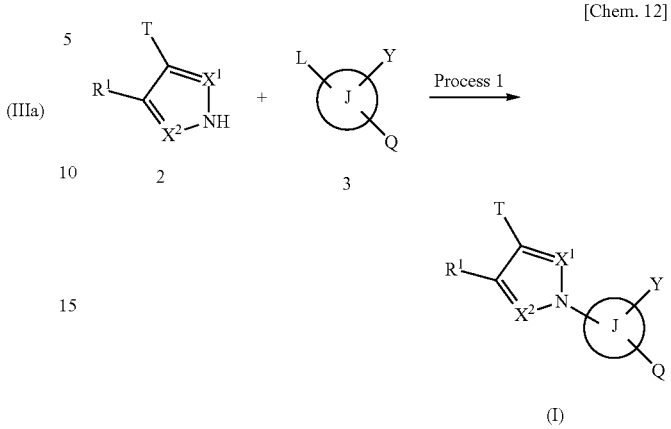

In the formula, L represents a halogen atom and T, ring J, Q, Y, X$^1$, X$^2$ and R$^1$ have the same meanings as defined above.
Process 1

A 5-membered heterocyclic derivative represented by the above general formula (I) of the present invention can be prepared by conducting a coupling reaction of Compound (2) and Compound (3) in an inert solvent or without any solvent in the presence of a base and optionally removing a protective group. As the inert solvent, N,N-dimethylformamide, tetrahydrofuran, N-methylpyrolidone, 1,2-dimethoxyethane, dimethylsulfoxide, 1,2-diethoxyethane, 1,4-dioxane, a mixed solvent thereof and the like can be illustrated. As the base, sodium hydride, potassium carbonate, cesium carbonate, sodium hydroxide, potassium hydroxide, sodium methoxide and the like can be illustrated. The reaction temperature is usually at room temperature to reflux temperature, and the reaction time is usually from 30 minutes to 7 days, varying based on a used starting material, solvent and reaction temperature or the like. In addition, in the present process, the reaction can be optionally conducted using a pressure-resistant reaction container.

A 5-membered heterocyclic derivative represented by the above general formula (I) of the present invention can be also prepared by conducting a coupling reaction of Compound (2) and Compound (3) in an inert solvent in the presence of a base, a catalytic or equivalent amount of copper iodide and a ligand and optionally removing a protective group. As the inert solvent, N,N-dimethylformamide, tetrahydrofuran, N-methylpyrolidone, 1,2-dimethoxyethane, a mixed solvent thereof and the like can be illustrated. As the base, potassium phosphate, potassium carbonate, cesium carbonate and the like can be illustrated. As the ligand, N,N-dimethylethylenediamine, (1R,2R)-(−)-N,N'-dimethylcyclohexane-1,2-diamine, (1S,2S)-(+)-N,N'-dimethylcyclohexane-1,2-diamine, proline, N,N-dimethylaminoglycine and the like can be illustrated. The reaction temperature is usually at room temperature to reflux temperature, and the reaction time is usually from 30 minutes to 7 days, varying based on a used starting material, solvent and reaction temperature or the like. In addition, in the present process, the reaction can be optionally conducted by using a pressure-resistant reaction container.

The above reaction can be also conducted by a method described in the following literature (a).
(a) Hui Zhang; Qian Cai; and Dawei Ma, J. Org. Chem., Vol. 70, No. 13, 2005, 5173.

[Chem. 13]

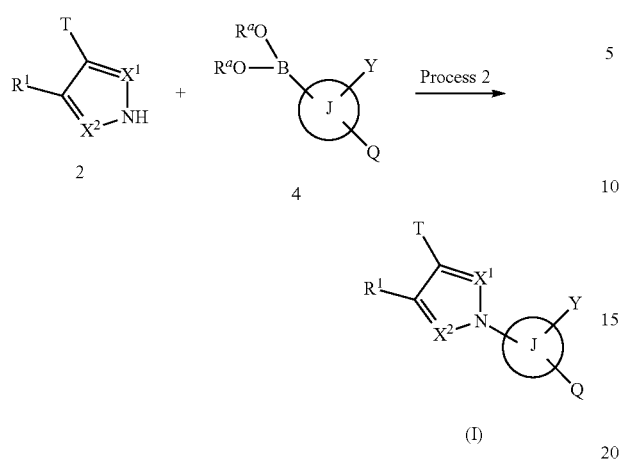

(I)

In the formula, $R^a$ represents a hydrogen atom or lower alkyl with the proviso that two $R^a$ may be different and both $R^a$ may bind together to form a ring, and T, ring J, Q, Y, $X^1$, $X^2$ and $R^1$ have the same meanings as defined above.

Process 2

A 5-membered heterocyclic derivative represented by the above general formula (I) of the present invention can be also prepared by conducting a coupling reaction of Compound (2) and Compound (4) in an inert solvent in the presence of a base and a catalytic amount of copper acetate and optionally removing a protective group. As the inert solvent, dichloromethane, 1,2-dichloroethane, N,N-dimethyl-formamide, tetrahydrofuran, N-methylpyrolidone, 1,2-dimethoxyethane, water, a mixed solvent thereof and the like can be illustrated. As the base, triethylamine, N,N-diisopropylethylamine, pyridine, 2,6-lutidine, 1,8-diazabicyclo[5,4,0]-7-undecene and the like can be illustrated. There are cases when it is better to use a dehydrating agent such as Molecular sieves in this reaction. The reaction temperature is usually at room temperature to reflux temperature, and the reaction time is usually from 30 minutes to 7 days, varying based on a used starting material, solvent and reaction temperature or the like. In addition, in the present process, the reaction can be optionally conducted using a pressure-resistant reaction container.

The above reaction can be also conducted by a method described in the following literature (b).

(b) Hartwig, John F.; Kawatsura, Motoi; Hauck, Sheila I. et al. Journal of Organic Chemistry, 1999, 64 (15), 5575-5580.

[Synthetic Method 2]

Among the 5-membered heterocyclic derivatives represented by the above general formula (I) of the present invention, Compound (1a) wherein T represents cyano can be also prepared, for example, by Synthetic method 2.

[Chem. 14]

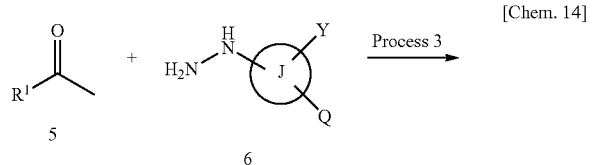

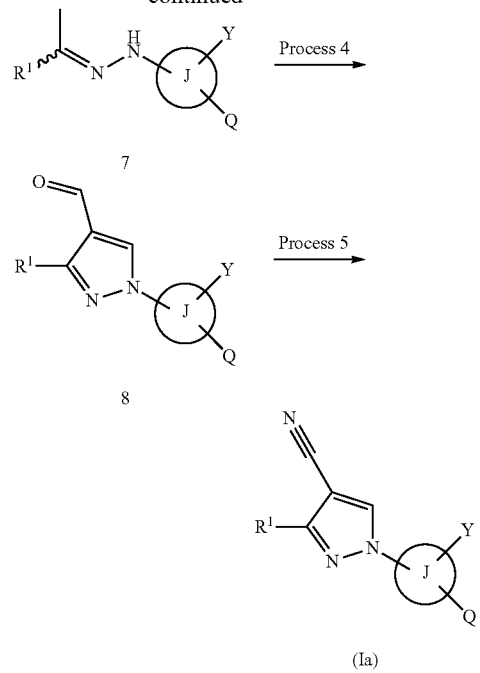

In the formula, ring J, Q, $R^1$ and Y have the same meanings as defined above.

Process 3

Compound (7) can be also prepared by subjecting Compound (5) to condensation with Compound (6) in an inert solvent or without any solvent in the presence or absence of an acid. As the inert solvent, methanol, ethanol, isopropanol, butanol, diethyl ether, tetrahydrofuran, 1,4-dioxane, 1,2-dimethoxyethane, N,N-dimethylformamide, acetonitrile, benzene, toluene, xylene, N-methylpyrolidone, dichloroethane, chloroform, acetic acid, water, a mixed solvent thereof and the like can be illustrated. As the acid, hydrochloric acid, sulfuric acid, acetic acid, trifluoroacetic acid and the like can be illustrated. The reaction temperature is usually at 0° C. to reflux temperature, and the reaction time is usually from 30 minutes to 7 days, varying based on a used starting material, solvent and reaction temperature or the like.

Process 4

Formylpyrazole compound (8) can be also prepared by allowing Compound (7) to react in an inert solvent in the presence of N,N-dimethylformamide and phosphoryl chloride. As the inert solvent, N,N-dimethylformamide, acetonitrile, benzene, toluene, xylene, chlorobenzene, dichloromethane, 1,2-dichloroethane, chloroform, a mixed solvent thereof and the like can be illustrated. The reaction temperature is usually at 0° C. to reflux temperature, and the reaction time is usually from 30 minutes to 7 days, varying based on a used starting material, solvent and reaction temperature or the like.

Process 5

A 5-membered heterocyclic derivative (Ia) of the present invention can be prepared by subjecting Formylpyrazole compound (8) and hydroxylamine or a hydrochloride salt thereof to cyanation in an inert solvent in the presence or absence of a base in the presence of a dehydrating agent. As the inert solvent, N,N-dimethylformamide, acetonitrile, benzene, toluene, chlorobenzene, dichloromethane, 1,2-dichloroethane, chloroform, N-methylpyrolidone, a mixed solvent thereof and the like can be illustrated. As the base, triethylamine, N,N-diisopropylethylamine, pyridine, 2,6-lutidine, 1,8-diazabicyclo[5,4,0]-7-undecene, potassium carbonate, sodium carbonate and the like can be illustrated. As the dehydrating agent, acetic anhydride, thionyl chloride, phosphoric chloride, N,N'-dicyclohexylcarbodiimide, N,N'-carbonyldiimidazole and the like can be illustrated. The reaction temperature is usually at 0° C. to reflux temperature, and the reaction time is usually from 30 minutes to 7 days, varying based on a used starting material, solvent and reaction temperature or the like.

The above cyanation reaction may be also conducted by allowing Formylpyrazole compound (8) and hydroxylamine or a hydrochloride salt thereof to react with sodium formate in a formic acid solvent. The reaction temperature is usually at 0° C. to reflux temperature, and the reaction time is usually from 30 minutes to 7 days, varying based on a used starting material, solvent and reaction temperature or the like.

[Synthetic Method 3]

Among the 5-membered heterocyclic derivatives represented by the above general formula (I) of the present invention, Compound (Ib) wherein $R^1$ represents -A-D-L-M or -A-D-E-G-L-M with the proviso that A represents a single bond and D represents optionally substituted lower alkenylene with the proviso that a double bond exists next to A, optionally substituted arylene or optionally substituted heteroarylene, and E G, L and M have the same meanings as defined above can be also prepared, for example, by Synthetic method 3. In Synthetic method 3, as an example, it is described using an example wherein $R^1$ represents -$A^a$-$D^a$-L-M in which $A^a$ represents a single bond, $D^a$ represents optionally substituted lower alkenylene, optionally substituted arylene or optionally substituted heteroarylene, and L and M have the same meanings as defined above.

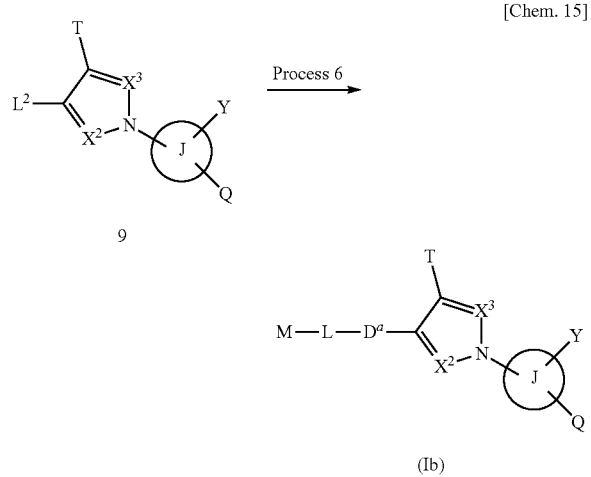

In the formula, $L^2$ represents a halogen atom or trifluoromethansulfonyl, $D^a$ represents optionally substituted lower alkenylene, optionally substituted arylene or optionally substituted heteroarylene, and L, M, T, ring J, Q, $X^1$, $X^2$ and Y have the same meanings as defined above.

Process 6 [Method 1]

A 5-membered heterocyclic derivative (Ib) of the present invention can be also prepared by conducting Suzuki-Miyaura coupling reaction of Compound (9) using the corresponding arylboronic acid reagent or hetero arylboronic acid reagent in an inert solvent in the presence of a base and a palladium catalyst. As the inert solvent, benzene, toluene, xylene, diethyl ether, tetrahydrofuran, 1,4-dioxane, 1,2-dimethoxyethane, dichloromethane, 1,2-dichloroethane, chloroform, methanol, ethanol, 2-propanol, butanol, N,N-dimethylformamide, N-methylpyrolidone, dimethylsulfoxide, water, a mixed solvent thereof and the like can be illustrated. As the base, sodium carbonate, potassium carbonate, sodium hydroxide, potassium hydroxide, sodium ethoxide, sodium methoxide, potassium fluoride, cesium fluoride, triethylamine, N,N-diisopropylethylamine, pyridine, 2,6-lutidine, 1,8-diazabicyclo-[5,4,0]-7-undecene and the like can be illustrated. As the palladium catalyst, tetrakis(triphenylphosphine) palladium, dichlorobis(triphenylphosphine)palladium, [1,1'-bis(diphenylphosphino)ferrocene]dichloropalladium and the like can be illustrated. The reaction temperature is usually at 0° C. to reflux temperature, and the reaction time is usually from 30 minutes to 7 days, varying based on a used starting material, solvent and reaction temperature or the like. In addition, in the present process, the reaction can be optionally conducted using a pressure-resistant reaction container.

Process 6 [Method 2]

A 5-membered heterocyclic derivative (Ib) of the present invention can be also prepared by conducting Mizorogi-Heck reaction of Compound (9) using the corresponding alkene in an inert solvent in the presence of a base and a palladium catalyst. As the inert solvent, benzene, toluene, xylene, diethyl ether, tetrahydrofuran, 1,4-dioxane, 1,2-dimethoxyethane, dichloromethane, 1,2-dichloroethane, chloroform, methanol, ethanol, 2-propanol, butanol, N,N-dimethylformamide, N-methylpyrolidone, dimethylsulfoxide, water, a mixed solvent thereof and the like can be illustrated. As the base, triethylamine, N,N-diisopropylethylamine, pyridine, 2,6-lutidine, 1,8-diazabicyclo[5,4,0]-7-undecene and the like can be illustrated. As the palladium catalyst, palladium acetate, palladium chloride, tetrakis(triphenylphosphine) palladium, dichlorobis(triphenylphosphine)palladium, [1,1'-bis(diphenylphosphino)ferrocene]-dichloropalladium and the like can be illustrated. In addition, in the present reaction can be also conducted using a ligand depending on the kind of palladium catalyst, and as the ligand, triphenylphosphine, tri-O-tolylphosphine, tri-t-butylphosphonium tetrafluoroborate and the like can be illustrated. The reaction temperature is usually at 0° C. to reflux temperature, and the reaction time is usually from 30 minutes to 7 days, varying based on a used starting material, solvent and reaction temperature or the like. In addition, in the present process, the reaction can be optionally conducted using a pressure-resistant reaction container.

A compound represented by the above general formula (2) used as the starting material in the above processes can be commercially available, or prepared by a known method or a similar method thereto. For example, Compound (2a) wherein $X^1$ represents CH and $X^2$ represents $CR^b$ wherein $R^b$ represents a hydrogen atom or lower alkyl can be also prepared by a method shown in the following Synthetic method 4.

[Synthetic Method 4]

-continued

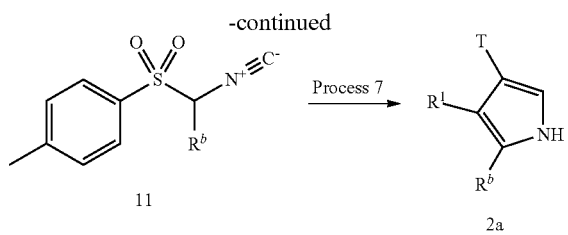

In the formula, $L^3$ represents a hydrogen atom or an electron withdrawing group such as alkoxycarbonyl and the like, $R^b$ represents a hydrogen atom or lower alkyl, and T and $R^1$ have the same meanings as defined above.

Process 7

Pyrrole compound (2a) can be also prepared by allowing Compound (10) and Isocyanide compound (11) to react in an inert solvent in the presence of a base. As the inert solvent, dichloromethane, dichloroethane, diethyl ether, tetrahydrofuran, 1,4-dioxane, 1,2-dimethoxyethane, acetonitrile, methanol, ethanol, N,N-dimethyl-formamide, dimethylsulfoxide, benzene, toluene, xylene, water, a mixed solvent thereof and the like can be illustrated. As the base, sodium hydride, sodium methoxide, sodium ethoxide, potassium t-butoxide, sodium t-butoxide, n-butyl lithium, sec-butyl lithium, tert-butyl lithium and the like can be illustrated. The reaction temperature is usually at 0° C. to reflux temperature, and the reaction time is usually from 30 minutes to 7 days, varying based on a used starting material, solvent and reaction temperature or the like.

[Synthetic Method 5]

Among Compound (10) used as the starting material in the above Process 4, Compound (10a) wherein $R^1$ represents -A-D-L-M or -A-D-E-G-L-M with the proviso that A represents a single bond can be also prepared by a method shown in the following Synthetic method 5.

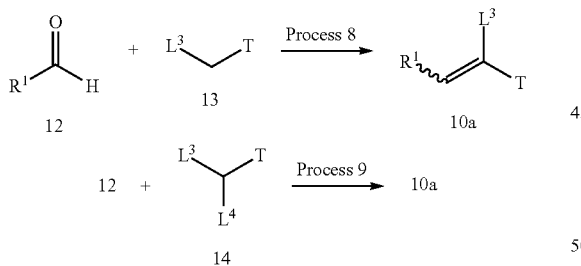

In the formula, $L^4$ represents Horner-Wadsworth-Emmons reagent such as phosphoric acid dimethyl ester, phosphoric acid diethyl ester and the like, or Wittig reagent such as triphenyl phosphonium, tributyl phosphonium and the like, and $L^3$, T and $R^1$ have the same meanings as defined above.

Process 8

Compound (10a) can be also prepared by allowing Aldehyde compound (12) and Compound (13) to react in an inert solvent in the presence or absence of a catalytic or equivalent amount of a base. As the inert solvent, methanol, ethanol, isopropanol, tetrahydrofuran, 1,4-dioxane, toluene, N-methylpyrolidone, a mixed solvent thereof and the like can be illustrated. As the base, piperidine, pyrrolidine, morpholine, triethylamine, pyridine, 2,6-lutidine, 1,8-diazabicyclo[5,4,0]-7-undecene, potassium carbonate, sodium carbonate, sodium hydroxide, potassium hydroxide, sodium methoxide, sodium ethoxide and the like can be illustrated. There are cases when it is better to use a dehydrating agent such as Molecular sieves in this reaction. The reaction temperature is usually at 0° C. to reflux temperature, and the reaction time is usually from 30 minutes to 7 days, varying based on a used starting material, solvent and reaction temperature or the like.

Process 9

Compound (10a) can be also prepared by subjecting Aldehyde compound (12) and Compound (14) to Horner-Wadsworth-Emmons reaction or Wittig reaction in an inert solvent in the presence or absence of a base. As the inert solvent, diethyl ether, tetrahydrofuran, 1,4-dioxane, 1,2-dimethoxyethane, N,N-dimethylformamide, dimethylsulfoxide, N-methylpyrolidone, acetonitrile, dichloromethane, dichloroethane, hexane, heptane, benzene, toluene, xylene, water, a mixed solvent thereof and the like can be illustrated. As the base, sodium hydride, sodium methoxide, sodium ethoxide, potassium t-butoxide, sodium t-butoxide, n-butyl lithium, sec-butyl lithium, tert-butyl lithium, sodium hydroxide, lithium hydroxide, potassium hexamethyldisilazide, hexamethyldisilazide, lithium hexamethyldisilazide and the like can be illustrated. The reaction temperature is usually at −20° C. to reflux temperature, and the reaction time is usually from 30 minutes to 7 days, varying based on a used starting material, solvent and reaction temperature or the like.

Among the compounds represented by the above general formula (2) used as the starting material in the above processes, Pyrazole compound (2b) wherein $R^1$ represents -A-D-L-M or -A-D-G-L-M with the proviso that A represents a single bond, $X^1$ represents CH, $X^2$ represents N and T represents cyano can be also prepared by a method shown in the following Synthetic method 6.

[Synthetic Method 6]

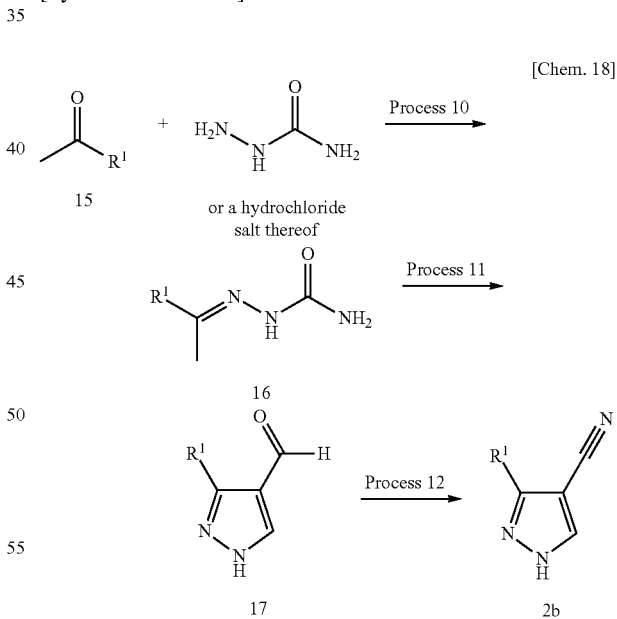

In the formula, $R^1$ has the same meaning as defined above.

Process 10

Semicarbazone (16) can be also prepared by allowing Acetyl compound (15) and semicarbazide or a hydrochloride salt thereof to react in an inert solvent or without any solvent in the presence of a base or an acid. As the inert solvent, methanol, ethanol, n-butanol, t-butanol, acetic acid, tetrahydrofuran, N,N-dimethylformamide, acetonitrile, water, a mixed solvent thereof and the like can be illustrated. As the base, sodium acetate, potassium acetate, sodium hydrogen carbonate, sodium carbonate, potassium carbonate, sodium methoxide, lithium hydroxide, pyridine, imidazole and the like can be illustrated. As the acid, acetic acid, trifluoroacetic acid and the like can be illustrated. The reaction temperature is usually at 0° C. to reflux temperature, and the reaction time is usually from 1 hour to 7 days, varying based on a used starting material, solvent and reaction temperature or the like.

Process 11

Folmylpylazole compound (17) can be also prepared by allowing Compound (16) to react in an inert solvent in the presence of N,N-dimethylformamide and phosphoryl chloride. As the inert solvent, N,N-dimethylformamide, acetonitrile, benzene, toluene, xylene, chlorobenzene, dichloromethane, 1,2-dichloroethane, chloroform, a mixed solvent thereof and the like can be illustrated. The reaction temperature is usually at 0° C. to reflux temperature, and the reaction time is usually from 30 minutes to 7 days, varying based on a used starting material, solvent and reaction temperature or the like.

Process 12

Cyanopylazole compound (2b) can be prepared by subjecting Folmylpylazole compound (17) and hydroxylamine or a hydrochloride salt thereof to cyanation in an inert solvent in the presence or absence of a base in the presence or absence of a dehydrating agent. As the inert solvent, N,N-dimethylformamide, acetonitrile, benzene, toluene, chlorobenzene, dichloromethane, 1,2-dichloroethane, chloroform, N-methylpyrrolidone, a mixed solvent thereof and the like can be illustrated. As the base, triethylamine, N,N-diisopropylethylamine, pyridine, 2,6-lutidine, 1,8-diazabicyclo[5,4,0]-7-undecene, potassium carbonate, sodium carbonate and the like can be illustrated. As the dehydrating agent, acetic anhydride, thionyl chloride, phosphoric chloride, N,N'-dicyclohexylcarbodiimide, N,N'-carbonylimidazole and the like can be illustrated. The reaction temperature is usually at 0° C. to reflux temperature, and the reaction time is usually from 30 minutes to 7 days, varying based on a used starting material, solvent and reaction temperature or the like.

The above cyanation reaction may be conducted by allowing Formylpyrazole compound (17) and hydroxylamine or a hydrochloride salt thereof to react with sodium formate in a formic acid solvent. The reaction temperature is usually at 0° C. to reflux temperature, and the reaction time is usually from 30 minutes to 7 days, varying based on a used starting material, solvent and reaction temperature or the like.

As the protective groups to be used in the present invention, various protective group generally used in organic reactions can be used. For example, as the protective groups of a hydroxyl group, in addition to a p-methoxybenzyl group, a benzyl group, a methoxymethyl group, an acetyl group, a pivaloyl group, a benzoyl group, a tert-butyldimethylsilyl group, a tert-butyldiphenylsilyl group, an allyl group and the like, when two hydroxyl groups are adjacent, an isopropylidene group, a cyclopentylidene group, a cyclohexylidene group and the like can be illustrated. As the protective groups of a thiol group, a p-methoxybenzyl group, a benzyl group, an acetyl group, a pivaloyl group, a benzoyl group, a benzyloxycarbonyl group and the like can be illustrated. As the protective groups of an amino group, a benzyloxycarbonyl group, a tert-butoxycarbonyl group, a benzyl group, a p-methoxybenzyl group, a trifluoroacetyl group, an acetyl group, a phthaloyl group and the like can be illustrated. As the protective groups of a carboxy group, a methyl group, an ethyl group, a benzyl group, a tert-butyldimethylsilyl group, an allyl group and the like can be illustrated.

A compound represented by the above general formula (I) of the present invention can be isolated or purified by conventional isolation techniques, such as fractional recrystallization, purification by chromatography, solvent extraction, solid-phase extraction and the like.

The 5-membered heterocyclic derivatives represented by the above general formula (I) of the present invention can be converted into pharmaceutically acceptable salts thereof in the usual way. As such a salt, an acid additive salt with a mineral acid such as hydrochloric acid, hydrobromic acid, hydroiodic acid, sulfuric acid, nitric acid, phosphoric acid and the like, an acid additive salt with an organic acid such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, benzoic acid, glutamic acid, aspartic acid and the like, an inorganic salt such as a sodium salt, a potassium salt, a magnesium salt, a zinc salt, a lithium salt, an aluminum salt and the like, a salt with an organic amine such as N-methyl-D-glucamine, N,N'-dibenzyl-ethylenediamine, 2-aminoethanol, tris(hydroxymethyl)aminomethane, arginine, lysine, piperadine, choline, diethylamine, 4-phenylcyclohexylamine and the like can be illustrated.

Of the 5-membered heterocyclic derivatives represented by the above general formula (I) of the present invention, in a compound having an unsaturated bond, there are two geometrical isomers, a compound of cis (Z) form and a compound of trans (E) form. In the present invention, either of the compounds can be employed, and a mixture thereof can be also employed.

Of the 5-membered heterocyclic derivatives represented by the above general formula (I) of the present invention, in a compound having a chiral carbon atom, there are a compound of R form and a compound of S form for each chiral carbon. In the present invention, either of the optical isomers can be employed, and a mixture of the optical isomers can be also employed.

Of the 5-membered heterocyclic derivatives represented by the above general formula (I) of the present invention, there can be some tautomers, the compounds of the present invention also include these tautomers.

In the present invention, the term "prodrug" means a compound modified from a parent compound by a pharmaceutically acceptable group usually used in a prodrug, for example, which is given a property such as improvement of stability, substantivity, oral absorbability or the like, and can be expected to be converted into the parent compound within an organism (in the liver, the intestine and the like) to exert the effect. A prodrug of a compound represented by the above general formula (I) of the present invention can be prepared by introducing an appropriate group forming a prodrug into any one or more groups selected from a hydroxy group, amino group, and other groups which can form a prodrug of the compound represented by the above general formula (I) using a corresponding reagent to produce a prodrug such as a halide compound or the like in the usual way, and then by suitably isolating and purificating in the usual way as occasion demands. Gekkan-Yakuji iyakuhin tekiseisiyou no tameno rinsyou yakubutudoutai (monthly pharmaceutical, clinical pharmacokinetics for the proper use of pharmaceutical products), 2003.3. extra number Vol 0.42, No. 4, p. 669-707, New drug Drug delivery system Published by CMC Co., Ltd., 2000.1.31., p. 67-173

As a group forming a prodrug used in a hydroxy group or an amino group, for example, (lower alkyl)-CO— such as acetyl, propionyl, butylyl, isobutylyl, pivaloyl and the like;

aryl-CO— such as benzoyl; (lower alkyl)-O-(lower alkylene)-CO—; (lower alkyl)-OCO-(lower alkylene)-CO—; (lower alkyl)-OCO— such as methyloxycarbonyl, ethyloxycarbonyl, propyloxycarbonyl, isopropyloxycarbonyl, tert-butyloxycarbonyl and the like; (lower alkyl)-O-(lower alkylene)-OCO—; (lower alkyl)-COO-(lower alkylene) such as acetyloxymethyl, pivaloyloxymethyl, 1-(acetyloxy)ethyl, 1-(pivaloyloxy)ethyl and the like; (lower alkyl)-OCO-(lower alkylene) such as methoxycarbonyloxymethyl, 1-(methoxycarbonyloxy)ethyl, ethoxycarbonyloxymethyl, 1-(ethoxycarbonyloxy)ethyl, isopropyloxycarbonyloxymethyl, 1-(isopropyloxycarbonyloxy)ethyl, tert-butyloxycarbonyloxymethyl, 1-(tert-butyloxycarbonyloxy)ethyl and the like; cycloalkyl-OCOO-(lower alkylene) such as cyclohexyloxycarbonyloxymethyl, 1-(cyclohexyloxycarbonyl)ethyl and the like; an ester or an amide with an amino acid such as glycine and the like; and the like can be illustrated.

As a group forming a prodrug used in a carboxy group, for example, lower alkyl such as methyl, ethyl, propyl, isopropyl, butyl, tert-butyl and the like; (lower alkyl)-COO-(lower alkylene) such as pivaloyloxymethyl, acetyloxymethyl, 1-(pivaloyloxy)ethyl, 1-(acetyloxy)ethyl and the like; (lower alkyl)-OCOO-(lower alkylene) such as ethyloxycarbonyloxymethyl, 1-(ethyloxycarbonyloxy)ethyl, isopropyloxycarbonyloxymethyl, 1-(isopropyloxycarbonyloxy)ethyl, tert-butyloxycarbonyloxymethyl, 1-(tert-butyloxycarbonyloxy)ethyl and the like; cycloalkyl-OCOO-(lower alkylene) such as cyclohexyloxycarbonylmethyl, 1-(cyclohexyloxycarbonyl)ethyl and the like; and the like can be illustrated.

A 5-membered heterocyclic derivative represented by the general formula (I) or a prodrug thereof, or a pharmaceutically acceptable salt thereof can be sometimes obtained as a hydrate or solvate thereof in the courses of purification or preparing salts thereof. A 5-membered heterocyclic derivative represented by the general formula (I) of the present invention or a prodrug thereof, or a pharmaceutically acceptable salt thereof includes a hydrate thereof or a solvate thereof with a pharmaceutically acceptable solvent. As the pharmaceutically acceptable solvents, ethanol and the like can be illustrated.

A pharmaceutical composition of the present invention is useful as an agent for the prevention or treatment of diseases associated with high blood uric acid levels such as hyperuricemia, gouty tophus, gouty arthritis, renal disorder associated with hyperuricemia, urinary calculi or the like, especially for hyperuricemia.

When the pharmaceutical compositions of the present invention are employed in the practical prevention or treatment, the dosage of a compound represented by the above general formula (I) or a prodrug thereof or a pharmaceutically acceptable salt thereof as the active ingredient is appropriately decided depending on the age, sex, body weight and degree of symptoms and treatment of each patient, for example, which is approximately within the range of from 1 to 2,000 mg per day per adult human in the case of oral administration, and the daily dose can be divided into one to several doses per day and administered.

When the pharmaceutical compositions of the present invention are employed in the practical prevention or treatment, various dosage forms are orally or parenterally used depending on their uses, for example, formulations for oral administration such as powders, fine granules, granules, tablets, capsules, dry syrups or the like is preferable.

These pharmaceutical compositions can be prepared optionally by admixing using an appropriate pharmaceutical additive such as excipients, disintegrators, binders, lubricants and the like, and formulating the mixture in accordance with conventional methods.

For example, powders can be formulated by, if desired, admixing well an active ingredient with appropriate excipients, lubricants and the like. For example, tablets can be formulated by tableting an active ingredient with appropriate excipients, disintegrators, binders, lubricants and the like in accordance with conventional methods, further if desired, can be suitably coated to provide film-coated tablets, sugar-coated tablets, enteric-coated tablets and the like. For example, capsules can be formulated by admixing well an active ingredient with appropriate excipients, lubricants and the like, or formulating fine granules, granules in accordance with conventional methods, and filling it in appropriate capsules. Furthermore, in the case of such an oral administration drug, it can be also formulated by conducting quick-release or sustained-release formulation depending on the preventions or the treatment methods.

A compound represented by the above general formula (I) of the present invention, or a prodrug thereof or a pharmaceutically acceptable salt thereof can be used further in combination with any other drug for the treatment of hyperuricemia or drug for the treatment of gout. As the drug for the treatment of hyperuricemia which can be used in the present invention, for example, urinary alkalizers such as sodium hydrogen carbonate, potassium citrate and sodium citrate and the like can be illustrated. In addition, as the drug for the treatment of gout, colchicine, or non-steroidal anti-inflammatory drugs such as indomethacin, naproxen, fenbufen, pranoprofen, oxaprozin, ketoprofen, etoricoxib, tenoxicam and the like and steroids and the like can be illustrated. In the present invention, an active ingredient of the present invention can be also used further in combination with at least one of these drugs, and a pharmaceutical composition comprising combination with at least one of these drugs includes any dosage forms of not only a single preparation comprising together with the active ingredient of the present invention but also a combination formulation consisting of a pharmaceutical composition comprising the active ingredient of the present invention and a separately-prepared pharmaceutical composition for simultaneous administration or administration at different dosage intervals. Furthermore, when used in combination with any drug other than the active ingredient of the present invention, the dosage of the compound of the present invention can be reduced depending on the dosage of the other drug used in combination, as the case may be, an advantageous effect more than an additive effect in the prevention or treatment of the above diseases can be obtained, or an adverse effect of the other drug used in combination can be avoided or declined.

Effect of the Invention

The 5-membered heterocyclic derivatives represented by the above general formula (I) of the present invention exert an excellent xanthine oxidase inhibitory activity and suppress the production of uric acid. In addition, a preferable compound of the present invention can also exert an excellent URAT1 inhibitory activity and enhance the uric acid excretion. Therefore, the 5-membered heterocyclic derivatives represented by the general formula (I) of the present invention or a prodrugs thereof, or pharmaceutically acceptable salts thereof can extremely suppress increase in serum uric acid level and are useful as an agent for the prevention or treatment of diseases associated with abnormal serum uric acid level such as hyperiuricemia or the like.

BEST MODE TO OPERATE THE INVENTION

The present invention is further illustrated in more detail by way of the following Reference Examples, Examples and Test Examples. However, the present invention is not limited thereto.

Reference Example 1

4-Fluoro-2-methoxymethoxybenzoic acid ethyl ester

To a solution of 4-fluoro-2-hydroxybenzoic acid (3.0 g) in ethanol (40 mL) was added thionyl chloride (5.61 mL) at 0° C., and this mixture was heated to reflux for 24 hours. This reaction mixture was concentrated, and this residue was poured into water, and this mixture was extracted with ethyl acetate. This organic layer was washed with water and brine, dried over anhydrous magnesium sulfate. The solvent was removed under reduced pressure to give 4-fluoro-2-hydroxybenzoic acid ethyl ester (3.5 g). To a solution of 4-fluoro-2-hydroxybenzoic acid ethyl ester (3.5 g) in dichloromethane (30 mL) were added N,N-diisopropylethylamine (5.0 g) and (chloromethyl)methyl ether (2.3 g) at 0° C., and this reaction mixture was stirred at room temperature overnight. This reaction mixture was poured into water, and the resulting mixture was extracted with ethyl acetate. This organic layer was washed with water and brine, and dried over anhydrous magnesium sulfate. The solvent was removed under reduced pressure. The residue was purified by column chromatography on silica gel (eluent: ethyl acetate/n-hexane) to give the title compound (2.8 g).

Reference Example 2

1-(Toluene-4-sulfonyl)ethylisocyanide

To a solution of toluene-4-sulfonylmethylisocyanide (15 g), methyl iodide (109 g) benzyl trimethyl ammonium chloride (3.5 g) in dichloromethane (300 mL) was added 5 mol/L aqueous sodium hydroxide solution (307 mL) under ice cooling, and this mixture was stirred at same temperature for 2 hours. To this reaction mixture was added water and this mixture was extracted with diethyl ether. This organic layer was washed with water and brine, and dried over anhydrous magnesium sulfate. The solvent was removed under reduced pressure to give the title compound (16 g).

Reference Example 3

2-Heptenenitrile

To a suspension of sodium hydride (60%, 0.48 g) in tetrahydrofuran (15 mL) was added a solution of cyanomethanephosphonic acid diethyl ester (1.9 g) in tetrahydrofuran (3 mL) under cooling to ice-brine. This reaction mixture was stirred at same temperature for 5 minutes, to this reaction mixture was added pentanal (0.86 g). After stirring at same temperature for 45 minutes, to this reaction mixture was added water. This reaction mixture was extracted with diethyl ether, and this organic layer was washed with brine, and dried over anhydrous magnesium sulfate. The solvent was removed under reduced pressure. The residue was purified by column chromatography on silica gel (eluent: hexane/ethyl acetate=5/1) to give the title compound (0.56 g).

Reference Example 4

4-Butyl-5-methyl-1H-pyrrole-3-carbonitrile

To a suspension of sodium hydride (60%, 0.096 g) in diethyl ether (3 mL) were added a solution of 1-(toluene-4-sulfonyl)ethylisocyanide (0.42 g) and 2-heptenenitrile (0.22 g) in a mixed solvent of diethyl ether (3 mL) and dimethylsulfoxide (3 mL) at room temperature, and this mixture was stirred at room temperature for 1 hour. To this reaction mixture was added water (15 mL). This mixture was extracted with ethyl acetate, and this organic layer was washed with brine, and dried over anhydrous magnesium sulfate. The solvent was removed under reduced pressure. The residue was purified by column chromatography on silica gel (eluent: ethyl acetate/n-hexane) to give the title compound (0.19 g).

Reference Example 5

2-Cyano-3-(3-fluorophenyl)acrylic acid ethyl ester

A solution of cyanoacetic acid ethyl ester (1.1 g), 3-fluorobenzaldehyde (1.5 g) and pyrrolidine (0.043 g) in ethanol (10 mL) was stirred at room temperature for 2 hours. The precipitated solid was collected by filtration, and this obtained solid was washed with ethanol (40 mL) to give the title compound (2.1 g).

Reference Example 6

4-(3-Fluorophenyl)-1H-pyrrole-3-carbonitrile

To a solution of 2-cyano-3-(3-fluorophenyl)acrylic acid ethyl ester (2.1 g) in methanol (20 mL) was added sodium methoxide (28% methanol solution, 2.2 mL) at 0° C., this mixture was stirred at same temperature for 15 minutes. To this reaction mixture was added a solution of toluene-4-sulfonylmethylisocyanide (2.0 g) in dichloromethane (20 mL) in a dropwise manner over 10 minutes at 0° C., and this mixture was stirred at same temperature for 30 minutes. To this reaction mixture was added 1 mol/L hydrochloric acid, this mixture was extracted with dichloromethane. This organic layer was washed with brine, and dried over anhydrous magnesium sulfate. The solvent was removed under reduced pressure. The residue was purified by column chromatography on silica gel (eluent: ethyl acetate/n-hexane) to give the title compound (0.60 g).

Reference Example 7

4-Cyano-1H-pyrrole-3-carboxylic acid

To a solution of 4-cyano-1H-pyrrole-3-carboxylic acid ethyl ester (1.1 g) in methanol (65 mL) was added 1 mol/L aqueous sodium hydroxide solution (65 mL), and this mixture was stirred at 50° C. for 5 hours. To this reaction mixture was added 1 mol/L hydrochloric acid, this mixture was extracted with ethyl acetate. This organic layer was washed with brine, and dried over anhydrous magnesium sulfate. The solvent was removed under reduced pressure. This obtained residue was washed with diethyl ether to give the title compound (0.72 g).

Reference Example 8

4-Cyano-1H-pyrrole-3-carboxylic acid methylamide

To a solution of 4-cyano-1H-pyrrole-3-carboxylic acid (0.034 g), methylamine hydrochloride (0.034 g), triethylamine (0.084 g) and 1-hydroxybenzotriazole (0.034 g) in tetrahydrofuran (2.5 mL) was added N-ethyl-N'-3-dimethylaminopropylcarbodiimide (0.058 g) at room temperature, and this mixture was stirred at same temperature overnight. This reaction mixture was poured into 1 mol/L hydrochloric acid, and this mixture was extracted with ethyl acetate. This organic layer was washed with a saturated aqueous sodium bicarbonate solution and brine, and dried over anhydrous magnesium sulfate. The solvent was removed under reduced pressure. The residue was purified by column chromatography on silica gel (eluent: ethyl acetate/n-hexane) to give the title compound (0.035 g).

Reference Example 9

3-Benzyloxy-1H-pyrazole-4-carboxylic acid ethyl ester

A suspension of 1-acetyl-3-oxo-2,3-dihydro-1H-pyrazole-4-carboxilic acid ethyl ester (2.7 g, This compound was prepared in a similar manner to that described in Bioorganic & Medicinal Chemistry Letters (2002), 12 (16), 2105-2108), benzylbromide (2.5 g), potassium carbonate (2.1 g) in N,N-dimethylformamide (20 mL) was stirred at 40° C. for 20 hours. To this reaction mixture was added 1 mol/L hydrochloric acid, and this mixture was extracted with ethyl acetate. This organic layer was washed with brine, and dried over anhydrous magnesium sulfate. The solvent was removed under reduced pressure. The residue was purified by column chromatography on aminopropyl silica gel (eluent: ethyl acetate/n-hexane) to give the title compound (1.6 g).

Reference Example 10

3-Benzyloxy-1-benzyloxymethyl-1H-pyrazole-4-carboxylic acid ethyl ester

A suspension of 3-benzyloxy-1H-pyrazole-4-carboxylic acid ethyl ester (0.74 g), benzylchloromethylether (0.56 g) and N,N-diisopropylethylamine (0.78 g) in N,N-dimethylformamide (15 mL) was stirred at 90° C. for 20 hours. To this reaction mixture was added 2 mol/L hydrochloric acid under ice cooling, and this mixture was extracted with ethyl acetate. This organic layer was washed with brine, and dried over anhydrous magnesium sulfate. The solvent was removed under reduced pressure. The residue was purified by column chromatography on aminopropyl silica gel (eluent: ethyl acetate/n-hexane) to give the title compound (0.65 g).

Reference Example 11

(3-Benzyloxy-1-benzyloxymethyl-1H-pyrazole-4-yl) methanol

To a suspension of lithium aluminum hydride (0.13 g) in tetrahydrofuran (5 mL) was added 3-benzyloxy-1-benzyloxymethyl-1H-pyrazole-4-carboxylic acid ethyl ester (0.65 g) at room temperature, and this mixture was stirred at same temperature for 3 hours. To this reaction mixture was added water, and the insoluble material was removed by filtration. This filtrate was dried over anhydrous magnesium sulfate, and this solvent was removed under reduced pressure to give the title compound (0.57 g).

Reference Example 12

(3-Benzyloxy-1-benzyloxymethyl-1H-pyrazole-4-yl) carbaldehyde

To a solution of (3-benzyloxy-1-benzyloxymethyl-1H-pyrazole-4-yl)-methanol (0.57 g) in dichloromethane (20 mL) was added manganese oxide (0.77 g), and this mixture was stirred at 50° C. for 20 hours. The insoluble material was removed by suction through a Celite pad, and this filtrate was concentrated under reduced pressure to give the title compound (0.57 g).

Reference Example 13

3-Benzyloxy-1H-pyrazole-4-carbonitrile

To a solution of (3-benzyloxy-1-benzyloxymethyl-1H-pyrazole-4-yl)-carb-aldehyde (0.57 g) in formic acid (5 mL) were added hydroxylamine hydrochloride (0.13 g) and sodium formate (0.24 g), and this mixture was heated to reflux for 5 hours. To this reaction mixture was added water, and this mixture was extracted with ethyl acetate. This organic layer was washed with brine, and dried over anhydrous magnesium sulfate. The solvent was removed under reduced pressure to give the title compound (0.045 g).

Reference Example 14

3-Acetyl[b]benzothiophene-4-carboxyphenylhydrazone

A suspension of 3-acetyl[b]benzothiophene (1.5 g) and 4-hydrazino benzoic acid (1.3 g) in ethanol (20 mL) was heated to reflux for 30 hours. To this reaction mixture was added water at room temperature, and this mixture was extracted with ethyl acetate. This organic layer was washed with brine, and dried over anhydrous magnesium sulfate. The solvent was removed under reduced pressure. The obtained residue was washed with n-hexane/diethylether=1/1, and this insoluble material was collected by filtration to give the title compound (1.7 g).

Reference Example 15

4-(3-Benzo[b]thiophene-3-yl-4-formylpyrazole-1-yl) benzoic acid

Phosphoryl chloride (3.0 g) was added to N,N-dimethylformamide under ice cooling, and this mixture was stirred at same temperature for 0.5 hours. To this reaction mixture was added 3-acetyl[b]benzothiophene-4-carboxyphenylhydrazone (1.7 g), and this mixture was stirred at room temperature for 30 hours. To this reaction mixture was added water, and this mixture was stirred for 0.5 hours. And then this insoluble material was collected by filtration, and dried under reduced pressure to give the title compound (0.3 g).

Reference Example 16

3-(2-Benzyloxy-phenyl)-2-cyano-acrylic acid ethyl ester

The title compound was prepared in a similar manner to that described in Reference Example 5 using the corresponding starting materials.

Reference Example 17

4-(2-Benzyloxyphenyl)-1H-pyrrole-3-carbonitrile

The title compound was prepared in a similar manner to that described in Reference Example 6 using the corresponding starting materials.

Reference Example 18

5-Bromo-2-methoxymethoxy-benzoic acid ethyl ester

The title compound was prepared in a similar manner to that described in Reference Example 1 using the corresponding starting materials.

Reference Examples 19 to 25

The title compounds were prepared in a similar manner to that described in Reference Example 6 using the corresponding starting materials.

Reference Examples 26 to 32

The title compounds were prepared in a similar manner to that described in Reference Example 8 using the corresponding starting materials.

Reference Examples 33 to 51

The title compounds were prepared in a similar manner to that described in Reference Example 6 using the corresponding starting materials.

Reference Examples 52 to 61

The title compounds were prepared in a similar manner to that described in Reference Example 4 using the corresponding starting materials.

Reference Example 62

2-(1-Cyclohexylethylidene)-1-hydradinecarboxamide

To a mixture of cyclohexylmethylketone (1.5 g), semicarbazide hydrochloride (1.86 g) and water (23 mL) was added sodium acetate (3.75 g), and this mixture was stirred at room temperature overnight. The insoluble material was collected by filtration, washed with water, dried under reduced pressure to give the title compound (1.9 g).

Reference Example 63

3-Cyclohexyl-1H-pyrazole-4-carbardehyde

To a solution of 2-(1-cyclohexylethyliden)-1-hydradinecarboxamide (1.92 g) in N,N-dimethylformamide (46 mL) was added phosphoryl chloride (4.82 g) under ice cooling, and this mixture was stirred at 80° C. overnight. This reaction mixture was poured into water, and this mixture was extracted with ethyl acetate. This organic layer was dried over anhydrous magnesium sulfate. The solvent was removed under reduced pressure. The residue was purified by column chromatography on silica gel (eluent: ethyl acetate/n-hexane) to give the title compound (1.2 g).

Reference Example 64

3-Cyclohexyl-1H-pyrazole-4-carbonitrile

To a mixture of 3-cyclohexyl-1H-pyrazole-4-carbardehyde (1.2 g), hydroxylamine hydrochloride (1.4 g) and tetrahydrofuran (12 mL) was added pyridine (2.66 g), and this mixture was heated to reflux overnight. To this reaction mixture was added acetic anhydride (2.75 g), and this mixture was heated to reflux for 12 hours. To this reaction mixture was added 1 mol/L aqueous sodium hydroxide solution. After stirring 30 minutes, to this mixture was added 2 mol/L hydrochloric acid until pH became 1. This obtained solid was collected by filtration, and this solid was washed with water, dried under reduced pressure to give the title compound (1.2 g).

Reference Example 65

2-Bromo-5-fluoroisonicotinic acid

To a solution of 2-bromo-5-fluoropyridine (5.0 g) in tetrahydrofuran (100 mL) was 2.6 mol/L n-butyllithium tetrahydrofuran solution (12 mL) in a dropwise manner at −70° C., and this mixture was stirred at same temperature for 2 hours. To this reaction mixture was added excessive amounts of dry-ice at −70° C., and this mixture was stirred at room temperature for 12 hours. This mixture was poured into water, and this mixture was extracted with diethyl ether. To this obtained aqueous layer was added 1 mol/L hydrochloric acid (2 mL), and this mixture was extracted with ethyl acetate. This organic layer was concentrated to give the title compound (5.2 g).

Reference Example 66

2-Bromo-5-fluoroisonicotinic acid ethyl ester

To a solution of 2-bromo-5-fluoroisonicotinic acid (5.2 g) in N,N-dimethylformamide (100 mL) were added potassium carbonate (9.8 g) and iodoethane (7.4 g) at room temperature, and this mixture was stirred at same temperature for 24 hours. This reaction mixture was poured into water, and this mixture was extracted with ethyl acetate. This organic layer was washed with water and brine, dried over anhydrous magnesium sulfate. The solvent was removed under reduced pressure to give the title compound (2.9 g).

Reference Example 67

5-Benzyloxy-2-bromoisonicotinic acid ethyl ester

To a solution of benzylalcohol (1.5 g) in tetrahydrofuran (30 mL) was added sodium hydride (55%, 0.3 g) under ice cooling, and this mixture was stirred at same temperature for 5 minutes. To this reaction mixture was added a solution of 2-bromo-5-fluoroisonicotinic acid ethyl ester (2.9 g) in tetrahydrofuran (30 mL), and this mixture was stirred at room temperature for 2 hours. This reaction mixture was poured into water, and this mixture was extracted with ethyl acetate. This organic layer was washed with water and brine, dried over anhydrous magnesium sulfate. The solvent was removed under reduced pressure. The residue was purified by column chromatography on silica gel (eluent: ethyl acetate/n-hexane) to give the title compound (2.4 g).

Reference Example 68

4-(tert-butyldiphenylsilanyloxymethyl)-1H-pyrrole-3-carbonitrile

To a suspension of sodium hydride (60%, 0.12 g) in diethyl ether (5 mL) were added a solution of 4-(tert-butyldiphenylsilanyloxy)-buta-2-ennitrile (0.81 g) and p-toluensulfonylmethylisocyanide (0.49 g) in diethyl ether (5 mL) and dimethylsulfoxide (5 mL). After stirring at room temperature for 5 hours, to this reaction mixture was added water and this reaction mixture was extracted with ethyl acetate. This organic layer was washed with brine, dried over anhydrous magnesium sulfate. The solvent was removed under reduced pressure. The residue was purified by column chromatography on silica gel (eluent: n-hexane/ethyl acetate=60/40-39/61) to give the title compound (0.50 g).

Reference Example 69

4-Thiophene-2-yl-1H-pyrazole-3-carbonitrile

After a solution of trimethylsilyldiazomethane in hexane (0.6 mol/L, 5 mL) was added to tetrahydrofuran (20 mL) under an argon atmosphere, to this reaction mixture was added a solution of n-butyl lithium in hexane (2.6 mol/L, 1.08 mL) in a dropwise manner over 5 minutes at −78° C., and this mixture was stirred at same temperature for 20 minutes. And then to this reaction mixture was added a solution of 2-thiophene-2-ylmethylene malononitrile (0.32 g) in tetrahydrofuran (5 mL) in a dropwise manner over 20 minutes. To this reaction mixture was added saturated aqueous ammonium chloride solution, and this mixture was extracted with ethyl acetate. This organic layer was washed with brine, dried over anhydrous magnesium sulfate, and filtered. The filtrate was concentrated under reduced pressure. This residue was washed with hexane to give 4-thiophene-2-yl-5-trimethylsilanyl-1H-pyrazole-3-carbonitrile (0.496 g). To the 4-thiophene-2-yl-5-trimethylsilanyl-1H-pyrazole-3-carbonitrile were added methanol (20 mL) and 1.0 mol/L aqueous sodium hydroxide solution (20 mL), and this mixture was heated to reflux for 2 hours. This reaction mixture was acidified (pH1) with adding 1.0 mol/L hydrochloric acid, the precipitated solid was collected by filtration. This obtained solid was washed with water, dried under reduced pressure at 50° C. to give the title compound (0.154 g).

Reference Example 70

1-(2-Chloropyridine-4-yl)-4-phenyl-1H-pyrrole-3-carbonitrile

To a solution of 4-phenyl-1H-pyrrole-3-carbonitrile (0.168 g), cupper (I) iodide (0.019 g), N,N-dimethyl grycine (0.021 g) and cesium carbonate (0.325 g) in dimethylsulfoxide (10 mL) was added 2-chloro-4-iodopyridine (0.287 g) at room temperature, and this mixture was at 180° C. in a sealed tube under microwave irradiation for 5 minutes. After cooling to ambient temperature, this reaction mixture was diluted with dichloromethane and water, and the insoluble material was removed by filtered though a Celite pad. This organic layer was separated and this organic solvent was removed under reduced pressure. The residue was purified by column chromatography on silica gel (eluent: ethyl acetate/hexane=80/20) to give the title compound (0.16 g).

Reference Examples 71 to 74

The title compounds were prepared in a similar manner to that described in Reference Example 4 using the corresponding starting materials.

Reference Examples 75 to 91

The title compounds were prepared in a similar manner to that described in Reference Example 6 using the corresponding starting materials.

Reference Examples 92 to 96

The title compounds were prepared in a similar manner to that described in Reference Example 64 using the corresponding starting materials.

Reference Examples 97 to 98

The title compounds were prepared in a similar manner to that described in Reference Example 69 using the corresponding starting materials.

Example 1

4-(3-Butyl-4-cyano-2-methylpyrrole-1-yl)benzoic acid ethyl ester

A suspension of 4-butyl-5-methyl-1H-pyrrole-3-carbonitrile (0.081 g), 4-fluoro-benzoic acid ethyl ester (0.10 g) and cesium carbonate (0.21 g) in N,N-dimethylformamide (3 mL) was stirred at 70° C. overnight. This reaction mixture was poured into water, and this mixture was extracted with ethyl acetate. This organic layer was washed with brine, dried over anhydrous magnesium sulfate. The solvent was removed under reduced pressure. The residue was purified by column chromatography on silica gel (eluent: ethyl acetate/n-hexane=1/6) to give the title compound (0.032 g).

Example 2

4-(3-Butyl-4-cyano-2-methylpyrrole-1-yl)benzoic acid

A suspension of 4-(3-butyl-4-cyano-2-methylpyrrole-1-yl)benzoic acid ethyl ester (0.030 g) and lithium hydroxide mono hydrate (0.041 g) in ethanol (2 mL) and water (1 mL) was stirred at 50° C. for 2 hours. To this reaction mixture was added 1 mol/L hydrochloric acid (5 mL), and this mixture was stirred at room temperature for 30 minutes. This reaction mixture was extracted with ethyl acetate, and this organic layer was washed with water, dried over anhydrous magnesium sulfate. The solvent was removed under reduced pressure to give the title compound (0.027 g).

Example 3

4-(4-Bromo-3-cyanopyrazole-1-yl)benzoic acid ethyl ester

A suspension of 4-bromo-1H-pyrazole-3-carbonitrile (0.52 g), 4-fluoro-benzoic acid ethyl ester (0.56 g) and cesium carbonate (1.5 g) in N,N-dimethylformamide (10 mL) was stirred at 100° C. for 2 hours. After cooling to ambient temperature, this reaction mixture was poured into water, and this mixture was extracted with ethyl acetate. This organic layer was washed with brine, dried over anhydrous magnesium sulfate. The organic layer was through an aminopropyl silica gel, and this filtrate was concentrated under reduced pressure. This obtained residue was washed with a mixed solvent of n-hexane/diethyl ether=5/1 to give the title compound (0.25 g).

Example 4

4-[3-cyano-4-(3,4-methylenedioxyphenyl)pyrazole-1-yl]benzoic acid ethyl ester

A suspension of 4-(4-bromo-3-cyanopyrazole-1-yl)benzoic acid ethyl ester (0.17 g), (3,4-methylenedioxyphenyl) boronic acid (0.11 g), tetrakis(triphenylphosphine) palladium (0.12 g) and sodium carbonate (0.17 g) in a mixed solvent of water (0.5 mL) and N,N-dimethylformamide (5 mL) was stirred at 70° C. for 12 hours. To this reaction mixture was added dilute hydrochloric acid, and this mixture was extracted with ethyl acetate. This organic layer was washed with brine, dried over anhydrous magnesium sulfate. The solvent was removed under reduced pressure. The residue was purified by column chromatography on aminopropyl silica gel (eluent: ethyl acetate/n-hexane=1/5) to give the title compound (0.05 g).

Example 5

4-[3-Cyano-4-(3,4-methylenedioxyphenyl)pyrazole-1-yl] benzoic acid

The title compound was prepared in a similar manner to that described in Example 2 using the corresponding starting materials.

Example 6

4-(3-Benzyloxy-4-cyanopyrazole-1-yl)benzoic acid ethyl ester

The title compound was prepared in a similar manner to that described in Example 1 using the corresponding starting materials.

Example 7

4-(3-Benzyloxy-4-cyanopyrazole-1-yl)benzoic acid

The title compound was prepared in a similar manner to that described in Example 2 using the corresponding starting materials.

Example 8

4-(3-Benzo[b]thiophene-3-yl-4-cyanopyrazole-1-yl) benzoic acid

A solution of 4-(3-benzo[b]thiophene-3-yl-4-formylpyrazole-1-yl)benzoic acid (0.26 g), hydroxylamine hydrochloride (0.058 g) and sodium formate (0.10 g) in formic acid (5 mL) was heated under reflux for 24 hours. To this reaction mixture was added water at room temperature, and this mixture was extracted with ethyl acetate. This organic layer was washed with brine, dried over anhydrous magnesium sulfate. The solvent was removed under reduced pressure. This obtained residue was dissolved with pyridine (5 mL), to this mixture was added trifluoroacetic anhydride (0.48 g) in a dropwise manner under ice cooling, and this mixture was stirred at room temperature for 5 hours. To this reaction mixture was added 2 mol/L hydrochloric acid, and this mixture was extracted with ethyl acetate. This organic layer was washed with brine, dried over anhydrous magnesium sulfate. The solvent was removed under reduced pressure. The obtained residue was washed with n-hexane/diethyl ether=1/1 to give the title compound (0.13 g).

Example 9

4-[4-(2-Benzyloxyphenyl)-3-cyanopyrrole-1-yl]-2-methoxymethoxy-benzoic acid ethyl ester To a solution of 4-(2-benzyloxyphenyl)-1H-pyrrole-3-carbonitrile (1.5 g), 4-fluoro-2-methoxymethoxybenzoic acid ethyl ester (1.4 g) in N,N-dimethylformamide (25 mL) was added cesium carbonate, and this mixture was stirred at 65° C. for 15 hours. This reaction mixture was poured into water, the precipitated solid was collected by filtration, and washed with water and n-hexane, dried under reduced pressure at 50° C. to give the title compound (2.3 g).

Example 10

4-[3-Cyano-4-(2-hydroxyphenyl)pyrrole-1-yl]-2-methoxymethoxy benzoic acid ethyl ester To a solution of 4-[4-(2-benzyloxyphenyl)-3-cyanopyrrole-1-yl]-2-methoxymethoxy-benzoic acid ethyl ester (2.3 g) in a mixed solvent of ethyl acetate (20 mL) and methanol (20 mL) was added palladium-carbon powder under an argon atmosphere, and this mixture was stirred at room temperature under a hydrogen atmosphere for 5 hours. The insoluble material was removed by filtration, and this filtrate was concentrated under reduced pressure to give the title compound (1.4 g)

Example 11

4-[3-Cyano-4-(2-hydroxyphenyl)pyrrole-1-yl]-2-hydroxy benzoic acid ethyl ester

To a solution of 4-[3-cyano-4-(2-hydroxyphenyl)pyrrole-1-yl]-2-methoxymethoxy benzoic acid ethyl ester (0.12 g) in a mixed solvent of tetrahydrofuran (3 mL) and ethanol (5 mL) was added 2 mol/L hydrochloric acid (2 mL), and this mixture was stirred at 70° C. for 18 hours. To this reaction mixture was added water, the precipitated solid was collected by filtration, and this solid was washed with water, dried under reduced pressure at 50° C. to give the title compound (0.054 g).

Example 12

4-[3-Cyano-4-(2-hydroxyphenyl)pyrrole-1-yl]-2-hydroxy benzoic acid

The title compound was prepared in a similar manner to that described in Example 2 using the corresponding starting materials.

Example 13

4-{3-Cyano-4-[2-(2-methoxyethoxy)phenyl]pyrrole-1-yl}-2-methoxymethoxy-benzoic acid ethyl ester To a solution of 4-[4-(2-hydroxyphenyl)-3-cyanopyrrole-1-yl]-2-methoxymethoxy benzoic acid ethyl ester (0.12 g)

and potassium carbonate (0.10 g) in N,N-dimethylformamide (1 mL) was added 1-bromo-3-methoxy-propane (0.092 g), and this mixture was stirred at 70° C. for 18 hours. This reaction mixture was poured into water, and this mixture was extracted with ethyl acetate. This organic layer was washed with brine, dried over anhydrous magnesium sulfate and concentrated under reduced pressure to give the title compound (0.12 g).

Example 14

4-{3-Cyano-4-[2-(2-methoxyethoxy)phenyl]pyrrole-1-yl}-2-hydroxy benzoic acid ethyl ester The title compound (0.072 g) was prepared in a similar manner to that described in Example 11 using the corresponding starting materials.

Example 15

4-{3-Cyano-4-[2-(2-methoxyethoxy)phenyl]pyrrole-1-yl}-2-hydroxy benzoic acid

To a solution of 4-{3-cyano-4-[2-(2-methoxyethoxy)phenyl]pyrrole-1-yl}-2-hydroxy benzoic acid ethyl ester (0.072 g) in a mixed solvent of ethanol (9 mL) and tetrahydrofuran (3 mL) was added 1 mol/mL aqueous lithium hydroxide solution (2.7 mL), and this mixture was stirred at room temperature for 48 hours. This reaction mixture was poured into 1 mol/L hydrochloric acid (2.7 mL), and to this mixture was added water (30 mL). The precipitated solid was collected by filtration. This obtained solid was washed with water, dried under reduced pressure at 50° C. to give the title compound (0.051 g).

Example 16

4-(3-Cyano-4-methoxypyrrole-1-yl)benzoic acid ethyl ester

The title compound was prepared in a similar manner to that described in Example 1 using the corresponding starting materials.

Example 17

4-(3-Benzyloxy-4-cyano-pyrrole-1-yl)benzoic acid ethyl ester

To a solution of 4-(3-cyano-4-methoxypyrrole-1-yl)benzoic acid ethyl ester (0.081 g) in dichloromethane (3 mL) was added boron tribromide (0.33 mL, 1 mol/L dichloromethane solution) under ice-cooling, and this mixture was stirred at same temperature for 2 hours. To this reaction mixture was added water, and this mixture was extracted with diethyl ether. This organic layer was washed with brine, dried over anhydrous magnesium sulfate. The solvent was removed under reduced pressure. The residue was purified by column chromatography on silica gel (eluent: ethyl acetate/n-hexane=1/1) to give 4-(3-cyano-4-hydroxypyrrole-1-yl)benzoic acid ethyl ester (0.052 g). To a solution of 4-(3-cyano-4-hydroxypyrrole-1-yl)benzoic acid ethyl ester (0.052 g) in N,N-dimethylformamide (4 mL) were added benzylbromide (0.038 g) and cesium carbonate (0.13 g) at room temperature, and this mixture was stirred at 80° C. for 5 hours. To this reaction mixture was added water at room temperature, and the precipitated solid was collected by filtration, and washed with methanol (5 mL) to give the title compound (0.016 g).

Example 18

4-(3-Cyano-4-benzyloxypyrrole-1-yl)benzoic acid

The title compound was prepared in a similar manner to that described in Example 2 using the corresponding starting materials.

Example 19

2-(3-Cyano-4-phenylpyrrole-1-yl)isonicotinic acid ethyl ester

To a solution of 4-phenyl-1H-pyrrole-3-carbonitrile (0.1 g) in toluene (0.70 mL) were added 2-bromo-isonicotinic acid ethyl ester (0.19 g), potassium phosphate (0.31 g), (1R, 2R)-(−)-N,N'-dimethylcyclohexane-1,2-diamine (0.02 g) and copper iodide (0.007 g) at room temperature, and this mixture was stirred at 110° C. for 24 hours. The insoluble material was removed by filtration through Celite, and this filtrate was concentrated. This obtained residue was purified by column chromatography on silica gel (eluent: ethyl acetate/n-hexane=10/90-66/34) to give the title compound (0.066 g).

Example 20

2-(3-Cyano-4-phenylpyrrole-1-yl)isonicotinic acid

The title compound (0.041 g) was prepared in a similar manner to that described in Example 2 using the corresponding starting materials.

Example 21

5-(3-Cyano-4-phenylpyrrole-1-yl)-2-methoxymethoxy-benzoic acid ethyl ester

A mixture of 4-phenyl-1H-pyrrole-3-carbonitrile (0.2 g), 5-bromo-2-methoxymethoxy-benzoic acid ethyl ester (0.36 g), copper iodide (0.023 g), N,N-dimethylgrycine (0.025 g), cesium carbonate (0.39 g) and dimethylsulfoxide (3 mL) was stirred at 75° C. for 12 hours. After cooling to ambient temperature, the insoluble material was removed by filtration through Celite pad, and this filtrate was concentrated. This obtained residue was purified by column chromatography on silica gel (eluent: ethyl acetate/n-hexane=10/90-66/34) to give the title compound (0.27 g).

Example 22

5-(3-Cyano-4-phenylpyrrole-1-yl)-2-hydroxy-benzoic acid

The title compound (0.16 g) was prepared in a similar manner to that described in Example 2 and Example 11 using the corresponding starting materials.

Example 23

3-(3-Cyano-4-phenylpyrrole-1-yl)benzoic acid ethyl ester

The title compound was prepared in a similar manner to that described in Example 21 using the corresponding starting materials.

Example 24

3-(3-Cyano-4-phenylpyrrole-1-yl)benzoic acid

The title compound was prepared in a similar manner to that described in Example 15 using the corresponding starting materials.

Example 25

4-(3-Amino-4-cyanopyrazole-1-yl)benzoic acid ethyl ester

The title compound was prepared in a similar manner to that described in Example 1 using the corresponding starting materials.

Example 26

4-(3-Acetylamino-4-cyanopyrazole-1-yl)benzoic acid ethyl ester

To a solution of 4-(3-amino-4-cyanopyrazole-1-yl)benzoic acid ethyl ester (0.1 g) in tetrahydrofuran (4 mL) were added acetyl chloride (0.12 g) and pyridine (0.15 g), and this mixture was stirred at room temperature for 12 hours. This reaction mixture was poured into water, and the precipitated solid was collected by filtration. This obtained solid was washed with ethyl acetate, dried under reduced pressure at 50° C. to give the title compound (0.088 g).

Example 27

4-(3-Acetylamino-4-cyanopyrazole-1-yl)benzoic acid

The title compound was prepared in a similar manner to that described in Example 2 using the corresponding starting materials.

Example 28

1-(5-Formylfuran-2-yl)-4-phenyl-1H-pyrrole-3-carbonitrile

The title compound was prepared in a similar manner to that described in Example 1 using 5-bromofuran-2-carboaldehyde instead of 4-fluoro benzoic acid ethyl ester.

Example 29

5-(3-Cyano-4-phenylpyrrole-1-yl)furan-2-carboxlic acid

To a solution of 1-(5-formylfuran-2-yl)-4-phenyl-1H-pyrrole-3-carbonitrile (0.14 g) in tetrahydrofuran (4 mL) were added silver oxide (0.15 g) and sodium hydroxide aqueous solution (2 mol/L, 0.4 mL), and this mixture was stirred at room temperature for 6 hours. The insoluble material was removed by filtration, and this filtrate was concentrated. To this residue were added water (15 mL) and hydrochloric acid (2 mol/L, 2 mL), this mixture was extracted with ethyl acetate. This organic layer was washed with brine, dried over anhydrous magnesium sulfate and concentrated under reduced pressure. This residue was purified by column chromatography on silica gel (eluent: methanol/dichloromethane=1/10-1/5) to give the title compound (0.040 g).

Examples 30 to 32

The title compounds were prepared in a similar manner to that described in Example 1 using the corresponding starting materials.

Examples 33 to 35

The title compounds were prepared in a similar manner to that described in Example 10 using the corresponding starting materials.

Examples 36 to 52

The title compounds were prepared in a similar manner to that described in Example 13 using the corresponding starting materials.

Examples 53 to 54

The title compounds were prepared in a similar manner to that described in Example 1 using the corresponding starting materials.

Example 55

The title compound was prepared in a similar manner to that described in Example 10 using the compound of Example 54 instead of 4-[4-(2-benzyloxyphenyl)-3-cyanopyrrole-1-yl]-2-methoxymethoxy-benzoic acid ethyl ester.

Examples 56 to 60

The title compounds were prepared in a similar manner to that described in Example 1 using the corresponding starting materials.

Examples 61 to 62

The title compounds were prepared in a similar manner to that described in Example 13 using the corresponding starting materials.

Example 63

The title compound was prepared in a similar manner to that described in Example 1 using the corresponding starting materials.

Example 64

4-[3-Cyano-4-(3-hydroxymethylphenyl)pyrrole-1-yl]benzoic acid ethyl ester

3-Cyano-5-[1-(4-ethoxycarbonylphenyl)-1H-pyrrole-3-yl]benzoic acid was prepared in a similar manner to that described in Example 10 using 4-[3-cyano-4-(3-benzyloxymethylphenyl)pyrrole-1-yl]benzoic acid ethyl ester. To a solution of the obtained carboxylic acid (1.0 g) in tetrahydrofuran (30 mL) was added boran-tetrahydrofuran complex (1.2 mol/L tetrahydrofuran solution, 3.75 mL) at 0° C., and this mixture was stirred at room temperature for 2 hours. To this reaction mixture was added saturated aqueous sodium bicarbonate solution, and this mixture was extracted with diethyl ether. This organic layer was washed with brine, dried over anhydrous magnesium sulfate and concentrated under reduced pressure. This residue was purified by column chromatography on silica gel (eluent: methanol/dichloromethane=1/20) to give the title compound (0.21 g).

Examples 65 to 73

The title compounds were prepared in a similar manner to that described in Example 1 using the corresponding starting materials.

Examples 74 to 75

The title compounds were prepared in a similar manner to that described in Example 17 using the corresponding starting materials.

Examples 76 to 90

The title compounds were prepared in a similar manner to that described in Example 1 using the corresponding starting materials.

Examples 91 to 92

The title compounds were prepared that, reacted in a similar manner to that described in Example 55 using the corresponding starting materials and separated by column chromatography on silica gel (eluent: ethyl acetate/n-hexane=10/90-66/34).

Examples 93 to 94

The title compounds were prepared in a similar manner to that described in Example 26 using the corresponding starting materials.

Examples 95 to 116

The title compounds were prepared in a similar manner to that described in Example 9 using the corresponding starting materials.

Example 117

The title compound was prepared in a similar manner to that described in Example 55 using the corresponding starting materials.

Examples 118 to 123

The title compounds were prepared in a similar manner to that described in Example 9 using the corresponding starting materials.

Example 124

The title compound was prepared in a similar manner to that described in Example 55 using the corresponding starting materials.

Example 125

The title compound was prepared in a similar manner to that described in Example 9 using the corresponding starting materials.

Example 126

The title compound was prepared in a similar manner to that described in Example 55 using the corresponding starting materials.

Examples 127 to 134

The title compounds were prepared in a similar manner to that described in Example 9 using the corresponding starting materials.

Examples 135 to 136

The title compounds were prepared in a similar manner to that described in Example 10 using the corresponding starting materials.

Example 137

The title compound was prepared in a similar manner to that described in Example 13 using the corresponding starting materials.

Examples 138 to 142

The title compounds were prepared in a similar manner to that described in Example 9 using the corresponding starting materials.

Examples 143 to 263

The title compounds were prepared in a similar manner to that described in Example 2 using the corresponding starting materials.

Example 264

The title compound was prepared in a similar manner to that described in Example 29 using the corresponding starting materials.

Examples 265 to 359

The title compounds were prepared in a similar manner to that described in Example 11 and Example 12 using the corresponding starting materials.

Examples 360 to 370

The title compounds were prepared in a similar manner to that described in Example 2 using the corresponding starting materials.

Examples 371 to 375

The title compounds were prepared in a similar manner to that described in Example 2 using the corresponding ester that was prepared in a similar manner to that described in Example 1 using 6-chloronicotinic acid ethyl ester instead of 4-fluoro-2-methoxymethoxy benzoic acid ethyl ester.

Example 376

4-(3-Cyano-4-phenylpyrrole-1-yl)benzamide

To a solution of 4-(3-cyano-4-phenylpyrrole-1-yl)benzoic acid (0.14 g) in tetrahydrofuran (2.5 mL) was added 1,1'-carbonyldiimidazole (0.16 g). After stirring for 30 minutes, to this reaction mixture was added aqueous ammonia (28% solution 0.75 mL), and this mixture was stirred 2 hours. To this reaction mixture was added water (10 mL), the precipitated white solid was collected by filtration, and wash with methanol, dried to give the title compound (0.13 g).

Example 377

5-(3-Cyano-4-phenylpyrrole-1-yl)pyridine-2-carboxilic acid ethyl ester

The title compound was prepared in a similar manner to that described in Example 19 using the corresponding starting materials.

Example 378

4-(3-Cyano-4-phenylpyrrole-1-yl)-2-nitro-benzoic acid ethyl ester

The title compound (0.137 g) was prepared in a similar manner to that described in Example 1 using 4-fluoro-2-nitro benzoic acid ethyl ester instead of 4-fluoro benzoic acid ethyl ester.

Example 379

2-Amino-4-(3-cyano-4-phenylpyrrole-1-yl)benzoic acid ethyl ester

To a solution of 4-(3-cyano-4-phenylpyrrole-1-yl)-2-nitro-benzoic acid ethyl ester (0.090 g) in a mixed solvent of methanol (2.5 mL) and ethyl acetate (2.5 mL) was added 10% palladium-carbon powder (0.016 g) under an argon atmosphere, and this mixture was stirred at 40° C. under a hydrogen atmosphere for 3 hours. After this reaction mixture was replaced under an argon atmosphere, the insoluble material was removed by suction through a Celite pad. This filtrate was concentrated under reduced pressure. The residue was purified by column chromatography on aminopropyl silica gel (eluent: ethyl acetate/hexane=50/50) to give the title compound (0.070 g).

Example 380

4-(3-Cyano-4-phenylpyrrole-1-yl)-2-methanesulfonylamino-benzoic acid ethyl ester To a solution of 2-amino-4-(3-cyano-4-phenylpyrrole-1-yl)benzoic acid ethyl ester (0.050 g) and triethylamine (0.046 g) in dichloromethane (2 mL) was added methane sulfonylchloride (0.043 g) under ice-cooling, and this mixture was stirred at room temperature for 3 days. This reaction mixture was concentrated under reduced pressure. The residue was purified by column chromatography on silica gel (eluent: ethyl acetate/n-hexane=75/25) to give the title compound (0.015 g).

Example 381

2-Acetylamino-4-(3-cyano-4-phenylpyrrole-1-yl) benzoic acid ethyl ester

The title compound was prepared in a similar manner to that described in Example 380 using acetyl chloride instead of methane sulfonylchloride.

Example 382

4-Phenyl-1-[4-(1H-tetrazole-5-yl)pyridine-2-yl]-1H-pyrrole-3-carbonitrile

To a solution of 2-(3-cyano-4-phenylpyrrole-1-yl)isonicotinamide (0.058 g) and sodium azide (0.039 g) in a mixed solvent of acetonitrile (1.0 mL) and tetrahydrofuran (0.5 mL) was added tetrachlorosilane (0.068 g) at room temperature, and this mixture was stirred at 80° C. overnight. To this reaction mixture was added water, this obtained solid was collected by filtration. After washing with water, this solid was dried at 50° C. under reduced pressure to give the title compound (0.051 g).

Example 383

5-Benzyloxy-2-(3-cyano-4-phenylpyrrole-1-yl)isonicotinic acid ethyl ester

To a solution of 3-cyano-4-phenylpyrrole (0.20 g) in dimethylsulfoxide (2 mL) was added 5-benzyloxy-2-bromoisonicotinic acid ethyl ester (0.30 g), cesium carbonate (0.30 g), copper iodide (0.010 g) and N,N-dimethyl glycine (0.020 g) at room temperature, and this mixture was stirred at 110° C. for 8 hours. The insoluble material was removed by suction through a Celite pad. This filtrate was poured into water, and this mixture was extracted with ethyl acetate. This organic layer was washed with water and brine, dried over anhydrous magnesium sulfate and concentrated under reduced pressure. The residue was purified by column chromatography on silica gel (eluent: ethyl acetate/n-hexane=10/90-60/40) to give the title compound (0.20 g).

Example 384

2-(3-Cyano-4-phenylpyrrole-1-yl)-5-hydroxyisonicotinic acid ethyl ester

To a solution of 5-benzyloxy-2-(3-cyano-4-phenylpyrrole-1-yl)isonicotinic acid ethyl ester in a mixed solvent of methanol (2 mL) and ethyl acetate (2 mL) was added palladium-carbon powder (0.020 g), and this mixture was stirred at room temperature under a hydrogen atmosphere for 30 minutes. The insoluble material was removed by suction through a Celite pad. This filtrate was concentrated under reduced pressure. This obtained solid was washed with diethyl ether, dried to give the title compound (0.040 g).

Example 385

2-(3-Cyano-4-phenylpyrrole-1-yl)-5-hydroxyisonicotinic acid

To a solution of 2-(3-cyano-4-phenylpyrrole-1-yl)-5-hydroxyisonicotinic acid ethyl ester (0.050 g) in a mixed solvent of tetrahydrofuran (3.6 mL) and ethanol (1.2 mL) was added 1 mol/L aqueous lithium hydroxide solution (1.2 mL) at room temperature, and this mixture was stirred at same temperature for 5 hours. This mixture was poured into water, this mixture was washed with diethyl ether. To this aqueous layer was added 1 mol/L hydrochloric acid (1.2 mL), and the precipitated solid was collected by filtration, and washed with water and n-hexane. This solid was dried under reduced pressure at 50° C. to give the title compound (0.030 g).

Example 386

4-(3-Cyano-4-hydroxymethylpyrrole-1-yl)benzoic acid ethyl ester

A suspension of 4-(tert-butyldiphenylsilanyloxymethyl)-1H-pyrrole-3-carbonitrile (0.3 g), 4-fluorobenzoic acid ethyl ester (0.35 g) and cesium carbonate (0.81 g) in N,N-dimethylformamide (2 mL) was stirred at 70° C. overnight. To this reaction mixture was added water, and this mixture was extracted with ethyl acetate. This organic layer was washed with water and brine, concentrated under reduced pressure. The residue was purified by column chromatography on silica gel (eluent: hexane/ethyl acetate=80/20-30/70) to give the title compound (0.0310 g).

Example 387

4-(3-Cyano-4-ethoxymethylpyrrole-1-yl)benzoic acid

To a solution of 4-(3-cyano-4-hydroxymethylpyrrole-1-yl)benzoic acid ethyl ester (0.022 g) in tetrahydrofuran (1 mL) were added triethylamine (0.0082 g) and methane sulfonylchloride (0.0093 g) under ice-cooling. After warming to ambient temperature, this mixture was stirred for 30 minutes. The insoluble material of this reaction mixture was removed by filtration, and this filtrate was added to a mixture of ethanol (1.125 g) and sodium hydride (60%, 0.13 g), and this mixture was stirred for 5 hours. To this reaction mixture was added water, and this mixture was stirred at room temperature for 1 hours. To this reaction mixture was added 2 mol/L hydrochloric acid (3 mL), this mixture was extracted with ethyl acetate. This organic layer was washed with brine, concentrated under reduced pressure. The residue was purified by column chromatography on silica gel (eluent: dichloromethane/methanol=88/12-81/19) to give the title compound (0.010 g).

Example 388

4-(3-Cyano-4-phenylpyrrole-1-yl)pyridine-2-carboxylic acid methyl ester

To a solution of 1-(2-chloropyridine-4-yl)-4-phenyl-1H-pyrrole-3-carbonitrile (0.070 g), palladium (II) acetate (0.006 g) and triethylamine (0.056 g) in methanol (1 mL) and dimethylsulfoxide (1 mL) was added 1,3-bis(diphenylphosphino)propane (0.025 g) an under argon atmosphere at room temperature, and this mixture was stirred under a carbon monoxide atmosphere at 75° C. for 1 days. After cooling to ambient temperature, this reaction mixture was diluted with dichloromethane and water. After the insoluble material was removed by suction through a Celite pad, this organic layer was separated and concentrated under reduced pressure. The residue was purified by column chromatography on silica gel (eluent: ethyl acetate/hexane=67/33) to give the title compound (0.053 g).

Examples 389 to 392

The title compounds were prepared in a similar manner to that described in Example 1 using the corresponding starting materials.

Example 393

The title compound was prepared in a similar manner to that described in Example 11 using the corresponding starting materials.

Examples 394 to 397

The title compounds were prepared in a similar manner to that described in Example 1 using the corresponding starting materials.

Examples 398 to 401

The title compounds were prepared in a similar manner to that described in Example 9 using the corresponding starting materials.

Examples 402 to 403

The title compounds were prepared that, reacted in a similar manner to that described in Example 55 using the corresponding starting materials and separated by column chromatography on silica gel (eluent: ethyl acetate/n-hexane=25/75).

Examples 404 to 407

The title compounds were prepared in a similar manner to that described in Example 9 using the corresponding starting materials.

Examples 408 to 412

The title compounds were prepared in a similar manner to that described in Example 21 using 4-iodo-2-methoxymethoxy-benzoic acid methyl ester and the corresponding starting materials.

Examples 413 to 414

The title compounds were prepared in a similar manner to that described in Example 9 using the corresponding starting materials.

Examples 415 to 416

The title compounds were prepared in a similar manner to that described in Example 9 using the corresponding starting materials and 2,4-difluoro-6-methoxymethoxy-benzoic acid ethyl ester instead of 4-fluoro-2-methoxymethoxybenzoic acid ethyl ester.

Example 417

The title compound was prepared in a similar manner to that described in Example 378 using the corresponding starting materials.

Example 418

The title compound was prepared in a similar manner to that described in Example 379 using the corresponding starting materials.

Examples 419 to 432

The title compounds were prepared in a similar manner to that described in Example 21 using 2-bromoisonicotinic acid ethyl ester and the corresponding starting materials.

Examples 433 to 435

The title compounds were prepared in a similar manner to that described in Example 384 using the corresponding starting materials.

Examples 436 to 441

The title compounds were prepared in a similar manner to that described in Example 13 using the corresponding starting materials.

Examples 442 to 449

The title compounds were prepared in a similar manner to that described in Example 383 using the corresponding starting materials.

Example 450

The title compound was prepared in a similar manner to that described in Example 19 using 2-bromo-5-fluoroisonicotinic acid ethyl ester and the corresponding starting materials.

Examples 451 to 467

The title compounds were prepared in a similar manner to that described in Example 2 using the corresponding starting materials.

Example 468

After carboxylic acid derivative was prepared in a similar manner to that described in Example 2, to this compound was added 2 mol/L hydrochloric acid (0.165 mL), and this mixture was stirred at 50° C. overnight. The precipitated solid was collected by filtration, and washed with methanol to give the title compound (0.080 g).

Examples 469 to 487

The title compounds were prepared in a similar manner to that described in Example 468 using the corresponding starting materials.

Examples 488 to 489

The title compounds were prepared in a similar manner to that described in Example 2 using the corresponding starting materials.

Examples 490 to 491

The title compounds were prepared in a similar manner to that described in Example 379 using the corresponding starting materials.

Examples 492 to 498

The title compounds were prepared in a similar manner to that described in Example 2 using the corresponding starting materials.

Example 499

The title compound was prepared in a similar manner to that described in Example 55 using the corresponding starting materials.

Examples 500 to 521

The title compounds were prepared in a similar manner to that described in Example 2 using the corresponding starting materials.

Examples 522 to 524

The title compounds were prepared in a similar manner to that described in Example 385 using the corresponding starting materials.

Examples 525 to 526

The title compounds were prepared in a similar manner to that described in Example 2 using the corresponding starting materials.

Examples 527 to 528

The title compounds were prepared in a similar manner to that described in Example 376 using the corresponding starting materials.

Example 529

The title compound was prepared in a similar manner to that described in Example 55 using the compound of Example 528.

Examples 530 to 531

The title compounds were prepared in a similar manner to that described in Example 529 using the corresponding starting materials.

Examples 532 to 548

The title compounds were prepared in a similar manner to that described in Example 376 using the corresponding starting materials.

Example 549

After the amide derivative was prepared in a similar manner to that described in Example 376 using the compound of Example 461, this title compound was prepared in a similar manner to that described in Example 11.

Examples 550 to 552

The title compounds were prepared in a similar manner to that described in Example 549 using the corresponding starting materials.

Example 553

After the amide derivative was prepared in a similar manner to that described in Example 376 using the compound of Example 488, this title compound was prepared in a similar manner to that described in Example 379.

Tables 1 to 9 and 68 show the chemical structures and $^1$H-NMR data of the above compounds of Reference Examples 1 to 61 excluding 3 and 62 to 70, Table 69 shows the chemical structures of the compounds of Reference Examples 71 to 98, Tables 10 to 67, 70 to 71 and 76 to 90 show the chemical structures and $^1$H-NMR data including some mass spectrum data of the above compounds of Examples 1 to 376 excluding 11 and 14, 377 to 388 and 451 to 553, Tables 72 to 75 show the chemical structure of the compounds of Examples 389 to 450, respectively.

The abbreviations in these Tables: "Ref No.", "Ex No.", "Strc", "Solv" and "MS" represent Reference Example number, Example number, chemical structure, measurement solvent of ¹H-NMR and mass spectrum, respectively.

TABLE 1

| Ref.No | Strc. | (Solv) ¹H-NMR δ ppm: |
|---|---|---|
| 1 | | (CDCl3) 1.37 (3H, t, J = 7.02 Hz), 3.52 (3H, s), 4.35 (2H, q, J = 7.02 Hz), 4.25 (2H, s), 6.07-6.78 (1H, m), 6.94 (1H, dd, J = 2.4, 10.8 Hz), 7.83 (1H, d, J = 7.0, 8.9 Hz) |
| 2 | | (CDCl3) 1.77 (3H, d, J = 6.9 Hz), 2.49 (3H, s), 4.59 (1H, q, J = 6.9 Hz), 7.40-7.48 (2H, m), 7.84-7.92 (2H, m) |
| 4 | | (CDCl3) 0.92 (3H, t, J = 7.2 Hz), 1.28-1.40 (2H, m), 1.48-1.58 (2H, m), 2.17 (3H, s), 2.46-2.52 (2H, m), 7.08 (1H, d, J = 2.7 Hz), 8.08 (1H, br) |
| 5 | | (CDCl3) 1.41 (3H, t, J = 7.3 Hz), 4.40 (2H, q, J = 7.3 Hz), 7.20-7.35 (1H, m), 7.45-7.55 (1H, m), 7.65-7.85 (2H, m), 8.21 (1H, s) |
| 6 | | (CDCl3) 6.90-7.10 (2H, m), 7.25-7.55 (5H, m), 8.71 (1H, brs.) |
| 7 | | (DMSO-d6) 7.45-7.80 (2 H, m), 12.20 (1 H, brs.), 12.48 (1 H, brs.) |
| 8 | | (DMSO-d6) 2.60-2.81 (3 H, m), 7.35-7.70 (2 H, m), 7.80-8.05 (1 H, m), 11.90 (1 H, brs.) |
| 9 | | (CDCl3) 1.20-1.50 (3 H, m), 4.15-4.40 (2 H, m), 5.20-5.50 (2 H, m), 7.15-7.60 (6 H, m), 7.88 (1 H, s) |

TABLE 2

| Ref.No | Strc. | (Solv) ¹H-NMR δ ppm: |
|---|---|---|
| 10 | | (CDCl3) 1.25-1.45 (3H, m), 4.15-4.40 (2H, m), 4.45-4.95 (2H, m), 5.15-5.55 (4H, m), 7.00-8.00 (11H, m) |
| 11 | | (CDCl3) 4.40-4.60 (4 H, m), 5.20-5.40 (4 H, m), 7.10-7.60 (11 H, m) |
| 12 | | (CDCl3) 4.57 (2 H, s), 5.32 (2 H, s), 5.38 (2 H, s), 7.20-7.55 (10 H, m), 7.88 (1 H, s), 9.82 (1 H, s) |
| 13 | | (DMSO-d6) 5.27 (2 H, s), 7.25-7.55 (5 H, m), 8.38 (1 H, s), 12.94 (1 H, brs.) |
| 14 | | (DMSO-d6) 2.44 (3 H, s), 7.20-7.65 (4 H, m), 7.75-8.15 (4 H, m), 8.75-9.00 (1 H, m), 9.75 (1 H, s), 12.30 (1 H, brs.) |

TABLE 3
| Ref. No | Strc. | (Solv) $^1$H-NMR δ ppm: |
|---|---|---|
| 15 | 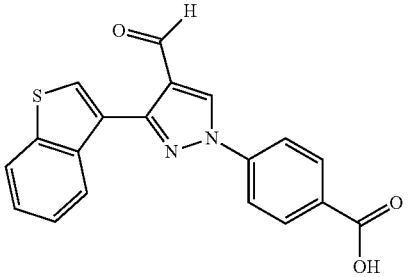 [SMILES: O=Cc1cn(-c2ccc(C(=O)O)cc2)nc1-c1csc2ccccc12] | (DMSO-d6) 7.35-7.65 (2H, m), 8.05-8.30 (5H, m), 8.40-8.60 (1H, m), 8.66 (1H, s), 9.56 (1H, s), 10.03 (1H, s), 13.18 (1H, brs.) |
| 16 | 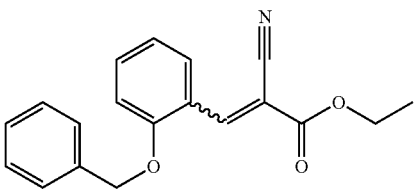 [SMILES: CCOC(=O)C(C#N)=Cc1ccccc1OCc1ccccc1] | (CDCl3) 1.27 (3H, t, J = 7.1 Hz), 4.29 (2H, q, J = 7.1 Hz), 5.28 (2H, s), 7.10-7.70 (8H, m), 8.15 (1H, d, J = 7.6 Hz), 8.68 (1H, s) |
| 17 | 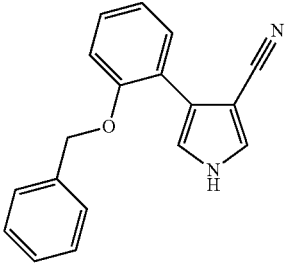 [SMILES: N#Cc1c[nH]cc1-c1ccccc1OCc1ccccc1] | (DMSO-d6) 5.14 (2H, s), 6.85-7.75 (11H, m), 11.94 (1H, brs) |
| 18 | 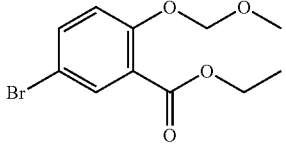 [SMILES: CCOC(=O)c1cc(Br)ccc1OCOC] | (CDCl3) 1.38 (3H, t, J = 7.2 Hz), 4.36 (2H, q, J = 7.2 Hz), 3.51 (3H, s), 5.22 (2H, s), 7.09) 1H, d, J = 8.9 Hz), 7.52 (1H, dd, J = 8.9 Hz, 2.7 Hz), 7.88 (1H, d, J = 2.5 Hz) |
| 19 | 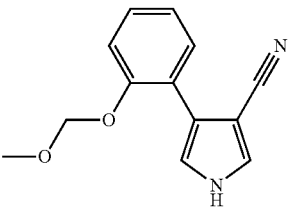 [SMILES: COCOc1ccccc1-c1c[nH]cc1C#N] | (CDCl3) 3.48 (3H, s), 5.23 (2H, s), 6.95-7.70 (6H, m), 8.64 (1H, brs.) |
| 20 | 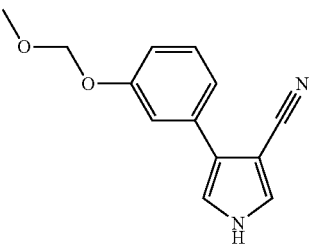 [SMILES: COCOc1cccc(-c2c[nH]cc2C#N)c1] | (CDCl3) 3.50 (3H, s), 5.22 (2H, s), 6.90-7.10 (2H, m), 7.20-7.45 (4H, m), 8.66 (1H, brs.) |

TABLE 3-continued

| Ref. No | Strc. | (Solv) $^1$H-NMR δ ppm: |
|---|---|---|
| 21 | | (CDCl3) 3.49 (3H, s), 5.20 (2H, s), 7.30-7.65 (6H, m), 8.65 (1H, brs.) |

TABLE 4

| Ref. No | Strc. | (Solv) $^1$H-NMR δ ppm: |
|---|---|---|
| 22 | | (DMSO-d6) 6.95-7.80 (9H, m), 11.86 (1H), brs.) |
| 23 | | (CDCl3) 5.39 (2H, s), 6.95-7.15 (1H, m), 7.25-7.60 (7H, m), 7.80-8.40 (3H, m), 8.81 (1H, brs.) |
| 24 | | (CDCl3) 3.79 (3H, s), 6.15-6.40 (1H, m), 6.95-7.15 (1H, m), 8.12 (1H, brs.) |
| 25 | | (DMSO-d6) 7.45-7.95 (7H, m), 12.40 (1H, brs.) |
| 26 | | (DMSO-d6) 2.80-3.20 (6H, m), 7.10-7.35 (1H, m), 7.50-7.75 (1H, m), 11.99 (1H, brs.) |

TABLE 4-continued

| Ref. No | Strc. | (Solv) ¹H-NMR δ ppm: |
|---|---|---|
| 27 | *N-benzyl-4-cyano-1H-pyrrole-3-carboxamide* | (DMSO-d6) 4.41 (2H, d, J = 5.9 Hz), 7.15-7.45 (5H, m), 7.56 (1H, d, J = 1.9 Hz), 7.64 (1H, d, J = 1.9 Hz), 8.53 (1H, t, J = 5.9 Hz), 11.95 (1H, brs.) |
| 28 | *N-benzyl-4-cyano-N-methyl-1H-pyrrole-3-carboxamide* | (DMSO-d6) 2.80-3.15 (3H, m), 4.66 (2H, s), 7.15-7.45 (6H, m), 7.60-7.75 (1H, m), 12.00 (1H, brs.) |
| 29 | *4-cyano-N-(2-methoxyethyl)-1H-pyrrole-3-carboxamide* | (DMSO-d6) 3.20-3.50 (7H, m), 7.45-7.70 (2H, m), 7.95-8.15 (1H, m), 11.94 (1H, brs.) |

TABLE 5

| Ref. No | Strc. | (Solv) ¹H-NMR δ ppm: |
|---|---|---|
| 30 | *4-cyano-N-(2-methoxyethyl)-N-methyl-1H-pyrrole-3-carboxamide* | (DMSO-d6) 2.80-3.70 (10H, m), 7.15-7.35 (1H, m), 7.55-7.75 (1H, m), 11.98 (1H, brs.) |
| 31 | *4-(piperidine-1-carbonyl)-1H-pyrrole-3-carbonitrile* | (DMSO-d6) 1.35-1.75 (6H, m), 3.35-3.65 (4H, m), 7.05-7.25 (1H, m), 7.55-7.75 (1H, m), 12.00 (1H, brs.) |
| 32 | *4-(morpholine-4-carbonyl)-1H-pyrrole-3-carbonitrile* | (DMSO-d6) 3.45-3.75 (8H, m), 7.15-7.35 (1H, m), 7.55-7.80 (1H, m), 12.07 (1H, brs.) |
| 33 | *4-(2,4-dimethoxyphenyl)-1H-pyrrole-3-carbonitrile* | (CDCl3) 6.45-6.65 (2H, m), 6.95-7.15 (1H, m), 7.25-7.60 (2H, m), 8.57 (1H, brs.) |

TABLE 5-continued
| Ref. No | Strc. | (Solv) ¹H-NMR δ ppm: |
|---|---|---|
| 34 | 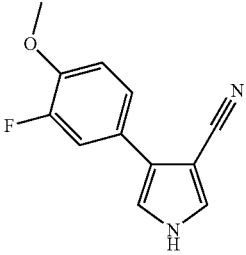 [SMILES: COc1ccc(-c2c[nH]cc2C#N)cc1F] | (CDCl3) 3.92 (3H, s), 6.80-7.15 (2H, m), 7.20-7.50 (3H, m), 8.67 (1H, brs.) |
| 35 | 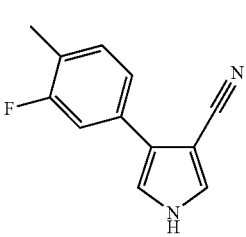 | (CDCl3) 2.20-2.40 (3H, m), 6.90-7.05 (1H, m), 7.15-7.45 (4H, m), 8.64 (1H, brs.) |
| 36 | 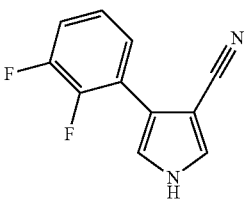 [SMILES: N#Cc1c[nH]cc1-c1cccc(F)c1F] | (DMSO-d6) 7.00-7.70 (5H, m), 8.79 (1H, brs.) |
TABLE 6
| Ref. No | Strc. | (Solv) ¹H-NMR δ ppm: |
|---|---|---|
| 37 | 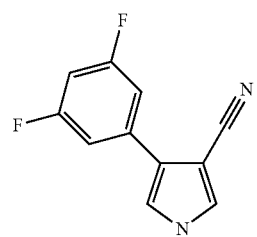 | (DMSO-d6) 7.05-7.60 (4H, m), 7.70-7.85 (1H, m), 12.09 (1H, brs.) |
| 38 | 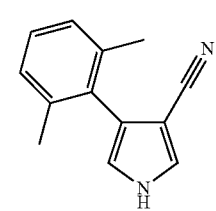 | (DMSO-d6) 2.06 (6H, s), 6.75-6.90 (1H, m), 7.00-7.25 (3H, m), 7.60-7.80 (1H, m), 11.81 (1H, brs.) |
| 39 | 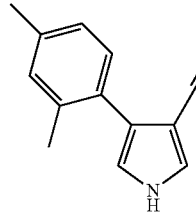 | (CDCl3) 2.30 (3H, s), 2.34 (3H, s), 6.65-6.80 (1H, m), 6.95-7.40 (4H, m), 8.78 (1H, brs.) |
| 40 |  | (DMSO-d6) 7.00-7.90 (5H, m), 12.08 (1H, brs.) |
| 41 | 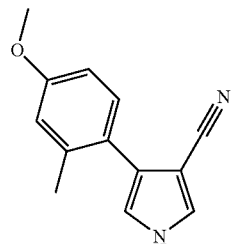 | (CDCl3) 2.32 (3H, s), 3.82 (3H, s), 6.65-6.90 (3H, m), 7.15-7.40 (2H, m), 8.72 (1H, brs.) |
| 42 | 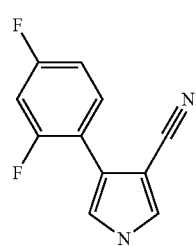 | (CDCl3) 6.85-7.25 (3H, m), 7.35-7.60 (2H, m), 8.89 (1H, brs.) |

TABLE 7

| Ref. No. | Strc. | (Solv) ¹H-NMR δ ppm: |
|---|---|---|
| 43 | (4-methoxy-2-fluorophenyl pyrrole-3-carbonitrile) | (CDCl3) 3.83 (3 H, s), 6.60-6.90 (2 H, m), 7.00-7.20 (1 H, m), 7.30-7.50 (1 H, m), 7.60-7.80 (1 H, m), 8.67 (1 H, brs.) |
| 44 | (5-methoxy-2-fluorophenyl pyrrole-3-carbonitrile) | (CDCl3) 3.84 (3 H, s), 6.70-6.85 (1 H, m), 6.95-7.25 (2 H, m), 7.30-7.50 (2 H, m), 8.74 (1 H, brs.) |
| 45 | (2-methoxynaphthyl pyrrole-3-carbonitrile) | (CDCl3) 3.97 (3 H, s), 6.80-7.00 (1 H, m), 7.25-7.55 (4 H, m), 7.65-8.00 (3 H, m), 8.76 (1 H, brs.) |
| 46 | (benzothiophen-2-yl pyrrole-3-carbonitrile) | (CDCl3) 7.00-7.50 (4 H, m), 7.65-7.89 (3 H, m), 8.66 (1 H, brs.) |
| 47 | (benzofuran-2-yl pyrrole-3-carbonitrile) | (CDCl3) 7.15-7.65 (7 H, m), 8.73 (1 H, brs.) |
| 48 | (benzothiophen-3-yl pyrrole-3-carbonitrile) | (CDCl3) 7.00-7.20 (1 H, m), 7.30-7.55 (3 H, m), 7.65 (1 H, s), 7.80-8.00 (2 H, m), 8.78 (1 H, brs.) |

TABLE 8

| Ref. No. | Strc. | (Solv) ¹H-NMR δ ppm: |
|---|---|---|
| 49 | (2-methoxystyryl pyrrole-3-carbonitrile) | (DMSO-d6) 3.82 (3 H, s), 6.80-7.75 (8 H, m), 11.81 (1 H, brs.) |
| 50 | (4-methoxystyryl pyrrole-3-carbonitrile) | (CDCl3) 3.83 (3 H, s), 6.75-7.50 (8 H, m), 8.49 (1 H, brs.) |
| 51 | (ethyl 4-trifluoromethyl pyrrole-3-carboxylate) | (CDCl3) 1.35 (3 H, t, J = 7.1 Hz), 4.31 (2 H, q, J = 7.1 Hz), 7.05-7.25 (1 H, m), 7.40-7.60 (1 H, m) |
| 52 | (4-benzyl pyrrole-3-carbonitrile) | (CDCl3) 6.44-6.48 (1H, m), 7.18-7.34 (6H, m), 8.43 (1H, br) |
| 53 | (4-propyl pyrrole-3-carbonitrile) | (CDCl3) 0.88-1.00 (3H, m), 1.56-1.72 (2H, m), 2.46-2.60 (2H, m), 6.52-6.58 (1H, m), 7.16-7.24 (1H, m), 8.40 (1H, br) |
| 54 | (2-methyl-4-propyl pyrrole-3-carbonitrile) | (CDCl3) 0.92 (3H, t, J = 7.5 Hz), 1.54-1.64 (2H, m), 2.44-2.50 (2H, m), 7.08 (1H, d, J = 3.4 Hz), 7.90-8.30 (1H, br) |

TABLE 8-continued
| Ref. No. | Strc. | (Solv) ¹H-NMR δ ppm: |
|---|---|---|
| 55 | 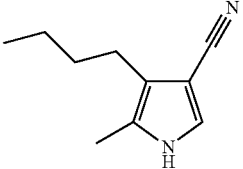 | (CDCl3) 0.92 (3H, t, J = 7.2 Hz), 1.28-1.40 (2H, m), 1.48-1.58 (2H, m), 2.17 (3H, s), 2.46-2.52 (2H, m), 7.08 (1H, d, J = 2.7 Hz), 8.08 (1H, br) |
| 56 | 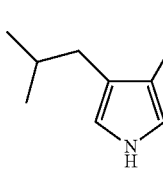 | (CDCl3) 0.92 (6H, d, J = 6.6 Hz), 1.84-1.96 (1H, m), 2.44 (2H, d, J = 7.0 Hz), 6.54-6.58 (1H, m), 7.18-7.24 (1H, m), 8.20-8.70 (1H, br) |
TABLE 9
| Ref. No. | Strc. | (Solv) ¹H-NMR δ ppm: |
|---|---|---|
| 57 | 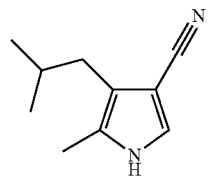 | (CDCl3) 0.88-0.96 (6H, m), 1.84-1.96 (1H, m), 2.14-2.20 (3H, m), 2.34-2.40 (2H, m), 7.08-7.12 (1H, m), 7.90-8.20 (1H, m) |
| 58 | 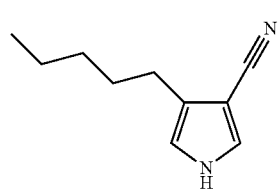 | (CDCl3) 0.90 (3H, t, J = 7.00), 1.26-1.40 (4H, m), 1.58-1.68 (2H, m), 2.52-2.60 (2H, m), 6.54-6.58 (1H, m), 7.18-7.22 (1H, m), 7.42-7.48 (2H, m), 7.86-7.92 (2H, m), 8.20-8.60 (1H, m) |
| 59 | 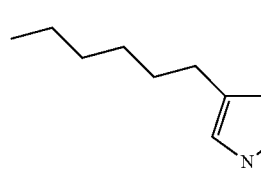 | (CDCl3) 0.88 (3H, t, J = 6.8 Hz), 1.25-1.40 (6H, m), 1.56-1.66 (2H, m), 2.52-2.60 (2H, m), 6.54-6.58 (1H, m), 7.18-7.22 (1H, m), 8.20-8.60 (1H, br) |
| 60 | 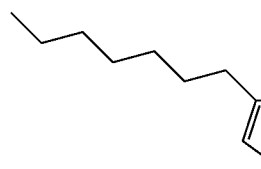 | (CDCl3) 0.88 (3H, t, J = 7.0 Hz), 1.20-1.40 (8H, m), 1.56-1.68 (2H, m), 2.52-2.60 (2H, m), 6.54-6.58 (1H, m), 7.19-7.22 (1H, m), 8.10-8.65 (1H, br) |

TABLE 9-continued

| Ref. No. | Strc. | (Solv) $^1$H-NMR δ ppm: |
|---|---|---|
| 61 | | (CDCl3) 4.53 (2H, s), 4.60 (2H, s), 6.74-6.78 (1H, m), 7.18-7.22 (1H, m), 7.24-7.42 (5H, m), 8.50-8.90 (1H, br) |

TABLE 10

| Ex. No. | Strc. | (Solv) $^1$H-NMR δ ppm: |
|---|---|---|
| 1 | | (CDCl3) 0.96 (3H, t, J = 7.3 Hz), 1.30-1.45 (2H, m), 1.42 (3H, t, J = 7.1 Hz), 1.54-1.64 (2H, m), 2.10 (3H, s), 2.52-2.58 (2H, m), 4.42 (2H, q, J = 7.1 Hz), 7.19 (1H, s), 7.30-7.36 (2H, m), 8.14-8.20 (2H, m) |
| 2 | | (DMSO-d6) 7.38 (3H, t, J = 7.4 Hz), 1.28-1.40 (2H, m), 1.46-1.58 (2H, m), 2.10 (3H, s), 2.40-2.60 (2H, m), 7.52-7.58 (2H, m), 7.76 (1H, s), 8.04-8.08 (2H, m), 13.17 (1H, brs) |
| 3 | | (CDCl3) 1.30-1.55 (3 H, m), 4.30-4.55 (2 H, m), 7.65-7.85 (2 H, m), 8.00-8.30 (3 H, m) |
| 4 | | (CDCl3) 1.43 (3 H, t, J = 7.1 Hz), 4.42 (2 H, q, J = 7.1 Hz), 6.03 (2 H, s), 6.92 (1 H, d, J = 8.0 Hz), 7.13 (1 H, d, J = 1.8 Hz), 7.18 (1 H, dd, J = 8.0, 1.8 Hz), 7.75-7.95 (2 H, m), 8.05-8.30 (3 H, m) |

TABLE 10-continued

| Ex. No. | Strc. | (Solv) ¹H-NMR δ ppm: |
|---|---|---|
| 5 | [structure: 4-(benzo[1,3]dioxol-5-yl)-3-cyano-1-(4-carboxyphenyl)pyrazole] | (DMSO-d6) 6.11 (2 H, s), 7.10 (1 H, d, J = 8.1 Hz), 7.29 (1 H, dd, J = 8.1, 1.8 Hz), 7.33 (1 H, d, J = 1.8 Hz), 7.95-8.25 (4 H, m), 9.25 (1 H, s) |
| 6 | [structure: 3-benzyloxy-4-cyano-1-(4-ethoxycarbonylphenyl)pyrazole] | (CDCl3) 1.41 (3 H, q, J = 6.9 Hz), 4.41 (2 H, q, J = 6.9 Hz), 5.42 (2 H, s), 7.25-7.80 (7 H, m), 8.10-8.25 (3 H, m) |

TABLE 11

| Ex. No. | Strc. | (Solv) ¹H-NMR δ ppm: |
|---|---|---|
| 7 | [structure: 3-benzyloxy-4-cyano-1-(4-carboxyphenyl)pyrazole] | (DMSO-d6) 5.43 (2 H, s), 7.25-7.65 (5 H, m), 7.80-8.25 (4 H, m), 9.31 (1 H, s), 13.15 (1 H, brs.) |
| 8 | [structure: 3-(benzothiophen-3-yl)-4-cyano-1-(4-carboxyphenyl)pyrazole] | (DMSO-d6) 7.35-7.70 (2 H, m), 8.00-8.30 (5 H, m), 8.45 (1 H, s), 8.55-8.70 (1 H, m), 9.65 (1 H, s), 13.23 (1 H, brs.) |
| 9 | [structure: pyrrole with 2-benzyloxyphenyl, cyano, and ethyl ester/methoxymethoxy phenyl substituents] | (DMSO-d6) 1.30 (3H, t, J = 7.1 Hz), 3.44 (3H, s), 4.29 (2H, q, J = 7.1 Hz), 5.17 (2H, s), 5.41 (2H, s), 6.95-7.05 (1H, m), 7.30-7.60 (10H, m), 7.81 (1H, d, J = 8.4 Hz), 8.11 (1H, d, J = 2.5 Hz), 8.51 (1H, d, J = 2.5 Hz) |

TABLE 11-continued

| Ex. No. | Strc. | (Solv) $^1$H-NMR δ ppm: |
|---|---|---|
| 10 | | (DMSO-d6) 1.31 (3H, t, J = 7.1 Hz), 3.44 (3H, s), 4.29 (2H, q, J = 7.1 Hz), 5.42 (2H, s), 6.70-8.55 (9H, m), 9.62 (1H, brs) |
| 12 | | (DMSO-d6) 6.74 (1H, d, J = 7.4 Hz), 7.14 (2H, d, J = 7.9 Hz), 7.23 (1H, t, J = 7.9 Hz), 7.34 (1H, d, J = 7.4 Hz), 7.42 (1H, s), 7.98 (1H, d, J = 7.9 Hz), 8.04 (1H, d, J = 2.6 Hz), 8.49 (1H, d, J = 2.6 Hz), 9.58 (1H, brs) |
| 13 | | (DMSO-d6) 1.31 (3H, t, J = 7.1 Hz), 3.25-3.40 (3H, m), 3.44 (3H, s), 3.65-3.75 (2H, m), 4.10-4.20 (2H, m), 5.41 (2H, s), 6.90-8.55 (9H, m) |

TABLE 12

| Ex. No. | Strc. | (Solv) $^1$H-NMR δ ppm: |
|---|---|---|
| 15 | | (DMSO-d6) 3.69-3.71 (2H, m), 4.15-4.17 (2H, m), 6.92-6.94 (1H, m), 7.33-7.40 (4H, m), 7.43-7.44 (1H, d, J = 2.1 Hz), 7.91 (1H, d, J = 8.8 Hz), 8.16 (1H, d, J = 2.5 Hz), 8.51 (1H, d, J = 2.8 Hz) |

TABLE 12-continued
| Ex. No. | Strc. | (Solv) $^1$H-NMR δ ppm: |
|---|---|---|
| 16 | 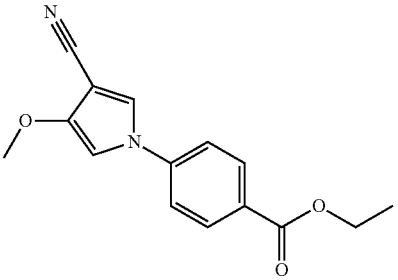 [SMILES: CCOC(=O)c1ccc(-n2cc(C#N)c(OC)c2)cc1] | (CDCl3) 1.42 (3 H, t, J = 7.2 Hz), 3.86 (3 H, s), 4.41 (2 H, q, J = 7.2 Hz), 6.50-6.75 (1 H, m), 7.25-7.55 (3 H, m), 8.00-8.30 (2 H, m) |
| 17 | 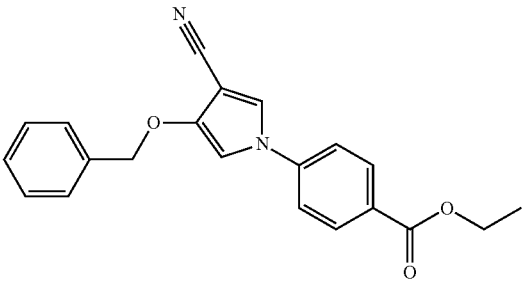 [SMILES: CCOC(=O)c1ccc(-n2cc(C#N)c(OCc3ccccc3)c2)cc1] | (CDCl3) 1.41 (3 H, t, J = 7.2 Hz), 4.40 (2 H, q, J = 7.2 Hz), 5.07 (2 H, s), 6.50-6.70 (1 H, m), 7.25-7.55 (8 H, m), 8.00-8.25 (2 H, m) |
| 18 | 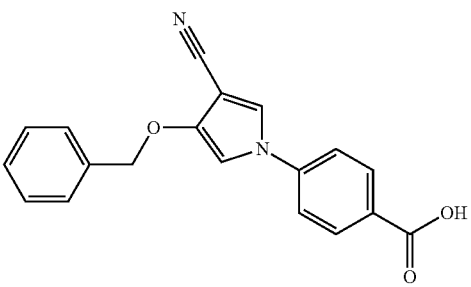 [SMILES: N#Cc1cn(-c2ccc(C(=O)O)cc2)cc1OCc1ccccc1] | (DMSO-d6) 5.08 (2 H, s), 7.30-7.55 (6 H, m), 7.77 (2 H, d, J = 8.7 Hz), 8.04 (2 H, d, J = 8.7 Hz), 8.15-8.30 (1 H, m), 13.11 (1 H, brs.) MS m/z: 317 (M − H)− |
| 19 | 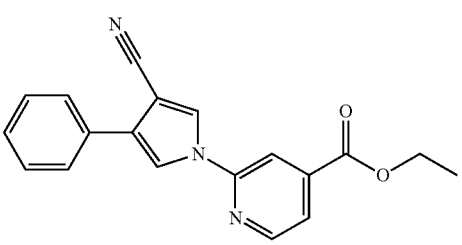 [SMILES: CCOC(=O)c1cccc(-n2cc(C#N)c(-c3ccccc3)c2)c1] | (DMSO-d6) 1.39 (3H, t, J = 7.1 Hz), 4.43 (2H, q, J = 7.1 Hz), 7.30-7.60 (3H, m), 7.70-7.95 (3H, m), 8.40-8.45 (2H, m), 8.70-8.80 (2H, m), 14.03 (1H, brs.) |
| 20 | 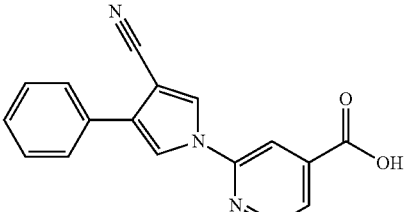 | (DMSO-d6) 7.30-7.40 (1H, m), 7.45-7.55 (2H, m), 7.70-7.90 (3H, m), 8.30-8.40 (2H, m), 8.65-8.80 (2H, m) |

TABLE 13

| Ex. No. | Strc. | (Solv) ¹H-NMR δ ppm: |
|---|---|---|
| 21 | | (DMSO-d6) 1.33 (3H, t, J = 7.1 Hz), 3.43 (3H, s), 4.32 (2H, q, J = 7.1 Hz), 5.32 (2H, s), 7.30-7.55 (4H, m), 7.70-7.80 (2H, m), 7.85-8.00 (3H, m), 8.35 (1H, d, J = 2.4 Hz) |
| 22 | | (DMSO-d6) 7.13 (1H, d, J = 8.9 Hz), 7.25-7.55 (3H, m), 7.65-7.80 (2H, m), 7.87 (1H, dd, J = 8.9 Hz, 2.9 Hz), 7.92 (1H, d, J = 2.5 Hz), 8.04 (1H, d, J = 2.9 Hz), 8.30 (1H, d, J = 2.5 Hz) |
| 23 | | (DMSO-d6) 1.35 (3H, t, J = 7.1 Hz), 4.37 (2H, J = 7.1 Hz), 7.30-7.80 (6H, m), 7.90-8.55 (5H, m) |
| 24 | | (DMSO-d6) 7.30-8.55 (11H, m), 13.34 (1H, brs.) |
| 25 | | (DMSO-d6) 1.31 (3H, t, J = 7.1 Hz), 4.31 (2H, q, J = 7.1 Hz), 6.13 (2H, s), 7.80-8.10 (4H, m), 9.09 (1H, s) |
| 26 | | (DMSO-d6) 1.34 (3H, t, J = 7.1 Hz), 2.10 (3H, s), 4.33 (2H, q, J = 7.1 Hz), 7.90-8.00 (2H, m), 8.10-8.15 (2H, m), 9.40 (1H, s), 10.88 (1H, brs) |

TABLE 13-continued

| Ex. No. | Strc. | (Solv) ¹H-NMR δ ppm: |
|---|---|---|
| 27 | | (DMSO-d6) 2.10 (3H, s), 7.92 (2H, d, J = 8.9 Hz), 8.08 (2H, d, J = 8.9 Hz), 9.37 (1H, s), 10.8 (1H, s-br), 13.1 (1H, s-br) |

TABLE 14

| Ex. No. | Strc. | (Solv) ¹H-NMR δ ppm: |
|---|---|---|
| 28 | | (CDCl3) 6.39 (1H, d, J = 3.8 Hz), 7.35 (1H, d, J = 3.8 Hz), 7.35-7.40 (1H, m), 7.41 (1H, d, J = 2.5 Hz), 7.43-7.49 (2H, m), 7.65-7.70 (2H, m), 7.76 (1H, d, J = 2.5 Hz), 9.60 (1H, s) |
| 29 | | (DMSO-d6) 6.66 (1H, d, J = 3.4 Hz), 7.23 (1H, br), 7.34-4.39 (1H, m), 7.45-7.50 (2H, m), 7.69-7.73 (2H, m), 7.86 (1H, d, J = 2.3 Hz), 8.28 (1H, d, J = 2.3 Hz) |
| 30 | | (CDCl3) 1.43 (3 H, t, J = 7.1 Hz), 3.51 (3 H, s), 4.42 (2 H, q, J = 7.1 Hz), 5.27 (2 H, s), 7.05-7.75 (8 H, m), 8.10-8.30 (2 H, m), |
| 31 | | (CDCl3) 1.43 (3 H, t, J = 7.2 Hz), 3.52 (3 H, s), 4.42 (2 H, q, J = 7.2 Hz), 5.24 (2 H, s), 6.95-7.15 (1 H, m), 7.25-7.75 (7 H, m), 8.10-8.30 (2 H, m) |

TABLE 14-continued

| Ex. No. | Strc. | (Solv) $^1$H-NMR δ ppm: |
|---|---|---|
| 32 | | (CDCl3) 1.43 (3 H, t, J = 7.0 Hz), 3.51 (3 H, s), 4.42 (2 H, q, J = 7.0 Hz), 5.22 (2 H, s), 7.05-7.30 (3 H, m), 7.40-7.75 (5 H, m), 8.10-8.30 (2 H, m m) |
| 33 | | (DMSO-d6) 1.34 (3 H, t, J = 7.2 Hz), 4.34 (2 H, q, J = 7.2 Hz), 6.80-7.25 (3 H, m), 7.40-7.55 (1 H, m), 7.84 (1 H, d, J = 2.5 Hz), 7.88 (2 H, d, J = 8.8 Hz), 8.09 (2 H, d, J = 8.8 Hz), 8.46 (1 H, d, J = 2.5 Hz), 9.85 (1 H, s) |
| 34 | | (DMSO-d6) 1.35 (3 H, t, J = 7.0 Hz), 4.35 (2 H, q, J = 7.0 Hz), 6.65-6.85 (1 H, m), 7.05-7.35 (3 H, m), 7.85-8.15 (5 H, m), 8.40-8.60 (1 H, m), 9.60 (1 H, s) |

TABLE 15

| Ex. No. | Strc. | (Solv) $^1$H-NMR δ ppm: |
|---|---|---|
| 35 | | (DMSO-d6) 1.34 (3 H, t, J = 7.0 Hz), 4.34 (2 H, q, J = 7.0 Hz), 6.86 (2 H, d, J = 8.5 Hz), 7.54 (2 H, d, J = 8.5 Hz), 7.85-8.15 (5 H, m), 8.40-8.55 (1 H, m), 9.55-9.70 (1 H, m) |
| 36 | | (CDCl3) 1.42 (3 H, t, J = 7.2 Hz), 2.02 (3 H, s), 2.10-2.30 (2 H, m), 4.16 (2 H, t, J = 6.3 Hz), 4.25 (2 H, t, J = 6.5 Hz), 4.42 (2 H, q, J = 7.2 Hz), 6.90-7.15 (2 H, m), 7.27-7.70 (6 H, m), 8.10-8.30 (2 H, m) |

TABLE 15-continued

| Ex. No. | Strc. | (Solv) $^1$H-NMR δ ppm: |
|---|---|---|
| 37 | | (CDCl3) 1.43 (3 H, t, J = 7.2 Hz), 2.06 (3 H, s), 2.10-2.20 (2 H, m), 4.13 (2 H, t, J = 6.1 Hz), 4.29 (2 H, t, J = 6.3 Hz), 4.42 (2 H, q, J = 7.2 Hz), 6.80-7.00 (1 H, m), 7.27-7.40 (4 H, m), 7.45-7.55 (2 H, m), 7.60-7.70 |
| 38 | | (DMSO-d6) 1.35 (3 H, t, J = 7.2 Hz), 1.95-2.15 (5 H, m), 4.00-4.25 (4 H, m), 4.35 (2 H, q, J = 7.2 Hz), 6.95-7.15 (2 H, m), 7.50-8.20 (7 H, m), 8.40-8.60 (1 H, m) |
| 39 | | (CDCl3) 1.42 (3 H, t, J = 7.2 Hz), 2.02 (3 H, s), 4.20-4.35 (2 H, m), 4.42 (2 H, q, J = 7.2 Hz), 4.45-4.60 (2 H, m), 6.95-7.15 (2 H, m), 7.25-7.80 (6 H, m), 8.10-8.25 (2 H, m) |
| 40 | | (CDCl3) 1.35-1.55 (3 H, m), 2.12 (3 H, s), 4.20-4.55 (6 H, m), 6.81-7.00 (1 H, m), 7.27-7.40 (4 H, m), 7.45-7.55 (2 H, m), 7.60-7.70 (1 H, m), 8.10-8.30 (2 H, m) |

TABLE 15-continued

| Ex. No. | Strc. | (Solv) $^1$H-NMR δ ppm: |
|---|---|---|
| 41 | | (CDCl3) 1.35-1.50 (3 H, m), 2.12 (3 H, s), 4.15-4.50 (6 H, m), 6.95-7.05 (2 H, m), 7.20-7.30 (1 H, m), 7.40-7.70 (5 H, m), 8.10-8.30 (2 H, m) |

TABLE 16

| Ex. No. | Strc. | (Solv) $^1$H-NMR δ ppm: |
|---|---|---|
| 42 | | (CDCl3) 1.43 (3 H, t, J = 7.1 Hz), 3.84 (3 H, s), 4.42 (2 H, q, J = 7.1 Hz), 4.74 (2 H, s), 6.80-6.95 (1 H, m), 7.05-7.40 (2 H, m), 7.50-8.30 (7 H, m) |
| 43 | | (CDCl3) 1.43 (3 H, t, J = 7.0 Hz), 3.83 (3 H, s), 4.42 (2 H, q, J = 7.0 Hz), 4.71 (2 H, s), 6.80-7.00 (1 H, m), 7.28-7.75 (7 H, m), 8.10-8.30 (2 H, m) |
| 44 | | (CDCl3) 1.43 (3 H, t, J = 7.3 Hz), 3.83 (3 H, s), 4.42 (2H, q, J = 7.3 Hz), 4.68 (2 H, s), 6.90-7.25 (3 H, m), 7.40-7.70 (5 H, m), 8.10-8.25 (2 H, m) |

TABLE 16-continued

| Ex. No. | Strc. | (Solv) ¹H-NMR δ ppm: |
|---|---|---|
| 45 | | (CDCl3) 1.43 (3 H, t, J = 7.1 Hz), 4.42 (2 H, q, J = 7.1 Hz), 5.29 (2 H, s), 6.90-7.75 (11 H, m), 8.05-8.30 (2 H, m) |
| 46 | | (CDCl3) 1.43 (3 H, t, J = 7.2 Hz), 4.42 (2 H, q, J = 7.2 Hz), 5.15 (2 H, s), 6.85-7.05 (1 H, m), 7.15-7.75 (10 H, m), 8.10-8.30 (2 H, m) |
| 47 | | (CDCl3) 1.43 (3 H, t, J = 7.0 Hz), 4.42 (2 H, q, J = 7.0 Hz), 5.31 (2 H, s), 6.95-7.90 (11 H, m), 8.00-8.25 (2 H, m) |

TABLE 17

| Ex. No. | Strc. | (Solv) ¹H-NMR δ ppm: |
|---|---|---|
| 48 | | (CDCl3) 1.42 (3 H, t, J = 7.1 Hz), 4.42 (2 H, q, J = 7.1 Hz), 5.17 (2 H, s), 7.00-7.85 (11 H, m), 8.00-8.25 (2 H, m) |

TABLE 17-continued
| Ex. No. | Strc. | (Solv) $^1$H-NMR δ ppm: |
|---|---|---|
| 49 | 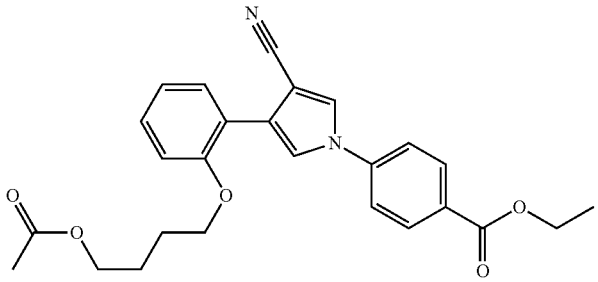 [SMILES: CCOC(=O)c1ccc(-n2cc(C#N)c(-c3ccccc3OCCCCOC(C)=O)c2)cc1] | (CDCl3) 1.43 (3 H, t, J = 7.2 Hz), 1.70-2.10 (7 H, m), 3.95-4.25 (4 H, m), 4.42 (2 H, q, J = 7.2 Hz), 6.90-7.15 (2 H, m), 7.25-7.45 (2 H, m), 7.49 (2 H, d, J = 8.5 Hz), 7.55-7.75 (2 H, m), 8.19 (2 H, d, J = 8.5 Hz) |
| 50 | 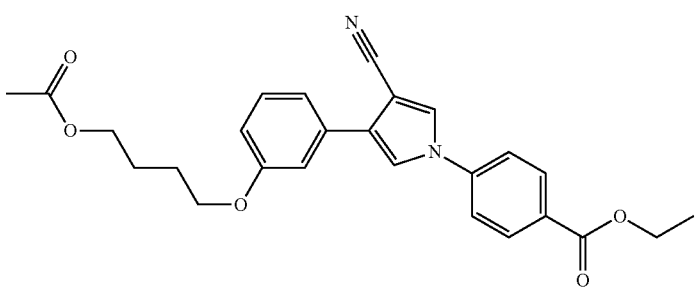 [SMILES: CCOC(=O)c1ccc(-n2cc(C#N)c(-c3cccc(OCCCCOC(C)=O)c3)c2)cc1] | (CDCl3) 1.43 (3 H, t, J = 7.2 Hz), 1.75-2.00 (4 H, m), 2.06 (3 H, s), 4.00-4.25 (4 H, m), 4.42 (2 H, q, J = 7.2 Hz), 6.80-6.95 (1 H, m), 7.15-7.73 (7 H, m), 8.10-8.30 (2 H, m) |
| 51 | 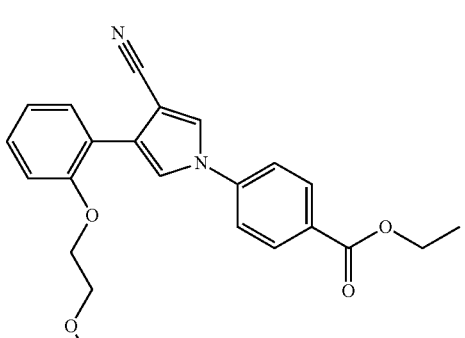 | (CDCl3) 1.35-1.50 (3 H, m), 3.44 (3 H, s), 3.75-3.90 (2 H, m), 4.10-4.60 (4 H, m), 6.95-7.35 (3 H, m), 7.45-7.90 (5 H, m), 8.05-8.30 (2 H, m) |
| 52 | 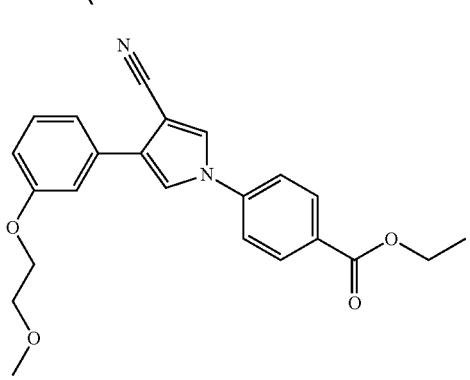 | (CDCl3) 1.43 (3 H, t, J = 7.1 Hz), 3.47 (3 H, s), 3.70-3.90 (2 H, m), 4.10-4.30 (2 H, m), 4.42 (2 H, q, J = 7.1 Hz), 6.85-7.00 (1 H, m), 7.20-7.75 (7 H, m), 8.10-8.30 (2 H, m) |
| 53 | 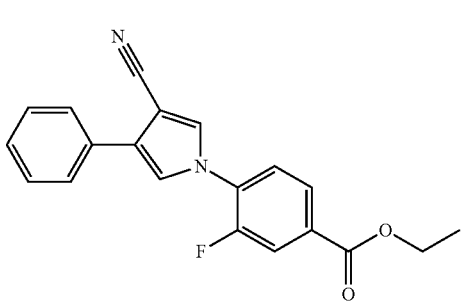 [SMILES: CCOC(=O)c1ccc(-n2cc(C#N)c(-c3ccccc3)c2)c(F)c1] | (CDCl3) 1.30-1.55 (3 H, m), 4.30-4.55 (2 H, m), 7.30-7.75 (8 H, m), 7.85-8.10 (2 H, m) |

TABLE 17-continued
| Ex. No. | Strc. | (Solv) $^1$H-NMR δ ppm: |
|---|---|---|
| 54 | 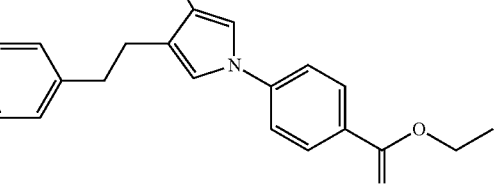 | (CDCl3) 1.43 (3 H, t, J = 7.1 Hz), 4.42 (2 H, q, J = 7.1 Hz), 6.90-7.70 (11 H, m), 8.05-8.30 (2 H, m) |
TABLE 18
| Ex. No. | Strc. | (Solv) $^1$H-NMR δ ppm: |
|---|---|---|
| 55 | 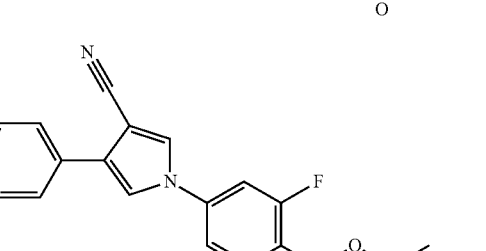 | (CDCl3) 1.41 (3 H, t, J = 7.2 Hz), 2.80-3.10 (4 H, m), 4.40 (2 H, q, J = 7.2 Hz), 6.70-6.90 (1 H, m), 7.15-7.60 (8 H, m), 8.05-8.20 (2 H, m) |
| 56 | 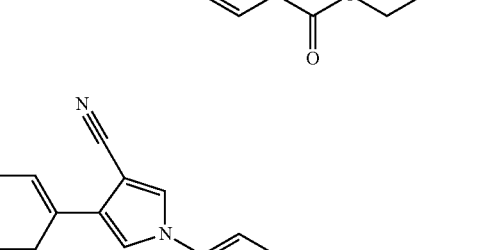 | (CDCl3) 1.43 (3 H, t, J = 7.1 Hz), 4.43 (2 H, q, J = 7.1 Hz), 7.27-7.80 (9 H, m), 8.00-8.20 (1 H, m) |
| 57 | 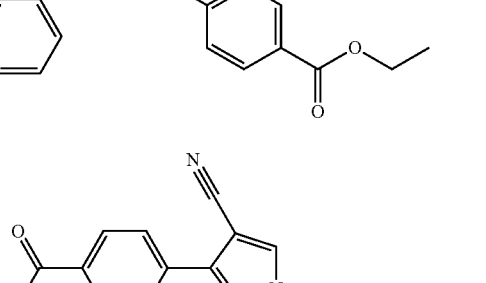 | (CDCl3) 1.43 (3 H, t, J = 7.2 Hz), 4.43 (2 H, q, J = 7.2 Hz), 7.28-8.30 (13 H, m) |
| 58 |  | (CDCl3) 1.43 (3 H, t, J = 7.2 Hz), 3.95 (3 H, s), 4.43 (2 H, q, J = 7.2 Hz), 7.40 (1 H, d, J = 1.9 Hz), 7.51 (2 H, d, J = 8.5 Hz), 7.69 (1 H, d, J = 1.9 Hz), 7.78 (2 H, d, J = 8.2 Hz), 8.11 (2 H, d, J = 8.2 Hz), 8.20 (2 H, d, J = 8.5 Hz) |

TABLE 18-continued

| Ex. No. | Strc. | (Solv) ¹H-NMR δ ppm: |
|---|---|---|
| 59 | | (CDCl3) 1.43 (3 H, t, J = 7.2 Hz), 4.43 (2 H, q, J = 7.2 Hz), 7.30-8.35 (10 H, m) |
| 60 | | (CDCl3) 1.43 (3 H, t, J = 7.2 Hz), 4.43 (2 H, q, J = 7.2 Hz), 7.30-7.90 (8 H, m), 8.10-8.35 (2 H, m) |
| 61 | | (CDCl3) 1.18 (3 H, t, J = 7.0 Hz), 1.42 (3 H, t, J = 7.1 Hz), 3.58 (2 H, q, J = 7.0 Hz), 3.80-3.95 (2 H, m), 4.10-4.35 (2 H, m), 4.42 (2 H, q, J = 7.1 Hz), 6.95-7.35 (3 H, m), 7.45-7.90 (5 H, m), 8.05-8.30 (2 H, m) |

TABLE 19

| Ex. No. | Strc. | (Solv) ¹H-NMR δ ppm: |
|---|---|---|
| 62 | | (CDCl3) 1.25 (3 H, t, J = 7.0 Hz), 1.43 (3 H, t, J = 7.2 Hz), 3.62 (2 H, q, J = 7.0 Hz), 3.70-3.95 (2 H, m), 4.10-4.30 (2 H, m), 4.42 (2 H, q, J = 7.2 Hz), 6.80-7.05 (1 H, m), 7.20-7.45 (4 H, m), 7.49 (2 H, d, J = 8.5 Hz), 7 |

TABLE 19-continued

| Ex. No. | Strc. | (Solv) $^1$H-NMR δ ppm: |
|---|---|---|
| 63 | | (CDCl3) 1.35-1.50 (3 H, m), 4.30-4.55 (2 H, m), 5.41 (2 H, s), 7.25-8.40 (15 H, m) |
| 64 | | (DMSO-d6) 1.35 (3 H, t, J = 7.2 Hz), 4.35 (2 H, q, J = 7.2 Hz), 4.56 (2 H, d, J = 5.7 Hz), 5.25 (1 H, t, J = 5.7 Hz), 7.25-7.75 (4 H, m), 7.85-8.20 (5 H, m), 8.45-8.60 (1 H, m) |
| 65 | | (CDCl3) 1.43 (3 H, t, J = 7.1 Hz), 4.42 (2 H, q, J = 7.1 Hz), 7.40-8.00 (9 H, m), 8.10-8.30 (2 H, m) |
| 66 | | (CDCl3) 1.30-1.55 (3 H, m), 2.90-3.15 (3 H, m), 4.30-4.55 (2 H, m), 6.35 (1 H, brs.), 7.35-7.90 (4 H, m), 8.10-8.30 (2 H, m) |
| 67 | | (CDCl3) 1.42 (3 H, t, J = 7.2 Hz), 2.90-3.40 (6 H, m), 4.42 (2 H, q, J = 7.2 Hz), 7.30-7.65 (4 H, m), 8.10-8.30 (2 H, m) |

TABLE 19-continued
| Ex. No. | Strc. | (Solv) ¹H-NMR δ ppm: |
|---|---|---|
| 68 | 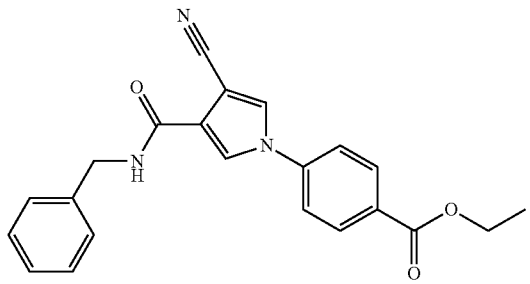 [SMILES: CCOC(=O)c1ccc(-n2cc(C#N)c(C(=O)NCc3ccccc3)c2)cc1] | (CDCl3) 1.42 (3 H, t, J = 7.0 Hz), 4.42 (2 H, q, J = 7.0 Hz), 4.55-4.80 (2 H, m), 6.67 (1 H, brs.), 7.20-7.45 (5 H, m), 7.47 (2 H, d, J = 8.5 Hz), 7.50-7.90 (2 H, m), 8.19 (2 H, d, J = 8.5 Hz) |
TABLE 20
| Ex. No. | Strc. | (Solv) ¹H-NMR δ ppm: |
|---|---|---|
| 69 | 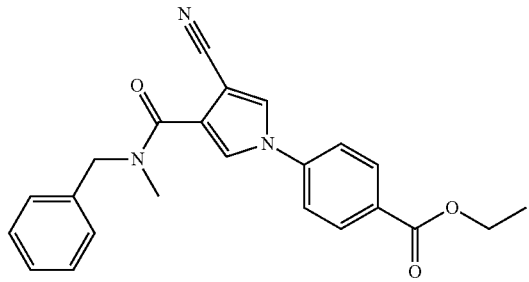 [SMILES: CCOC(=O)c1ccc(-n2cc(C#N)c(C(=O)N(C)Cc3ccccc3)c2)cc1] | (CDCl3) 1.41 (3 H, t, J = 7.3 Hz), 3.08 (3 H, s), 4.41 (2 H, q, J = 7.3 Hz), 4.77 (2 H, s), 7.10-7.65 (9 H, m), 8.05-8.30 (2 H, m) |
| 70 | 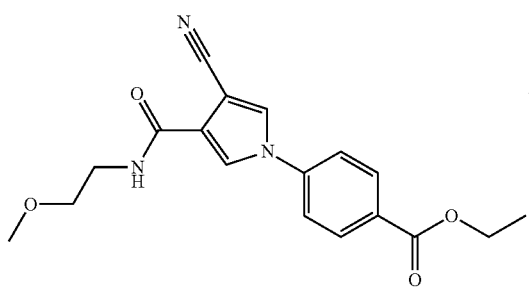 [SMILES: CCOC(=O)c1ccc(-n2cc(C#N)c(C(=O)NCCOC)c2)cc1] | (CDCl3) 1.42 (3 H, t, J = 7.0 Hz), 3.42 (3 H, s) 3.50-3.75 (4 H, m), 4.42 (2 H, q, J = 7.0 Hz), 6.69 (1 H, brs.), 7.35-7.85 (4 H, m), 8.10-8.30 (2 H, m) |
| 71 | 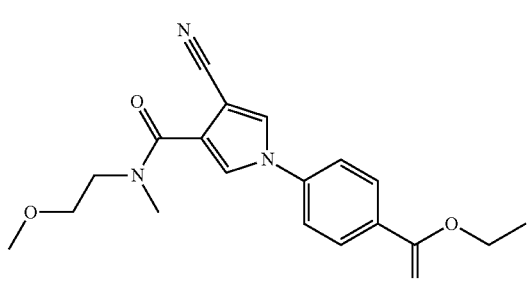 | (CDCl3) 1.42 (3 H, t, J = 7.3 Hz), 2.95-3.85 (10 H, m), 4.42 (2 H, q, J = 7.3 Hz), 7.30-7.65 (4 H, m), 8.05-8.30 (2 H, m) |

TABLE 20-continued

| Ex. No. | Strc. | (Solv) $^1$H-NMR δ ppm: |
|---|---|---|
| 72 | | (CDCl3) 1.42 (3 H, t, J = 7.1 Hz), 1.55-1.80 (6 H, m), 3.50-3.80 (4 H, m), 4.42 (2 H, q, J = 7.1 Hz), 7.30-7.65 (4 H, m), 8.05-8.30 (2 H, m) |
| 73 | | (CDCl3) 1.42 (3 H, t, J = 7.0 Hz), 3.55-3.95 (8 H, m), 4.42 (2 H, q, J = 7.0 Hz), 7.30-7.70 (4 H, m), 8.10-8.30 (2 H, m) |
| 74 | | (CDCl3) 1.04 (6 H, d, J = 6.6 Hz), 1.42 (3 H, t, J = 7.3 Hz), 2.05-2.24 (1 H, m), 3.72 (2 H, d, J = 6.6 Hz), 4.40 (2 H, q, J = 7.3 Hz), 6.50-6.70 (1 H, m), 7.30-7.50 (3 H, m), 8.05-8.25 (2 H, m) |
| 75 | | (CDCl3) 1.42 (3 H, t, J = 7.1 Hz), 3.46 (3 H, s), 3.70-3.85 (2 H, m), 4.05-4.25 (2 H, m), 4.40 (2 H, q, J = 7.1 Hz), 6.55-6.75 (1 H, m), 7.30-7.49 (3 H, m), 8.05-8.25 (2 H, m) |

TABLE 21

| Ex. No. | Strc. | (Solv) ¹H-NMR δ ppm: |
|---|---|---|
| 76 | | (CDCl3) 1.41 (3H, q, J = 7.1 Hz), 3.96 (2H, s), 4.40 (2H, q, J = 7.1 Hz, 6.76-6.80 (1H, m), 7.22-7.28 (1H, m), 7.28-7.40 (6H, m), 7.53 (1H, d, J = 2.6 Hz), 8.10-8.14 (2H, m) |
| 77 | | (CDCl3) 1.41 (3H, q, J = 7.2 Hz), 2.26 (3H, d, J = 2.3 Hz), 4.41 (2H, q, J = 7.2 Hz), 6.90-6.92 (1H, m), 7.38-7.44 (2H, m), 7.50 (1H, d, J = 2.3 Hz), 8.12-8.18 (2H, m) |
| 78 | | (CDCl3) 1.42 (3H, t, J = 7.1 Hz), 2.18 (3H, d, J = 0.77 Hz), 4.42 (2H, q, J = 7.1 Hz), 6.30-6.33 (1H, m), 7.25 (1H, d, J = .2.0 Hz), 7.32-7.38 (2H, m), 8.14-8.20 (2H, m) |
| 79 | | (CDCl3) 1.00 (3H, t, J = 7.3 Hz), 1.42 (3H, t, J = 7.1 Hz), 1.65-1.75 (2H, m), 2.55-2.65 (2H, m), 4.41 (2H, q, J = 7.1 Hz), 6.88-6.92 (1H, m), 7.38-7.44 (2H, m), 7.51 (1H, d, J = 2.4 Hz), 8.12-8.18 (2H, m) |

TABLE 21-continued

| Ex. No. | Strc. | (Solv) $^1$H-NMR δ ppm: |
|---|---|---|
| 80 | | (CDCl3) 0.98 (3H, t, J = 7.5 Hz), 1.42 (3H, t, J = 7.2 Hz), 1.58-1.70 (2H, m), 2.10 (3H, s), 2.50-2.56 (2H, m), 4.42 (2H, q, J = 7.2 Hz), 7.19 (1H, s), 7.32-7.36 (2H, m), 8.14-8.18 (2H, m) |
| 81 | | (CDCl3) 0.96 (3H, t, J = 7.3 Hz), 1.36-1.46 (5H, m), 1.60-1.74 (2H, m), 2.58-2.64 (2H, m), 4.41 (2H, q, J = 7.2 Hz), 6.88-6.92 (1H, m), 7.38-7.44 (2H, m), 7.51 (1H, d, J = 2.6 Hz), 8.12-8.18 (2H, m) |

TABLE 22

| Ex. No. | Strc. | (Solv) $^1$H-NMR δ ppm: |
|---|---|---|
| 82 | | (CDCl3) 0.97 (6H, d, J = 6.8 Hz), 1.42 (3H, t, J = 7.2 Hz), 1.90-2.02 (1H, m), 2.49 (2H, d, J = 6.8 Hz), 4.41 (2H, q, J = 7.2 Hz), 6.89 (1H, d, J = 2.5 Hz), 7.40-7.44 (2H, m), 7.52 (1H, d, J = 2.5 Hz), 8.12-8.18 (2H, m) |
| 83 | | (CDCl3) 0.96 (6H, d, J = 6.9 Hz), 1.44 (3H, t, J = 7.1 Hz), 1.88-2.00 (1H, m), 2.42 (2H, d, J = 7.3 Hz), 4.42 (2H, q, J = 7.1 Hz), 7.20 (1H, s), 7.32-7.36 (2H, m), 8.14-8.18 (2H, m) |

TABLE 22-continued

| Ex. No. | Strc. | (Solv) $^1$H-NMR δ ppm: |
|---|---|---|
| 84 | | (CDCl3) 1.42 (3H, t, J = 7.1 Hz), 2.10 (3H, s), 2.17 (3H, s), 4.42 (2H, q, J = 7.1 Hz), 7.19 (1H, s), 7.30-7.36 (2H, m), 8.14-8.18 (2H, m) |
| 85 | | (CDCl3) 1.42 (3H, t, J = 7.2 Hz), 4.42 (2H, q, J = 7.2 Hz), 6.49 (1H, dd, J = 2.0, 3.6 Hz), 6.84-6.87 (1H, m), 7.40 (1H, d, J = 2.4 Hz), 7.42-7.44 (1H, m), 7.46-7.52 (2H, m), 7.59 (1H, d, J = 2.4 Hz), 8.16-8.20 (2H, m) |
| 86 | | (CDCl3) 0.88-0.94 (3H, m), 1.34-1.40 (4H, m), 1.42 (3H, t, J = 7.1 Hz), 1.62-1.72 (2H, m), 2.58-2.64 (2H, m), 4.41 (2H, q, J = 7.1 Hz), 6.88-6.92 (1H, m), 7.38-7.44 (2H, m), 7.50 (1H, d, J = 2.5 Hz), 8.12-8.16 (2H, m) |
| 87 | | (CDCl3) 0.86-0.94 (3H, m), 1.28-1.44 (9H, m), 1.62-1.72 (2H, m), 2.58-2.64 (2H, m), 4.40 (2H, q, J = 7.2 Hz), 6.88-6.91 (1H, m), 7.39-7.44 (2H, m), 7.50 (1H, d, J = 2.6 Hz), 8.12-8.16 (2H, m) |
| 88 | | (CDCl3) 0.89 (3H, t, J = 6.9 Hz), 1.24-1.48 (11H, m), 1.62-1.72 (2H, m), 2.56-2.66 (2H, m), 4.40 (2H, q, J = 6.9 Hz), 6.88-6.94 (1H, m), 7.38-7.46 (2H, m), 7.48-7.54 (1H, m), 8.12-8.18 (2H, m) |

TABLE 23

| Ex. No. | Str. | (Solv) $^1$H-NMR δ ppm: |
|---|---|---|
| 89 | | (CDCl3) 1.41 (3H, t, J = 7.1 Hz), 4.41 (2H, q, J = 7.1 Hz), 4.57 (2H, s), 4.65 (2H, s), 7.14 (1H, d, J = 2.6 Hz), 7.28-7.33 (1H, m), 7.34-7.39 (2H, m), 7.39-7.44 (4H, m), 7.55 (1H, d, J = 2.6 Hz), 8.12-8.18 (2H, m) |
| 90 | | (DMSO-d6) 1.30-1.40 (6H, m), 4.03 (2H, q, J = 7.1 Hz), 4.32 (2H, q, J = 7.1 Hz), 7.37 (1H, d, J = 2.7 Hz), 7.75-7.85 (2H, m), 8.00-8.10 (2H, m), 8.23 (1H, d, J = 2.7 Hz) |
| 91 | | (DMSO-d6) 1.32 (3H, t, J = 7.1 Hz), 2.80-2.90 (2H, m), 2.90-3.05 (2H, m), 4.33 (2H, q, J = 7.1 Hz), 6.10-6.20 (1H, m), 6.30-6.40 (1H, m), 7.50-7.60 (2H, m), 8.00-8.10 (2H, m), 8.33 (1H, d, J = 2.4 Hz) |
| 92 | | (DMSO-d6) 1.32 (3H, t, J = 7.1 Hz), 1.40-2.70 (8H, m), 3.55-3.65 (1H, m), 3.70-3.80 (2H, m), 4.32 (2H, q, J = 7.1 Hz), 7.54 (1H, d, J = 2.3 Hz), 7.75-7.85 (2H, m), 8.00-8.10 (2H, m), 8.32 (1H, d, J = 2.3 Hz) |
| 93 | | (DMSO-d6) 1.35 (3H, t, J = 7.1 Hz), 4.34 (2H, q, J = 7.1 Hz), 7.50-7.70 (3H, m), 7.95-8.20 (6H, m), 9.47 (1H, brs), 11.32 (1H, brs) |

TABLE 23-continued

| Ex. No. | Strc. | (Solv) $^1$H-NMR δ ppm: |
|---|---|---|
| 94 | | (DMSO-d6) 1.34 (3H, t, J = 7.1 Hz), 3.73 (2H, s), 4.33 (2H, q, J = 7.1 Hz), 7.20-7.40 (5H, m), 7.90-8.00 (2H, m), 8.05-8.15 (2H, m), 9.39 (1H, s), 11.11 (1H, brs) |

TABLE 24

| Ex. No. | Strc. | (Solv) $^1$H-NMR δ ppm: |
|---|---|---|
| 95 | | (CDCl3) 3.56 (3 H, s), 3.93 (3 H, s), 5.34 (2 H, s), 6.95-7.75 (8 H, m), 7.85-8.05 (1 H, m) |
| 96 | | (CDCl3) 1.30-1.50 (3 H, m), 3.55 (3 H, s), 3.86 (3 H, s), 3.89 (3 H, s), 4.25-4.50 (2 H, m), 5.31 (2 H, s), 6.45-6.70 (2 H, m), 7.00-7.70 (5 H, m), 7.80-8.05 (1 H, m) |
| 97 | | (CDCl3) 1.40 (3 H, t, J = 7.2 Hz), 3.56 (3 H, s), 4.39 (2 H, q, J = 7.2 Hz), 5.32 (2 H, s), 6.85-7.45 (5 H, m), 7.55-8.05 (3 H, m) |

TABLE 24-continued

| Ex. No. | Strc. | (Solv) $^1$H-NMR δ ppm: |
|---|---|---|
| 98 | | (CDCl3) 1.40 (3 H, t, J = 7.1 Hz), 3.56 (3 H, s), 3.93 (3 H, s), 4.39 (2 H, q, J = 7.1 Hz), 5.33 (2 H, s), 6.95-7.70 (7 H, m), 7.80-8.05 (1 H, m) |
| 99 | | (CDCl3) 1.40 (3 H, t, J = 7.0 Hz), 2.31 (3 H, s), 3.56 (3 H, s), 4.39 (2 H, q, J = 7.0 Hz), 5.33 (2 H, s), 7.00-7.45 (6 H, m), 7.55-7.70 (1 H, m), 7.80-8.05 (1 H, m) |
| 100 | | (CDCl3) 1.41 (3 H, t, J = 7.1 Hz), 3.56 (3 H, s), 4.39 (2 H, q, J = 7.1 Hz), 5.33 (2 H, s), 7.00-7.75 (7 H, m), 7.85-8.05 (1 H, m) |
| 101 | | (CDCl3) 1.41 (3 H, t, J = 7.2 Hz), 3.56 (3 H, s), 4.39 (2 H, q, J = 7.2 Hz), 5.33 (2 H, s), 6.70-6.90 (1 H, m), 7.00-7.35 (5 H, m), 7.55-7.70 (1 H, m), 7.85-8.05 (1 H, m) |

TABLE 25

| Ex. No. | Strc. | (Solv) $^1$H-NMR δ ppm: |
|---|---|---|
| 102 | | (CDCl3) 1.40 (3 H, t, J = 7.1 Hz), 2.20 (6 H, s), 3.56 (3 H, s), 4.39 (2 H, q, J = 7.1 Hz), 5.32 (2 H, s), 6.90-7.35 (6 H, m), 7.60-7.75 (1 H, m), 7.85-8.05 (1 H, m) |

TABLE 25-continued

| Ex. No. | Strc. | (Solv) $^1$H-NMR δ ppm: |
|---|---|---|
| 103 | | (CDCl3) 1.40 (3 H, t, J = 7.1 Hz), 2.25-2.45 (6 H, m), 3.55 (3 H, s), 4.39 (2 H, q, J = 7.1 Hz), 5.31 (2 H, s), 6.90-7.40 (6 H, m), 7.55-7.70 (1 H, m), 7.85-8.05 (1 H, m) |
| 104 | | (CDCl3) 1.40 (3 H, t, J = 7.1 Hz), 3.55 (3 H, s), 4.39 (2 H, q, J = 7.1 Hz), 5.32 (2 H, s), 6.90-7.45 (6 H, m), 7.60-7.75 (1 H, m), 7.85-8.05 (1 H, m) |
| 105 | | (CDCl3) 1.40 (3 H, t, J = 7.0 Hz), 2.20-2.45 (3 H, m), 3.56 (3 H, s), 4.39 (2 H, q, J = 7.0 Hz), 5.32 (2 H, s), 6.95-7.35 (6 H, m), 7.55-7.74 (1 H, m), 7.85-8.05 (1 H, m) |
| 106 | | (CDCl3) 1.40 (3 H, t, J = 7.1 Hz), 2.38 (3 H, s), 3.55 (3 H, s), 3.84 (3 H, s), 4.39 (2 H, q, J = 7.1 Hz), 5.32 (2 H, s), 6.70-7.35 (6 H, m), 7.55-7.70 (1 H, m), 7.85-8.05 (1 H, m) |
| 107 | | (CDCl3) 1.41 (3 H, t, J = 7.2 Hz), 3.56 (3 H, s), 4.39 (2 H, q, J = 7.2 Hz), 5.32 (2 H, s), 6.90-7.75 (7 H, m), 7.85-8.05 (1 H, m) |

TABLE 25-continued

| Ex. No. | Strc. | (Solv) $^1$H-NMR δ ppm: |
|---|---|---|
| 108 | | (CDCl3) 1.41 (3 H, t, J = 7.3 Hz), 3.56 (3 H, s), 4.39 (2 H, q, J = 7.3 Hz), 5.33 (2 H, s), 7.00-7.75 (8 H, m), 7.85-8.05 (1 H, m) |

TABLE 26

| Ex. No. | Strc. | (Solv) $^1$H-NMR δ ppm: |
|---|---|---|
| 109 | | (CDCl3) 1.40 (3 H, t, J = 7.1 Hz), 3.56 (3 H, s), 3.88 (3 H, s), 4.39 (2 H, q, J = 7.1 Hz), 5.33 (2 H, s), 6.80-7.45 (7 H, m), 7.55-7.70 (1 H, m), 7.85-8.05 (1 H, m) |
| 110 | | (CDCl3) 1.41 (3 H, t, J = 7.1 Hz), 2.42 (3 H, s), 3.56 (3 H, s), 4.39 (2 H, q, J = 7.1 Hz), 5.33 (2 H, s), 7.00-7.70 (8 H, m), 7.85-8.00 (1 H, m) |
| 111 | | (CDCl3) 1.41 (3 H, t, J = 7.0 Hz), 3.57 (3 H, s), 4.40 (2 H, q, J = 7.0 Hz), 5.34 (2 H, s), 7.00-7.40 (3 H, m), 7.50-8.05 (6 H, m) |

TABLE 26-continued

| Ex. No. | Strc. | (Solv) ¹H-NMR δ ppm: |
|---|---|---|
| 112 | | (CDCl3) 1.40 (3 H, t, J = 7.3 Hz), 3.55 (3 H, s), 3.86 (3 H, s), 4.38 (2 H, q, J = 7.3 Hz), 5.31 (2 H, s), 6.45-6.65 (1 H, m), 6.90-7.45 (3 H, m), 7.80-8.00 (1 H, m) |
| 113 | | (CDCl3) 1.40 (3 H, t, J = 7.2 Hz), 3.56 (3 H, s), 3.85 (3 H, s), 4.39 (2 H, q, J = 7.2 Hz), 5.32 (2 H, s), 6.65-7.40 (5 H, m), 7.55-8.05 (3 H, m) |
| 114 | | (CDCl3) 1.40 (3 H, t, J = 7.2 Hz), 3.56 (3 H, s), 3.86 (3 H, s), 4.39 (2 H, q, J = 7.2 Hz), 5.32 (2 H, s), 6.70-7.75 (7 H, m), 7.85-8.05 (1 H, m) |
| 115 | | (CDCl3) 1.41 (3 H, t, J = 7.1 Hz), 3.56 (3 H, s), 3.93 (3 H, s), 3.97 (3 H, s), 4.39 (2 H, q, J = 7.1 Hz), 5.33 (2 H, s), 6.85-7.35 (6 H, m), 7.50-7.70 (1 H, m), 7.85-8.05 (1 H, m) |

TABLE 27

| Ex. No. | Strc. | (Solv) ¹H-NMR δ ppm: |
|---|---|---|
| 116 | | (CDCl3) 1.41 (3 H, t, J = 7.3 Hz), 3.55 (3 H, s), 4.00 (3 H, s), 4.39 (2 H, q, J = 7.3 Hz), 5.32 (2 H, s), 7.05-7.55 (6 H, m), 7.65-8.05 (5 H, m) |

TABLE 27-continued

| Ex. No. | Strc. | (Solv) $^1$H-NMR δ ppm: |
|---|---|---|
| 117 | | (CDCl3) 1.39 (3 H, t, J = 7.2 Hz), 2.80-3.10 (4 H, m), 3.55 (3 H, s), 4.37 (2 H, q, J = 7.2 Hz), 5.30 (2 H, s), 6.65-7.60 (9 H, m), 7.80-8.00 (1H, m) |
| 118 | | (CDCl3) 1.40 (3 H, t, J = 7.0 Hz), 3.56 (3 H, s), 4.39 (2 H, q, J = 7.0 Hz), 5.32 (2 H, s), 6.90-7.65 (11 H, m), 7.80-8.05 (1 H, m) |
| 119 | | (CDCl3) 1.41 (3 H, t, J = 7.2 Hz), 3.57 (3 H, s), 4.40 (2 H, q, J = 7.2 Hz), 5.34 (2 H, s), 7.00-7.45 (5 H, m), 7.55-8.05 (5 H, m) |
| 120 | | (CDCl3) 1.41 (3 H, t, J = 7.3 Hz), 3.57 (3 H, s), 4.40 (2 H, q, J = 7.3 Hz), 5.35 (2 H, s), 7.05-7.75 (9 H, m), 7.85-8.05 (1 H, m) |
| 121 | | (CDCl3) 1.41 (3 H, t, J = 7.2 Hz), 3.56 (3 H, s), 4.40 (2 H, q, J = 7.2 Hz), 5.33 (2 H, s), 7.05-8.10 (10 H, m) |

TABLE 27-continued

| Ex. No. | Strc. | (Solv) ¹H-NMR δ ppm: |
|---|---|---|
| 122 | | (CDCl3) 1.41 (3 H, t, J = 7.2 Hz), 3.57 (3 H, s), 3.87 (3 H, s), 4.39 (2 H, q, J = 7.2 Hz), 5.34 (2 H, s), 7.05-7.45 (6 H, m), 7.55-8.05 (4 H, m) |

TABLE 28

| Ex. No. | Strc. | (Solv) ¹H-NMR δ ppm: |
|---|---|---|
| 123 | | (CDCl3) 1.40 (3 H, t, J = 7.2 Hz), 3.56 (3 H, s), 3.90 (3 H, s), 4.39 (2 H, q, J = 7.2 Hz), 5.32 (2 H, s), 6.80-7.35 (7 H, m), 7.45-7.65 (3 H, m), 7.80-8.06 (1 H, m) |
| 124 | | (CDCl3) 1.39 (3 H, t, J = 7.0 Hz), 2.75-3.10 (4 H, m), 3.55 (3 H, s), 3.85 (3 H, s), 4.37 (2 H, q, J = 7.0 Hz), 5.30 (2 H, s), 6.70-7.30 (7 H, m), 7.40-7.55 (1 H, m), 7.80-8.00 (1 H, m) |
| 125 | | (CDCl3) 1.40 (3 H, t, J = 7.3 Hz), 3.56 (3 H, s), 3.84 (3 H, s), 4.39 (2 H, q, J = 7.3 Hz), 5.32 (2 H, s), 6.75-7.65 (10 H, m), 7.80-8.05 (1 H, m) |

TABLE 28-continued

| Ex. No. | Strc. | (Solv) $^1$H-NMR δ ppm: |
|---|---|---|
| 126 | | (CDCl3) 1.39 (3 H, t, J = 7.2 Hz), 2.75-3.05 (4 H, m), 3.55 (3 H, s), 3.79 (3 H, s), 4.37 (2 H, q, J = 7.2 Hz), 5.30 (2 H, s), 6.65-7.25 (7 H, m), 7.40-7.55 (1 H, m), 7.80-8.00 (1 H, m) |
| 127 | | (CDCl3) 1.25-1.50 (6 H, m), 3.55 (3 H, s), 4.20-4.55 (4 H, m), 5.32 (2 H, s), 7.08 (1 H, dd, J = 8.2, 2.2 Hz), 7.25 (1 H, d, J = 2.2 Hz), 7.35-7.50 (1 H, m), 7.70-7.80 (1 H, m), 7.92 (1 H, d, J = 8.2 Hz) |
| 128 | | (CDCl3) 1.30-1.55 (6 H, m), 3.55 (3 H, s), 4.25-4.55 (4 H, m), 5.31 (2 H, s), 6.95-7.35 (2 H, m), 7.45-8.05 (3 H, m) |
| 129 | | (CDCl3) 1.40 (3 H, t, J = 7.1 Hz), 3.55 (3 H, s), 4.39 (2 H, q, J = 7.1 Hz), 5.32 (2 H, s), 6.95-7.70 (4 H, m), 7.85-8.05 (1 H, m) |

TABLE 29

| Ex. No. | Strc. | (Solv) $^1$H-NMR δ ppm: |
|---|---|---|
| 130 | | (DMSO-d6) 1.30 (3H, t, J = 7.1 Hz), 3.44 (3H, s), 4.29 (2H, q, J = 7.1 Hz), 5.41 (2H, s), 6.08 (2H, s), 7.00-7.60 (5H, m), 7.75-8.55 (3H, m), |

TABLE 29-continued

| Ex. No. | Strc. | (Solv) $^1$H-NMR δ ppm: |
|---|---|---|
| 131 | | (DMSO-d6) 1.30 (3H, t, J = 7.1 Hz), 3.44 (3H, s), 4.29 (2H, q, J = 7.1 Hz), 5.40 (2H, s), 6.12 (2H, s), 6.90-7.00 (2H, m), 7.24 (1H, dd, J = 7.5 Hz, 1.4 Hz), 7.42 (1H, d, J = 8.5 Hz, 2.2 Hz), 7.50 (1H, d, J = 2.0 Hz), 7.81 (1H, d, J = 8.5 Hz), 7.83 (1H, d, J = 2.2 Hz), 7.87 (1H, d, J = 2.2 Hz), 8.16 (1H, d, J = 2.2 Hz) |
| 132 | | (DMSO-d6) 1.32 (3H, t, J = 7.1 Hz), 3.44 (3H, s), 4.29 (2H, q, J = 7.1 Hz), 5.41 (2H, s), 7.45-7.70 (6H, m), 7.82 (1H, d, J = 8.7 Hz), 7.90-8.10 (4H, m), 8.61 (1H, d, J = 2.4 Hz) |
| 133 | | (DMSO-d6) 1.31 (3H, t, J = 7.1 Hz), 3.44 (3H, s), 4.29 (2H, q, J = 7.1 Hz), 5.41 (2H, s), 7.45-7.60 (2H, m), 7.80-8.00 (5H, m), 8.30 (1H, d, J = 2.3 Hz), 8.58 (1H, d, J = 2.3 Hz) |
| 134 | | (DMSO-d6) 1.30 (3H, t, J = 7.1 Hz), 3.45 (3H, s), 3.88 (3H, s), 4.29 (2H, q, J = 7.1 Hz), 5.42 (2H, s), 7.49 (1H, dd, J = 8.9 Hz, 2.0 Hz), 7.55 (1H, d, J = 2.0 Hz), 7.82 (1H, d, J = 8.5 Hz), 7.90 (2H, d, J = 8.1 Hz), 8.05 (2H, d, J = 8.1 Hz), 8.26 (1H, d, J = 2.3 Hz), 8.57 (1H, d, J = 2.3 Hz) |
| 135 | | (DMSO-d6) 1.31 (3H, t, J = 7.1 Hz), 3.44 (3H, s), 4.28 (2H, q, J = 7.1 Hz), 5.40 (2H, s), 6.80-7.90 (8H, m), 8.42 (1H, d, J = 2.2 Hz), 9.86 (1H, brs) |

TABLE 30

| Ex. No. | Strc. | (Solv) ¹H-NMR δ ppm: |
|---|---|---|
| 136 | | (DMSO-d6) 1.31 (3H, t, J = 7.1 Hz), 3.44 (3H, s), 4.29 (2H, q, J = 7.1 Hz), 5.41 (2H, s), 6.80-6.90 (2H, m), 7.40-7.95 (6H, m), 8.44 (1H, d, J = 2.3 Hz), 9.62 (1H, brs) |
| 137 | | (DMSO-d6) 1.31 (3H, t, J = 7.1 Hz), 3.44 (3H, s), 4.28 (2H, q, J = 7.1), 5.40 (2H, s), 6.80-7.85 (7H, m), 8.42 (1H, d, J = 2.4 Hz) |
| 138 | | (CDCl3) 1.40 (3H, t, J = 7.1 Hz), 3.56 (3H, s), 4.39 (2H, q, J = 7.1 Hz), 5.33 (2H, s), 7.00-7.15 (2H, m), 7.20-7.35 (3H, m), 7.45-7.55 (1H, m), 7.59 (1H, d, J = 2.3 Hz), 7.93 (1H, d, J = 8.4 Hz) |
| 139 | | (DMSO-d6) 1.31 (3H, t, J = 7.1 Hz), 3.44 (3H, s), 4.30 (2H, q, J = 7.1 Hz), 5.41 (2H, s), 7.40-7.60 (3H, m), 7.65-7.90 (3H, m), 8.08 (1H, d, J = 2.4 Hz), 8.47 (1H, d, J = 2.4 Hz) |
| 140 | | (CDCl3) 1.39 (3H, t, J = 7.1 Hz), 3.53 (3H, s), 3.95 (2H, s), 4.37 (2H, q, J = 7.1 Hz), 6.74 (1H, m), 6.98 (1H, dd, J = 2.2, 8.4 Hz), 7.16 (1H, d, J = 2.4 Hz), 7.20-7.36 (5H, m), 7.49 (1H, d, J = 2.4 Hz), 7.87 (1H, d, J = 8.4 Hz) |

TABLE 30-continued

| Ex. No. | Strc. | (Solv) $^1$H-NMR δ ppm: |
|---|---|---|
| 141 | | (CDCl3) 1.40 (3H, t, J = 7.2 Hz), 3.55 (3H, s), 4.38 (2H, q, J = 7.2 Hz), 5.31 (2H, s), 6.60-6.63 (1H, m), 7.02-7.10 (2H, m), 7.22-7.24 (1H, m), 7.54-7.57 (1H, m), 7.89-7.93 (1H, m) |
| 142 | | (CDCl3) 1.39 (3H, t, J = 7.1 Hz), 3.54 (3H, s), 4.37 (3H, q, J = 7.10 Hz), 5.30 (2H, m), 6.86-6.90 (1H, m), 7.01 (1H, dd, J = 2.2, 8.4 Hz), 7.19 (1H, d, J = 2.1 Hz), 7.47 (1H, d, J = 2.2 Hz), 7.90 (1H, d, J = 8.4 Hz) |

TABLE 31

| Ex. No. | Strc. | (Solv) $^1$H-NMR δ ppm:/MS (m/z) |
|---|---|---|
| 143 | | (DMSO-d6) 3.39 (3 H, s), 5.24 (2 H, s), 7.05-7.55 (4 H, m), 7.82 (1 H, d, J = 2.4 Hz), 7.86 (2H, d, J = 8.8 Hz), 8.07 (2 H, d, J = 8.8 Hz), 8.45 (1 H, d, J = 2.4 Hz), 13.12 (1 H, brs.)/MS (m/z): 347 (M − H)− |
| 144 | | (DMSO-d6) 3.41 (3 H, s), 5.25 (2 H, s), 6.90-7.10 (1 H, m), 7.35-7.45 (3 H, m), 7.90 (2 H, d, J = 8.5 Hz), 8.08 (2 H, d, J = 8.5 Hz), 8.12 (1 H, d, J = 2.4 Hz), 8.50 (1 H, d, J = 2.4 Hz), 13.13 (1 H, brs.)/MS (m/z): 347 (M − H)− |

TABLE 31-continued

| Ex. No. | Strc. | (Solv) $^1$H-NMR δ ppm:/MS (m/z) |
|---|---|---|
| 145 | | (DMSO-d6) 3.40 (3 H, s), 5.24 (2 H, s), 7.13 (2 H, d, J = 8.2 Hz), 7.66 (2 H, d, J = 8.2 Hz), 7.88 (2 H, d, J = 8.2 Hz), 7.95-8.05 (1 H, m), 8.07 (2 H, d, J = 8.2 Hz), 8.40-8.55 (1 H, m), 13.12 (1 H, brs.)/MS (m/z): 347 (M − H)− |
| 146 | | (DMSO-d6) 6.80-7.05 (2 H, m), 7.10-7.25 (1 H, m), 7.40-7.55 (1 H, m), 7.75-7.95 (3 H, m), 8.07 (2 H, d, J = 8.5 Hz), 8.37-8.50 (1 H, m), 9.82 (1 H, brs.), 13.11 (1 H, brs.)/MS (m/z): 303 (M − H)− |
| 147 | | (DMSO-d6) 6.65-6.85 (1 H, m), 7.10-7.30 (3 H, m), 7.89 (2 H, d, J = 8.7 Hz), 8.03 (1 H, d, J = 2.2 Hz), 8.07 (2 H, d, J = 8.7 Hz), 8.48 (1 H, d, J = 2.2 Hz), 9.57 (1 H, brs.), 13.12 (1 H, brs.)/MS (m/z): 303 (M − H)− |
| 148 | | (DMSO-d6) 6.85 (2 H, d, J = 8.4 Hz), 7.54 (2 H, d, J = 8.4 Hz), 7.87 (2 H, d, J = 8.5 Hz), 7.93 (1 H, d, J = 2.1 Hz), 8.06 (2 H, d, J = 8.5 Hz), 8.44 (1 H, d, J = 2.1 Hz), 9.58 (1 H, brs.), 13.11 (1 H, brs.)/MS (m/z): 303 (M − H)− |
| 149 | | (DMSO-d6) 1.85-2.00 (2 H, m), 3.45-3.65 (2 H, m), 4.05-4.20 (2 H, m), 4.52 (1 H, brs.), 6.95-7.20 (2 H, m), 7.25-7.40 (1 H, m), 7.45-7.55 (1 H, m), 7.75-8.20 (5 H, m), 8.40-8.50 (1 H, m), 13.11 (1 H, brs.)/MS (m/z): 361 (M − H)− |

TABLE 32
| Ex. No. | Strc. | ¹H-NMR δ ppm: DMSO-d6/MS (m/z) |
|---|---|---|
| 150 | 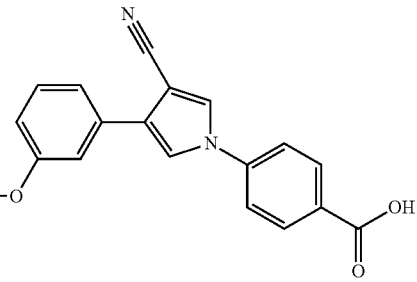 | 1.80-2.00 (2 H, m) 3.50-3.65 (2 H, m) 4.05-4.15 (2 H, m) 4.55 (1 H, brs.) 6.85-7.00 (1 H, m) 7.25-7.45 (3 H, m) 7.90 (2 H, d, J = 8.4 Hz) 8.08 (2 H, d, J = 8.4 Hz) 8.10-8.20 (1 H, m) 8.45-8.55 (1 H, m) 13.13 (1 H, brs.)/MS (m/z): 361 (M − H)− |
| 151 | 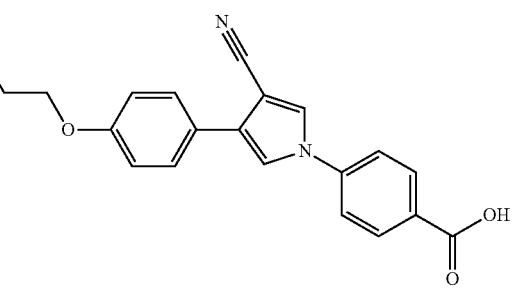 | 1.80-1.95 (2 H, m), 3.50-3.65 (2 H, m), 4.00-4.15 (2 H, m) 4.60-4.75 (1 H, m), 7.03 (2 H, d, J = 8.7 Hz), 7.65 (2 H, d, J = 8.7 Hz), 7.70 (2 H, d, J = 8.5 Hz), 7.93 (1 H, d, J = 2.5 Hz), 8.04 (2 H, d, J = 8.5 Hz), 8.37 (1 H, d, J = 2.5)/MS (m/z): 347 (M − H)− |
| 152 | 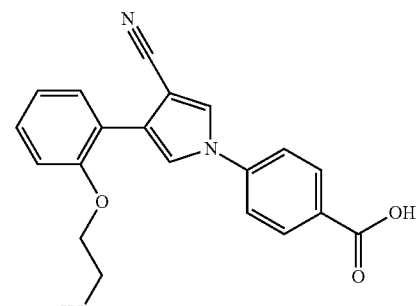 | 3.75-3.90 (2 H, m), 4.05-4.20 (2 H, m), 4.93 (1 H, brs.), 6.95-7.40 (3 H, m), 7.50-8.20 (6 H, m), 8.40-8.55 (1 H, m), 13.12 (1 H, brs.)/MS (m/z): 347 (M − H)− |
| 153 | 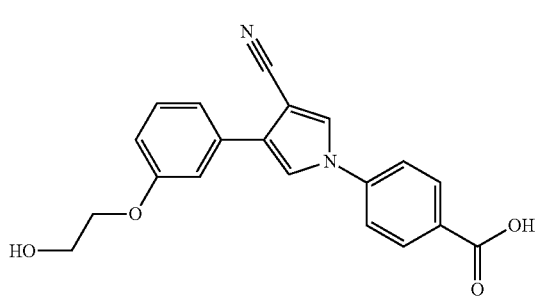 [SMILES: N#Cc1cn(-c2ccc(C(=O)O)cc2)cc1-c1cccc(OCCO)c1] | 3.65-3.85 (2 H, m), 3.95-4.15 (2 H, m), 4.85-4.95 (1 H, m), 6.85-7.00 (1 H, m), 7.25-7.45 (3 H, m), 7.90 (2 H, d, J = 8.7 Hz), 8.08 (2 H, d, J = 8.7 Hz), 8.15 (1 H, d, J = 2.4 Hz), 8.51 (1 H, d, J = 2.4 Hz), 13.15 (1 H, brs.) |
| 154 | 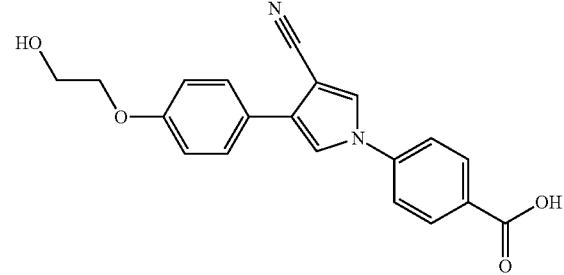 [SMILES: N#Cc1cn(-c2ccc(C(=O)O)cc2)cc1-c1ccc(OCCO)cc1] | 3.65-3.80 (2 H, m), 3.90-4.15 (2 H, m), 4.88 (1 H, brs.), 7.05 (2 H, d, J = 8.7 Hz), 7.66 (2 H, d, J = 8.7 Hz), 7.85 (2 H, d, J = 8.4 Hz), 7.95-8.05 (1 H, m), 8.07 (2 H, d, J = 8.4 Hz), 8.40-8.50 (1 H, m)/MS (m/z): 347 (M − H)− |

TABLE 32-continued

| Ex. No. | Strc. | $^1$H-NMR δ ppm: DMSO-d6/MS (m/z) |
|---|---|---|
| 155 | | 5.19 (2 H, s) 7.00-7.65 (9 H, m) 7.72 (2 H, d, J = 8.4 Hz) 7.75-7.85 (1 H, m) 8.04 (2 H, d, J = 8.4 Hz) 8.40-8.50 (1 H, m) 13.14 (1 H, brs.)/MS (m/z): 393 (M − H)− |

TABLE 33

| Ex.No. | Strc. | $^1$H-NMR δ ppm: DMSO-d6/MS (m/z) |
|---|---|---|
| 156 | | 5.17 (2 H, s), 6.90-7.10 (1 H, m), 7.25-7.60 (8 H, m), 7.90 (2 H, d, J = 8.4 Hz), 8.08 (2 H, d, J = 8.4 Hz), 8.10-8.25 (1 H, m), 8.45-8.60 (1 H, m), 13.15 (1 H, brs.)/MS (m/z): 393 (M − H)− |
| 157 | | 5.16 (2 H, s), 7.00-8.20 (14 H, m), 8.40-8.55 (1 H, m), 13.14 (1 H, brs.)/MS (m/z): 393 (M − H)− |
| 158 | | 4.78 (2 H, s), 6.95-7.40 (3 H, m), 7.65-7.80 (1 H, m), 7.88 (2 H, d, J = 8.2 Hz), 8.07 (2 H, d, J = 8.2 Hz), 8.20-8.30 (1 H, m), 8.45-8.55 (1 H, m), 12.90-13.50 (2 H, m)/MS (m/z): 361 (M − H)− |

TABLE 33-continued

| Ex.No. | Strc. | ¹H-NMR δ ppm: DMSO-d6/MS (m/z) |
|---|---|---|
| 159 | | 4.73 (2 H, s), 6.85-6.95 (1 H, m), 7.25-7.45 (3 H, m), 7.90 (2 H, d, J = 8.7 Hz), 8.08 (2 H, d, J = 8.7 Hz), 8.15 (1 H, d, J = 2.2 Hz), 8.51 (1 H, d, J = 2.2 Hz), 12.90-13.20 (2 H, m)/MS (m/z): 361 (M − H)− |
| 160 | | 4.72 (2 H, s), 7.03 (2 H, d, J = 8.5 Hz), 7.65 (2 H, d, J = 8.5 Hz), 7.80-8.15 (5 H, m), 8.40-8.55 (1 H, m), 12.60-13.40 (2 H, m)/MS (m/z): 361 (M − H)− |
| 161 | | 7.15-7.60 (10 H, m), 7.70 (2 H, d, J = 8.5 Hz), 8.02 (2 H, d, J = 8.5 Hz), 8.22-8.35 (1 H, m), 13.06 (1 H, brs.)/MS (m/z): 363 (M − H)− |

TABLE 34

| Ex.No. | Strc. | ¹H-NMR δ ppm: DMSO-d6/MS (m/z) |
|---|---|---|
| 162 | | 7.35-7.85 (8 H, m), 7.93 (2 H, d, J = 8.8 Hz), 8.00-8.15 (3 H, m), 8.25 (1 H, d, J = 2.5 Hz), 8.54 (1 H, d, J = 2.5 Hz), 13.11 (1 H, brs.)/MS (m/z): 363 (M − H)− |

TABLE 34-continued

| Ex. No. | Strc. | ¹H-NMR δ ppm: DMSO-d6/MS (m/z) |
|---|---|---|
| 163 | | 7.30-8.30 (14 H, m), 8.45-8.65 (1 H, m), 13.11 (1 H, brs.)/MS (m/z): 363 (M − H)− |
| 164 | | 6.90-7.70 (9 H, m), 7.81 (2 H, d, J = 8.7 Hz), 7.83 (1 H, d, J = 2.2 Hz), 8.05 (2 H, d, J = 8.7 Hz), 8.43 (1 H, d, J = 2.2 Hz), 13.13 (1 H, brs.)/MS (m/z): 379 (M − H)− |
| 165 | | 6.90-7.65 (9 H, m), 7.89 (2 H, d, J = 8.4 Hz), 8.07 (2 H, d, J = 8.4 Hz), 8.10-8.25 (1 H, m), 8.45-8.60 (1 H, m), 13.15 (1 H, brs.) |
| 166 | | 7.00-7.25 (5 H, m), 7.35-7.50 (2 H, m), 7.65-8.20 (7 H, m), 8.45-8.55 (1 H, m), 13.14 (1 H, brs.)/MS (m/z): 379 (M − H)− |
| 167 | | 2.30 (3 H, s), 5.19 (2 H, s), 6.95-8.20 (13 H, m), 8.35-8.50 (1 H, m), 13.13 (1 H, brs.)/MS (m/z): 407 (M − H)− |

TABLE 35

| Ex.No. | Strc. | ¹H-NMR δ ppm: DMSO-d6/MS (m/z) |
|---|---|---|
| 168 | | 2.26 (3 H, s), 5.15 (2 H, s), 6.95-8.15 (13 H, m), 8.35-8.55 (1 H, m), 13.14 (1 H, brs.)/MS (m/z): 407 (M − H)− |
| 169 | | 2.31 (3 H, s), 5.14 (2 H, s), 6.95-8.15 (13 H, m), 8.35-8.50 (1 H, m), 13.12 (1 H, brs.)/MS (m/z): 407 (M − H)− |
| 170 | | 5.25 (2 H, s) 7.00-7.85 (11 H, m) 7.95-8.15 (2 H, m) 8.35-8.50 (1 H, m), 13.16 (1 H, brs.)/MS (m/z): 411 (M − H)− |
| 171 | | 5.22 (2 H, s), 7.00-8.15 (13 H, m), 8.40-8.50 (1 H, m), 13.13 (1 H, brs.)/MS (m/z): 411 (M − H)− |

TABLE 35-continued
| Ex.No. | Strc. | ¹H-NMR δ ppm: DMSO-d6/MS (m/z) |
|---|---|---|
| 172 | 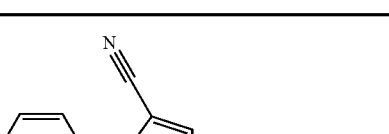 | 5.17 (2 H, s), 7.00-7.45 (5 H, m), 7.50-7.85 (6 H, m). 7.95-8.15 (2 H, m), 8.35-8.50 (1 H, m), 13.14 (1 H, brs.)/MS (m/z): 411 (M − H)− |
TABLE 36
| Ex.No. | Strc. | ¹H-NMR δ ppm: DMSO-d6/MS (m/z) |
|---|---|---|
| 173 | 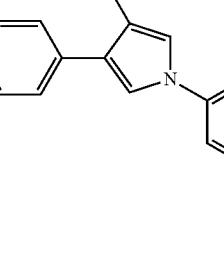 | 5.36 (2 H, s), 6.95-7.65 (7 H, m), 7.80-8.20 (5 H, m), 8.45-8.55 (1 H, m), 13.15 (1 H, brs.)/MS (m/z): 399 (M − H)− |
| 174 | 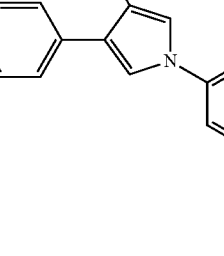 | 5.16 (2 H, s), 6.90-7.70 (7 H, m), 7.90 (2 H, d, J = 8.7 Hz), 8.08 (2 H, d, J = 8.7 Hz), 8.10-8.20 (1 H, m), 8.45-8.55 (1 H, m), 13.14 (1 H, brs.)/MS (m/z): 399 (M − H)− |
| 175 | 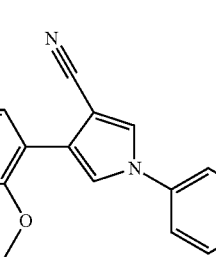 | 5.38 (2 H, s), 6.95-8.15 (12 H, m), 8.35-8.50 (1 H, m), 13.12 (1 H, brs.)/MS (m/z): 399 (M − H)− |

TABLE 36-continued

| Ex.No. | Strc. | ¹H-NMR δ ppm: DMSO-d6/MS (m/z) |
|---|---|---|
| 176 | | 5.18 (2 H, s), 7.00-7.65 (7 H, m), 7.73 (2 H, d, J = 8.8 Hz), 7.75-7.85 (1 H, m), 8.05 (2 H, d, J = 8.8 Hz), 8.40-8.50 (1 H, m), 13.13 (1 H, brs.)/MS (m/z): 399 (M − H)− |
| 177 | | 5.26 (2 H, s), 7.05-7.80 (11 H, m), 7.90-8.05 (2 H, m), 8.30-8.45 (1 H, m)/MS (m/z): 427 (M − H)− |

TABLE 37

| Ex.No. | Strc. | ¹H-NMR δ ppm: DMSO-d6/MS (m/z) |
|---|---|---|
| 178 | | 5.21 (2 H, s), 7.00-8.15 (13 H, m), 8.40-8.50 (1 H, m) 13.13 (1 H, brs.)/MS (m/z): 427 (M − H)− |
| 179 | | 5.19 (2 H, s), 7.00-7.85 (11 H, m), 7.95-8.15 (2 H, m), 8.35-8.50 (1 H, m), 13.12 (1 H, brs.)/MS (m/z): 427 (M − H)− |

TABLE 37-continued

| Ex.No. | Strc. | ¹H-NMR δ ppm: DMSO-d6/MS (m/z) |
|---|---|---|
| 180 | | 5.35 (2 H, s), 6.95-8.20 (13 H, m), 8.35-8.55 (1 H, m), 13.13 (1 H, brs.)/MS (m/z): 461 (M − H)− |
| 181 | | 5.30 (2 H, s), 7.05-8.15 (13 H, m), 8.40-8.50 (1 H, m), 13.12 (1 H, brs.)/MS (m/z): 461 (M − H)− |
| 182 | | 5.31 (2 H, s), 7.00-8.15 (13 H. m), 8.35-8.55 (1 H, m), 13.12 (1 H, s)/MS (m/z): 461 (M − H)− |

TABLE 38

| Ex.No. | Strc. | $^1$H-NMR δ ppm: DMSO-d6/MS (m/z) |
|---|---|---|
| 183 | | 3.80 (3 H, s), 5.16 (2 H, s), 6.85-7.85 (11 H, m), 7.95-8.15 (2 H, m), 8.35-8.50 (1 H, m), 13.14 (1 H, brs.)/MS (m/z): 423 (M − H)− |
| 184 | | 3.70 (3 H, s), 5.16 (2 H, s), 6.80-7.65 (8 H, m), 7.74 (2 H, d, J = 8.5 Hz), 7.75-7.90 (1 H, m), 8.04 (2 H, d, J = 8.5 Hz), 8.40-8.50 (1 H, m), 13.13 (1 H, brs.)/MS (m/z): 423 (M − H)− |
| 185 | | 3.76 (3 H, s), 5.11 (2 H, s), 6.85-8.15 (13 H, m), 8.35-8.50 (1 H, m), 13.12 (1 H, brs.)/MS (m/z): 423 (M − H)− |
| 186 | | 2.36 (3 H, s), 5.15 (2 H, s), 6.95-7.55 (8 H, m), 7.85-8.25 (5 H, m), 8.45-8.55 (1 H, m), 13.13 (1 H, brs.)/MS (m/z): 407 (M − H)− |

TABLE 38-continued
| Ex.No. | Strc. | $^1$H-NMR δ ppm: DMSO-d6/MS (m/z) |
|---|---|---|
| 187 | 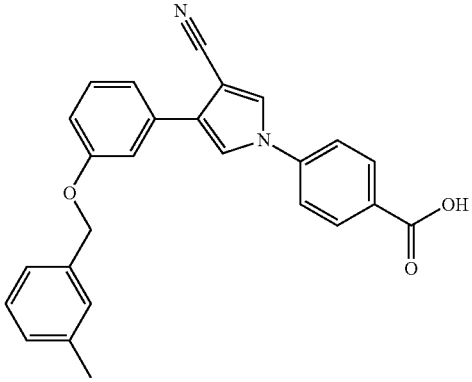 [SMILES: Cc1cccc(COc2cccc(-c3cn(-c4ccc(C(=O)O)cc4)cc3C#N)c2)c1] | 2.33 (3 H, s) 5.12 (2 H, s) 6.95-7.50 (8 H, m) 7.80-8.25 (5 H, m) 8.45-8.60 (1 H, m) 13.14 (1 H, brs.)/MS (m/z): 407 (M − H)− |
TABLE 39
| Ex.No. | Strc. | $^1$H-NMR δ ppm: DMSO-d6/MS (m/z) |
|---|---|---|
| 188 | 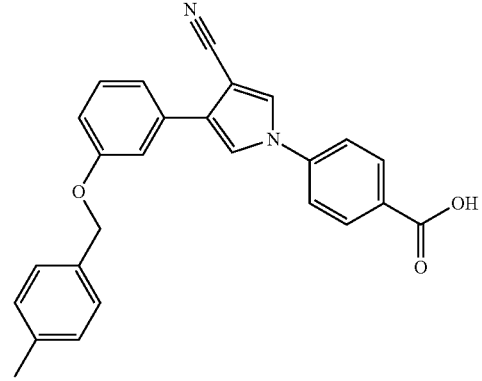 [SMILES: Cc1ccc(COc2cccc(-c3cn(-c4ccc(C(=O)O)cc4)cc3C#N)c2)cc1] | 2.31 (3 H, s), 5.11 (2 H, s), 6.90-7.05 (1 H, m), 7.15-7.50 (7 H, m), 7.90 (2 H, d, J = 8.7 Hz), 8.08 (2 H, d, J = 8.7 Hz), 8.14 (1 H, d, J = 2.2 Hz), 8.50 (1 H, d, J = 2.2 Hz), 13.14 (1 H, brs.)/MS (m/z): 407 (M − H)− |
| 189 | 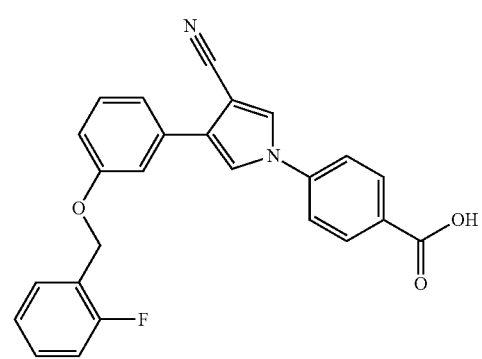 [SMILES: N#Cc1cn(-c2ccc(C(=O)O)cc2)cc1-c1cccc(OCc2ccccc2F)c1] | 5.21 (2 H, s), 6.95-7.70 (8 H, m), 7.90 (2 H, d, J = 8.5 Hz), 8.08 (2 H, d, J = 8.5 Hz), 8.10-8.20 (1 H, m), 8.45-8.55 (1 H, m), 13.13 (1 H, brs.)/MS (m/z): 411 (M − H)− |

TABLE 39-continued
| Ex.No. | Strc. | ¹H-NMR δ ppm: DMSO-d6/MS (m/z) |
|---|---|---|
| 190 | 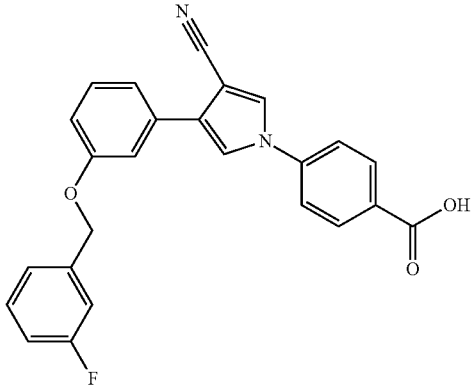 [SMILES: N#Cc1cn(-c2ccc(C(=O)O)cc2)cc1-c1cccc(OCc2cccc(F)c2)c1] | 5.20 (2 H, s), 6.90-7.60 (8 H, m), 7.80-8.25 (5 H, m), 8.45-8.60 (1 H, m), 13.14 (1 H, brs.)/MS (m/z): 411 (M − H)− |
| 191 | 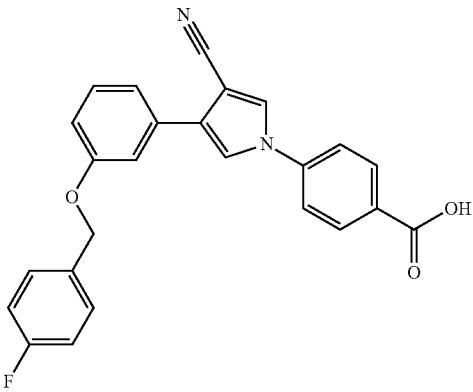 [SMILES: N#Cc1cn(-c2ccc(C(=O)O)cc2)cc1-c1cccc(OCc2ccc(F)cc2)c1] | 5.15 (2 H, s), 6.90-7.65 (8 H, m), 7.90 (2 H, d, J = 8.2 Hz), 8.08 (2 H, d, J = 8.2 Hz), 8.10-8.20 (1 H, m), 8.40-8.60 (1 H, m), 13.14 (1 H, brs.)/MS (m/z): 411 (M − H)− |
| 192 | 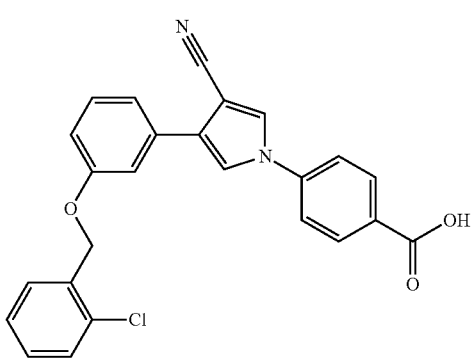 [SMILES: N#Cc1cn(-c2ccc(C(=O)O)cc2)cc1-c1cccc(OCc2ccccc2Cl)c1] | 5.23 (2 H, s), 6.90-7.15 (1 H, m), 7.25-8.75 (13 H, m), 13.13 (1 H, brs.)/MS (m/z): 427(M − H)− |

TABLE 40
| Ex.No. | Strc. | ¹H-NMR δ ppm: DMSO-d6/MS (m/z) |
|---|---|---|
| 193 | 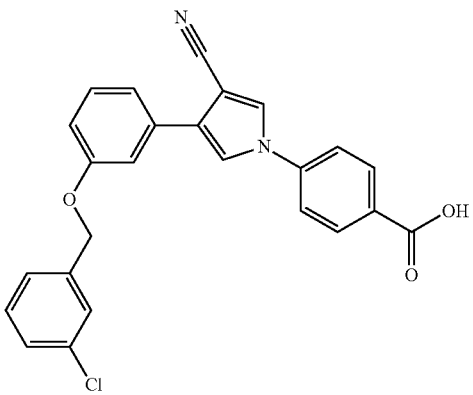 [SMILES: N#Cc1cn(-c2ccc(C(=O)O)cc2)cc1-c1cccc(OCc2cccc(Cl)c2)c1] | 5.19 (2 H, s), 6.90-7.10 (1 H, m), 7.25-7.65 (7 H, m), 7.90 (2 H, d, J = 8.2 Hz), 8.08 (2 H, d, J = 8.2 Hz), 8.10-8.20 (1 H, m), 8.45-8.55 (1 H, m), 13.14 (1 H, brs.)/MS (m/z): 427(M − H)− |
| 194 | 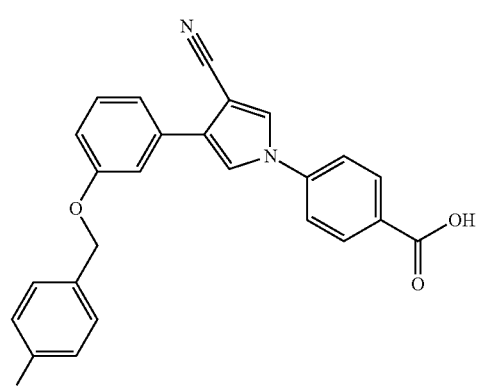 | 5.17 (2 H, s), 6.90-7.10 (1 H, m), 7.25-7.60 (7 H, m), 7.90 (2 H, d, J = 8.7 Hz), 8.08 (2 H, d, J = 8.7 Hz), 8.15 (1 H, d, J = 2.2 Hz), 8.50 (1 H, d, J = 2.2 Hz), 13.14 (1 H, brs.)/MS (m/z): 427(M − H)− |
| 195 | 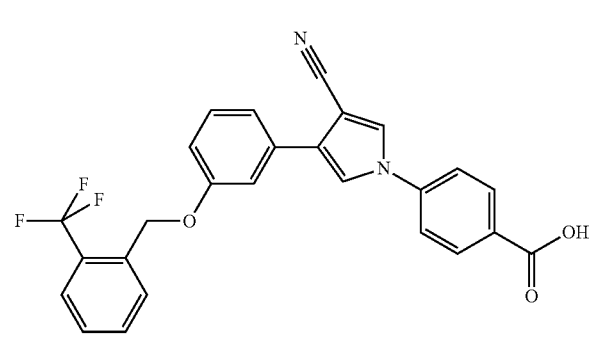 [SMILES: N#Cc1cn(-c2ccc(C(=O)O)cc2)cc1-c1cccc(OCc2ccccc2C(F)(F)F)c1] | 5.30 (2 H, s), 6.90-7.10 (1 H, m), 7.25-8.25 (12 H, m), 8.40-8.60 (1 H, m), 13.14 (1 H, brs.)/MS (m/z): 461(M − H)− |
| 196 | 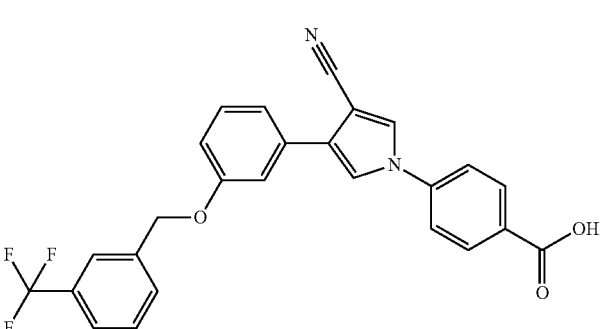 | 5.28 (2 H, s), 6.95-7.15 (1 H, m), 7.30-8.25 (12 H, m), 8.40-8.60 (1 H, m), 13.14 (1 H, brs.)/MS (m/z): 461 (M − H)− |

TABLE 40-continued
| Ex.No. | Strc. | ¹H-NMR δ ppm: DMSO-d6/MS (m/z) |
|---|---|---|
| 197 |  | 5.30 (2 H, s), 6.95-7.10 (1 H, m), 7.25-8.25 (12 H, m), 8.40-8.60 (1 H, m), 13.14 (1 H, brs.)/MS (m/z): 461(M − H)− |
TABLE 41
| Ex.No. | Strc. | ¹H-NMR δ ppm: DMSO-d6/MS (m/z) |
|---|---|---|
| 198 |  | 3.77 (3 H, s), 5.14 (2 H, s), 6.85-7.15 (4 H, m), 7.25-7.50 (4 H, m), 7.90 (2 H, d, J = 8.5 Hz), 8.08 (2 H, d, J = 8.5 Hz), 8.15 (1 H, d, J = 2.2 Hz), 8.50 (1 H, d, J = 2.2 Hz), 13.14 (1 H, brs.)/MS (m/z): 423(M − H)− |
| 199 | | 1.40-1.95 (4 H, m), 3.25-3.60 (2 H, m), 3.90-4.20 (2 H, m), 4.46 (1 H, brs.), 6.90-7.60 (4 H, m), 7.70-8.20 (5 H, m), 8.34-8.55 (1 H, m), 13.15 (1 H, brs.)/MS (m/z): 375(M − H)− |
| 200 | 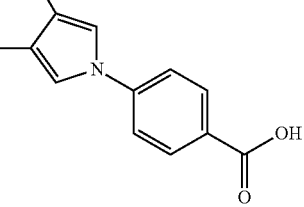 | 1 50-1.90 (4 H, m), 3.40-3.55 (2 H, m), 3.95-4.15 (2 H, m), 4.47 (1 H, brs.), 6.80-7 00 (1 H, m), 7.20-7.50 (3 H, m), 7.70-7.85 (2 H, m), 7.95-8.15 (3 H, m), 8.40-8.50 (1 H, m)/MS (m/z): 375 (M − H)− |

TABLE 41-continued

| Ex.No. | Strc. | $^1$H-NMR δ ppm: DMSO-d6/MS (m/z) |
|---|---|---|
| 201 | | 3.32 (3 H, s), 3.65-3.85 (2 H, m), 4.10-4.30 (2 H, m), 6.95-7.45 (3 H, m), 7.55-8.20 (6 H, m), 8.40-8.55 (1 H, m), 13.17 (1 H, brs.)/MS (m/z): 361(M − H)− |
| 202 | | 3.33 (3 H, s), 3.60-3.80 (2 H, m), 4.05-4.25 (2 H, m), 6.85-7.00 (1 H, m), 7.25-7.50 (3 H, m), 7.80-8.25 (5 H, m), 8.40-8.60 (1 H, m), 13.17 (1 H, brs.)/MS (m/z): 361(M − H)− |
| 203 | | 7.30-7.55 (3 H, m), 7.65-8.05 (6 H, m), 8.20-8.35 (1 H, m), 13.55 (1 H, brs.)/MS (m/z): 305(M − H)− |

TABLE 42

| Ex.No. | Strc. | $^1$H-NMR δ ppm: DMSO-d6/MS (m/z) |
|---|---|---|
| 204 | | 2.32 (3 H, s), 7.20-8.20 (10 H, m), 13.22 (1 H, brs.)/MS (m/z): 301 (M − H)− |

TABLE 42-continued

| Ex.No. | Strc. | ¹H-NMR δ ppm: DMSO-d6/MS (m/z) |
|---|---|---|
| 205 | | 7.25-8.35 (9 H, m), 8.50-8.75 (1 H, m), 13.76 (1 H, brs.)/MS (m/z): 355(M − H)− |
| 206 | | 6.95-8.20 (12 H, m), 8.35-8.55 (1 H, m), 13.17 (1 H, brs.)/MS (m/z): 313(M − H)− |
| 207 | | 2.75-3.05 (4 H, m), 7.10-7.60 (6 H, m), 7.76 (2 H, d, J = 8.2 Hz), 8.04 (2 H, d, J = 8.2 Hz), 8.25-8.40 (1 H, m), 13.12 (1 H, brs.)/MS (m/z): 315(M − H)− |
| 208 | | 7.25-8.25 (9 H, m), 8.45-8.65 (1 H, m), 13.37 (1 H, brs.)/MS (m/z): 305(M − H)− |
| 209 | | 7.50-7.70 (4 H, m), 7.85-8.20 (8 H, m), 8.55-8.65 (1 H, m), 13.14 (1 H, brs.)/MS (m/z): 337(M − H)− |

TABLE 42-continued

| Ex.No. | Strc. | ¹H-NMR δ ppm: DMSO-d6/MS (m/z) |
|---|---|---|
| 210 | | 7.75-8.35 (9 H, m), 8.45-8.65 (1 H, m), 12.70-13.40 (2 H, m)/MS (m/z): 331 (M − H)− |

TABLE 43

| Ex.No. | Strc. | ¹H-NMR δ ppm: DMSO-d6/MS (m/z) |
|---|---|---|
| 211 | | 7.65-8.40 (9 H, m), 8.50-8.65 (1 H, m), 13.20 (1 H, brs.)/MS (m/z): 312 (M − H)− |
| 212 | | 7.85-8.15 (8 H, m), 8.34 (1 H, d, J = 2.2 Hz), 8.59 (1 H, d, J = 2.2 Hz), 13.21 (1 H, brs.)/MS (m/z): 312(M − H)− |
| 213 | | 1.05 (3 H, t, J = 6.9 Hz), 3.49 (2 H, q, J = 6.9 Hz), 3.72-3.85 (2 H, m), 4.10-4.25 (2 H, m), 6.95-7.45 (3 H, m), 7.55-7.70 (1 H, m), 7.83 (2 H, d, J = 8.8 Hz), 7.90-8.00 (1 H, m), 8.07 (2 H, d, J = 8.8 Hz), 8.40-8.55 (1 H, m)/MS (m/z): 375(M − H)− |

TABLE 43-continued

| Ex.No. | Strc. | ¹H-NMR δ ppm: DMSO-d6/MS (m/z) |
|---|---|---|
| 214 | | 4.30-4.50 (4 H, m), 6.85-7.45 (8 H, m), 7.55-7.70 (3 H, m), 7.80-7.95 (3 H, m), 8.35-8.50 (1 H, m), 13.10 (1 H, brs.)/MS (m/z): 375(M − H)− |
| 215 | | 1.14 (3 H, t, J = 6.9 Hz), 3.52 (2 H, q, J = 6.9 Hz), 3.65-3.85 (2 H, m), 4.05-4.25 (2 H, m), 6.80-7.05 (1 H, m), 7.20-7.50 (3 H, m), 7.80-8.25 (5 H, m), 8.45-8.60 (1 H, m), 13.17 (1 H, brs.)/MS (m/z): 375(M − H)− |

TABLE 44

| Ex.No. | Strc. | ¹H-NMR δ ppm: DMSO-d6/MS (m/z) |
|---|---|---|
| 216 | | 4.25-4.50 (4 H, m), 6.85-7.10 (4 H, m), 7.20-7.50 (5 H, m), 7.90 (2 H, d, J = 8.5 Hz), 8.08 (2 H, d, J = 8.5 Hz), 8.10-8.25 (1 H, m), 8.45-8.60 (1 H, m), 13.17 (1 H, brs.)/MS (m/z): 423(M − H)− |

TABLE 44-continued

| Ex.No. | Strc. | ¹H-NMR δ ppm: DMSO-d6/MS (m/z) |
|---|---|---|
| 217 | | 7.50-7.70 (1 H, m), 7.85-8.65 (9 H, m), 12.90-13.35 (2 H, m)/MS (m/z): 331 (M − H)− |
| 218 | | 7.40-8.15 (9 H, m), 8.35-8.50 (1 H, m), 12.60-13.30 (2 H, m)/MS (m/z): 331 (M − H)− |
| 219 | | 4.45-4.65 (2 H, m), 5.15-5.35 (1 H, m), 7.20-8.20 (9 H, m), 8.40-8.60 (1 H, m), 13.13 (1 H, brs.)/MS (m/z): 317(M − H)− |
| 220 | | 3.81 (3 H, s), 7.30-7.45 (1 H, m), 7.78 (2 H, d, J = 8.5 Hz), 8.03 (2 H, d, J = 8.5 Hz), 8.15-8.30 (1 H, m), 13.10 (1 H, brs.)/MS (m/z): 241 (M − H)− |
| 221 | | 1.29 (3 H, t, J = 7.1 Hz), 4.26 (2 H, q, J = 7.1 Hz), 7.93 (2 H, d, J = 8.4 Hz), 8.05 (2 H, d, J = 8.4 Hz), 8.10-8.35 (2 H, m), 13.15 (1 H, brs.)/MS (m/z): 326 (M − H)− |

TABLE 45

| Ex.No. | Strc. | ¹H-NMR δ ppm: DMSO-d6/MS (m/z) |
|---|---|---|
| 222 | | 7.75-8.60 (6 H, m), 12.80-13.40 (2 H, m)/ MS (m/z): 255 (M − H)− |
| 223 | | 7.88 (2 H, d, J = 8.5 Hz), 8.08 (2 H, d, J = 8.5 Hz), 8.35-8.70 (2 H, m) 13.26 (1 H, brs.)/ MS (m/z): 279 (M − H)− |
| 224 | | 7.50-7.75 (3 H, m), 7.85-8.25 (7 H, m), 8.55-8.70 (1 H, m), 13.24 (1 H, brs.)/MS (m/z): 315 (M − H)− |
| 225 | | 2.65-2.85 (3 H, m), 7.70-7.85 (2 H, m), 8.00-8.25 (4 H, m), 8.35-8.45 (1 H, m), 13.13 (1 H, brs.)/MS (m/z): 268 (M − H)− |
| 226 | | 2.85-3.30 (6 H, m), 7.75-8.15 (5 H, m), 8.43 (1 H, s), 13.11 (1 H, brs.)/MS (m/z): 282 (M − H)− |

TABLE 45-continued

| Ex.No. | Strc. | ¹H-NMR δ ppm: DMSO-d6/MS (m/z) |
|---|---|---|
| 227 | | 4.35-4.60 (2 H, m), 7.15-7.50 (5 H, m), 7.65-7.85 (2 H, m), 8.00-8.80 (5 H, m), 13.13 (1 H, brs.)/MS (m/z): 344 (M − H)− |
| 228 | | 3.00-3.25 (3 H, m), 4.60-4.80 (2 H, m), 7.20-7.45 (5 H, m), 7.70-8.15 (5 H, m), 8.40-8.50 (1 H, m), 13.16 (1 H, brs.)/MS (m/z): 358 (M − H)− |

TABLE 46

| Ex. No. | Strc. | ¹H-NMR δ ppm: DMSO-d6/MS (m/z) |
|---|---|---|
| 229 | | 3.15-3.60 (7 H, m), 7.70-7.85 (2 H, m), 8.00-8.50 (5 H, m), 13.16 (1 H, brs.)/MS (m/z): 312 (M − H)− |
| 230 | | 2.85-3.75 (10 H, m), 7.70-8.15 (5 H, m), 8.42 (1 H, s), 13.15 (1 H, brs.)/MS (m/z): 326 (M − H)− |

TABLE 46-continued
| Ex. No. | Strc. | $^1$H-NMR δ ppm: DMSO-d6/MS (m/z) |
|---|---|---|
| 231 | 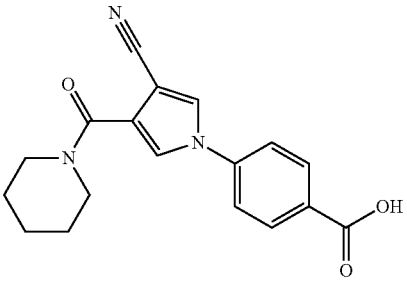 [SMILES: N#Cc1cn(-c2ccc(C(=O)O)cc2)cc1C(=O)N1CCCCC1] | 1.40-1.75 (6 H, m), 3.45-3.65 (4 H, m), 7.75-8.15 (5 H, m), 8.35-8.50 (1 H, m)/MS (m/z): 322 (M − H)− |
| 232 | 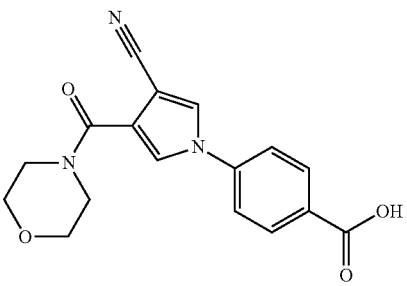 [SMILES: N#Cc1cn(-c2ccc(C(=O)O)cc2)cc1C(=O)N1CCOCC1] | 3.55-3.75 (8 H, m), 7.75-8.15 (5 H, m), 8.35-8.50 (1 H, m)/MS (m/z): 324 (M − H)− |
| 233 | 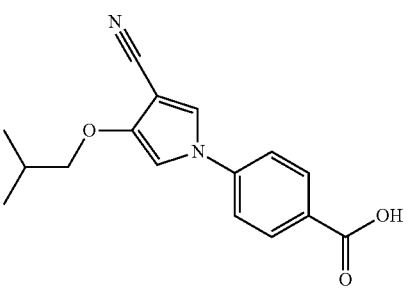 [SMILES: CC(C)COc1cn(-c2ccc(C(=O)O)cc2)cc1C#N] | 0.98 (6 H, d, J = 6.6 Hz), 1.90-2.20 (1 H, m), 3.77 (2 H, d, J = 6.6 Hz), 7.25-7.45 (1 H, m), 7.65-8.30 (5 H, m), 13.06 (1 H, brs.)/MS (m/z): 283 (M − H)− |
| 234 | 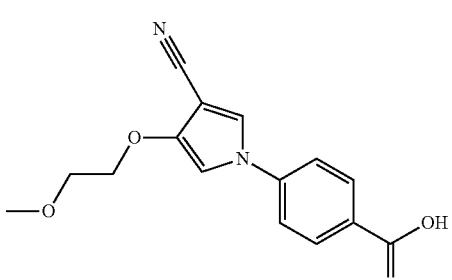 | 3.33 (3 H, s), 3.55-3.80 (2 H, m), 4.00-4.20 (2 H, m), 7.30-7.45 (1 H, m), 7.76 (2 H, d, J = 8.5 Hz), 8.03 (2 H, d, J = 8.5 Hz), 8.10-8.30 (1 H, m), 13.07 (1 H, brs.)/MS (m/z): 285 (M − H)− |
TABLE 47
| Ex. No. | Strc. | $^1$H-NMR δ ppm: DMSO-d6/MS (m/z) |
|---|---|---|
| 235 | 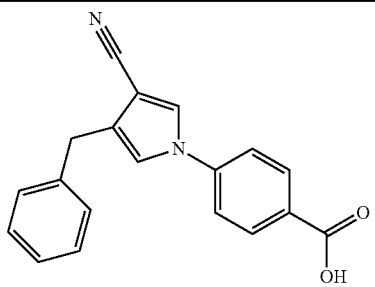 | 3.89 (2H, s), 7.18-7.24 (1H, m), 7.25-7.35 (4H, m), 7.56 (1H, d, J = 2.7 Hz), 7.73-7.80 (2H, m), 8.00-8.06 (2H, m), 8.32 (1H, d, J = 2.7 Hz), 12.12 (1H, brs) |

TABLE 47-continued

| Ex. No. | Strc. | ¹H-NMR δ ppm: DMSO-d6/MS (m/z) |
|---|---|---|
| 236 | | 2.15 (3H, d, J = 0.8), 7.22 (1H, d, J = 2.3, 8.8 Hz), 7.27 (1H, d, J = 2.3 Hz), 7.49-7.52 (1H, m), 7.87 (1H, d, J = 8.8 Hz), 8.29 (1H, d, J = 2.3 Hz), 11.56 (1H, brs) |
| 237 | | 2.17-2.19 (3H, m), 6.44-6.47 (1H, m), 7.57-7.61 (2H, m), 7.83 (1H, d, J = 1.9 Hz), 8.05-8.09 (2H, m), 13.20 (1H, brs) |
| 238 | | 0.95 (3H, t, J = 7.4 Hz), 1.58-1.70 (2H, m), 2.44-2.56 (2H, m), 7.48 (1H, m), 7.74-7.82 (2H, m), 7.98-8.06 (2H, m), 8.26-8.32 (1H, m), 13.11 (1H, br) |
| 239 | | 0.92 (3H, t, J = 7.5 Hz), 1.50-1.60 (2H, m), 2.11 (3H, s), 2.45-2.50 (2H, m), 7.54-7.60 (2H, m), 7.77 (1H, s), 8.04-8.08 (2H, m), 13.20 (1H, br) |
| 240 | | 0.92 (3H, t, J = 7.3 Hz), 1.30-1.42 (2H, m), 1.56-1.68 (2H, m), 2.46-2.58 (2H, m), 7.48-7.52 (1H, m), 7.74-7.82 (2H, m), 8.00-8.06 (2H, m), 8.28-8.30 (1H, m), 13.11 (1H, br) |

TABLE 47-continued

| Ex. No. | Strc. | ¹H-NMR δ ppm: DMSO-d6/MS (m/z) |
|---|---|---|
| 241 | | 0.93 (6H, d, J = 6.6 Hz), 1.84-1.96 (1H, m), 2.41 (2H, d, J = 6.8 Hz), 7.50 (1H, d, J = 2.3 Hz), 7.76-7.82 (2H, m), 8.00-8.06 (2H, m), 8.30 (1H, d, J = 2.3 Hz), 13.11 (1H, brs) |

TABLE 48

| Ex. No. | Strc. | ¹H-NMR δ ppm: DMSO-d6/MS (m/z) |
|---|---|---|
| 242 | | 0.92 (6H, d, J = 6.6 Hz), 1.76-1.88 (1H, m), 2.09 (3H, s), 2.37 (2H, d, J = 7.0 Hz), 7.54-7.60 (2H, m), 7.77 (1H, s), 8.04-8.10 (2H, m), 1.08 (1H, brs) |
| 243 | | 2.08-2.12 (6H, m), 7.52-7.58 (2H, m), 7.76 (1H, s), 8.04-8.08 (2H, m), 13.18 (1H, brs) |
| 244 | | 6.62 (1H, dd, J = 1.9, 3.4 Hz), 6.72-6.76 (1H, m), 7.74-7.78 (1H, m), 7.84-7.92 (2H, m), 8.03 (1H, d, J = 2.5 Hz), 8.04-8.10 (2H, m), 8.49 (1H, d, J = 2.5 Hz) |

TABLE 48-continued

| Ex. No. | Strc. | $^1$H-NMR δ ppm: DMSO-d6/MS (m/z) |
|---|---|---|
| 245 | | 0.89 (3H, t, J = 7.0 Hz), 1.30-1.36 (4H, m), 1.58-1.68 (2H, m), 2.50-2.56 (2H, m), 7.48-7.52 (1H, m), 7.74-7.82 (2H, m), 8.00-8.06 (2H, m), 8.26-8.30 (1H, m), 13.07 (1H, brs) |
| 246 | | 0.84-0.90 (3H, m), 1.24-1.40 (6H, m), 1.56-1.66 (2H, m), 2.48-2.56 (2H, m), 7.49 (1H, d, J = 2.4 Hz), 7.74-7.80 (2H, m), 8.00-8.06 (2H, m), 8.28 (1H, m), 13.07 (1H, brs) |
| 247 | | 0.82-0.90 (3H, m), 1.20-1.40 (8H, m), 1.56-1.68 (2H, m), 2.46-2.56 (2H, m), 7.48-7.54 (1H, m), 7.74-7.80 (2H, m), 8.00-8.06 (2H, m), 8.26-8.30 (1H, m), 13.08 (1H, brs) |
| 248 | | 4.50 (2H, s), 4.55 (2H, s), 7.26-7.42 (5H, m), 7.73 (1H, d, J = 2.3 Hz), 7.78-7.84 (2H, m), 8.02-8.08 (2H, m), 8.37 (1H, d, J = 2.3 Hz), 13.11 (1H, brs) |

TABLE 49

| Ex. No. | Strc. | ¹H-NMR δ ppm: DMSO-d6/MS (m/z) |
|---|---|---|
| 249 | | 6.11 (2 H, s), 7.10 (1 H, d, J = 8.1 Hz), 7.29 (1 H, dd, J = 8.1, 1.8 Hz), 7.33 (1 H, d, J = 1.8 Hz), 7.95-8.25 (4 H, m), 9.25 (1 H, s) |
| 250 | | 7.50-7.60 (2H, m), 7.67 (2H, d, J = 7.0 Hz), 7.85-7.95 (3H, m), 8.00-8.10 (3H, m), 8.14 (1H, d, J = 2.2 Hz), 8.20-8.35 (1H, m), 8.43 (1H, d, J = 2.2 Hz) |
| 251 | | 3.87 (3 H, s), 7.05-7.35 (2 H, m), 7.45-7.60 (1 H, m), 7.70 (1 H, s), 7.85-8.20 (6 H, m), 8.40-8.60 (1 H, m) |
| 252 | | 1.51 (6 H, d, J = 6.6 Hz), 4.70-5.00 (1 H, m), 7.05-7.35 (2 H, m), 7.50-7.70 (1 H, m), 7.81 (1 H, s), 7.85-8.20 (6 H, m), 8.40-8.60 (1 H, m), 13.12 (1 H, brs.) |
| 253 | | 7.35-7.60 (2 H, m), 7.80-8.20 (8 H, m), 8.45-8.70 (1 H, m), 13.14 (1 H, brs.) |

TABLE 49-continued
| Ex. No. | Strc. | $^1$H-NMR δ ppm: DMSO-d6/MS (m/z) |
|---|---|---|
| 254 | 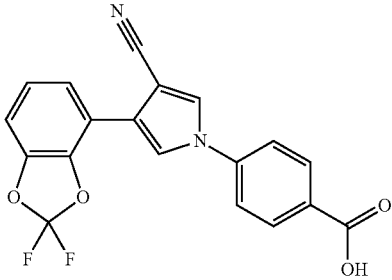 [SMILES: N#Cc1cn(-c2ccc(C(=O)O)cc2)cc1-c1cccc2c1OC(F)(F)O2] | 7.25-7.60 (3H, m), 7.80-8.15 (5H, m), 8.50-8.65 (1H, m), 13.17 (1H, brs.) |
| 255 | 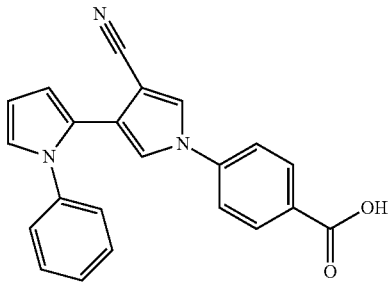 [SMILES: N#Cc1cn(-c2ccc(C(=O)O)cc2)cc1-c1cccn1-c1ccccc1] | 6.20-6.60 (2 H, m), 7.05-7.75 (9 H, m), 7.95-8.10 (2 H, m), 8.20-8.45 (1 H, m), 13.14 (1 H, brs.) |
TABLE 50
| Ex. No. | Strc. | $^1$H-NMR δ ppm: DMSO-d6/MS (m/z) |
|---|---|---|
| 256 | 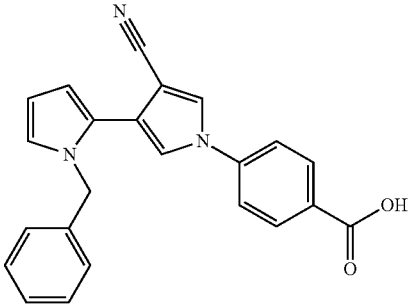 [SMILES: N#Cc1cn(-c2ccc(C(=O)O)cc2)cc1-c1cccn1Cc1ccccc1] | 5.32 (2 H, s), 6.05-6.50 (2 H, m), 6.85-7.05 (3 H, m), 7.15-7.35 (3 H, m), 7.45-7.85 (3 H, m), 7.95-8.15 (2 H, m), 8.29-8.50 (1 H, m), 13.13 (1 H, brs.) |
| 257 | 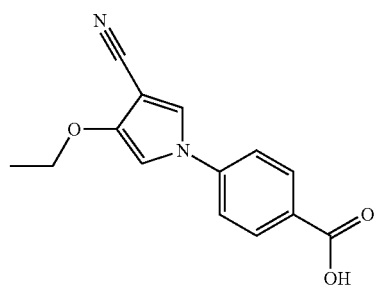 [SMILES: CCOc1cn(-c2ccc(C(=O)O)cc2)cc1C#N] | 1.36 (3H, t, J = 7.0 Hz), 4.03 (2H, q, J = 7.0 Hz), 7.36 (1H, d, J = 2.4 Hz), 7.76 (2H, d, J = 8.5 Hz), 8.02 (2H, d, J = 8.5 Hz), 8.21 (1H, d, J = 2.4 Hz), 13.1 (1H, brs) |

TABLE 50-continued

| Ex. No. | Strc. | ¹H-NMR δ ppm: DMSO-d6/MS (m/z) |
|---|---|---|
| 258 | | 2.86 (2H, t, J = 6.9 Hz), 2.97 (2H, t, J = 6.9 Hz), 6.16 (1H, d, J = 3.2 Hz), 6.35-6.36 (1H, m), 7.53-7.54 (2H, m), 7.75 (2H, d, J = 8.5 Hz), 8.02 (2H, d, J = 8.5 Hz), 8.30 (1H, d, J = 2.1 Hz), 13.1 (1H, brs) |
| 259 | | 1.35-1.50 (1H, m), 1.70-1.90 (4H, m), 1.90-2.05 (1H, m), 2.50-2.70 (2H, m), 3.55-3.65 (1H, m), 3.70-3.85 (2H, m), 7.52 (1H, d, J = 2.3 Hz), 7.77 (2H, d, J = 8.7 Hz), 8.02 (2H, d, J = 8.7 Hz), 8.30 (1H, d, J = 2.3 Hz), 13.12 (1H, brs) |
| 260 | | 6.11 (2H, s-br), 7.81 (2H, d, J = 8.8 Hz), 8.01 (2H, d, J = 8.8 Hz), 9.06 (1H, s), 13.0 (1H, brs) |
| 261 | | 2.30 (3H, s), 3.10 (3H, s), 7.92 (2H, d, J = 8.7 Hz), 8.04 (2H, d, J = 8.7 Hz), 8.28 (1H, s), 9.18 (1H, s), 13.06 (1H, brs) |
| 262 | | 7.50-7.70 (3H, m), 7.90-8.15 (6H, m), 9.46 (1H, s), 11.33 (1H, s), 13.19 (1H, brs) |

TABLE 51

| Ex. No. | Strc. | ¹H-NMR δ ppm: DMSO-d6/MS (m/z) |
|---|---|---|
| 263 | | 3.73 (2H, s), 7.25-7.35 (5H, m), 7.92 (2H, d, J = 8.8 Hz), 8.08 (2H, d, J = 8.8 Hz), 9.38 (1H, s), 11.1 (1H, s-br), 13.2 (1H, s-br) |
| 264 | | 6.58 (1H, d, J = 3.3 Hz), 6.92 (1H, br), 7.52 (1H, dd, J = 1.3, 5.0 Hz), 7.68 (1H, dd, J = 3.0, 5.0 Hz), 8.00 (1H, dd, J = 1.3, 3.0 Hz), 7.85 (1H, d, J = 2.4 Hz), 8.22 (1H, d, J = 2.4 Hz) |
| 265 | | 7.10-7.70 (6 H, m), 7.85-8.00 (1 H, m), 8.10-8.30 (1 H, m), 8.45-8.60 (1 H, m)/ MS (m/z): 321 (M − H)− |
| 266 | | 3.70-3.90 (6 H, m), 6.55-6.75 (2 H, m), 7.20-7.45 (3 H, m), 7.60-8.00 (2 H, m), 8.30-8.50 (1 H, m)/MS (m/z): 363 (M − H)− MS (m/z): 339 (M − H)− |
| 267 | | 7.20-7.50 (4H, m), 7.60-7.75 (1H, m), 7.85-8.00 (2H, m), 8.45-8.60 (1H, m)/MS (m/z): 339 (M − H)− |

TABLE 51-continued

| Ex. No. | Strc. | ¹H-NMR δ ppm: DMSO-d6/MS (m/z) |
|---|---|---|
| 268 | (4-(3-fluoro-4-methoxyphenyl)-3-cyano-pyrrol-1-yl attached to 2-hydroxy-4-benzoic acid) | 3.88 (3 H, s), 7.15-7.70 (5 H, m), 7.80-8.20 (2 H, m), 8.40-8.60 (1 H, m)/MS (m/z): 351 (M − H)− |
| 269 | (4-(3-fluoro-4-methylphenyl)-3-cyano-pyrrol-1-yl attached to 2-hydroxy-4-benzoic acid) | 2.27 (3 H, s), 7.25-7.65 (5 H, m), 7.80-8.00 (1 H, m), 8.10-8.25 (1 H, m), 8.45-8.60 (1 H, m)/MS (m/z): 335 (M − H)− |

TABLE 52

| Ex. No. | Strc. | ¹H-NMR δ ppm: DMSO-d6/MS (m/z) |
|---|---|---|
| 270 | (4-(2,3-difluorophenyl)-3-cyano-pyrrol-1-yl attached to 2-hydroxy-4-benzoic acid) | 7.20-7.60 (5 H, m), 7.85-8.10 (2 H, m), 8.50-8.65 (1 H, m)/MS (m/z): 339 (M − H)− |
| 271 | (4-(3,5-difluorophenyl)-3-cyano-pyrrol-1-yl attached to 2-hydroxy-4-benzoic acid) | 7.10-7.65 (5 H, m), 7.85-8.00 (1 H, m), 8.25-8.40 (1 H, m), 8.50-8.65 (1 H, m)/MS (m/z): 339 (M − H)− |

TABLE 52-continued

| Ex. No. | Strc. | $^1$H-NMR δ ppm: DMSO-d6/MS (m/z) |
|---|---|---|
| 272 | | 2.14 (6 H, s), 7.05-7.50 (5 H, m), 7.60-8.00 (2 H, m), 8.50-8.65 (1 H, m)/MS (m/z): 331 (M − H)− |
| 273 | | 2.25-2.40 (6 H, m), 7.00-7.50 (5 H, m), 7.65-8.00 (2 H, m), 8.40-8.55 (1 H, m)/MS (m/z): 331 (M − H)− |
| 274 | | 7.15-7.65 (5 H, m), 7.85-8.05 (2 H, m), 8.50-8.65 (1 H, m)/MS (m/z): 339 (M − H)− |
| 275 | | 2.20-2.35 (3 H, m), 7.10-7.50 (5 H, m), 7.80-8.00 (2 H, m), 8.47-8.60 (1 H, m)/MS (m/z): 335 (M − H)− |
| 276 | | 2.33 (3 H, s), 3.79 (3 H, s), 6.75-7.00 (2 H, m), 7.15-7.50 (3 H, m), 7.65-8.00 (2 H, m), 8.40-8.55 (1 H, m)/MS (m/z): 347 (M − H)− |

TABLE 53

| Ex. No. | Strc. | $^1$H-NMR δ ppm: DMSO-d6/MS (m/z) |
|---|---|---|
| 277 | | 7.20-7.60 (5 H, m), 7.80-8.15 (2 H, m), 8.50-8.65 (1 H, m)/MS (m/z): 339 (M − H)− |
| 278 | | 7.20-8.05 (7 H, m), 8.15-8.35 (1 H, m), 8.45-8.65 (1 H, m)/MS (m/z): 337 (M − H)− |
| 279 | | 3.82 (3 H, s), 6.85-7.00 (1 H, m), 7.25-7.50 (5 H, m), 7.85-8.00 (1 H, m), 8.10-8.20 (1 H, m), 8.45-8.60 (1 H, m)/MS (m/z): 333 (M − H)− |
| 280 | | 2.37 (3 H, s), 7.05-7.70 (6 H, m), 7.80-8.20 (2 H, m), 8.45-8.60 (1 H, m)/MS (m/z): 317 (M − H)− |
| 281 | | 7.25-8.70 (9 H, m)/MS (m/z): 371 (M − H)− |

TABLE 53-continued
| Ex. No. | Strc. | ¹H-NMR δ ppm: DMSO-d6/MS (m/z) |
|---|---|---|
| 282 | 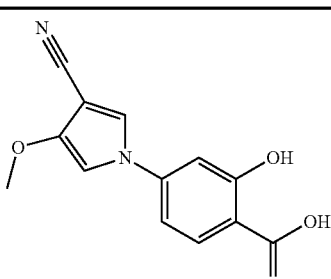 | 3.80 (3 H, s), 7.15-7.50 (3 H, m), 7.80-7.95 (1 H, m), 8.15-8.30 (1 H, m)/MS (m/z): 257 (M – H)– |
| 283 | 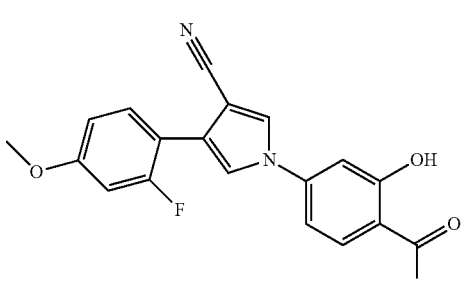 | 3.83 (3 H, s), 6.85-7.10 (2 H, m), 7.25-7.65 (3 H, m), 7.75-8.00 (2 H, m), 8.40-8.60 (1 H, m)/MS (m/z): 351 (M – H)– |
TABLE 54
| Ex. No. | Strc. | ¹H-NMR δ ppm: DMSO-d6/MS (m/z) |
|---|---|---|
| 284 | 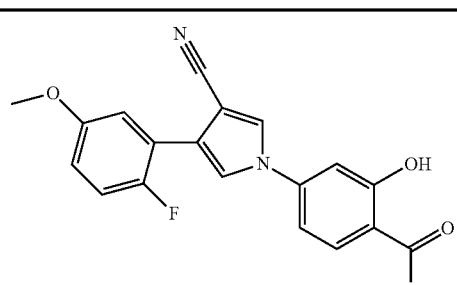 | 3.80 (3 H, s), 6.85-7.05 (1 H, m), 7.15-7.50 (4 H, m), 7.80-8.05 (2 H, m), 8.45-8.60 (1 H, m)/MS (m/z): 351 (M – H)– |
| 285 | 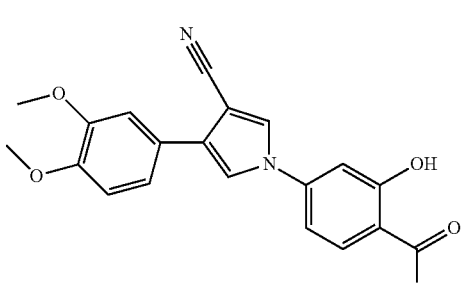 | 3.79 (3 H, s), 3.83 (3 H, s), 6.95-7.55 (5 H, m), 7.85-8.15 (2 H, m), 8.40-8.60 (1 H, m)/MS (m/z): 363 (M – H)– |

TABLE 54-continued

| Ex. No. | Strc. | ¹H-NMR δ ppm: DMSO-d6/MS (m/z) |
|---|---|---|
| 286 | | 3.90 (3 H, s), 7.25-8.15 (10 H, m), 8.50-8.65 (1 H, m)/MS (m/z): 383 (M − H)− |
| 287 | | 2.70-3.05 (4 H, m), 7.10-7.60 (8 H, m), 7.75-7.95 (1 H, m), 8.20-8.40 (1 H, m)/MS (m/z): 331 (M − H)− |
| 288 | | 6.95-7.65 (9 H, m), 7.80-8.10 (2 H, m), 8.35-8.55 (1 H, m)/MS (m/z): 329 (M − H)− |
| 289 | | 7.25-7.55 (4 H, m), 7.65-8.30 (5 H, m), 8.45-8.70 (1 H, m)/MS (m/z): 359 (M − H)− |
| 290 | | 7.10-8.05 (8 H, m), 8.15-.8.80 (2 H, m)/MS (m/z): 343 (M − H)− |

TABLE 55
| Ex. No. | Strc. | $^1$H-NMR δ ppm: DMSO-d6/MS (m/z) |
|---|---|---|
| 291 | 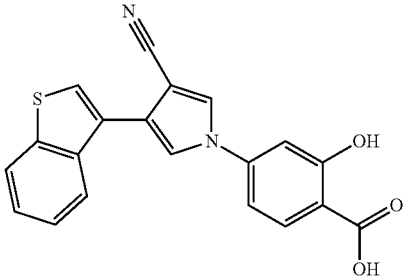 [SMILES: N#Cc1cn(-c2ccc(C(=O)O)c(O)c2)cc1-c1csc2ccccc12] | 7.30-7.60 (4 H, m), 7.79-8.20 (5 H, m), 8.50-8.70 (1 H, m)/MS (m/z): 359 (M − H)− |
| 292 | 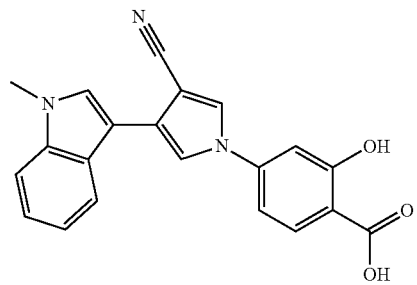 [SMILES: Cn1cc(-c2cn(-c3ccc(C(=O)O)c(O)c3)cc2C#N)c2ccccc21] | 3.87 (3 H, s), 7.05-8.10 (9 H, m), 8.40-8.60 (1 H, m)/MS (m/z): 356 (M − H)− |
| 293 | 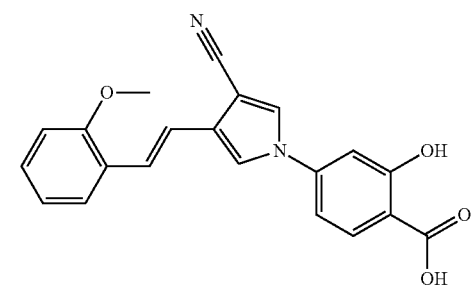 [SMILES: COc1ccccc1/C=C/c1cn(-c2ccc(C(=O)O)c(O)c2)cc1C#N] | 3.85 (3 H, s), 6.85-7.65 (8 H, m), 7.80-8.10 (2 H, m), 8.35-8.55 (1 H, m)/MS (m/z): 359 (M − H)− |
| 294 | 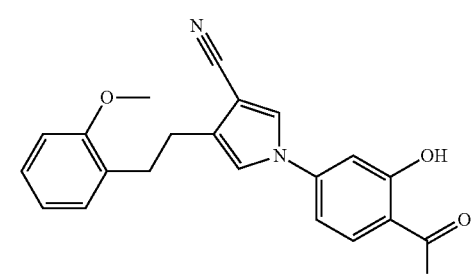 | 2.65-3.00 (4 H, m), 3.80 (3 H, s), 6.75-7.35 (6 H, m), 7.45-7.60 (1 H, m), 7.79-7.95 (1 H, m), 8.20-8.40 (1 H, m)/MS m/z): 361 (M − H)− |
| 295 | 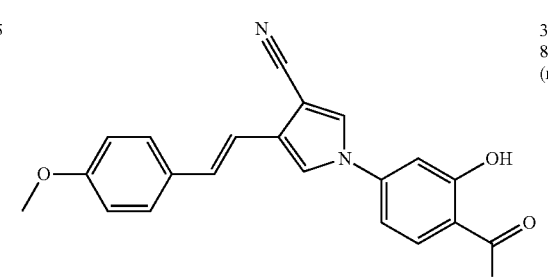 | 3.78 (3 H, s), 6.80-7.60 (8 H, m), 7.80-8.05 (2 H, m), 8.30-8.55 (1 H, m)/MS (m/z): 359 (M − H)− |

TABLE 55-continued
| Ex. No. | Strc. | ¹H-NMR δ ppm: DMSO-d6/MS (m/z) |
|---|---|---|
| 296 | 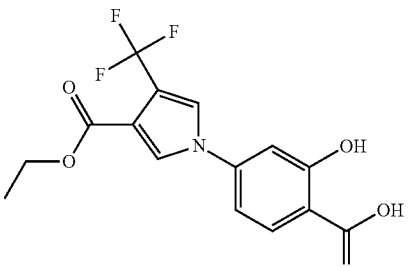 | 2.70-2.95 (4 H, m), 3.71 (3 H, s), 6.85 (2 H, d, J = 8.5 Hz), 7.16 (2 H, d, J = 8.5 Hz), 7.22 (1 H, dd, J = 8.7, 2.2 Hz), 7.27 (1 H, d, J = 2.2 Hz), 7.45-7.60 (1 H, m), 7.87 (1 H, d, J = 8.7 Hz), 8.20-8.40 (1 H, m)/MS (m/z): 361 (M − H)− |
| 297 | | 6.70-6.90 (2 H, m), 7.40-7.75 (3 H, m)/ MS (m/z): 314 (M − H)− |
TABLE 56
| Ex. No. | Strc. | ¹H-NMR δ ppm: DMSO-d6/MS (m/z) |
|---|---|---|
| 298 | 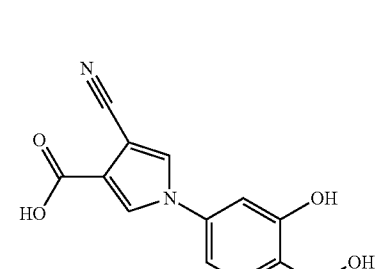 | 1.20-1.40 (3 H, m), 4.15-4.35 (2 H, m), 7.30-7.55 (2 H, m), 7.80-7.95 (1 H, m), 8.10-8.40 (2 H, m)/MS (m/z): 342 (M − H)− |
| 299 | | 7.25-7.55 (2 H, m), 7.80-8.00 (1 H, m), 8.10-8.65 (2 H, m)/MS (m/z): 271 (M − H)− |

TABLE 56-continued

| Ex. No. | Strc. | ¹H-NMR δ ppm: DMSO-d6/MS (m/z) |
|---|---|---|
| 300 | | 7.20-7.50 (2 H, m), 7.85-8.00 (1H, m), 8.30-8.75 (2 H, m)/MS (m/z): 295 (M − H)− |
| 301 | | 7.25-7.55 (5 H, m), 7.65-8.20 (4 H, m), 8.40-8.65 (1 H, m) |
| 302 | | 7.40-7.75 (5 H, m), 7.85-8.10 (3 H, m), 9.57 (1 H, s) |
| 303 | | 6.85-7.45 (10H, m), 7.60-7.70 (1H, m), 7.76 (1 H, d, J = 2.4 Hz), 7.82 (1H, d, J = 8.5 Hz), 8.37 (1H, d, J = 2.6 Hz) |
| 304 | | 6.30-6.40 (1H, m), 6.45-6.55 (1H, m), 7.00-7.55 (9H, m), 7.85 (1H, d, J = 6.4 Hz), 8.35 (1H, J = 2.4 Hz) |

TABLE 57

| Ex. No. | Strc. | ¹H-NMR δ ppm: DMSO-d6/MS (m/z) |
|---|---|---|
| 305 | (structure) | 4.25-4.35 (4H, m), 6.95 (1H, d, J = 8.7 Hz), 7.21 (1H, dd, J = 8.4 Hz, 2.2 Hz), 7.33 (1H, dd, J = 8.7 Hz, 2.2 Hz), 7.40 (1H, d, 2.2 Hz), 7.90 (1H, d, J = 8.7 Hz), 8.03 (1H, d, J = 2.4 Hz), 8.47 (1H, d, J = 2.4 Hz) |
| 306 | (structure) | 7.10-7.20 (1H, m), 7.35 (1H, dd, J = 8.7 Hz, 2.3 Hz), 7.40-7.50 (2H, m), 7.50-7.60 (1H, m), 7.91 (1H, d, J = 8.7 Hz), 8.08 (1H, d, J = 2.4 Hz), 8.52 (1H, d, J = 2.4 Hz) |
| 307 | (structure) | 2.36 (3H, s), 7.20-7.45 (6H, m), 7.81 (1H, s, J = 2.4 Hz), 7.90 (1H, d, J = 8.3 Hz), 8.51 (1H, s, J = 2.4 Hz) |
| 308 | (structure) | 7.25-7.70 (6H, m), 7.80-8.00 (2H, m), 8.45-8.60 (1H, m) |
| 309 | (structure) | 3.84 (3H, s), 6.95-7.20 (2H, m), 7.25-7.55 (4H, m), 7.75-7.95 (2H, m), 8.40-8.50 (1H, m) |

TABLE 57-continued

| Ex. No. | Strc. | ¹H-NMR δ ppm: DMSO-d6/MS (m/z) |
|---|---|---|
| 310 | | 2.48 (3H, s), 6.80-6.90 (1H, m), 7.15-7.50 (3H, m), 7.80-8.05 (2H, m), 8.45-8.55 (1H, m) |
| 311 | | 2.29 (3H, s), 7.03 (1H, d, J = 5.2 Hz), 7.34 (1H, dd, J = 8.7 Hz, 2.3 Hz), 7.42 (1H, d, J = 2.3 Hz), 7.50 (1H, d, J = 5.4 Hz), 7.84 (1H, d, J = 2.4 Hz), 7.91 (1H, d, J = 8.7 Hz), 8.52 (1H, d, J = 2.4 Hz) |

TABLE 58

| Ex. No. | Strc. | ¹H-NMR δ ppm: DMSO-d6/MS (m/z) |
|---|---|---|
| 312 | | 7.25-7.45 (2H, m), 7.50-8.00 (6H, m), 8.45-8.60 (1H, m) |
| 313 | | 7.10-7.50 (4H, m), 7.92 (1H, d, J = 8.6 Hz), 8.05-8.20 (1H, m), 8.45-8.65 (1H, m) |
| 314 | | 7.35-7.60 (3H, m), 7.65-7.85 (2H, m), 7.92 (1H, d, J = 8.5 Hz), 8.10-8.20 (1H, m), 8.45-8.55 (1H, m) |
| 315 | | 7.30-7.50 (4H, m), 7.65-8.00 (3H, m), 8.05-8.25 (1H, m), 8.45-8.60 (1H, m) |
| 316 | | 3.80 (3H, s), 7.00-7.10 (2H, m), 7.25-7.50 (2H, m), 7.60-7.75 (2H, m), 7.91 (1H, d, J = 8.7 Hz), 8.00-8.05 (1H, m), 8.40-8.50 (1H, m) |
| 317 | | 2.34 (3H, s), 7.28 (2H, d, J = 7.9 Hz), 7.30-7.50 (2H, m), 7.63 (2H, d, J = 7.9 Hz), 7.91 (1H, d, J = 8.3 Hz), 8.05-8.10 (1H, m), 8.45-8.60 (1H, m) |

TABLE 58-continued

| Ex. No. | Strc. | $^1$H-NMR δ ppm: DMSO-d6/MS (m/z) |
|---|---|---|
| 318 | | 7.30-7.50 (2H, m), 7.75-8.05 (5H, m), 8.20-8.40 (1H, m), 8.50-8.65 (1H, m) |

TABLE 59

| Ex. No. | Strc. | $^1$H-NMR δ ppm: DMSO-d6/MS (m/z) |
|---|---|---|
| 319 | | 7.25-7.55 (5H, m), 7.60-7.75 (1H, m), 7.35-8.05 (2H, m), 8.50-8.60 (1H, m) |
| 320 | | 7.25-7.40 (3H, m), 7.43 (1H, d, J = 2.2 Hz), 7.70-7.85 (2H, m), 7.92 (1H, d, J = 8.6 Hz), 8.10-8.15 (1H, m), 8.50-8.55 (1H, m) |
| 321 | | 6.07 (2H, s), 7.00-7.45 (5H, m), 7.85-8.00 (1H, m), 8.04 (1H, d, J = 2.5 Hz), 8.48 (1H, d, J = 2.5 Hz) |
| 322 | | 6.11 (2H, s), 6.90-7.05 (2H, m), 7.15-7.30 (2H, m), 7.35 (1H, d, J = 2.3 Hz), 7.80-7.95 (2H, m), 8.53 (1H, d, J = 2.3 Hz) |

TABLE 59-continued

| Ex. No. | Strc. | $^1$H-NMR δ ppm: DMSO-d6/MS (m/z) |
|---|---|---|
| 323 | | 6.90-7.60 (11H, m), 7.80-7.95 (1H, m), 8.17 (1H, d, J = 2.4 Hz), 8.52 (1H, d, J = 2.4 Hz) |
| 324 | | 7.05-7.45 (9H, m), 7.75-7.95 (3H, m), 8.09 (1H, d, J = 2.4 Hz), 8.51 (1H, d, J = 2.4 Hz) |
| 325 | | 7.35-7.65 (6H, m), 7.90-8.10 (5H, m), 8.61 (1H, d, J = 2.4 Hz) |

TABLE 60

| Ex. No. | Strc. | $^1$H-NMR δ ppm: DMSO-d6/MS (m/z) |
|---|---|---|
| 326 | | 7.35-7.55 (5H, m), 7.74 (2H, d, J = 7.9 Hz), 7.79 (2H, d, J = 8.3 Hz), 7.85 (2H, d, J = 8.3 Hz), 7.92 (1H, d, J = 7.9 Hz), 8.20 (1H, d, J = 2.4 Hz), 8.54 (1H, d, J = 2.4 Hz) |
| 327 | | 0.76 (3H, t, J = 7.4 Hz), 2.68 (2H, q, J = 7.4 Hz), 7.07 (1H, dd, J = 6.6, 2.3 Hz), 7.14 (1H, d, J = 2.3 Hz), 7.37-7.52 (5H, m), 7.85-8.00 (2H, m) |

TABLE 60-continued

| Ex. No. | Strc. | ¹H-NMR δ ppm: DMSO-d6/MS (m/z) |
|---|---|---|
| 328 | | 7.10-7.35 (7H,m), 7.40-7.85 (6H, m), 8.30 (1H, d, J = 2.2 Hz) |
| 329 | | 7.30-8.10 (12H, m), 8.27 (1H, d, J = 2.3 Hz), 8.56 (1H, d, J = 2.3 Hz) |
| 330 | | 7.65-8.10 (6H, m), 8.15-8.90 (3H, m) |
| 331 | | 7.25-7.50 (2H, m), 7.85-8.00 (5H, m), 8.34 (1H, d, J = 2.3 Hz), 8.59 (1H, d, J = 2.3 Hz) |

TABLE 61

| Ex. No. | Strc. | ¹H-NMR δ ppm: DMSO-d6/MS (m/z) |
|---|---|---|
| 332 | | 5.16 (2H, s), 6.95-7.05 (1H, m), 7.30-7.55 (10H, m), 7.85-8.00 (1H, m), 8.10-8.60 (2H, m) |
| 333 | | 5.19 (2H, s), 7.00-7.56 (11H, m), 7.81 (1H, d, J = 2.5 Hz), 7.87 (1H, d, J = 8.9 Hz), 8.45 (1H, d, J = 2.5 Hz) |
| 334 | | 5.16 (2H, s), 7.05-7.90 (12H, m), 8.02 (1H, d, J = 2.5 Hz), 8.48 (1H, d, J = 2.5 Hz) |
| 335 | | 1.37 (3H, t, J = 7.0 Hz), 4.09 (2H, q, J = 7.0 Hz), 6.85-7.50 (6H, m), 7.85-8.55 (3H, m) |
| 336 | | 0.99 (3H, t, J = 6.8 Hz), 1.78 (2H, sext, J = 6.8 Hz), 3.98 (2H, t, J = 6.8 Hz), 6.85-6.95 (1H, m), 7.25-7.50 (5H, m), 7.91 (1H, d, J = 8.5 Hz), 8.16 (1H, d, J = 2.5 Hz), 8.51 (1H, d, J = 2.5 Hz) | ns
TABLE 61-continued

| Ex. No. | Strc. | ¹H-NMR δ ppm: DMSO-d6/MS (m/z) |
|---|---|---|
| 337 | (structure) | 7.36 (1H, dd, J = 8.8, 2.0 Hz), 745 (1H, d, J = 2.0 Hz), 7.87 (2H, d, J = 8.2 Hz), 7.92 (1H, d, J = 8.8 Hz), 8.02 (2H, d, J = 8.2 Hz), 8.27 (1H, d, J = 2.5 Hz), 8.57 (1H, d, J = 2.3 Hz) |

TABLE 62

| Ex. No. | Strc. | ¹H-NMR δ ppm: DMSO-d6/MS (m/z) |
|---|---|---|
| 338 | (structure) | 6.80-7.50 (6H, m), 7.75-8.45 (3H, m), 9.83 (1H, brs) |
| 339 | (structure) | 6.80-7.60 (6H, m), 7.85-8.00 (2H, m), 8.45 (1H, d, J = 2.4 Hz), 9.60 (1H, brs) |
| 340 | (structure) | 1.35 (3H, t, J = 6.9 Hz), 4.06 (2H, q, J = 6.9 Hz), 6.95-7.95 (7H, m), 8.01 (1H, d, J = 2.4 Hz), 8.47 (1H, d, J = 2.4 Hz) |
| 341 | (structure) | 1.39 (3H, t, J = 6.8 Hz), 4.09 (2H, d, J = 6.8 Hz), 7.01 (1H, t, J = 8.0 Hz), 7.11 (1H, d, J = 8.3 Hz), 7.29-7.37 (3H, m), 7.46 (1H, dd, J = 5.3, 1.8 Hz), 7.81 (1H, d, J = 2.9 Hz), 7.90 (1H, d, J = 8.5 Hz), 8.44 (1H, d, J = 2.7 Hz) |
| 342 | (structure) | 0.99 (3H, t, J = 7.3 Hz), 1.74 (2H, q, J = 7.3 Hz), 3.97 (2H, t, J = 6.2 Hz), 7.02 (2H, d, J = 9.1 Hz), 7.33 (1H, dd, J = 6.6, 1.7 Hz), 7.40 (1H, d, J = 1.7 Hz), 7.64 (2H, d, J = 8.9 Hz), 7.89 (1H, d, J = 8.6 Hz), 8.01 (1H, d, J = 1.9 Hz), 8.47 (1H, d, J = 2.2 Hz) |
| 343 | (structure) | 1.3 (6H, d, J = 6.1 Hz), 4.69 (1H, quint, J = 6.1 Hz), 6.88-6.91 (1H, m), 7.25-7.45 (5H, m), 7.90 (1H, d, J = 8.5 Hz), 8.13 (1H, d, J = 2.5 Hz), 8.50 (1H, d, J = 2.5 Hz) |
| 344 | (structure) | 1.39 (3H, t, J = 7.0 Hz), 4.09 (2H, q, J = 7.0 Hz), 6.95-7.50 (6H, m), 7.79 (1H, d, J = 2.4 Hz), 7.89 (1H, d, J = 8.4 Hz), 8.42 (1H, d, J = 2.4 Hz), |

TABLE 63

| Ex.No. | Strc. | ¹H-NMR δ ppm: DMSO-d6/MS (m/z) |
|---|---|---|
| 345 | | 3.32 (3H, s), 3.65-3.80 (2H, m), 4.15-4.25 (2H, m), 7.00-7.65 (6H, m), 7.89 (1H, d, J = 8.6 Hz), 7.96 (1H, d, J = 2.3 Hz), 8.46 (1H, d, J = 2.3 Hz) |
| 346 | | 1.28 (6H, d, J = 5.6 Hz), 4.60-4.75 (1H, m), 6.95-7.70 (6H, m), 7.89 (1H, d, J = 8.7 Hz), 8.00 (1H, d, J = 2.4 Hz), 8.47 (1H, d, J = 2.4 Hz) |
| 347 | | 3.32 (3H, s), 3.55-3.70 (2H, m), 4.10-4.20 (2H, m), 7.00-7.70 (6H, m), 7.90 (1H, d, J = 8.7 Hz), 8.02 (1H, d, J = 2.4 Hz), 8.48 (1H, d, J = 2.4 Hz) |
| 348 | | 7.30-7.50 (2H, m), 7.76 (1H, d, J = 3.2 Hz), 7.85-8.00 (2H, m), 8.37 (1H, d, J = 2.3 Hz), 8.57 (1H, d, J = 2.3 Hz) |
| 349 | | 2.43 (3H, s), 7.15-7.55 (6H, m), 7.81 (1H, d, J = 2.3 Hz), 7.91 (1H, d, J = 8.3 Hz), 8.50 (1H, d, J = 2.3 Hz) |

TABLE 63-continued

| Ex.No. | Strc. | $^1$H-NMR δ ppm: DMSO-d6/MS (m/z) |
|---|---|---|
| 350 |  | 2.52 (3H, s), 7.30-7.50 (4H, m), 7.65-7.75 (2H, m), 7.92 (1H, d, J = 8.7 Hz), 8.12 (1H, d, J = 2.4 Hz), 8.51 (1H, d, J = 2.4 Hz) |
| 351 |  | 6.90-7.00 (1H, m), 7.38 (1H, dd, J = 8.7 Hz, 2.3 Hz), 7.45 (1H, d, J = 2.3 Hz), 7.65-7.75 (1H, m), 7.90 (1H, d, J = 8.7 Hz), 8.65-8.75 (1H, m) |

TABLE 64

| Ex. No. | Strc. | $^1$H-NMR δ ppm: DMSO-d6/MS (m/z) |
|---|---|---|
| 352 |  | 1.42 (9H, s), 7.40-7.50 (2H, m), 7.93 (1H, m), 9.39 (1H, s) |
| 353 |  | 7.05-7.15 (1H, m), 7.40-7.60 (2H, m), 7.90-8.00 (1H, m), 8.80-8.95 (1H, m) |
| 354 |  | 6.89 (1H, d, J = 2.5 Hz), 7.40-8.00 (3H, m), 8.67 (1H, d, J = 2.5 Hz) |
| 355 |  | 0.92 (3H, t, J = 7.0 Hz), 1.25-1.45 (2H, m), 1.50-1.70 (2H, m), 7.20-7.35 (2H, m), 7.45-7.55 (1H, m), 7.87 (1H, d, J = 7.7 Hz), 8.25-8.35 (1H, m) |
| 356 |  | 6.55-6.65 (1H, m), 6.70-6.80 (1H, m), 7.30-7.45 (2H, m), 7.70-7.80 (1H, m), 7.90 (1H, d, J = 8.6 Hz), 8.00-8.10 (1H, m), 8.45-8.55 (1H, m) |
| 357 |  | 3.87 (2H, s), 7.18-7.25 (2H, m), 7.25-7.35 (5H, m), 7.59 (1H, d, J = 2.5 Hz), 7.87 (1H, d, J = 8.4 Hz), 8.32 (1H, d, J = 8.3 Hz) |

TABLE 64-continued

| Ex. No. | Strc. | ¹H-NMR δ ppm: DMSO-d6/MS (m/z) |
|---|---|---|
| 358 | 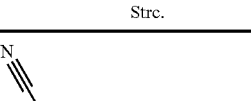 | 6.76 (1H, dd, J = 1.7, 3.1 Hz), 7.27 (1H, d, J = 2.2, 8.9 Hz), 7.34 (1H, d, J = 2.2 Hz), 7.70 (1H, dd, J = 2.3, 3.1 Hz), 7.89 (1H, d, J = 8.9 Hz), 8.39 (1H, dd, J = 1.7, 2.2 Hz) |

TABLE 65

| Ex. No. | Strc. | ¹H-NMR δ ppm: DMSO-d6/MS (m/z) |
|---|---|---|
| 359 | 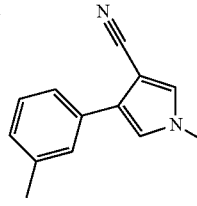 | 2.15 (3H, d, J = 0.8), 7.22 (1H, d, J = 2.3, 8.8 Hz), 7.27 (1H, d, J = 2.3 Hz), 7.49-7.52 (1H, m), 7.87 (1H, d, J = 8.8 Hz), 8.29 (1H, d, J = 2.3 Hz), 11.56 (1H, brs) |
| 360 | 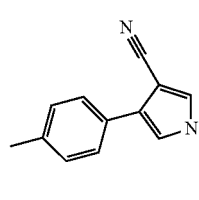 | 7.10-7.85 (4H, m), 8.25-8.80 (4H, m), 14.03 (1H, brs.) |
| 361 | 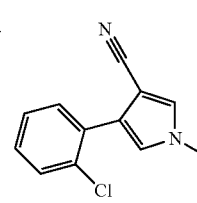 | 2.37 (3H, s), 7.25-7.40 (4H, m), 7.75-7.85 (1H, m), 7.95-8.05 (1H, m), 8.20-8.35 (1H, m), 8.65-8.75 (2H, m), 14.01 (1H, brs.) |

TABLE 65-continued

| Ex. No. | Strc. | ¹H-NMR δ ppm: DMSO-d6/MS (m/z) |
|---|---|---|
| 362 | 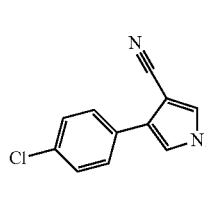 | 2.37 (3H, s), 7.10-7.25 (1H, m), 7.36 (1H, t, j = 7.7 Hz), 7.55-7.65 (2H, m), 7.81 (1H, dd, j = 5.0 Hz, 1.1 Hz), 8.30-8.35 (2H, m), 8.65-8.75 (2H, m), 14.01 (1H, brs.) |
| 363 | 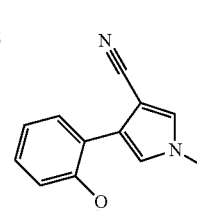 | 2.35 (3H, s), 7.28 (2H, d, j = 8.0 Hz), 7.65-7.70 (2H, m), 7.81 (1H, dd, j = 5.0 Hz, 1.2 Hz), 8.25-8.30 (2H, m), 8.65-8.75 (2H, m), 14.02 (1H, brs.) |
| 364 | | 7.40-7.50 (2H, m), 7.50-7.65 (2H, m), 7.82 (1H, dd, j = 5.1 Hz, 1.1 Hz), 8.14 (1H, d, j = 2.4 Hz), 8.25-8.30 (1H, m), 8.65-8.75 (1H, m), 8.76 (1H, d, j = 2.4 Hz), 14.02 (1H, brs.) |
| 365 | | 7.50-7.90 (5H, m), 8.25-8.80 (4H, m), 14.05 (1H, brs.) |
| 366 | | 3.84 (3H, s), 7.00-7.60 (4H, m), 7.75-8.75 (5H, m), 13.98 (1H, brs.) |

TABLE 66

| Ex. No. | Strc. | ¹H-NMR δ ppm: DMSO-d6/MS (m/z) |
|---|---|---|
| 367 | | 3.83 (3H, s), 6.90-7.00 (1H, m), 7.30-7.45 (3H, m), 7.75-7.85 (1H, m), 8.25-8.35 (1H, m), 8.39 (1H, d, j = 2.2 Hz), 8.65-8.75 (2H, m), 14.06 (1H, brs.) |

TABLE 66-continued

| Ex. No. | Strc. | ¹H-NMR δ ppm: DMSO-d6/MS (m/z) |
|---|---|---|
| 368 | (structure) | 3.80 (3H, s), 7.00-7.10 (2H, m), 7.65-7.90 (3H, m), 8.20-8.35 (2H, m), 8.47 (1H, d, j = 2.4 Hz), 8.69 (1H, d, j = 4.9 Hz) |
| 369 | (structure) | 4.28 (4H, s), 6.90-7.00 (1H, m), 7.20-7.30 (2H, m), 7.75-7.85 (1H, m), 8.20-8.35 (2H, m), 8.60-8.75 (2H, m), 13.98 (1H, brs.) |
| 370 | (structure) | 1.55-1.80 (4H, m), 2.15-2.45 (4H, m), 6.35-6.45 (1H, m), 7.77-7.80 (1H, m), 7.85-7.95 (1H, m), 8.20-8.30 (1H, m), 8.55-8.70 (2H, m), 13.95 (1H, brs.) |
| 371 | (structure) | 7.20-9.15 (10H, m), 13.50 (1H, brs.)/MS (m/z): 285 (M − H)− |
| 372 | (structure) | 7.10-7.25 (1H, m), 7.40-7.65 (2H, m), 8.00-8.10 (1H, m), 8.15-8.30 (1H, m), 8.40-8.55 (1H, m), 8.65-8.75 (1H, m), 8.95-9.05 (1H, m), 13.50 (1H, brs.)/MS (m/z): 294 (M − H)− |
| 373 | (structure) | 7.50-7.90 (3H, m), 7.95-8.10 (1H, m), 8.25-8.55 (2H, m), 8.60-8.75 (1H, m), 8.90-9.05 (1H, m), 13.49 (1H, brs.)/MS (m/z): 294 (M − H)− |

TABLE 67

| Ex. No. | Strc. | ¹H-NMR δ ppm: DMSO-d6/MS (m/z) |
|---|---|---|
| 374 | | 0.80-1.05 (3H, m), 1.25-1.45 (2H, m), 1.50-1.70 (2H, m), 2.40-2.65 (2H, m), 7.65-7.80 (1H, m), 7.85-8.00 (1H, m), 8.30-8.60 (2H, m), 8.85-9.05 (1H, m), 13.43 (1H, brs.)/MS (m/z): 268 (M − H)− |
| 375 | | 0.80-0.95 (3H, m), 1.20-1.45 (4H, m), 1.50-1.75 (2H, m), 2.40-2.60 (2H, m), 7.65-7.80 (1H, m), 7.85-8.00 (1H, m), 8.30-8.60 (2H, m), 8.85-9.05 (1H, m), 13.42 (1H, brs.)/MS (m/z): 282 (M − H)− |
| 376 | | 7.25-7.55 (4H, m), 7.65-8.15 (8H, m), 8.40-8.55 (1H, m)/MS (m/z): 286 (M − H)− |

TABLE 68

| Ref No. | Strc | (Solv) ¹H-NMR δ ppm: |
|---|---|---|
| 62 | | (DMSO-d6) 1.00-1.50 (5H, m), 1.55-1.85 (8H, m), 1.95-2.20 (1H, m), 6.14 (2H, brs.), 8.82 (1H, brs.) |
| 63 | | (CDCl3) 1.10-2.00 (10H, m), 3.10-3.30 (1H, m), 7.99 (1H, s), 9.97 (1H, s) |
| 64 | | (DMSO-d6) 1.00-2.00 (10H, m), 2.50-3.00 (1H, m), 7.50-9.00 (1H, m), 12.50-14.00 (1H, m) |

TABLE 68-continued

| Ref No. | Strc | (Solv) $^1$H-NMR δ ppm: |
|---|---|---|
| 65 | | (DMSO-d6) 7.52 (1H, d, J = 5.1 Hz), 8.27 (1H, d, J = 1.2 Hz) |
| 66 | | (DMSO-d6) 1.31 (3H, t, J = 7.1 Hz), 4.36 (2H, q, J = 7.1 Hz), 7.98 (1H, d, J = 5.2 Hz), 8.66 (1H, d, J = 1.9 Hz) |
| 67 | | (DMSO-d6) 1.26 (3H, t, J = 7.1 Hz), 4.29 (2H, q, J = 7.1 Hz), 5.33 (2H, s), 7.30-7.50 (5H, m), 7.78 (1H, s), 8.47 (1H, s) |
| 68 | | (CDCl3) 1.08 (9H, s), 4.72-4.74 (2H, m), 6.66-6.69 (1H, m), 7.22-7.25 (1H, m), 7.35-7.46 (6H, m), 7.66-7.74 (4H, m), 8.41 (1H, brs) |
| 69 | | (CDCl3) 7.05-7.20 (1H, m), 7.25-7.55 (2H, m), 7.81 (1H, s) |
| 70 | | (CDCl3) 7.25-7.60 (6H, m), 7.60-7.80 (3H, m), 8.40-8.60 (1H, m). |

TABLE 69

| Ref No. | Strc |
|---|---|
| 71 | |
| 72 | |

TABLE 69-continued
| Ref No. | Strc |
|---|---|
| 73 | 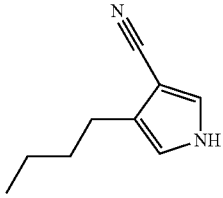 |
| 74 | 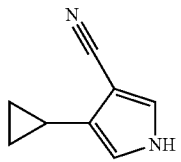 |
| 75 | 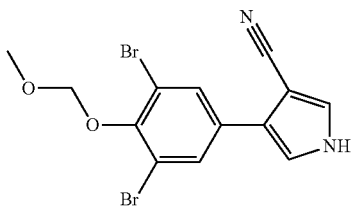 [SMILES: COCOc1c(Br)cc(-c2c[nH]cc2C#N)cc1Br] |
| 76 | 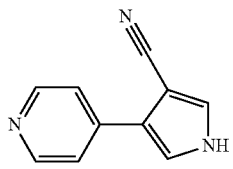 |
| 77 | 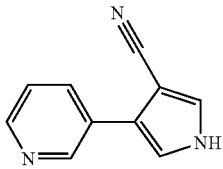 [SMILES: N#Cc1c[nH]cc1-c1cccnc1] |
| 78 | 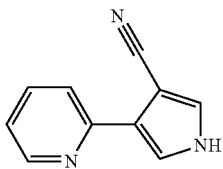 [SMILES: N#Cc1c[nH]cc1-c1ccccn1] |
| 79 | 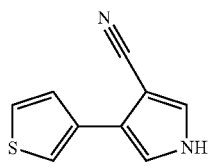 [SMILES: N#Cc1c[nH]cc1-c1ccsc1] |
| 80 | 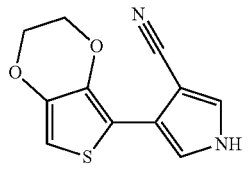 [SMILES: N#Cc1c[nH]cc1-c1scc2c1OCCO2] |
| 81 | 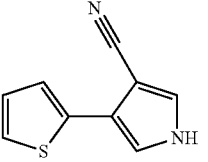 |
| 82 | 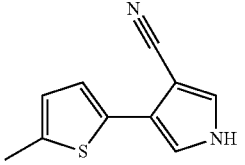 |
| 83 | 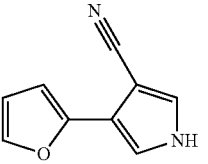 [SMILES: N#Cc1c[nH]cc1-c1cccs1] |
| 84 | 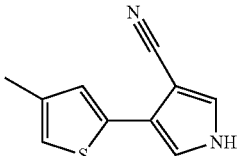 |
| 85 | 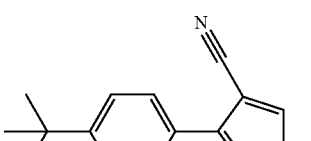 |
| 86 | 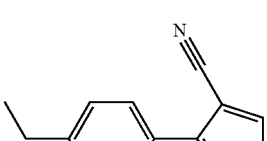 |
| 87 | 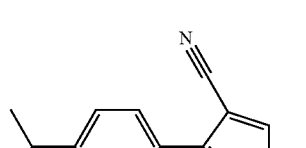 |
| 88 | 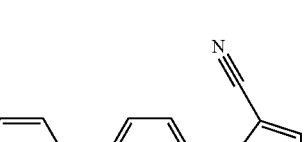 |

TABLE 69-continued
| Ref No. | Strc |
|---|---|
| 89 | 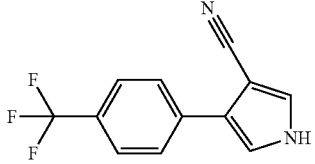 [SMILES: N#Cc1c[nH]cc1-c1ccc(C(F)(F)F)cc1] |
| 90 | 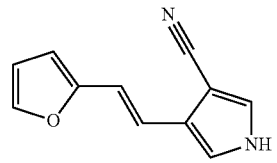 [SMILES: N#Cc1c[nH]cc1/C=C/c1ccco1] |
| 91 | 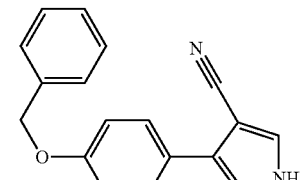 |
| 92 | 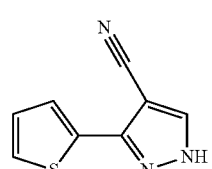 |
| 93 | 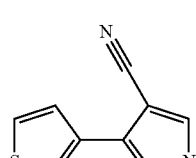 |
| 94 | 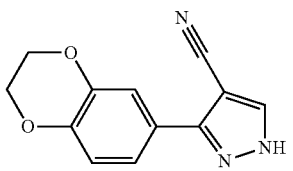 [SMILES: N#Cc1c[nH]nc1-c1ccc2c(c1)OCCO2] |
| 95 | 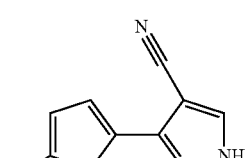 |
| 96 | 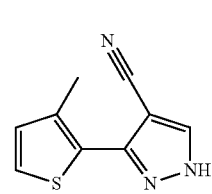 |
| 97 | 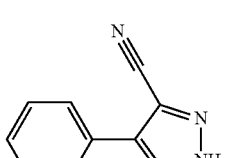 |
| 98 | 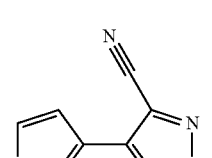 |
TABLE 70
| Ex No. | Strc | (Solv) $^1$H-NMR δ ppm: |
|---|---|---|
| 377 | 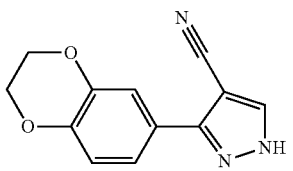 [SMILES: N#Cc1c[nH]nc1-c1ccc2c(c1)OCCO2] | (CDCl3) 1.40-1.55 (3H, m), 4.45-4.60 (2H, m), 7.25-7.55 (4H, m), 7.60-7.75 (3H, m), 7.80-8.00 (1H, m), 8.20-8.40 (1H, m), 8.80-9.00 (1H, m). |
| 378 | 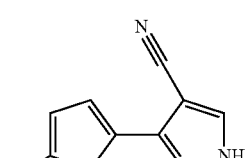 | (CDCl3) 1.38(3H, t, J = 7.2 Hz), 4.36 (2H, q, J = 7.2 Hz), 7.25-7.55 (4H, m), 7.60-7.80 (4H, m), 7.85-8.05 (2H, m). |

TABLE 70-continued
| Ex No. | Strc | (Solv) $^1$H-NMR δ ppm: |
|---|---|---|
| 379 | 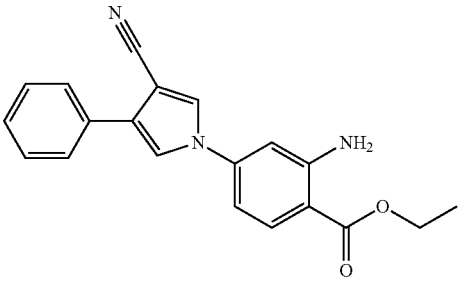 [SMILES: CCOC(=O)c1ccc(-n2cc(C#N)c(-c3ccccc3)c2)cc1N] | (CDCl3) 1.41 (3H, t, J = 7.2 Hz), 4.36 (2H, q, J = 7.2 Hz), 5.98 (2H, brs.), 6.60-6.75 (2H, m), 7.20-7.35 (2H, m), 7.40-7.50 (2H, m), 7.55-7.70 (3H, m), 7.95-8.05 (1H, m). |
| 380 | 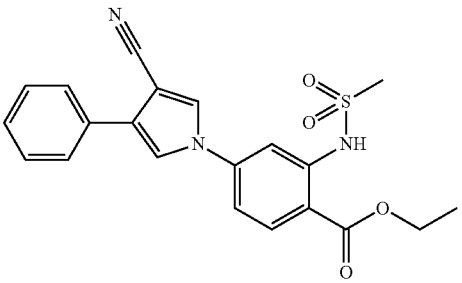 [SMILES: CCOC(=O)c1ccc(-n2cc(C#N)c(-c3ccccc3)c2)cc1NS(C)(=O)=O] | (CDCl3) 1.35-1.50 (3H, m), 3.13 (3H, s), 4.35-4.50 (2H, m), 7.10-7.50 (5H, m), 7.60-7.75 (3H, m), 7.80-7.95 (1H, m), 8.15-8.30 (1H, m), 10.75 (1H, brs.). |
| 381 | 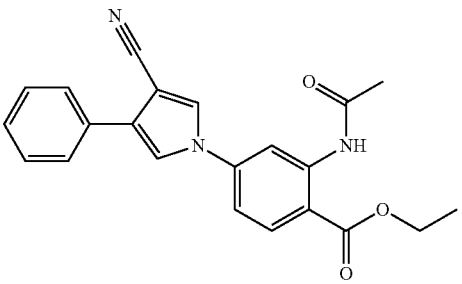 [SMILES: CCOC(=O)c1ccc(-n2cc(C#N)c(-c3ccccc3)c2)cc1NC(C)=O] | (CDCl3) 1.35-1.50 (3H, m), 2.29 (3H, s), 4.35-4.50 (2H, m), 7.05-7.20 (1H, m), 7.25-7.55 (4H, m), 7.60-7.75 (3H, m), 8.10-8.25 (1H, m), 8.90-9.10 (1H, m), 11.30 (1H, brs.). |
| 382 | 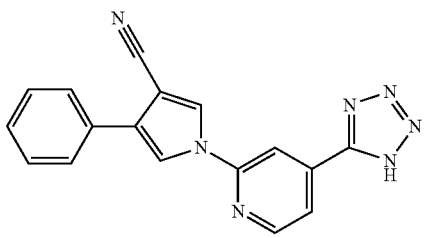 [SMILES: N#Cc1cn(-c2cc(-c3nnn[nH]3)ccn2)cc1-c1ccccc1] | (DMSO-d6) 7.30-7.60 (3H, m), 7.70-8.10 (3H, m), 8.25-8.60 (2H, m), 8.65-8.85 (2H, m). |
| 383 | 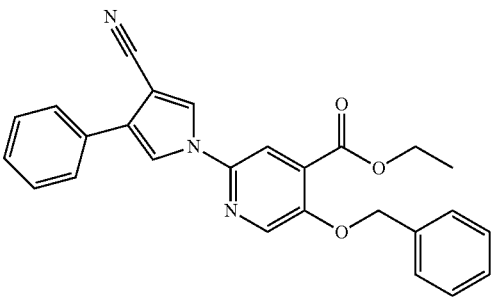 [SMILES: CCOC(=O)c1cc(-n2cc(C#N)c(-c3ccccc3)c2)ncc1OCc1ccccc1] | (DMSO-d6) 1.31 (3H, t, J = 7.1 Hz), 4.36 (2H, q, J = 7.1 Hz), 5.40 (2H, s), 7.30-7.80 (10H, m), 8.00-8.60 (4H, m) |

TABLE 71

| Ex No. | Strc | (Solv) $^1$H-NMR δ ppm: |
|---|---|---|
| 384 | | (DMSO-d6) 1.36 (3H, t, J = 7.1 Hz), 4.38 (2H, q, J = 7.1 Hz), 7.30-7.80 (5H, m), 8.01 (1H, s), 8.12 (1H, d, J = 2.4 Hz), 8.25 (1H, s), 8.49 (1H, d, J = 2.4 Hz) |
| 385 | | (DMSO-d6) 7.30-7.80 (5H, m), 8.07 (1H, s), 8.15 (1H, d, J = 2.3 Hz), 8.26 (1H, s), 8.49 (1H, d, J = 2.3 Hz) |
| 386 | | (CDCl3) 1.42 (3H, t, J = 7.22), 4.41 (2H, q, J = 7.22), 4.73-4.77 (2H, m), 7.15-7.18 (1H, m), 7.40-7.46 (2H, m), 7.55-7.58 (1H, m), 8.14-8.19 (2H, m) |
| 387 | | (DMSO-d6) 1.15 (3H, t, J = 7.1 Hz), 3.50 (2H, q, J = 7.1 Hz), 4.41 (2H, s), 7.60-7.67 (1H, m), 7.68-7.76 (2H, m), 7.96-8.06 (2H, m), 8.28-8.34 (1H, m) |
| 388 | | (CDCl3) 7.30-7.60 (5H, m), 7.60-7.90 (3H, m), 8.15-8.30 (1H, m), 8.75-8.95 (1H, m). |

TABLE 72
| Ex No. | Strc |
|---|---|
| 389 | |
| 390 | |
| 391 | |
| 392 | |
| 393 | |
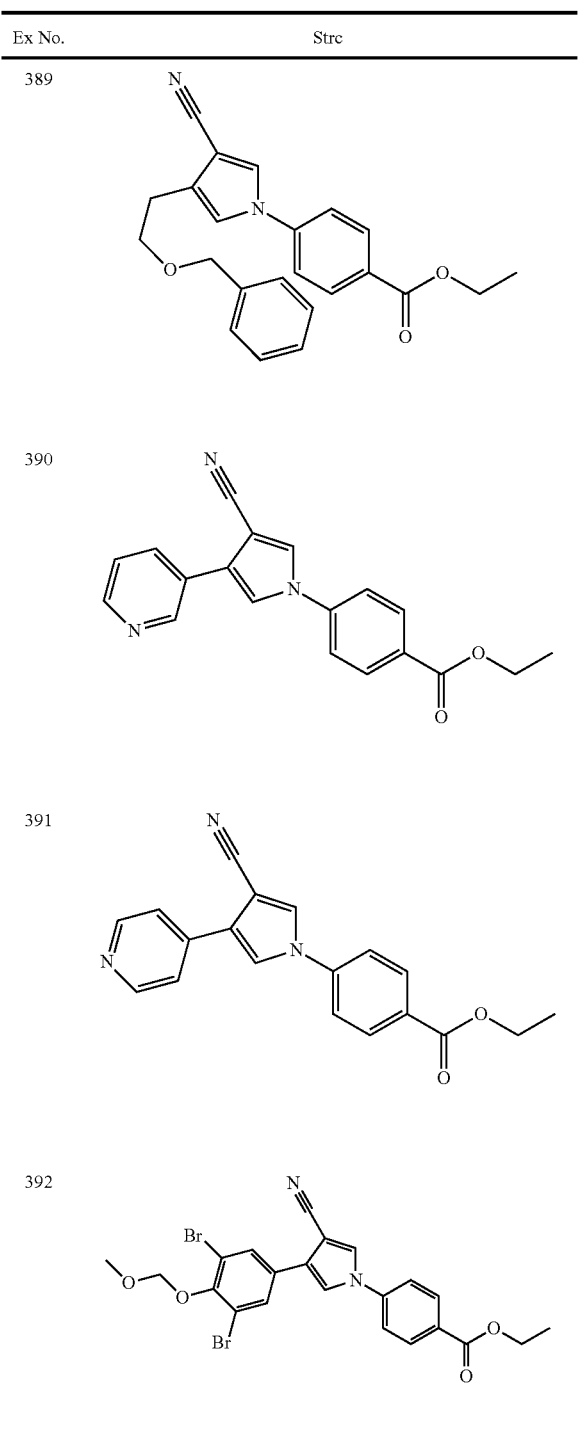
TABLE 72-continued
| Ex No. | Strc |
|---|---|
| 394 | |
| 395 | |
| 396 | |
| 397 | |
| 398 | |
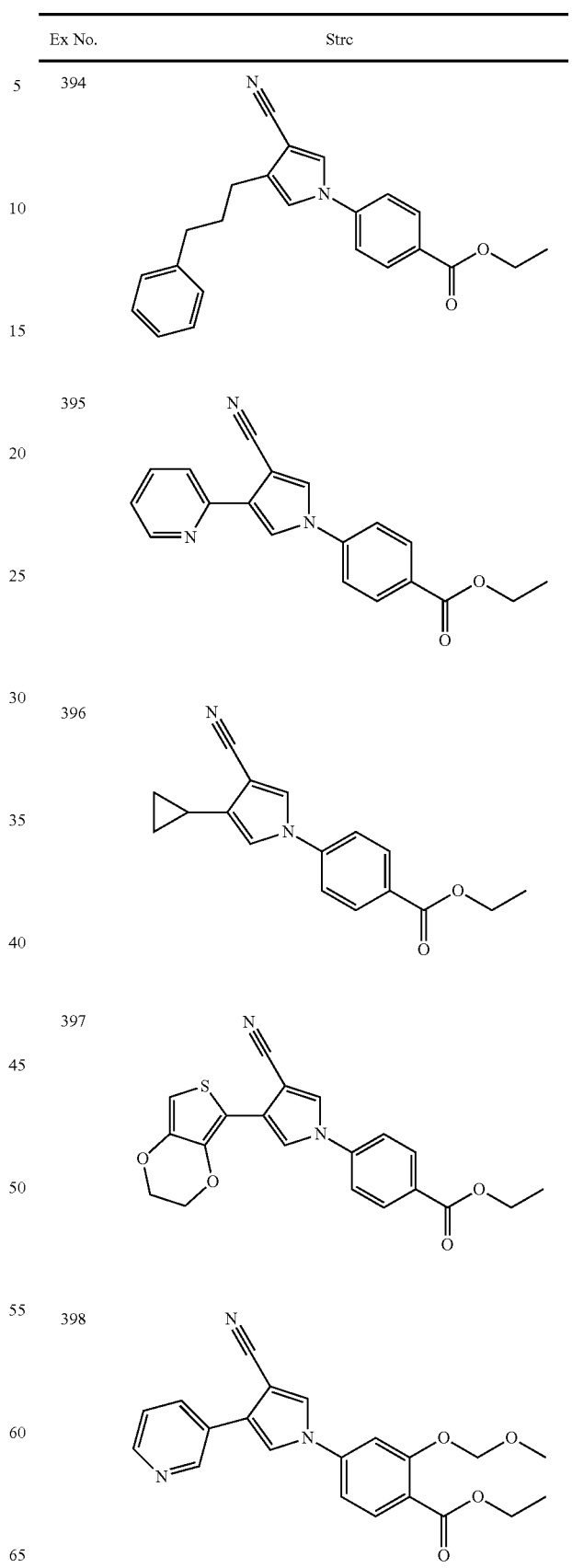

TABLE 72-continued
| Ex No. | Strc |
|---|---|
| 399 | 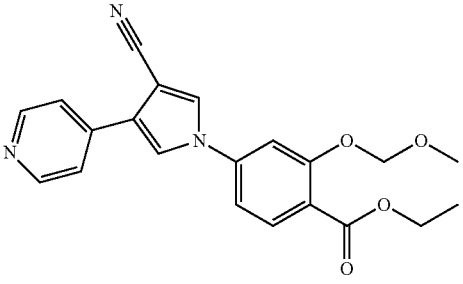 [SMILES: CCOC(=O)c1ccc(-n2cc(C#N)c(-c3ccncc3)c2)cc1OCOC] |
| 400 | 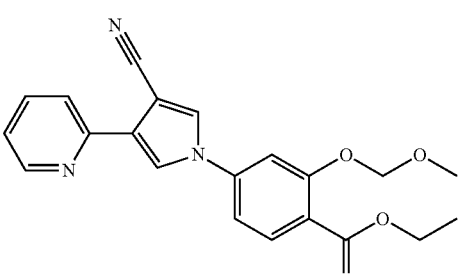 |
| 401 | 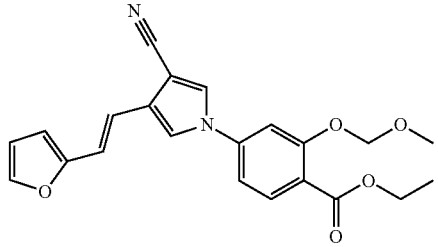 [SMILES: CCOC(=O)c1ccc(-n2cc(C#N)c(/C=C/c3ccco3)c2)cc1OCOC] |
| 402 | 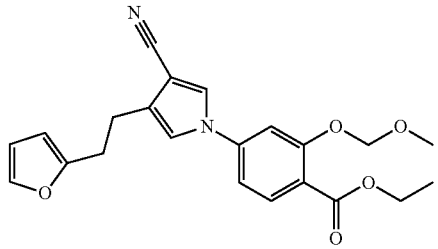 [SMILES: CCOC(=O)c1ccc(-n2cc(C#N)c(CCc3ccco3)c2)cc1OCOC] |
| 403 | 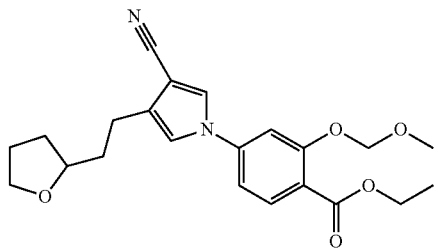 [SMILES: CCOC(=O)c1ccc(-n2cc(C#N)c(CCC3CCCO3)c2)cc1OCOC] |
TABLE 72-continued
| Ex No. | Strc |
|---|---|
| 404 | 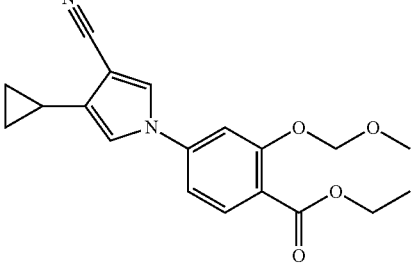 |
TABLE 73
| Ex No. | Strc |
|---|---|
| 405 | 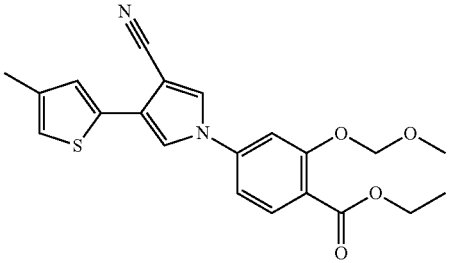 [SMILES: CCOC(=O)c1ccc(-n2cc(C#N)c(-c3cc(C)cs3)c2)cc1OCOC] |
| 406 | 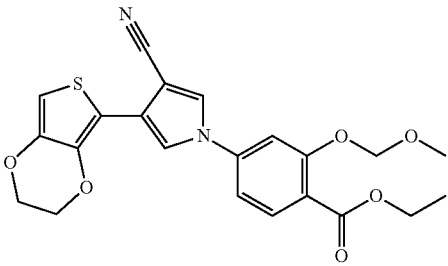 [SMILES: CCOC(=O)c1ccc(-n2cc(C#N)c(-c3scc4c3OCCO4)c2)cc1OCOC] |
| 407 | 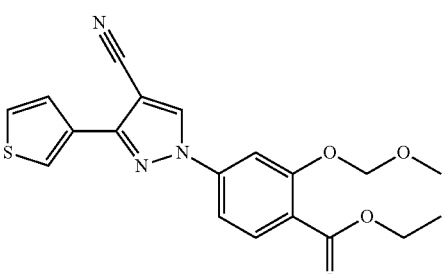 |
| 408 | 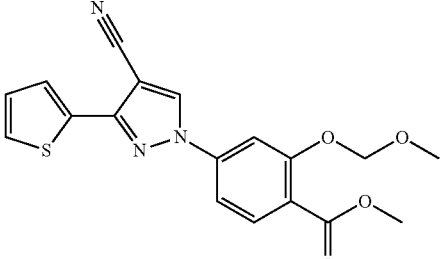 |

TABLE 73-continued
| Ex No. | Strc |
|---|---|
| 409 | 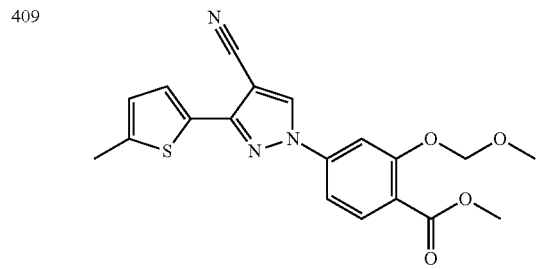 |
| 410 | 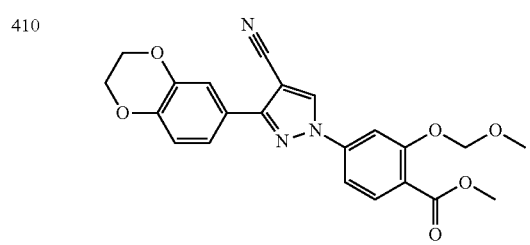 |
| 411 | 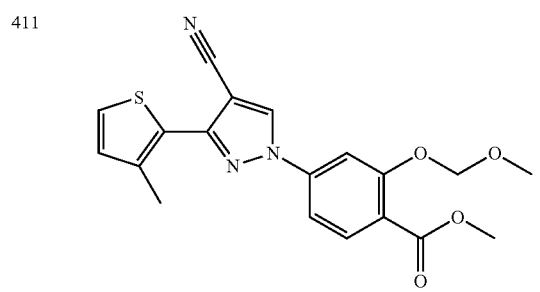 |
| 412 | 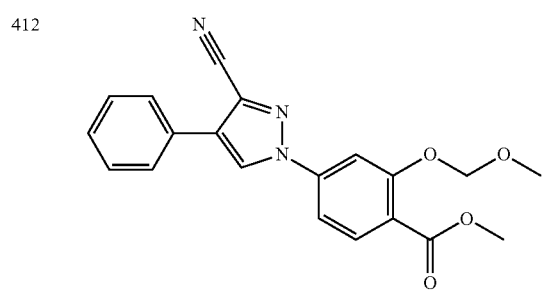 |
| 413 | 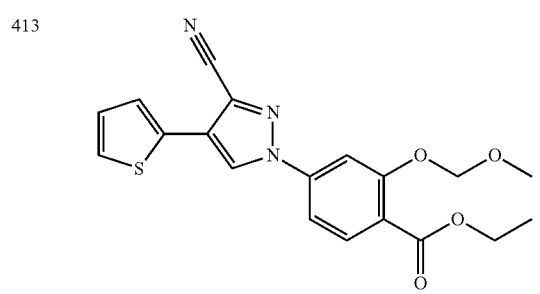 |
| 414 | 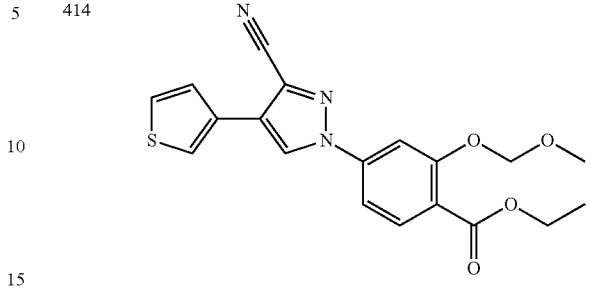 |
| 415 | 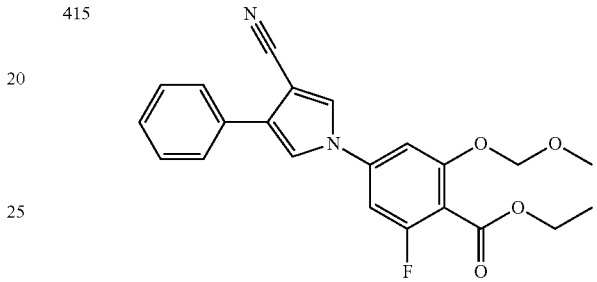 |
| 416 | 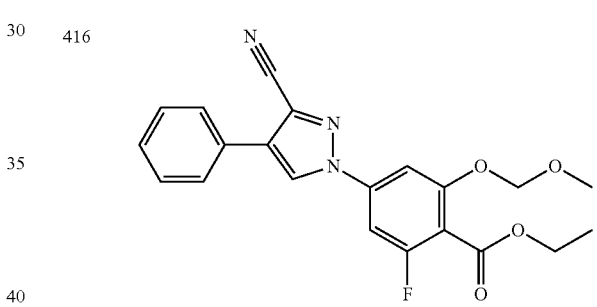 |
| 417 | 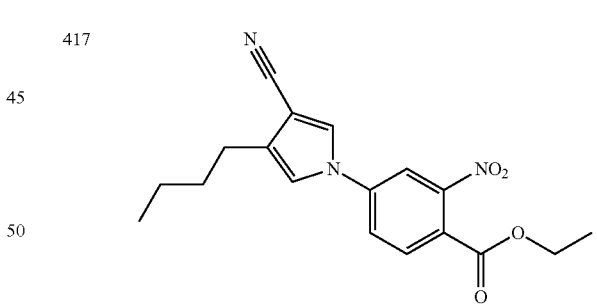 |
| 418 | 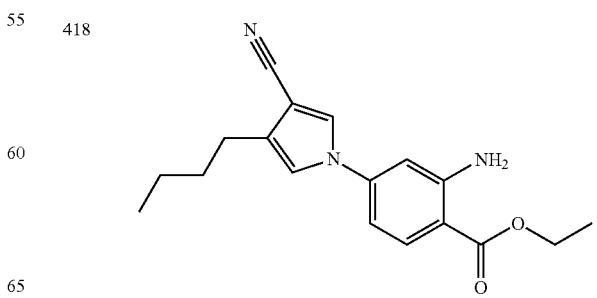 |

TABLE 73-continued
| Ex No. | Strc |
|---|---|
| 419 | 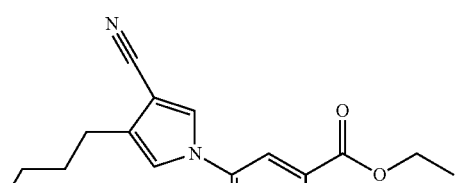 |
| 420 | 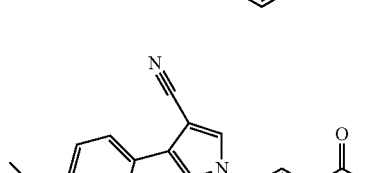 |
TABLE 74
| Ex No. | Strc |
|---|---|
| 421 | 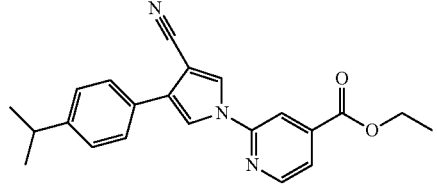 [SMILES: CCOC(=O)c1ccnc(-n2cc(C#N)c(-c3ccc(C(C)C)cc3)c2)c1] |
| 422 | 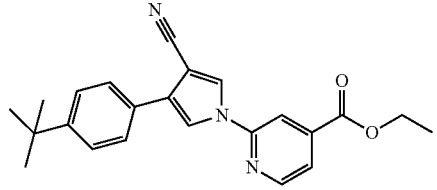 [SMILES: CCOC(=O)c1ccnc(-n2cc(C#N)c(-c3ccc(C(C)(C)C)cc3)c2)c1] |
| 423 | 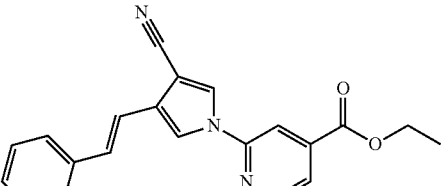 |
| 424 | 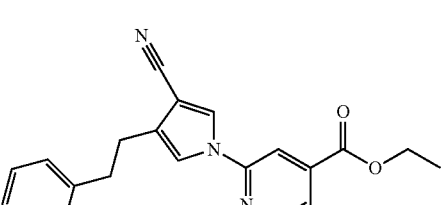 |
TABLE 74-continued
| Ex No. | Strc |
|---|---|
| 425 | |
| 426 | |
| 427 | |
| 428 | |
| 429 | |
| 430 | |

TABLE 74-continued
| Ex No. | Strc |
|---|---|
| 431 | 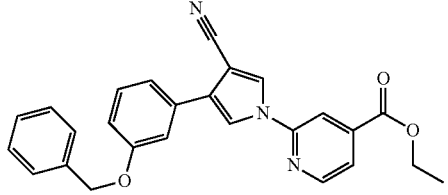 [SMILES: CCOC(=O)c1ccnc(-n2cc(C#N)c(-c3cccc(OCc4ccccc4)c3)c2)c1] |
| 432 | 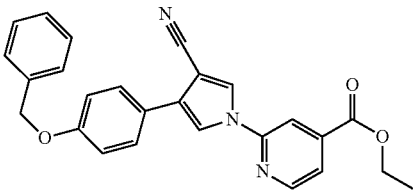 [SMILES: CCOC(=O)c1ccnc(-n2cc(C#N)c(-c3ccc(OCc4ccccc4)cc3)c2)c1] |
| 433 | 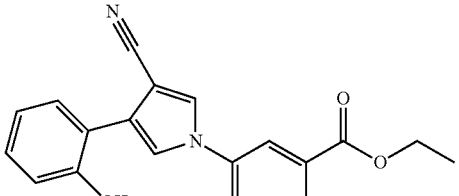 |
| 434 | 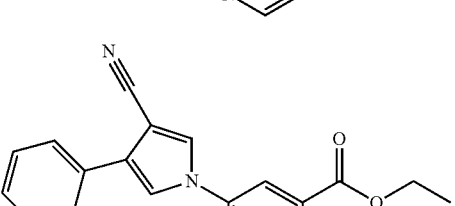 |
| 435 | 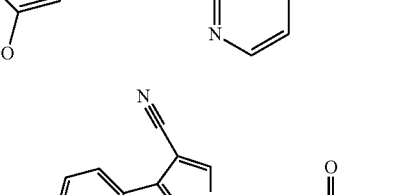 |
| 436 | 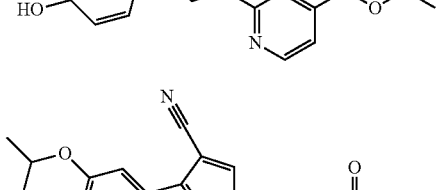 |
TABLE 75
| Ex No. | Strc |
|---|---|
| 437 | 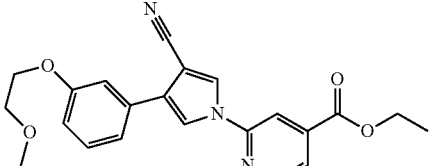 |
| 438 | 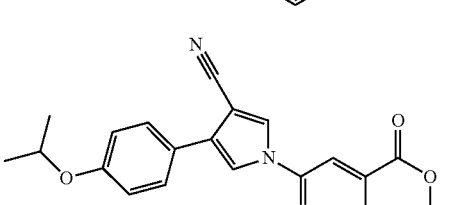 |
| 439 | 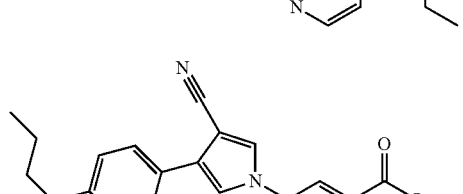 |
| 440 | 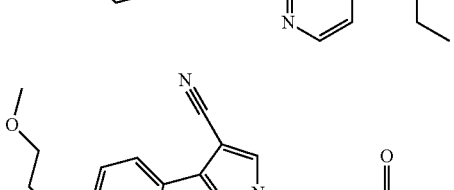 |
| 441 | 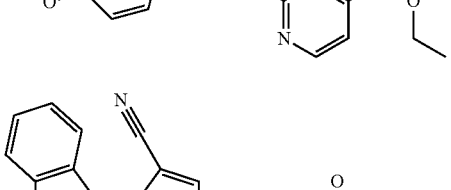 |
| 442 | 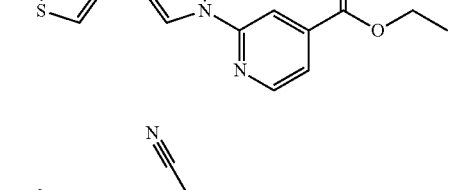 |
| 443 | 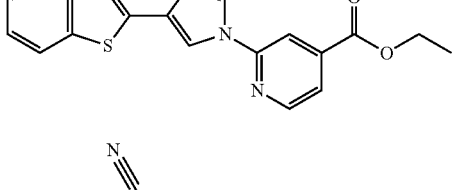 |
| 444 | 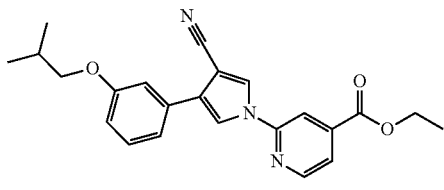 [SMILES: CCOC(=O)c1ccnc(-n2cc(C#N)c(-c3cccc(OCC(C)C)c3)c2)c1] |

TABLE 75-continued
| Ex No. | Strc |
|---|---|
| 445 | 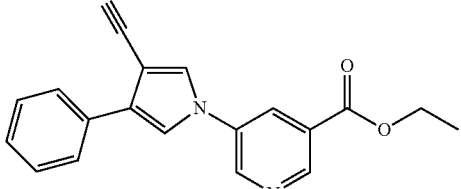 |
| 446 | 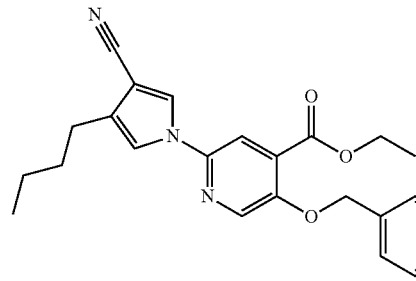 |
| 447 | 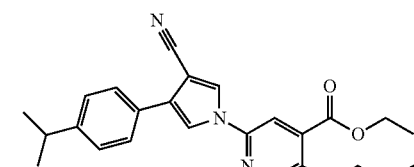 |
| 448 | 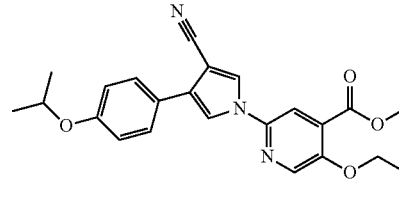 |
| 449 | 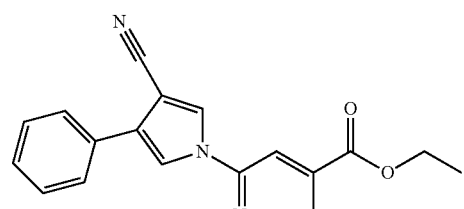 |
| 450 | 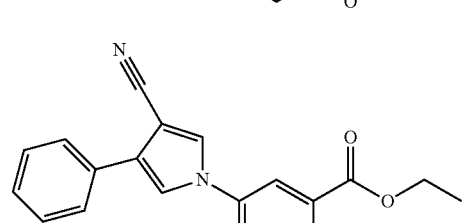 |
TABLE 76
| Ex No. | Strc | $^{1}$H-NMR δ ppm: DMSO-d6 |
|---|---|---|
| 451 | | 2.82 (2H, t, J = 6.8 Hz), 3.69 (2H, t, J = 6.8 Hz), 4.52 (2H, s), 7.20-7.40 (5H, m), 7.51 (1H, d, J = 2.4 Hz), 7.70-8.10 (4H, m), 8.29 (1H, d, J = 2.4 Hz), 13.00 (1H, brs) |
| 452 | | 7.45-7.60 (1H, m), 7.85-8.00 (2H, m), 8.05-8.20 (3H, m), 8.25 (1H, d, J = 2.4 Hz), 8.50-8.65 (2H, m), 8.90-9.05 (1H, m), 13.2 (1H, brs.) |

TABLE 76-continued
| Ex No. | Strc | ¹H-NMR δ ppm: DMSO-d6 |
|---|---|---|
| 453 | 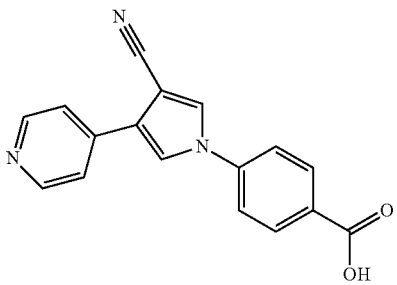 [SMILES: N#Cc1cn(-c2ccc(C(=O)O)cc2)cc1-c1ccncc1] | 7.90-8.00 (2H, m), 8.05-8.20 (2H, m), 8.25-8.35 (2H, m), 8.74 (1H, d, J = 2.3 Hz), 8.81 (1H, d, J = 2.3 Hz), 8.90-9.05 (2H, m) |
| 454 | 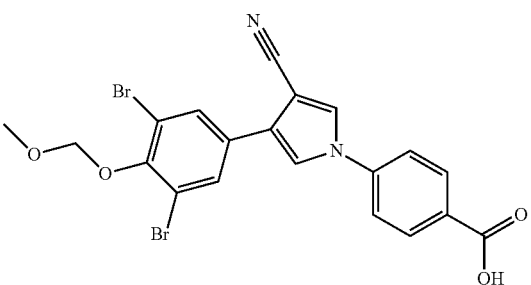 [SMILES: COCOc1c(Br)cc(-c2cn(-c3ccc(C(=O)O)cc3)cc2C#N)cc1Br] | 3.63 (3H, s), 5.18 (2H, s), 7.85-8.00 (2H, m), 8.00-8.15 (4H, m), 8.20-8.35 (1H, m), 8.45-8.60 (1H, m), 13.15 (1H, brs.). |
| 455 | 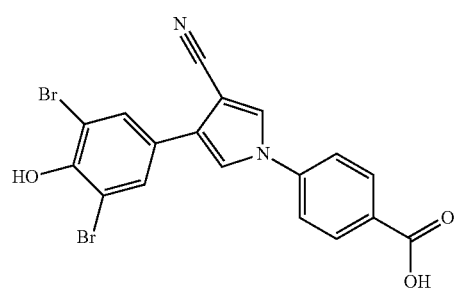 [SMILES: N#Cc1cn(-c2ccc(C(=O)O)cc2)cc1-c1cc(Br)c(O)c(Br)c1] | 7.80-8.25 (7H, m), 8.45-8.55 (1H, m), 10.13 (1H, brs.), 13.15 (1H, brs.). |
| 456 | 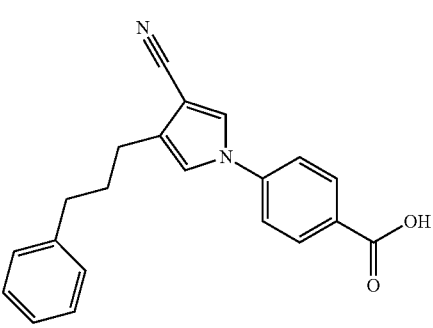 [SMILES: N#Cc1cn(-c2ccc(C(=O)O)cc2)cc1CCCc1ccccc1] | 1.90-2.00 (2H, m), 2.56 (2H, t, J = 7.6 Hz), 2.67 (2H, t, J = 7.6 Hz), 7.15-7.35 (5H, m), 7.53 (1H, d, J = 2.6 Hz), 7.76-7.82 (2H, m), 8.00-8.06 (2H, m), 8.29 (1H, d, J = 2.6 Hz), 13.06 (1H, brs) |
| 457 | 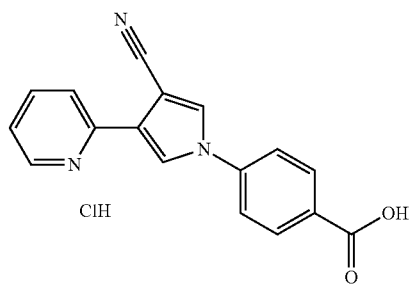 [SMILES: N#Cc1cn(-c2ccc(C(=O)O)cc2)cc1-c1ccccn1 ; Cl] | 7.30-7.45 (1H, m), 7.80-8.20 (6H, m), 8.30-8.75 (3H, m). |

TABLE 77

| Ex No. | Strc | ¹H-NMR δ ppm: DMSO-d6 |
| --- | --- | --- |
| 458 | | 0.60-0.75 (2H, m), 0.85-1.00 (2H, m), 1.65-1.85 (1H, m), 7.35-7.50 (1H, m), 7.76 (2H, d, J = 9.1 Hz), 8.02 (2H, d, J = 9.1 Hz), 8.25-8.30 (1H, m), 13.12 (1H, brs.). |
| 459 | | 4.10-4.45 (4H, m), 6.64 (1H, s), 7.75-7.90 (3H, m), 8.00-8.15 (2H, m), 8.40-8.55 (1H, m), 13.18 (1H, brs.). |
| 460 | | 7.30-7.60 (3H, m), 7.65-7.85 (2H, m), 8.10-8.45 (3H, m), 8.55-8.75 (1H, m), 9.10-9.30 (1H, m), 13.37 (1H, brs.). |
| 461 | | 3.44 (3H, s), 5.40 (2H, s), 7.30-7.55 (5H, m), 7.70-7.85 (3H, m), 8.06 (1H, d, J = 2.3 Hz), 8.48 (1H, d, J = 2.3 Hz), 12.84 (1H, brs.). |
| 462 | | 3.44 (3H, s), 5.40 (2H, s), 7.05-7.25 (1H, m), 7.35-7.65 (4H, m), 7.70-7.85 (1H, m), 7.90-8.10 (1H, m), 8.40-8.55 (1H, m), 12.84 (1H, brs.). |

TABLE 77-continued
| Ex No. | Strc | ¹H-NMR δ ppm: DMSO-d6 |
|---|---|---|
| 463 | 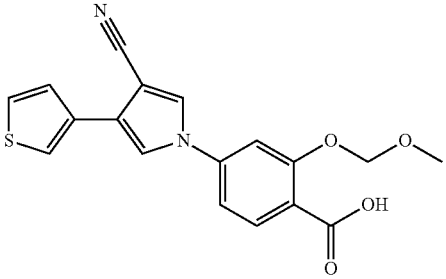 [SMILES: COCOc1cc(-n2cc(C#N)c(-c3ccsc3)c2)ccc1C(=O)O] | 3.44 (3H, s), 5.40 (2H, s), 7.35-7.60 (3H, m), 7.65-7.85 (3H, m), 8.06 (1H, d, J = 2.1 Hz), 8.44 (1H, d, J = 2.1 Hz), 12.84 (1H, brs.). |
| 464 | 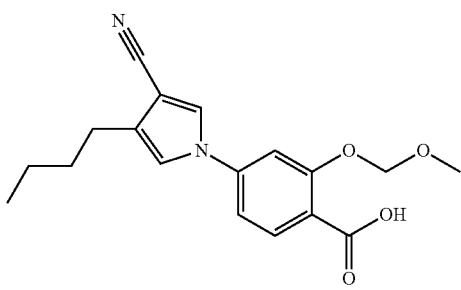 [SMILES: CCCCc1cn(-c2ccc(C(=O)O)c(OCOC)c2)cc1C#N] | 0.92 (3H, t, J = 7.5 Hz), 1.25-1.45 (2H, m), 1.50-1.70 (2H, m), 2.45-2.60 (2H, m), 3.42 (3H, s), 5.37 (2H. s), 7.25-7.50 (3H, m), 7.70-7.85 (1H, m), 8.15-8.35 (1H, m), 12.78 (1H, brs.). |
TABLE 78
| Ex No. | Strc | ¹H-NMR δ ppm: DMSO-d6 |
|---|---|---|
| 465 | 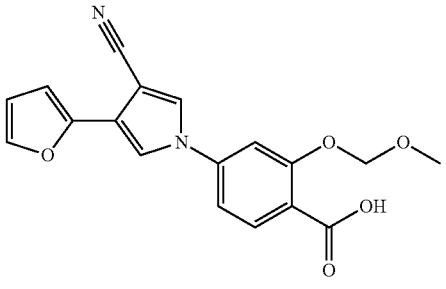 [SMILES: COCOc1cc(-n2cc(C#N)c(-c3ccco3)c2)ccc1C(=O)O] | 3.44 (3H, s), 5.40 (2H, s), 6.55-6.80 (2H, m), 7.35-7.55 (2H, m), 7.70-7.85 (2H, m), 7.90-8.10 (1H, m), 8.35-8.55 (1H, m), 12.86 (1H, brs.). |
| 466 | 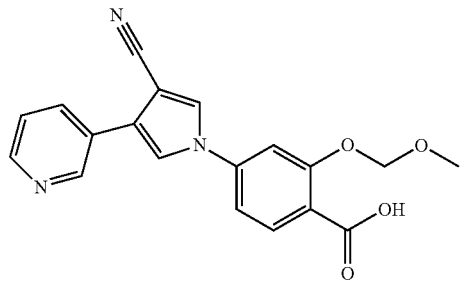 [SMILES: COCOc1cc(-n2cc(C#N)c(-c3cccnc3)c2)ccc1C(=O)O] | 3.44 (3H, s), 5.40 (2H, s), 7.40-7.60 (3H, m), 7.75-7.90 (1H, m), 8.00-8.30 (2H, m), 8.45-8.65 (2H, m), 8.85-9.05 (1H, m), 12.84 (1H, brs.). |
| 467 | 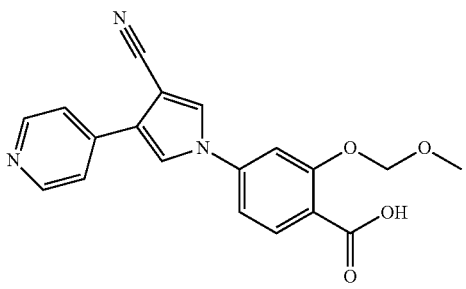 [SMILES: COCOc1cc(-n2cc(C#N)c(-c3ccncc3)c2)ccc1C(=O)O] | 3.44 (3H, s), 5.40 (2H, s), 7.35-7.60 (2H, m), 7.65-7.90 (3H, m), 8.25-8.40 (1H, m), 8.45-8.80 (3H, m), 12.89 (1H, brs.). |

TABLE 78-continued

| Ex No. | Strc | ¹H-NMR δ ppm: DMSO-d6 |
| --- | --- | --- |
| 468 | | 7.30-7.50 (2H, m), 7.60-7.75 (1H, m), 7.85-8.00 (1H, m), 8.15-8.40 (2H, m), 8.50-8.75 (2H, m), 8.95-9.10 (1H, m). |
| 469 | | 7.30-7.60 (2H, m), 7.85-8.05 (1H, m), 8.10-8.30 (2H, m), 8.60-9.00 (4H, m). |
| 470 | | 7.30-7.50 (3H, m), 7.85-8.05 (3H, m), 8.35-8.70 (3H, m). |
| 471 | | 6.45-6.65 (2H, m), 6.85 (1H, d, J = 16.5 Hz), 7.08 (1H, d, J = 16.5 Hz), 7.20-7.40 (2H, m), 7.60-7.75 (1H, m), 7.85-8.10 (2H, m), 8.35-8.55 (1H, m). |

TABLE 79

| Ex No. | Strc | ¹H-NMR δ ppm: DMSO-d6 |
| --- | --- | --- |
| 472 | | 2.75-3.05 (4H, m), 6.10-6.40 (2H, m), 7.10-7.35 (2H, m), 7.45-7.60 (2H, m), 7.75-7.90 (1H, m), 8.20-8.40 (1H, m). |

TABLE 79-continued

| Ex No. | Strc | $^1$H-NMR δ ppm: DMSO-d6 |
|---|---|---|
| 473 | | 1.35-1.50 (1H, m), 1.65-2.10 (5H, m), 2.40-2.75 (2H, m), 3.50-3.85 (3H, m), 7.15-7.35 (2H, m), 7.45-7.60 (1H, m), 7.75-7.95 (1H, m), 8.20-8.40 (1H, m). |
| 474 | | 0.60-1.00 (4H, m), 1.65-1.85 (1H, m), 7.15-7.50 (3H, m), 7.75-7.95 (1H, m), 8.20-8.65 (1H, m). |
| 475 | | 2.24 (3H, s), 7.05-7.50 (4H, m), 7.80-8.10 (2H, m), 8.40-8.60 (1H, m) |
| 476 | | 4.15-4.40 (4H, m), 6.64 (1H, s), 7.20-7.40 (2H, m), 7.75-7.95 (2H, m), 8.40-8.55 (1H, m). |
| 477 | | 7.45-7.60 (2H, m), 7.67 (1H, dd, J = 5.0 Hz, 1.3 Hz), 7.79 (1H, dd, J = 5.0 Hz, 2.9 Hz), 7.97 (1H, d, J = 8.5 Hz), 8.16 (1H, dd, J = 2.9 Hz, 1.3 Hz), 9.51 (1H, s) |

TABLE 79-continued

| Ex No. | Strc | ¹H-NMR δ ppm: DMSO-d6 |
|---|---|---|
| 478 | | 7.20-7.35 (1H, m), 7.40-7.55 (2H, m), 7.70-7.85 (2H, m), 7.90-8.05 (1H, m), 9.54 (1H, s). |

TABLE 80

| Ex No. | Strc | ¹H-NMR δ ppm: DMSO-d6 |
|---|---|---|
| 479 | | 2.52 (3H, s), 6.85-7.05 (1H, m), 7.35-7.65 (3H, m), 7.85-8.05 (1H, m) 9.51 (1H, s). |
| 480 | | 0.80-2.20 (10H, m), 2.75-2.95 (1H, m). 7.35-7.50 (2H, m), 7.85-8.00 (1H, m), 9.35 (1H, s) |
| 481 | | 4.15-4.45 (4H, m), 7.00-7.15 (1H, m), 7.35-7.55 (4H, m), 7.85-8.05 (1H, m), 9.52 (1H, s). |
| 482 | | 2.48 (3H, s), 7.00-7.20 (1H, m), 7.40-7.80 (3H, m), 7.85-8.05 (1H, m), 9.57 (1H, s). |

TABLE 80-continued

| Ex No. | Strc | ¹H-NMR δ ppm: DMSO-d6 |
| --- | --- | --- |
| 483 | | 7.35-7.65 (5H, m), 7.70-7.85 (2H, m), 7.90-8.10 (1H, m), 9.34 (1H, s). |
| 484 | | 7.15-7.30 (1H, m), 7.45-7.75 (4H, m), 7.85-8.05 (1H, m), 9.30 (1H, s). |
| 485 | | 7.40-7.65 (3H, m), 7.10-8.10 (3H, m), 9.31 (1H, s). |

TABLE 81

| Ex No. | Strc | ¹H-NMR δ ppm: DMSO-d6 |
| --- | --- | --- |
| 486 | | 7.15-7.55 (4H, m), 7.60-7.90 (4H, m), 8.15-8.35 (1H, m). |
| 487 | | 7.25-7.60 (4H, m), 7.65-7.85 (3H, m), 8.90-9.10 (1H, m). |

TABLE 81-continued
| Ex No. | Strc | ¹H-NMR δ ppm: DMSO-d6 |
|---|---|---|
| 488 | 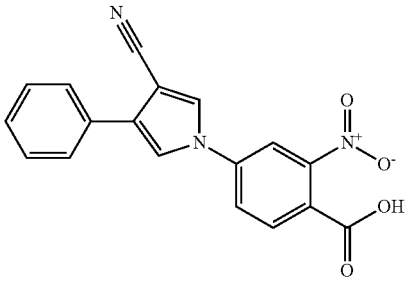 [SMILES: N#Cc1cn(-c2ccc(C(=O)O)c([N+](=O)[O-])c2)cc1-c1ccccc1] | 7.30-7.55 (3H, m), 7.65-7.80 (2H, m), 8.00-8.30 (3H, m), 8.35-8.50 (1H, m), 8.55-8.70 (1H, m), 14.02 (1H, brs.) |
| 489 | 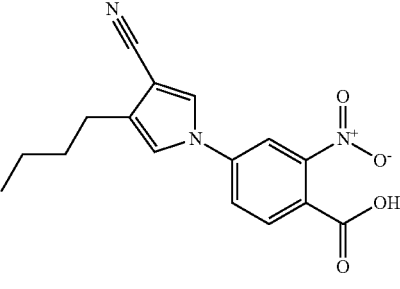 [SMILES: CCCCc1cn(-c2ccc(C(=O)O)c([N+](=O)[O-])c2)cc1C#N] | 0.80-1.05 (3H, m), 1.25-1.45 (2H, m), 1.50-1.70 (2H, m), 2.40-2.60 (2H, m), 7.50-7.70 (1H, m), 7.90-8.15 (2H, m), 8.20-8.45 (2H, m). |
| 490 | 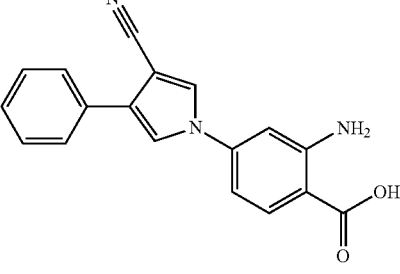 | 6.80-7.05 (2H, m), 7.25-7.55 (3H, m), 7.65-7.90 (4H, m), 8.20-8.35 (1H, m). |
| 491 | 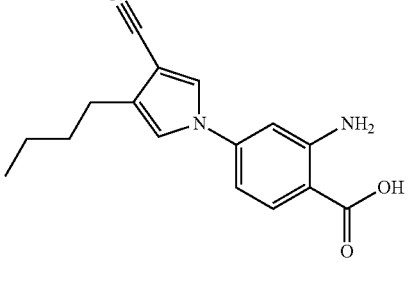 | 0.80-1.00 (3H, m), 1.25-1.45 (2H, m), 1.50-1.70 (2H, m), 2.40-2.60 (2H, m), 6.65-6.80 (1H, m), 6.85-7.00 (1H, m), 7.15-7.35 (1H, m), 7.70-7.85 (1H, m), 8.00-8.15 (1H, m). |
| 492 | 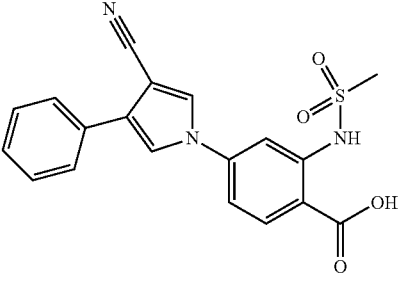 [SMILES: CS(=O)(=O)Nc1cc(-n2cc(C#N)c(-c3ccccc3)c2)ccc1C(=O)O] | 3.38 (3H, s). 7.25-7.80 (7H, m), 7.95-8.20 (2H, m), 8.40-8.60 (1H, m). |

TABLE 82

| Ex No. | Strc | ¹H-NMR δ ppm: DMSO-d6 |
|---|---|---|
| 493 | | 2.19 (3H, s), 7.25-7.55 (4H, m), 7.65-7.85 (2H, m), 7.90-8.20 (2H, m), 8.30-8.45 (1H, m), 8.65-8.80 (1H, m). |
| 494 | | 0.09 (3H, t, J = 7.4 Hz), 1.25-1.45 (2H, m), 1.50-1.70 (2H, m), 2.54 (2H, t, J = 7.4 Hz), 7.65-7.85 (2H, m), 8.00-8.75 (3H, m), 13.93 (1H, brs) |
| 495 | | 1.22 (3H, t, J = 7.6 Hz), 2.65 (2H, q, J = 7.6 Hz), 7.25-7.40 (2H, m), 7.75-7.75 (2H, m), 7.75-7.85 (1H, m), 8.25-8.40 (2H, m), 8.65-8.75 (2H, m), 14.0 (1H, brs.) |
| 496 | | 1.24 (6H, d, J = 7.0 Hz), 2.80-3.00 (1H, m), 7.25-7.40 (2H, m), 7.60-7.75 (2H, m), 7.75-7.85 (1H, m), 8.25-8.35 (2H, m), 8.65-8.75 (2H, m), 14.0 (1H, brs.) |
| 497 | | 1.32 (9H, s), 7.45-7.55 (2H, m), 7.65-7.75 (2H, m), 7.81 (1H, dd, J = 4.9 Hz, 1.1 Hz), 8.25-8.35 (2H, m), 8.65-8.75 (2H, m) |
| 498 | | 7.00-7.90 (8H, m), 8.15-8.80 (4H, m), 14.00 (1H, brs) |

TABLE 82-continued

| Ex No. | Strc | ¹H-NMR δ ppm: DMSO-d6 |
|---|---|---|
| 499 | | 2.80-3.00 (4H, m), 7.15-7.40 (5H, m), 7.70-8.75 (5H, m), 13.98 (1H, brs) |
| 500 | | 7.80-8.05 (5H, m), 8.30-8.85 (4H, m), 14.06 (1H, brs) |

TABLE 83

| Ex No. | Strc | ¹H-NMR δ ppm: DMSO-d6 |
|---|---|---|
| 501 | | 6.50-7.20 (4H, m), 7.65-8.75 (6H, m) |
| 502 | | 7.50-7.65 (1H, m), 7.84 (1H, dd, J = 5.0 Hz, 1.2 Hz), 8.15-8.25 (1H, m), 8.30-8.40 (1H, m), 8.45-8.65 (2H, m), 8.70-8.85 (2H, m), 8.95-9.05 (1H, m), 14.0 (1H, brs.) |
| 503 | | 7.90 (1H, dd, J = 5.0 Hz, 1.2 Hz), 8.25-8.45 (3H, m), 8.70-8.80 (1H, m), 8.85-9.00 (3H, m), 8.95-9.05 (1H, m) |
| 504 | | 3.83 (3H, s), 7.50-7.80 (2H, m), 8.10-8.25 (1H, m), 8.35-8.50 (1H, m), 8.55-8.70 (1H, m), 13.94 (1H, brs.). |

TABLE 83-continued

| Ex No. | Strc | ¹H-NMR δ ppm: DMSO-d6 |
|---|---|---|
| 505 | | 5.18 (2H, s), 6.90-7.90 (10H, m), 8.20-8.80 (4H, m) |
| 506 | | 5.18 (2H, s), 6.90-7.90 (10H, m), 8.20-8.80 (4H, m) |
| 507 | | 5.21 (2H, s), 7.00-7.85 (10H, m), 8.05-8.25 (2H, m), 8.60-8.75 (2H, m), 13.94 (1H, brs) |

TABLE 84

| Ex No. | Strc | ¹H-NMR δ ppm: DMSO-d6 |
|---|---|---|
| 508 | | 6.70-7.30 (4H, m), 7.75-8.75 (5H, m), 9.58 (1H, s) |
| 509 | | 6.85-7.85 (5H, m), 8.10-8.75 (4H, m), 9.89 (1H, s) |

TABLE 84-continued
| Ex No. | Strc | ¹H-NMR δ ppm: DMSO-d6 |
|---|---|---|
| 510 | 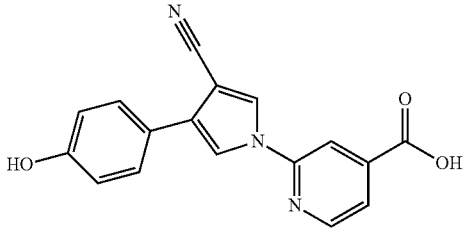 [SMILES: N#Cc1cn(-c2cc(C(=O)O)ccn2)cc1-c1ccc(O)cc1] | 6.80-7.85 (5H, m), 8.15-8.75 (4H, m), 9.61 (1H, s) |
| 511 | 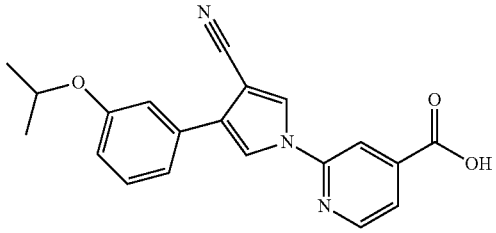 [SMILES: CC(C)Oc1cccc(-c2cn(-c3cc(C(=O)O)ccn3)cc2C#N)c1] | 1.32 (6H, d, J = 6.0 Hz), 4.60-4.80 (1H, m), 6.90-7.20 (2H, m), 7.25-7.40 (1H, m), 7.45-7.60 (1H, m), 8.08 (1H, d, J = 2.5 Hz), 8.20-8.25 (1H, m), 8.60-8.75 (2H, m) |
| 512 | 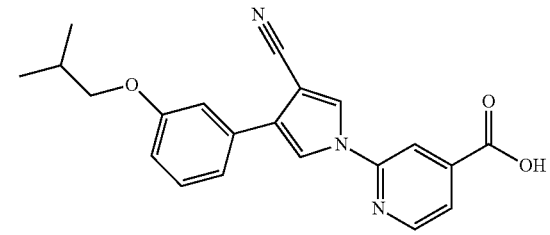 [SMILES: CC(C)COc1cccc(-c2cn(-c3cc(C(=O)O)ccn3)cc2C#N)c1] | 0.99 (6H, d, J = 6.8 Hz), 2.00-2.20 (1H, m), 3.84 (2H, d, J = 6.4 Hz), 6.95-7.20 (2H, m), 7.25-7.45 (1H, m), 7.50-7.65 (1H, m), 7.70-7.95 (1H, m), 8.14 (1H, d, J = 2.3 Hz), 8.20-8.30 (1H, m), 8.65-8.75 (2H, m), 1.92 (1H, brs.) |
| 513 | 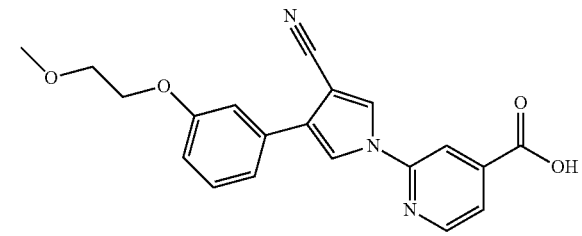 [SMILES: COCCOc1cccc(-c2cn(-c3cc(C(=O)O)ccn3)cc2C#N)c1] | 3.34 (3H, s), 3.70-3.80 (2H. m), 4.15-4.25 (2H, m), 7.00-7.25 (2H, m), 7.25-7.40 (1H, m), 7.63 (1H, dd, J = 7.7 Hz, 1.8 Hz), 7.81 (1H, dd, J = 5.1 Hz, 1.2 Hz), 8.15-8.10 (2H, m), 8.60-8.80 (2H, m), 13.98 (1H, brs.) |
| 514 | 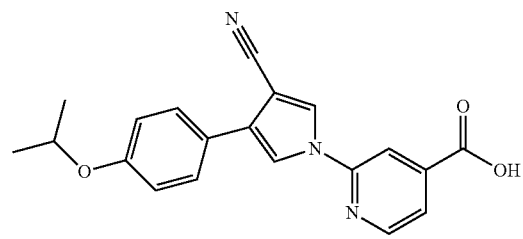 [SMILES: CC(C)Oc1ccc(-c2cn(-c3cc(C(=O)O)ccn3)cc2C#N)cc1] | 1.29 (6H, d, J = 6.0 Hz), 4.46-4.80 (1H, m), 6.90-7.85 (5H, m), 8.15-8.80 (4H, m) |
TABLE 85
| Ex No. | Strc | ¹H-NMR δ ppm: DMSO-d6 |
|---|---|---|
| 515 | 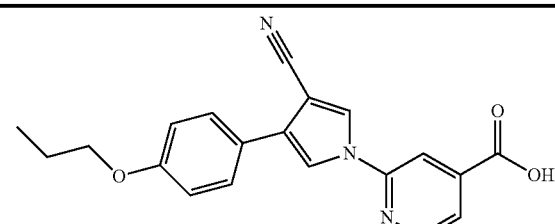 | 0.98 (3H, t, J = 7.4 Hz), 1.65-1.85 (2H, m), 3.98 (2H, t, J = 6.5 Hz), 6.95-7.85 (5H. m), 8.20-8.75 (4H, m) |

TABLE 85-continued
| Ex No. | Strc | ¹H-NMR δ ppm: DMSO-d6 |
|---|---|---|
| 516 | 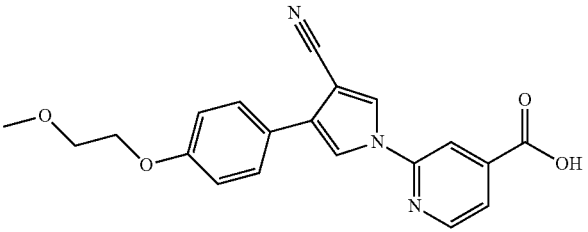 [SMILES: COCCOc1ccc(-c2cn(-c3cc(C(=O)O)ccn3)cc2C#N)cc1] | 3.30-3.40 (3H, m), 3.60-4.20 (4H, m), 6.95-7.85 (5H, m), 8.20-8.75 (4H, m) |
| 517 | 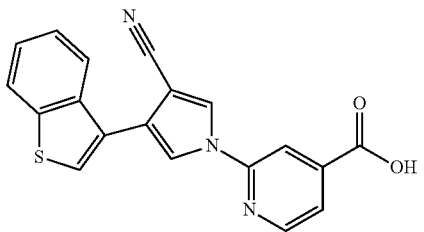 [SMILES: N#Cc1cn(-c2cc(C(=O)O)ccn2)cc1-c1csc2ccccc12] | 7.35-7.60 (2H, m), 7.75-8.15 (4H, m), 8.20-8.45 (2H, m), 8.65-8.85 (2H, m), 14.02 (1H, brs.) |
| 518 | 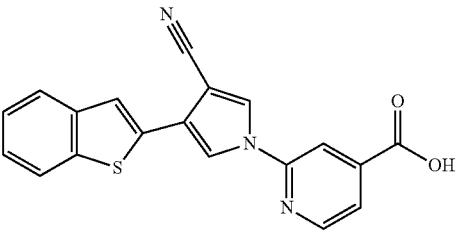 [SMILES: N#Cc1cn(-c2cc(C(=O)O)ccn2)cc1-c1cc2ccccc2s1] | 7.30-7.50 (2H, m), 7.75-8.10 (4H, m), 8.25-8.50 (2H, m), 8.65-8.85 (2H, m), 14.03 (1H, brs.). |
| 519 | 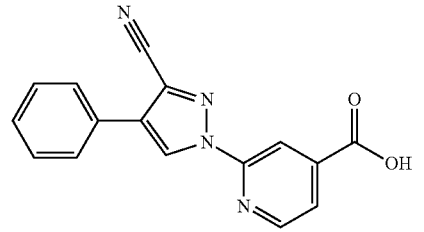 [SMILES: N#Cc1nn(-c2cc(C(=O)O)ccn2)cc1-c1ccccc1] | 7.35-7.65 (3H, m), 7.75-8.00 (3H, m), 8.30-8.45 (1H, m), 8.70-8.85 (1H, m), 9.34 (1H, s), 14.13 (1H, brs.). |
| 520 | 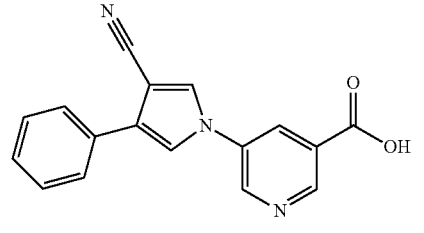 [SMILES: N#Cc1cn(-c2cncc(C(=O)O)c2)cc1-c1ccccc1] | 7.25-7.60 (3H, m), 7.65-7.85 (2H, m), 8.10-8.30 (1H, m), 8.50-8.70 (2H, m), 8.95-9.15 (1H, m), 9.20-9.35 (1H, m), 13.79 (1H, brs.). |
| 521 | 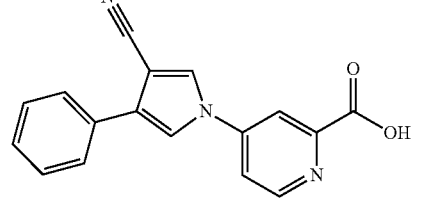 | 7.25-7.60 (3H, m), 7.65-8.10 (3H, m), 8.15-8.50 (2H, m), 8.60-9.00 (2H, m). |

TABLE 86
| Ex No. | Strc | $^1$H-NMR δ ppm: DMSO-d6 |
|---|---|---|
| 522 | 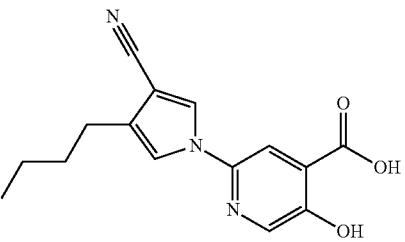 [SMILES: CCCCc1cn(-c2cc(C(=O)O)c(O)cn2)cc1C#N] | 0.91 (3H, t, J = 7.3 Hz), 1.25-1.45 (2H, m), 1.50-1.70 (2H, m), 2.40-2.60 (2H, m), 7.50-7.60 (1H, m), 7.89 (1H, s), 8.18 (1H, s), 8.20-8.30 (1H, m) |
| 523 | 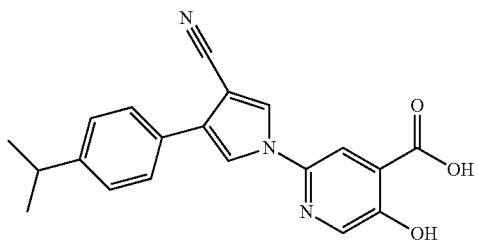 [SMILES: CC(C)c1ccc(-c2cn(-c3cc(C(=O)O)c(O)cn3)cc2C#N)cc1] | 1.24 (6H, d, J = 6.6 Hz), 2.80-3.00 (1H, m), 7.30-7.40 (2H, m), 7.60-7.75 (2H, m), 8.08 (1H, s), 8.11 (1H, d, J = 2.3 Hz), 8.29 (1H, s), 8.49 (1H, d, J = 2.3 Hz) |
| 524 | 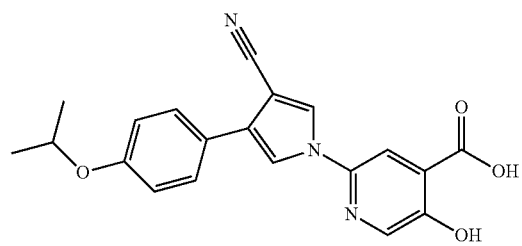 [SMILES: CC(C)Oc1ccc(-c2cn(-c3cc(C(=O)O)c(O)cn3)cc2C#N)cc1] | 1.28 (6H, d, J = 6.1 Hz), 4.55-4.75 (1H, m), 6.95-7.70 (4H, m), 8.00-8.55 (4H, m) |
| 525 | 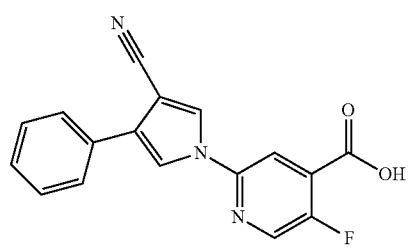 [SMILES: N#Cc1cn(-c2cc(C(=O)O)c(F)cn2)cc1-c1ccccc1] | 7.30-7.85 (5H, m), 8.20-8.35 (2H, m), 8.55-8.75 (2H, m) |
| 526 | 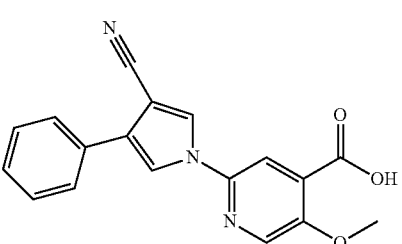 | 3.98 (3H, s), 7.25-7.80 (5H, m), 8.00-8.60 (4H, m), 13.79 (1H, brs) |
| 527 | 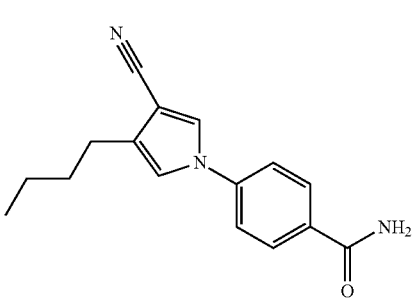 [SMILES: CCCCc1cn(-c2ccc(C(N)=O)cc2)cc1C#N] | 0.80-1.00 (3H, m), 1.25-1.45 (2H, m), 1.50-1.70 (2H, m), 2.40-2.60 (2H, m), 7.30-7.55 (2H, m), 7.65-7.80 (2H, m), 7.90-8.10 (3H, m), 8.20-8.30 (1H, m). |

TABLE 86-continued

| Ex No. | Strc | ¹H-NMR δ ppm: DMSO-d6 |
|---|---|---|
| 528 | | 5.17 (2H, s), 6.90-7.10 (1H, m), 7.25-7.55 (9H, m), 7.75-7.90 (2H, m), 7.95-8.20 (4H, m), 8.40-6.60 (1H, m). |

TABLE 87

| Ex No. | Strc | ¹H-NMR δ ppm: DMSO-d6 |
|---|---|---|
| 529 | | 6.75-6.95 (2H, m), 7.35-7.65 (3H, m), 7.70-8.20 (6H, m), 8.35-8.50 (1H, m), 9.60 (1H, s). |
| 530 | | 6.80-7.00 (2H, m), 7.10-7.25 (1H, m), 7.40-7.55 (2H, m), 7.75-7.90 (3H, m), 8.00-8.15 (3H, m), 8.35-8.50 (1H, m), 9.88 (1H, brs.). |
| 531 | | 6.65-6.80 (1H, m), 7.05-7.30 (3H, m), 7.40-7.55 (1H, m), 7.75-7.90 (2H, m), 7.95-8.15 (4H, m), 8.40-8.55 (1H, m), 9.61 (1H, brs.). |
| 532 | | 2.37 (3H, s), 7.20-7.55 (5H, m), 7.75-7.90 (3H, m), 7.95-8.15 (3H, m), 8.40-8.55 (1H, m). |

TABLE 87-continued

| Ex No. | Strc | ¹H-NMR δ ppm: DMSO-d6 |
|---|---|---|
| 533 | 4-[4-(2-methoxyphenyl)-3-cyano-1H-pyrrol-1-yl]benzamide | 3.84 (3H, s), 6.95-7.20 (2H, m), 7.30-7.55 (3H, m), 7.75-7.90 (3H, m), 7.95-8.15 (3H, m), 8.35-8.50 (1H, m). |
| 534 | 4-[4-(2-fluorophenyl)-3-cyano-1H-pyrrol-1-yl]benzamide | 7.25-7.55 (4H, m), 7.60-7.75 (1H, m), 7.80-8.15 (6H, m), 8.45-8.60 (1H, m). |
| 535 | 4-[4-(2-chlorophenyl)-3-cyano-1H-pyrrol-1-yl]benzamide | 7.35-7.70 (5H, m), 7.75-8.15 (6H, m), 8.40-8.60 (1H, m). |

TABLE 88

| Ex No. | Strc | ¹H-NMR δ ppm: DMSO-d6 |
|---|---|---|
| 536 | 4-[4-(2-trifluoromethylphenyl)-3-cyano-1H-pyrrol-1-yl]benzamide | 7.40-8.15 (1H, m), 8.40-8.60 (1H, m). |
| 537 | 4-[4-(3-methylphenyl)-3-cyano-1H-pyrrol-1-yl]benzamide | 2.37 (3H, s), 7.10-7.25 (1H, m), 7.30-7.65 (4H, m), 7.80-8.15 (6H, m), 8.40-8.60 (1H, m). |

TABLE 88-continued

| Ex No. | Strc | $^1$H-NMR δ ppm: DMSO-d6 |
|---|---|---|
| 538 | (structure: 4-[4-(3-methoxyphenyl)-3-cyano-1H-pyrrol-1-yl]benzamide) | 3.82 (3H, m), 6.85-7.00 (1H, m), 7.25-7.60 (4H, m), 7.75-7.95 (2H, m), 8.00-8.20 (4H, m), 8.40-8.60 (1H, m). |
| 539 | (structure: 4-[4-(3-fluorophenyl)-3-cyano-1H-pyrrol-1-yl]benzamide) | 7.10-7.30 (1H, m), 7.40-7.70 (4H, m), 7.80-7.95 (2H, m), 8.00-8.30 (4H, m), 8.45-8.60 (1H, m). |
| 540 | (structure: 4-[4-(3-chlorophenyl)-3-cyano-1H-pyrrol-1-yl]benzamide) | 7.35-7.60 (3H, m), 7.65-7.95 (4H, m), 8.00-8.30 (4H, m), 8.45-8.60 (1H, m). |
| 541 | (structure: 4-[4-(3-trifluoromethylphenyl)-3-cyano-1H-pyrrol-1-yl]benzamide) | 7.40-7.60 (1H, m), 7.65-8.20 (9H, m), 8.25-8.40 (1H, m), 8.45-8.65 (1H, m). |
| 542 | (structure: 4-[4-(4-methylphenyl)-3-cyano-1H-pyrrol-1-yl]benzamide) | 2.34 (3H, s), 7.20-7.35 (2H, m), 7.40-7.70 (3H, m), 7.75-8.15 (6H, m), 8.40-8.55 (1H, m). |

TABLE 89
| Ex No. | Strc | $^1$H-NMR δ ppm: DMSO-d6 |
|---|---|---|
| 543 | 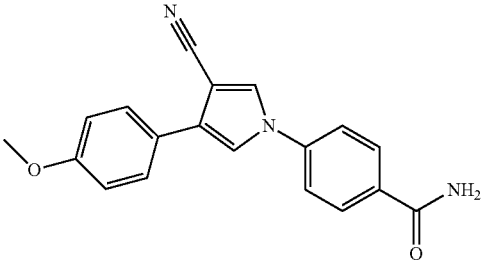 [SMILES: COc1ccc(-c2cn(-c3ccc(C(N)=O)cc3)cc2C#N)cc1] | 3.80 (3H, s), 6.95-7.15 (2H, m), 7.40-7.90 (5H, m), 7.95-8.15 (4H, m), 8.35-8.55 (1H, m). |
| 544 | 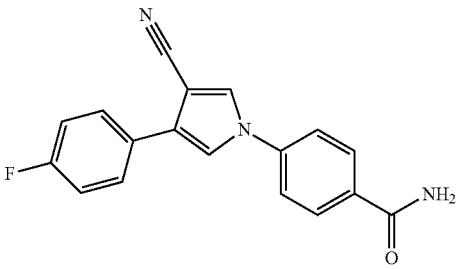 [SMILES: N#Cc1cn(-c2ccc(C(N)=O)cc2)cc1-c1ccc(F)cc1] | 7.25-7.55 (3H, m), 7.70-8.20 (8H, m), 8.40-8.60 (1H, m). |
| 545 | 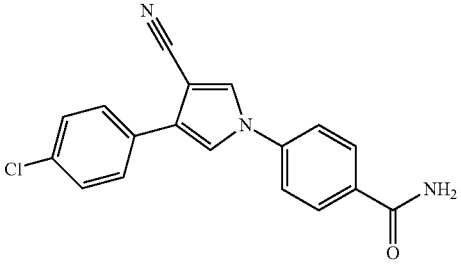 [SMILES: N#Cc1cn(-c2ccc(C(N)=O)cc2)cc1-c1ccc(Cl)cc1] | 7.40-7.65 (3H, m), 7.70-7.90 (4H, m), 7.95-8.25 (4H, m), 8.45-8.60 (1H, m). |
| 546 | 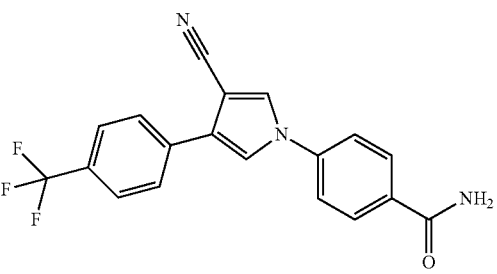 [SMILES: N#Cc1cn(-c2ccc(C(N)=O)cc2)cc1-c1ccc(C(F)(F)F)cc1] | 7.40-7.60 (1H, m), 7.75-8.15 (9H, m), 8.20-8.35 (1H, m), 3.50-8.65 (1H, m). |
| 547 | 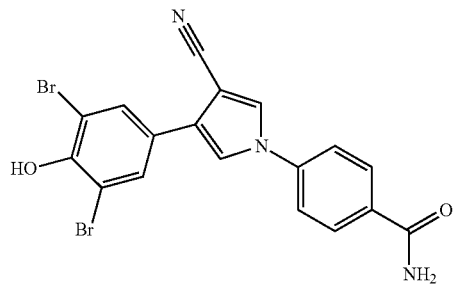 [SMILES: N#Cc1cn(-c2ccc(C(N)=O)cc2)cc1-c1cc(Br)c(O)c(Br)c1] | 7.35-7.55 (1H, m), 7.75-8.25 (8H, m), 8.40-8.60 (1H, m), 10.12 (1H, brs.). |

TABLE 89-continued

| Ex No. | Strc | $^1$H-NMR δ ppm: DMSO-d6 |
|---|---|---|
| 548 | | 7.35-7.60 (3H, m), 7.65-7.95 (4H, m), 8.00-8.30 (4H, m), 8.45-8.60 (1H, m). |
| 549 | | 7.25-7.55 (5H, m), 7.65-7.85 (2H, m) 7.90-8.20 (3H, m), 8.40-8.60 (2H, m), 13.56 (1H, brs.). |

TABLE 90

| Ex No. | Strc | $^1$H-NMR δ ppm: DMSO-d6 |
|---|---|---|
| 550 | | 7.05-7.65 (5H, m), 7.90-8.15 (3H, m), 8.35-8.60 (2H, m), 13.55 (1H, brs.). |
| 551 | | 7.20-7.40 (2H, m), 7.45-7.85 (3H, m). 7.90-8.20 (3H, m), 8.35-8.60 (2H, m), 13.56 (1H, brs.). |
| 552 | | 6.55-6.80 (2H, m), 7.20-7.40 (2H, m), 7.65-7.85 (1H, m), 7.90-8.10 (3H, m), 8.40-8.60 (2H, m), 13.54 (1H, brs.). |

TABLE 90-continued

| Ex No. | Strc | ¹H-NMR δ ppm: DMSO-d6 |
|---|---|---|
| 553 | (structure) | 6.75-7.05 (4H, m), 7.25-7.55 (3H, m), 7.60-7.95 (4H, m), 8.20-8.35 (1H, m). |

Test Example 1

Xanthine Oxidase Inhibitory Activity (1) Preparation of Test Compounds

Test compounds were dissolved in DMSO (Wako) at 40 mM concentration and then diluted to intended concentrations with phosphate-buffered saline (PBS).

(2) Method for Measurement

Xanthine oxidase (from bovine milk, Sigma) was prepared with phosphate-buffered saline (PBS) at 0.02 units/mL, and then the solution was added to 96 well plates at 50 μL/well. In addition, test compounds diluted with PBS were added at 50 μL/well. Xanthine (Wako) at 200 μM prepared with PBS was added at 100 μL/well, and the reaction was conducted for 10 minutes at room temperature. Absorbance at 290 nm was measured using a microplate reader SpectraMax Plus 384 (Molecular device). The absorbance under a condition without xanthine is 0%, and control without test compounds is 100%. Fifty % inhibitory concentration of a test compound ($IC_{50}$) was calculated (Tables 91 to 92). Ex. No in the table indicates Example number.

TABLE 91

| Ex. No | $IC_{50}$ (nM) |
|---|---|
| 2 | 17.1 |
| 7 | 5.8 |
| 8 | 7.5 |
| 12 | 5.5 |
| 15 | 13.9 |
| 18 | 7.1 |
| 20 | 52.1 |
| 22 | 120.3 |
| 27 | 7.1 |
| 143 | 4.6 |
| 144 | 5.8 |
| 145 | 4.9 |
| 146 | 4.0 |
| 147 | 2.1 |
| 148 | 2.5 |
| 149 | 6.0 |
| 150 | 5.0 |
| 151 | 63.2 |
| 152 | 4.0 |
| 153 | 2.4 |
| 154 | 4.0 |
| 155 | 52.4 |
| 156 | 52.9 |
| 157 | 33.8 |
| 158 | 5.1 |
| 159 | 2.7 |
| 160 | 2.1 |
| 161 | 31.9 |
| 162 | 55.1 |

TABLE 91-continued

| Ex. No | $IC_{50}$ (nM) |
|---|---|
| 163 | 41.7 |
| 164 | 33.2 |
| 165 | 32.2 |
| 166 | 52.2 |
| 167 | 83.8 |
| 168 | 70.0 |
| 169 | 56.8 |
| 170 | 37.5 |
| 171 | 39.8 |
| 172 | 49.1 |
| 173 | 41.4 |
| 174 | 17.6 |
| 175 | 27.7 |
| 176 | 13.7 |
| 177 | 54.4 |
| 179 | 143.2 |
| 180 | 255.4 |
| 183 | 67.3 |
| 184 | 71.9 |
| 188 | 132.1 |
| 189 | 63.4 |
| 190 | 116.5 |
| 191 | 90.3 |
| 193 | 70.4 |
| 198 | 111.3 |
| 199 | 19.2 |
| 200 | 5.9 |
| 201 | 11.1 |
| 202 | 6.0 |
| 203 | 6.6 |
| 206 | 7.1 |
| 207 | 3.8 |
| 208 | 5.2 |
| 209 | 7.1 |
| 210 | 5.1 |
| 211 | 4.6 |
| 212 | 5.4 |
| 213 | 16.8 |
| 214 | 47.0 |
| 215 | 6.7 |
| 216 | 20.9 |
| 217 | 5.0 |
| 219 | 5.0 |
| 220 | 11.1 |
| 221 | 45.4 |
| 224 | 10.7 |
| 225 | 7.2 |
| 226 | 19.7 |
| 227 | 3.6 |
| 228 | 4.6 |
| 229 | 7.2 |
| 230 | 13.0 |
| 231 | 7.0 |
| 232 | 26.9 |
| 233 | 2.3 |
| 234 | 4.0 |
| 235 | 8.6 |

TABLE 91-continued

| Ex. No | IC$_{50}$ (nM) |
|---|---|
| 236 | 81.2 |
| 238 | 3.6 |
| 239 | 15.0 |
| 240 | 3.3 |
| 241 | 3.6 |
| 242 | 9.0 |
| 244 | 3.6 |
| 245 | 2.8 |
| 246 | 8.9 |
| 247 | 8.9 |
| 248 | 11.9 |
| 249 | 9.4 |
| 250 | 25.6 |
| 251 | 23.0 |
| 252 | 33.2 |
| 253 | 5.4 |
| 254 | 6.9 |
| 255 | 10.1 |
| 256 | 15.2 |
| 257 | 4.1 |
| 258 | 3.9 |
| 259 | 4.7 |
| 261 | 5.3 |
| 262 | 3.1 |
| 263 | 4.6 |
| 265 | 7.3 |
| 266 | 10.4 |
| 267 | 11.6 |
| 268 | 13.3 |
| 269 | 23.4 |
| 270 | 24.2 |
| 271 | 15.1 |
| 272 | 10.1 |
| 273 | 14.6 |
| 274 | 5.0 |
| 275 | 7.2 |

TABLE 92

| Ex. No | IC$_{50}$ (nM) |
|---|---|
| 276 | 7.7 |
| 277 | 10.1 |
| 278 | 49.1 |
| 279 | 8.4 |
| 280 | 15.6 |
| 281 | 41.2 |
| 282 | 5.3 |
| 283 | 6.2 |
| 284 | 9.3 |
| 285 | 3.9 |
| 286 | 27.5 |
| 287 | 5.8 |
| 288 | 10.4 |
| 289 | 22.6 |
| 290 | 27.6 |
| 291 | 6.4 |
| 292 | 5.2 |
| 293 | 15.9 |
| 294 | 11.2 |
| 295 | 28.8 |
| 296 | 5.6 |
| 297 | 18.9 |
| 298 | 6.6 |
| 299 | 7.9 |
| 300 | 7.9 |
| 301 | 6.2 |
| 302 | 4.9 |
| 303 | 49.4 |
| 304 | 15.1 |
| 305 | 7.3 |
| 306 | 7.8 |
| 307 | 7.5 |
| 308 | 7.5 |
| 309 | 6.5 |
| 310 | 17.5 |
| 311 | 6.9 |
| 312 | 9.9 |
| 313 | 5.2 |
| 314 | 5.2 |
| 315 | 14.6 |
| 316 | 9.0 |
| 317 | 6.8 |
| 318 | 17.0 |
| 319 | 8.1 |
| 320 | 10.6 |
| 321 | 10.9 |
| 322 | 6.5 |
| 325 | 13.1 |
| 327 | 7.1 |
| 328 | 9.3 |
| 330 | 19.9 |
| 331 | 5.3 |
| 332 | 51.5 |
| 333 | 87.8 |
| 334 | 59.5 |
| 335 | 7.9 |
| 336 | 36.4 |
| 337 | 4.0 |
| 338 | 5.7 |
| 339 | 4.4 |
| 340 | 5.8 |
| 341 | 10.0 |
| 342 | 35.9 |
| 344 | 13.5 |
| 345 | 25.7 |
| 346 | 16.8 |
| 347 | 12.2 |
| 348 | 5.2 |
| 349 | 6.4 |
| 350 | 13.7 |
| 351 | 14.7 |
| 352 | 3.2 |
| 354 | 66.7 |
| 355 | 3.3 |
| 356 | 1.7 |
| 357 | 5.9 |
| 358 | 8.8 |
| 359 | 6.1 |
| 360 | 144.6 |
| 361 | 88.5 |
| 362 | 25.6 |
| 363 | 21.3 |
| 364 | 22.7 |
| 365 | 33.1 |
| 366 | 29.3 |
| 367 | 25.0 |
| 368 | 13.3 |
| 369 | 9.7 |
| 370 | 19.9 |
| 371 | 2.4 |

Test Example 2

Inhibitory Activity of Uric Acid Transport with Brush-Border Membrane Vesicles (BBMV)

Inhibitory activity of uric acid transport of test compounds was performed on the basis of methods described in a reference (Am. J. Physiol. 266 (Renal Fluid Electrolyte Physiol. 35): F797-F805, 1994) with a partial modification.

(1) Preparation of BBMV from Human Kidney Cortex

BBMV from human kidney cortex were purchased from KAC. Renal cortex was dissected from human kidney and cut into small pieces. Then, the cortex was homogenized in 5 volumes of ice-cold isotonic buffer (300 mM mannitol, 5 mM ethylene glycol-bis-(β-aminoethylether)-N,N,N',N'-tetraacetic acid (EGTA), 12 mM tris(hydroxymethyl)aminomethane (Tris).HCl, pH 7.4). After adding 1 M magnesium chloride to a final concentration of 12 mM, and then the suspension was mixed and allowed to stand on ice for 15 minutes. The homogenized solution was centrifuged at 2,500×g for 15 minutes at 4° C., furthermore, the supernatant was centrifuged at 30,000×g for 30 minutes at 4° C. The pellet was resuspended in ice-cold buffer 1 (150 mM mannitol, 2.5 mM EGTA, 6 mM Tris.HCl, pH 7.4). After adding 1 M magnesium chloride to a final concentration of 12 mM, and then the suspension was mixed and allowed to stand on ice for 15 minutes. After centrifugation again at 2,500×g for 15 minutes at 4° C., furthermore, the supernatant was centrifuged at 30,000×g for 30 minutes at 4° C. The pellet was resuspended in ice-cold buffer 2 (100 mM mannitol, 100 mM potassium gluconate, 20 mM 2-[4-(2-hydroxyethyl)-1-piperazinyl]-ethanesulfonic acid (Hepes)-Tris, pH 7.4). After centrifugation at 30,000×g for 30 minutes at 4° C., the pellet was resuspended in buffer 2, and then the protein concentration was determined (2) Preparation of Test Compounds Test compounds were dissolved in DMSO (Wako) at 40 mM concentration and then diluted to 2 times higher concentration than intended with Cl⁻ gradient buffer (100 mM mannitol, 100 mM potassium gluconate, 20 mM Hepes-Tris, pH 7.4). Cl⁻ gradient buffer without test compounds was used for control. Furthermore, an equal volume of Cl⁻ gradient buffer containing $^{14}$C-labeled uric acid (Moravek) and probenecid (Wako) was added to test compounds and control, and finally assay buffer including 40 μM uric acid and 5 μM probenecid was prepared. To measure the uptake of $^{14}$C-labeled uric acid through Cl⁻ gradient independent manner, assay buffer was prepared with Cl⁻ equilibrium buffer (100 mM mannitol, 60 mM potassium gluconate, 40 mM potassium chloride, 20 mM Hepes-Tris, pH 7.4) in place of Cl⁻ gradient buffer.

(3) Method for Measurement

BBMV were thawed on ice. After adding 8 mL of intravesicular buffer (100 mM mannitol, 60 mM potassium gluconate, 40 mM potassium chloride, 20 mM Hepes-Tris, pH 7.4) to 200 μL of prepared BBMV (protein concentration: 16 mg/mL), the BBMV were suspended through 25-gauge needle and allowed to equilibrate at room temperature for 60 minutes. After centrifugation at 30,000×g for 30 minutes at 4° C., the pellet was resuspended in 1.2 mL of intravesicular buffer. The suspension was kept on ice until the beginning of the measurement. The uptake of uric acid into BBMV was measured by the rapid-filtration technique. Requirement of BBMV (20 μL/l reaction) was warmed for 20 minutes at room temperature. The uptake of uric acid was initiated by mixing with 100 μL of assay buffer. After incubation for 20 seconds at room temperature, 3 mL of ice-cold stop solution (300 mM mannitol, 60 mM sodium sulfate, 100 μM probenecid (Wako), 5 mM Tris-H₂SO₄, pH 7.4) was added, and then the solutions were filtered rapidly through nitrocellulose filters (0.65 μm pore size, Sartorius) kept under suction. Furthermore, filters were washed twice with 3 mL of stop solution and dissolved in 10 mL of Filter-Count (PerkinElmer), and the radioactivity was counted in a liquid scintillation counter (PerkinElmer). The radioactivity associated with the filters in the absence of BBMV was used as corrections. In addition, percent inhibition of test compounds at 100 μM was calculated according to the formula described below (Table 93). Ex. No, Conc. and inhibition % in the table indicate Example number, concentration of test compounds (μM) and percent inhibition (%), respectively.

Percent inhibition (%)=[1−(B−C)/(A−C)]×100

A: Radioactivity in control
B: Radioactivity in the case of addition of test compounds
C: Radioactivity in Cl⁻ equilibrium buffer

TABLE 93

| Ex. No | Conc. (μM) | inhibition % |
|--------|------------|--------------|
| 20     | 100        | >90          |
| 306    | 100        | >90          |
| 355    | 100        | >90          |

Test Example 3

Inhibitory Activity of Uric Acid Transport with Human URAT1 Expressing Cells (1) Preparation of Transiently Human URAT1 Expressing Cells Full length human URAT1 cDNA (NCBI Accession No. NM_144585) was subcloned into expression vector, pcDNA3.1 (Invitrogen). Human URAT1 expression vector was transfected into COS7 cells (RIKEN CELL BANK RCB0539) using Lipofectamine 2000 (Invitrogen). COS7 cells were cultured in collagen-coated 24 well plates (Asahi Techno Glass) at 2×10⁵/well in D-MEM culture medium (Invitrogen) containing 10% fetal bovine serum (Sanko Junyaku) for 2 hours at 37° C. under the condition of 5% CO₂. For 1 well, 2 μL of Lipofectamine 2000 was diluted in 50 μL of OPTI-MEM (Invitrogen) and allowed to stand at room temperature for 7 minutes (hereinafter referred to as Lipo2000-OPTI). For 1 well, 0.8 μg of human URAT1 expression vector was diluted in 50 μL of OPTI-MEM (Invitrogen) and combined gently with Lipo2000-OPTI. After standing at room temperature for 25 minutes, the mixture was added to COS7 cells at 100 μL/well. Furthermore, COS7 cells were cultured for 2 days at 37° C. under the condition of 5% CO₂ and used for measuring inhibitory activity on the uptake.

(2) Preparation of Test Compounds

Test compounds were dissolved in DMSO (Wako) at 10 mM concentration and then diluted to 2 times higher concentration than intended with pre-treatment buffer (125 mM sodium gluconate, 4.8 mM potassium gluconate, 1.2 mM potassium dihydrogen phosphate, 1.2 mM magnesium sulfate, 1.3 mM calcium gluconate, 5.6 mM glucose, 25 mM Hepes, pH 7.4). Pre-treatment buffer without test compounds was used for control. In addition, an equal volume of pre-treatment buffer containing $^{14}$C-labeled uric acid (Moravek) was added to test compounds and control, and finally assay buffer including 20 μM uric acid was prepared.

(3) Method for Measurement

All tests were performed on hot-plate at 37° C. Pre-treatment buffer and assay buffer were incubated at 37° C. and then used for assays. Medium was removed from plates, and 700 mL of pre-treatment buffer was added, and the cells were pre-incubated for 10 minutes. After repeating same step, pre-treatment buffer was removed, and assay buffer was added at 400 μL/well. The uptake reaction was carried out for 5 minutes. After terminating the reaction, assay buffer was rapidly removed, and the cells were washed twice with addition of ice-cold pre-treatment buffer at 1.2 mL/well. Then, the cells were lysed by addition of 0.2 N sodium hydroxide at 300 μL/well. The lysed solutions were transferred into Picoplate (PerkinElmer), and Microscinti 40 (PerkinElmer) was added at 600 µL/well. After mixing, the radioactivity was counted in a liquid scintillation counter (PerkinElmer). The radioactivity in COST cells not transfected with URAT1 expression vector was also counted under the same condition as control. In addition, percent inhibition of test compounds at 100 µM was calculated according to the formula described below (Table 94). In the table Ex. No, Conc. and inhibition % indicate Example number, concentration of test compound (µM) and percent inhibiton (%), respectively.

Percent inhibition (%)=[1−(B−C)/(A−C)]×100

A: Radioactivity in control
B: Radioactivity in the case of addition of test compounds
C: Radioactivity in COST cells not transfected with URAT1 expression vector

TABLE 94

| Ex. No | Conc. (µM) | inhibition % |
|---|---|---|
| 20 | 100 | 77 |
| 306 | 100 | 91 |
| 355 | 100 | 89 |

Test Example 4

Serum Hypouricemic Effect (1) Method for Measurement

Test compounds at 1 mg/kg suspended in 0.5% methylcellulose solution were administered orally to overnight fasted male CD (SD) IGS rats (5-week-old, Charls River Japan). At 2 hours after administration, blood was collected under ether anesthesia from abdominal aorta, and serum was separated according to general method. Serum uric acid values were determined by use of uric acid measurement kit (Uric acid C-Test Wako: Wako), and percent decrease in uric acid was calculated according to the formula described below.

Percent decrease in uric acid (%)=(Serum uric acid values in control animals−Serum uric acid values in animals administered test compounds)×100/Serum uric acid values in control animals (2) Results Compounds of example 301 and 314 have over 50% hypouricemic effect at 2 hours after oral administration. As results described above, it is confirmed that compounds in the present invention have a potent effect reducing serum uric acid.

INDUSTRIAL APPLICABILITY

The 5-membered heterocyclic derivatives represented by the above general formula (I) of the present invention or prodrugs, or pharmaceutically acceptable salts thereof exert an excellent xanthine oxidase inhibitory activity, and therefore, can exert an inhibitory activity of uric acid production and lower the blood uric acid level. Therefore, the present invention can provide an agent for the prevention or treatment of hyperuricemia, gouty tophus, gouty arthritis, renal disorder associated with hyperuricemia, urinary calculi or the like.

The invention claimed is:
1. A 5-membered heterocyclic derivative represented by the general formula (I):

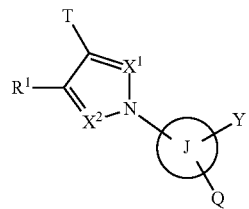

wherein
T represents nitro, cyano or trifluoromethyl;
ring J represents a phenyl ring or a 5 or 6-membered heteroaryl ring;
Q represents carboxy, lower alkoxycarbonyl, carbamoyl, mono(di)(lower alkyl)carbamoyl, sulfo, sulfamoyl or 5-tetrazolyl when ring J represents a phenyl ring; or Q represents carboxy, lower alkoxycarbonyl, carbamoyl, mono(di)(lower alkyl) carbamoyl or 5-tetrazolyl when ring J represents a 5 or 6-membered heteroaryl ring;
$X^1$ and $X^2$ independently represent $CR^2$ or N with the proviso that both of $X^1$ and $X^2$ do not represent N at the same time, and when two $R^2$ exist, these $R^2$ are optionally the same or different from each other, and with proviso that both of $X^1$ and $X^2$ do not represent $CR^2$ at the same time when ring J represents a phenyl ring;
$R^2$ represents a hydrogen atom or optionally substituted lower alkyl;
Y represents hydroxy, amino, a halogen atom, perfluoro (lower alkyl), optionally substituted lower alkyl, optionally substituted lower alkoxy, nitro, (lower alkyl)carbonylamino or (lower alkyl)sulfonylamino when ring J represents a phenyl ring; or Y represents a hydrogen atom, hydroxy, amino, a halogen atom, perfluoro(lower alkyl), optionally substituted lower alkyl, optionally substituted lower alkoxy, nitro, (lower alkyl)carbonylamino or (lower alkyl) sulfonylamino when ring J represents a 5 or 6-membered heteroaryl ring with the proviso that two or more Y optionally exist on ring J and these Y are optionally the same or different from each other;
$R^1$ represents cyano, perfluoro(lower alkyl), $-A^4$, -A-D-L-M, -A-D-E-G-L-M or $-N(-D-L-M)_2$ with the proviso that two (-D-L-M) are optionally different from each other;
$A^4$ represents thiol, —CHO, carboxy, —CONHR³, —N(R³)CHO, —N═CR³NHR⁴, —COCOOH, —COCONHR³, —SO₂NHR³, —N(R³)CONHR⁴ or —N(R³)SO₂NHR⁴ when ring J represents a phenyl ring; or $A^4$ represents thiol, —CHO, carboxy, —CONHR³, amino, —N(R³)CHO, —N═CR³NHR⁴, —COCOOH, —COCONHR³, —COCONHR³, —SO₂NHR³, —N(R³)CONHR⁴ or —N(R³)SO₂NHR⁴ when ring J represents a 5 or 6-membered heteroaryl ring;
A represents a single bond, —O—, —S—, —CO—, —COO—, —CON(R³)—, —SO₂—, —NH—, —N(R³)COO—, —N(R³)SO₂—, —N═CR³N(R⁴)—, —COCOO—, —COCON(R³)—, —SO₂N(R³)—, —N(R³)CON(R⁴)— or —N(R³)SO₂N(R⁴)—, wherein $R^3$ and $R^4$ independently represent a hydrogen atom or lower alkyl;
D represents optionally substituted lower alkylene, optionally substituted lower alkenylene, optionally substituted lower alkynylene, optionally substituted $C_{3-8}$ cycloalkylene, optionally substituted 3 to 8-membered heterocycloalkylene, optionally substituted $C_{6-10}$ arylene, optionally substituted 5 or 6-membered heteroarylene or optionally substituted 5 or 6-membered heteroarylene fused with a 6-membered ring with the proviso that D is optionally further substituted by -L-M or -E-G-L-M;

E represents a single bond, —O—, —S—, —CO—, —COO—, —CON($R^5$)—, —$SO_2$—, —N($R^5$)—, —N($R^5$)CO—, —N($R^5$)COO—, —N($R^5$)$SO_2$—, —OCON($R^5$)—, —OCOO—, —COCOO—, —COCON($R^5$)—, —$SO_2$N($R^5$)—, —N($R^5$)CON($R^6$)— or —N($R^5$)$SO_2$N($R^6$)—, wherein $R^5$ and $R^6$ independently represent a hydrogen atom or lower alkyl;

G represents optionally substituted lower alkylene, optionally substituted lower alkenylene, optionally substituted lower alkynylene, optionally substituted $C_{3-8}$ cycloalkylene, optionally substituted 3 to 8-membered heterocycloalkylene, optionally substituted $C_{6-10}$ arylene, optionally substituted 5 or 6-membered heteroarylene or optionally substituted 5 or 6-membered heteroarylene fused with a 6-membered ring;

L represents a single bond, —O—, —S—, —CO—, —COO—, —CON($R^8$)—, —$SO_2$—, —N($R^8$)—, —N($R^8$)CO—, —N($R^8$)COO—, —N($R^8$)$SO_2$—, —OCO—, —OCON($R^8$)—, —OCOO—, —COCOO—, —COCON($R^8$)—, —$SO_2$N($R^8$)—, —N($R^8$)CON($R^9$)— or —N($R^8$)$SO_2$N($R^9$)—, wherein $R^8$ and $R^9$ independently represent a hydrogen atom or lower alkyl; and M represents a hydrogen atom, optionally substituted lower alkyl, optionally substituted lower alkenyl, optionally substituted lower alkynyl, optionally substituted $C_{3-8}$ cycloalkyl(lower alkyl), optionally substituted 3 to 8-membered heterocycloalkyl(lower alkyl), optionally substituted $C_{6-10}$ aryl(lower alkyl), optionally substituted 5 or 6-membered heteroaryl(lower alkyl), or optionally substituted 5 or 6-membered heteroaryl fused with a 6-membered ring (lower alkyl), optionally substituted $C_{3-8}$ cycloalkyl, optionally substituted 3 to 8-membered heterocycloalkyl, optionally substituted $C_{6-10}$ aryl, optionally substituted 5 or 6-membered heteroaryl or optionally substituted 5 or 6-membered heteroaryl fused with a 6-membered ring with the proviso that when M is a hydrogen atom, L is a single bond, —O—, —S—, —CO—, —COO—, —CON($R^8$)—, —N($R^8$)—, —N($R^8$)CO—, —OCO—, —OCON($R^8$)—, —COCOO—, —COCON($R^8$)—, —$SO_2$N($R^8$)—, —N($R^8$)CON($R^9$)— or —N($R^8$)$SO_2$N($R^9$)—; with the proviso that when $R^1$ and $R^2$ bound to the neighboring atoms exist, these $R^1$ and $R^2$ optionally bind together to form a ring; respectively, or a pharmaceutically acceptable salt thereof.

2. A 5-membered heterocyclic derivative as claimed in claim 1, wherein Y represents, hydroxy, amino, a halogen atom, perfluoro(lower alkyl), optionally substituted lower alkyl or optionally substituted lower alkoxy when J represents a phenyl ring; or Y represents a hydrogen atom, hydroxy, amino, a halogen atom, perfluoro(lower alkyl), optionally substituted lower alkyl or optionally substituted lower alkoxy when ring J represents a 5 or 6-membered heteroaryl ring with the proviso that two or more Y optionally exist on ring J and these Y are optionally the same or different from each other, or a pharmaceutically acceptable salt thereof.

3. A 5-membered heterocyclic derivative as claimed in claim 2, wherein

Q represents carboxy, carbamoyl or 5-tetrazolyl;

Y represents hydroxy, amino, a halogen atom, perfluoro(lower alkyl), optionally substituted lower alkyl, or lower alkoxy which optionally has 1 to 3 of the same or different substituents selected from the group consisting of a fluorine atom, hydroxy and amino when ring J represents a phenyl ring; or Y represents a hydrogen atom, hydroxy amino, a halogen atom, perfluoro(lower alkyl), optionally substituted lower alkyl, or lower alkoxy which optionally has 1 to 3 of the same or different substituents selected from the group consisting of a fluorine atom, hydroxy and amino when ring J represents a 5 or 6-membered heteroaryl ring with the proviso that two or more Y optionally exist on ring J and these Y are optionally the same or different from each other;

$R^1$ represents perfluoro(lower alkyl), -$A^A$, -A-D-L-M, -A-D-E-G-L-M or —N(-D-L-M)$_2$ with the proviso that two (-D-L-M) are optionally different from each other;

$A^A$ represents thiol, —CHO, —CONH$R^3$, —N($R^3$)CHO, —N=C($R^3$)NH$R^4$, —COCOOH, —COCONH$R^3$, —$SO_2$NH$R^3$, —N($R^3$)CONH$R^4$ or —N($R^3$)$SO_2$NH$R^4$ when ring J represents a phenyl ring; or $A^A$ represents thiol, —CHO, —CONH$R^3$, amino, —N($R^3$)CHO, —N=C($R^3$)N$R^4$, —COCOOH, —COCONH$R^3$, —$SO_2$NH$R^3$, —N($R^3$)CONH$R^4$ or —N($R^3$)$SO_2$NH$R^4$ when ring J represents a 5 or 6-membered heteroaryl ring;

A represents a single bond, —O—, —S—, —CO—, —CON($R^3$)—, —$SO_2$—, —NH—, —N($R^3$)COO—, —N($R^3$)$SO_2$—, —N=C$R^3$N($R^4$)—, —COCOO—, —COCON($R^3$)—, —$SO_2$N($R^3$)—, —N($R^3$)CON($R^4$)— or —N($R^3$)$SO_2$N($R^4$)—, wherein $R^3$ and $R^4$ independently represent a hydrogen atom or lower alkyl;

D represents optionally substituted lower alkylene, optionally substituted lower alkenylene, optionally substituted lower alkynylene, optionally substituted $C_{3-8}$ cycloalkylene, optionally substituted 3 to 8-membered heterocycloalkylene, optionally substituted $C_{6-10}$ arylene, optionally substituted 5 or 6-membered heteroarylene or optionally substituted 5 or 6-membered heteroarylene fused with a 6-membered ring with the proviso that D is optionally further substituted by -L-M or -E-G-L-M;

E represents a single bond, —O—, —S—, —CO—, —COO—, —CON($R^5$)—, —$SO_2$—, —N($R^5$)—, —N($R^5$)CO—, —N($R^5$)COO—, —N($R^5$)$SO_2$—, —OCON($R^5$)—, —OCOO—, —COCOO—, —COCON($R^5$)—, —$SO_2$N($R^5$)—, —N($R^5$)CON($R^6$)— or —N($R^5$)$SO_2$N($R^6$)—, wherein $R^5$ and $R^6$ independently represent a hydrogen atom or lower alkyl;

G represents optionally substituted lower alkylene, optionally substituted lower alkenylene, optionally substituted lower alkynylene, optionally substituted $C_{3-8}$ cycloalkylene, optionally substituted 3 to 8-membered heterocycloalkylene, optionally substituted $C_{6-10}$ arylene, optionally substituted 5 or 6-membered heteroarylene or optionally substituted 5 or 6-membered heteroarylene fused with a 6-membered ring;

L represents a single bond, —O—, —S—, —CO—, —COO—, —CON($R^8$)—, —$SO_2$—, —N($R^8$)—, —N($R^8$)CO—, —N($R^8$)COO—, —N($R^8$)$SO_2$—, —OCO—, —OCON($R^8$)—, —OCOO—, —COCOO—, —COCON($R^8$)—, —$SO_2$N($R^8$)—, —N($R^8$)CON($R^9$)— or —N($R^8$)$SO_2$N($R^9$)—, wherein $R^8$ and $R^9$ independently represent a hydrogen atom or lower alkyl; and M represents a hydrogen atom, optionally substituted lower alkyl, optionally substituted lower alkenyl, optionally substituted lower alkynyl, optionally substituted $C_{3-8}$ cycloalkyl(lower alkyl), optionally substituted 3 to 8-membered heterocycloalkyl(lower alkyl), optionally substituted $C_{6-10}$ aryl(lower alkyl), optionally substituted 5 or 6-membered heteroaryl(lower alkyl), or optionally substituted 5 or 6-membered heteroaryl fused with a 6-membered ring (lower alkyl), optionally substituted $C_{3-8}$ cycloalkyl, optionally substituted 3 to 8-membered heterocycloalkyl, optionally substituted $C_{6-10}$ aryl, optionally substituted 5 or 6-membered heteroaryl or optionally substituted 5 or 6-membered heteroaryl fused with a 6-membered ring with the proviso that when M is a hydrogen atom, L is a single bond, —O—, —S—, —CO—, —COO—, —CON($R^8$)—, —N($R^8$)—, —N($R^8$)CO—, —OCO—, —OCON($R^8$)—, —COCOO—, —COCON($R^8$)—, —$SO_2$N($R^8$)—, —N($R^8$)CON($R^9$)— or —N($R^8$)$SO_2$N($R^9$)— with the proviso that when $R^1$ and $R^2$ bound to the neighboring atoms exist, these $R^1$ and $R^2$ optionally bind together to form a ring; respectively, or a pharmaceutically acceptable salt thereof.

4. A 5-membered heterocyclic derivative as claimed in claim 2, wherein $X^1$ represents N; and $X^2$ represents $CR^2$ wherein $R^2$ represents a hydrogen atom or optionally substituted lower alkyl; or a pharmaceutically acceptable salt thereof.

5. A 5-membered heterocyclic derivative as claimed in claim 2, wherein $X^1$ represents CH; and $X^2$ represents N; or a pharmaceutically acceptable salt thereof.

6. A 5-membered heterocyclic derivative as claimed in claim 2, wherein ring J represents a 5 or 6-membered heteroaryl ring, and $X^1$ and $X^2$ independently represent $CR^2$ wherein these $R^2$ are optionally different from each other and represent a hydrogen atom or optionally substituted lower alkyl; or a pharmaceutically acceptable salt thereof.

7. A 5-membered heterocyclic derivative as claimed in claim 6, wherein $X^1$ and $X^2$ represent CH, or a pharmaceutically acceptable salt thereof.

8. A 5-membered heterocyclic derivative as claimed in claim 1, wherein T represents cyano, or a pharmaceutically acceptable salt thereof.

9. A 5-membered heterocyclic derivative as claimed in claim 1, wherein Q represents carboxy, or a pharmaceutically acceptable salt thereof.

10. A 5-membered heterocyclic derivative as claimed in claim 9, wherein the group represented by the general formula:

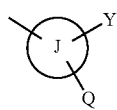
(II)

is a group represented by the following general formula (IIa) or (IIb):

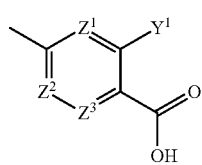
(IIa)

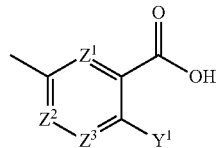
(IIb)

wherein
$Z^1$, $Z^2$ and $Z^3$ independently represent $CR^{12}$ or N; and
$Y^1$ represents hydroxy, amino, a halogen atom, optionally substituted lower alkyl, or lower alkoxy which optionally has 1 to 3 of the same or different substituents selected from the group consisting of a fluorine atom, hydroxy and amino when ring J represents a phenyl ring; or $Y^1$ represents a hydrogen atom, hydroxy, amino, a halogen atom, optionally substituted lower alkyl, or lower alkoxy which optionally has 1 to 3 of the same or different substituents selected from the group consisting of a fluorine atom, hydroxy and amino when ring J represents a 6-membered heteroaryl ring; and
$R^{12}$ represent a hydrogen atom, hydroxy, amino, a halogen atom, optionally substituted lower alkyl, or lower alkoxy which optionally has 1 to 3 of the same or different substituents selected from the group consisting of a fluorine atom, hydroxy and amino with the proviso that when two or more $R^{12}$ exist, these $R^{12}$ are optionally the same or different from each other, or a pharmaceutically acceptable salt thereof.

11. A 5-membered heterocyclic derivative as claimed in claim 10, wherein the group represented by the general formula (II) is a group represented by the general formula (IIa) wherein $Z^1$, $Z^2$ and $Z^3$ independently represent $CR^{12}$ in which $R^{12}$ represents a hydrogen atom or a halogen atom; and $Y^1$ represents hydroxy or amino, or a pharmaceutically acceptable salt thereof.

12. A 5-membered heterocyclic derivative as claimed in claim 10, wherein the group represented by the general formula (II) is a group represented by the general formula (IIb) wherein $Z^1$, $Z^2$ and $Z^3$ independently represent $CR^{12}$ in which $R^{12}$ represents a hydrogen atom or a halogen atom; and $Y^1$ represents hydroxy or amino, or a pharmaceutically acceptable salt thereof.

13. A 5-membered heterocyclic derivative as claimed in claim 10, wherein the group represented by the general formula (II) is a group represented by the general formula (IIa) wherein one of $Z^1$ and $Z^2$ represents N; the other represents CH; $Z^3$ represents CH; and $Y^1$ represents a hydrogen atom, hydroxy or amino, or a pharmaceutically acceptable salt thereof.

14. A 5-membered heterocyclic derivative as claimed in claim 10, wherein the group represented by the general formula (II) is a group represented by the general formula (IIb) wherein $Z^1$ and $Z^3$ independently represent $CR^{12}$ in which $R^{12}$ represents a hydrogen atom or a halogen atom; $Z^2$ represents N; and $Y^1$ represents a hydrogen atom, hydroxy or amino, or a pharmaceutically acceptable salt thereof.

15. A 5-membered heterocyclic derivative as claimed in claim 9, wherein ring J represents a 5-membered heteroaryl ring having 1 to 3 different or the same hetero atoms selected from the group consisting of an oxygen atom, a nitrogen atom and a sulfur atom in the ring, or a pharmaceutically acceptable salt thereof.

16. A 5-membered heterocyclic derivative as claimed in claim 15, wherein the group represented by the general formula:

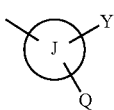

is a group represented by the following general formula (IIc):

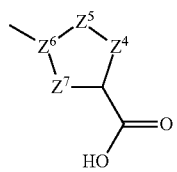

wherein $Z^4$, $Z^5$ and $Z^7$ independently represent an oxygen atom, a nitrogen atom, a sulfur atom with the proviso that both of $Z^4$ and $Z^5$ are not atoms selected from an oxygen atom or a sulfur atom at the same time, or $CR^{14}$ in which $R^{14}$ represents a hydrogen atom, hydroxy, amino, a halogen atom, optionally substituted lower alkyl or optionally substituted lower alkoxy with the proviso that when two or more $R^{14}$ exist, these $R^{14}$ are optionally the same or different from each other; $Z^6$ represents a carbon atom; and $Z^4$, $Z^5$, $Z^6$ and $Z^7$ bind together with the carbon atom bound by a carboxy group to form a 5-membered heteroaryl ring, or a pharmaceutically acceptable salt thereof.

17. A 5-membered heterocyclic derivative as claimed in claim 1, wherein $R^1$ represents -A-D-L-M or -A-D-E-G-L-M wherein A represents a single bond; and D, E, G, L and M have the same meanings as defined in claim 1, or a pharmaceutically acceptable salt thereof.

18. A 5-membered heterocyclic derivative as claimed in claim 1, wherein $R^1$ represents -A-D-L-M or -A-D-E-G-L-M wherein A represents —O—; and D, E, G, L and M have the same meanings as defined in claim 1, or a pharmaceutically acceptable salt thereof.

19. A 5-membered heterocyclic derivative as claimed in claim 1, wherein $R^1$ represents -A-D-L-M or -A-D-E-G-L-M wherein A represents —CO— or —CON($R^3$)—; and D, E, G, L, M and $R^3$ have the same meanings as defined in claim 1, or a pharmaceutically acceptable salt thereof.

20. A 5-membered heterocyclic derivative as claimed in claim 1, wherein $R^1$ represents -A-D-L-M, -A-D-E-G-L-M or —N(-D-L-M)$_2$ with the proviso that two (-D-L-M) are optionally different from each other, wherein A represents —N($R^3$)SO$_2$— or —N=CR$^3$N($R^4$)—; and D, E, G, L, M, $R^3$ and $R^4$ have the same meanings as defined in claim 1, or a pharmaceutically acceptable salt thereof.

21. A xanthine oxidase inhibitor comprising as an active ingredient a 5-membered heterocyclic derivative as claimed in claim 20, or a pharmaceutically acceptable salt thereof.

22. A 5-membered heterocyclic derivative as claimed in claim 1, wherein ring J represents a phenyl ring, or a pharmaceutically acceptable salt thereof.

23. A 5-membered heterocyclic derivative as claimed in claim 1, wherein ring J represents a 5 or 6-membered heteroaryl ring, or a pharmaceutically acceptable salt thereof.

24. A pharmaceutical composition comprising as an active ingredient a 5-membered heterocyclic derivative as claimed in claim 1, or a pharmaceutically acceptable salt thereof.

* * * * *